United States Patent
Ahmad et al.

(10) Patent No.: US 9,453,002 B2
(45) Date of Patent: *Sep. 27, 2016

(54) SUBSTITUTED IMIDAZOLES AS N-TYPE CALCIUM CHANNEL BLOCKERS

(71) Applicant: Janssen Pharmaceutica NV, Beerse (BE)

(72) Inventors: Ishtiyaque Ahmad, Bangalore (IN); Rajagopal Bakthavatchalam, Madison, CT (US); Sivaramakrishna Battula, Yeswanthpur (IN); Henricus Jacobus Maria Gijsen, Breda (NL); Saravanan Vadivelu, Yeswanthpur (IN); Mark Wall, Lansdale, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/968,480

(22) Filed: Aug. 16, 2013

(65) Prior Publication Data

US 2015/0051225 A1    Feb. 19, 2015

(51) Int. Cl.
*A61K 31/54* (2006.01)
*C07D 405/14* (2006.01)
*C07D 405/04* (2006.01)

(52) U.S. Cl.
CPC .......... *C07D 405/14* (2013.01); *C07D 405/04* (2013.01)

(58) Field of Classification Search
CPC  C07D 405/04; C07D 405/14; C07D 409/14; C07D 417/14; C07D 409/04
See application file for complete search history.

(56) References Cited

U.S. PATENT DOCUMENTS

2014/0163031 A1*  6/2014  Wall et al. ................. 514/236.5

FOREIGN PATENT DOCUMENTS

| WO | WO 2005/033073 | 4/2005 |
|---|---|---|
| WO | WO 2006/105442 | 10/2006 |

OTHER PUBLICATIONS

International Search Report mailed Oct. 31, 2013 for Application No. PCT/US2013/055282.
Belardetti, F., et al., "A Fluorescence-Based High-Throughput Screening Assay for the Identification of T-Type Calcium Channel Blockers", Assay and Drug Development Technologies, vol. 7, pp. 266-280 (2009).
Dai, G., et al. "A High-Throughput Assay for Evaluating State Dependence and Subtype Selectivity of Cav2 Calcium Channel Inhibitors", Assay and Drug Development Technologies, vol. 6, No. 2, pp. 195-212 (2008).
Dixon, W. J., "Efficient Analysis of Experimental Observations", Ann. Rev. Pharmacology.& Toxicology, vol. 20, pp. 441-462 (1980).
Finley, M., et al., "An Integrated Multiassay Approach to the Discovery of Small-Molecular N-Type Voltage-Gated Calcium Channel Antagonists", Assay and Drug Development Technologies, vol. 8(6), pp. 685-694 (2010).
Kim, Sun Ho., et al., An Experimental Model for Peripheral Neuropathy Produced by Segmental Spinal Nerve Ligation in the Rat, Pain, vol. 50, pp. 355-363 (1992).
Nielsen, C., et al., "Anti-Allodynic Efficacy of the χ-Conopeptide, Xen2174 in Rats with Neuropathic Pain", Pain, vol. 118, pp. 112-124 (2005).
Subasinghe, N., et al., "A Novel Series of Pyrazolylpiperidine N-Type Calcium Channel Blockers", Bioorganic & Medical Chemistry Letters, vol. 22, pp. 4080-4083 (2012).

* cited by examiner

*Primary Examiner* — Jean Cornet

(57) ABSTRACT

Disclosed are compounds, compositions and methods for treating various diseases, syndromes, conditions and disorders, including pain. Such compounds are represented by Formula (I) as follows:

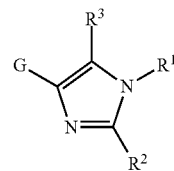

Formula (I)

wherein $R^1$, $R^2$, $R^3$, and G are defined herein.

24 Claims, No Drawings

SUBSTITUTED IMIDAZOLES AS N-TYPE CALCIUM CHANNEL BLOCKERS

CROSS-REFERENCE TO RELATED APPLICATIONS

Not applicable.

STATEMENT REGARDING FEDERALLY SPONSORED RESEARCH OR DEVELOPMENT

The research and development of the invention described below was not federally sponsored.

BACKGROUND OF THE INVENTION

Calcium ions play a fundamental role in the physiology and biochemistry of organisms and of cells. The entry of calcium into cells through ion channels mediates a variety of cellular and physiological responses, including gene expression, signal transduction, neurotransmitter release, muscle contraction and hormone secretion. Ion channels are classified by gating, or what opens and closes the channel to the flux of ions. Voltage-gated ion channels open or close depending on the voltage gradient across the plasma membrane, whereas ligand-gated ion channels open or close depending on the binding of ligands to the channel. The classification of voltage-gated calcium channels divides them into three groups: (i) high voltage-activated channels, which include L-, N-, P- and Q-type channels; (ii) intermediate voltage-activated R-type channels; and (iii) low voltage-activated T-type channels.

The N-type calcium channel is distributed mainly in central and peripheral neurons, being localized primarily to presynaptic nerve terminals. This channel regulates the calcium flux required for depolarization-evoked release of neurotransmitters from synaptic endings. The transmission of pain signals from the periphery to the central nervous system (CNS) is mediated, inter alia, by N-type calcium channels located in the spinal cord. Inhibition of the N-type calcium channel in the superficial dorsal horn leads to a decrease in membrane excitability and neurotransmitter release, resulting in pain relief. In addition, knock-out mice lacking the N-type calcium channel exhibit reduced nociceptive behaviors in animal models of pain.

N-type calcium channels have been shown to mediate the development and maintenance of the neuronal sensitization processes associated with neuropathic pain and therefore provide attractive targets for the development of analgesic drugs. Three N-type calcium channel modulators are currently approved for the treatment of pain: ω-conotoxin MVIIA (ziconotide), marketed as Prialt®, potently and selectively blocks the N-type calcium channel and is indicated for the management of severe chronic pain; gabapentin, marketed as Neurontin®, and pregabalin, marketed as Lyrica®, bind with high affinity to the α2δ subunit of the N-type calcium channel and are indicated for the treatment of fibromyalgia, diabetic nerve pain and/or post-herpetic neuralgia pain.

It is an object of the present invention to provide N-Type calcium channel blockers. It is also an object of the invention to provide a method of treating, ameliorating or preventing pain by the administration of a compound of Formula (I). And, it is an object of the invention to provide a pharmaceutical composition comprising a compound of Formula (I), useful for treating, ameliorating or preventing pain.

SUMMARY OF THE INVENTION

The present invention is directed to a compound of Formula (I)

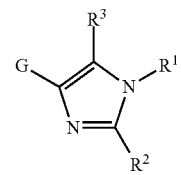

Formula (I)

wherein $R^1$ is i) phenyl optionally independently substituted with one to three substituents that are selected from the group consisting of chloro, fluoro, bromo, cyano, trifluoromethyl, $C_{1-4}$alkyl, difluoromethoxy, and $C_{1-4}$alkoxy; provided that when phenyl of group (i) is substituted with a single substituent, that substituent is at the 4-position;

ii) a heteroaryl selected from the group consisting of pyridinyl, pyrimidinyl, pyridazinyl, and pyrazinyl; wherein said heteroaryl is optionally independently substituted with one or two substituents that are chloro, fluoro, bromo, cyano, trifluoromethyl, $C_{1-4}$alkyl, or $C_{1-4}$alkoxy;

iii) pyrimidin-5-ylmethyl;

iv) phenylmethyl, wherein the phenyl portion of phenylmethyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylmethyl of group (iv) is substituted with a single substituent, that substituent is at the 4-position;

v) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylsulfonyl of group (v) is substituted with a single substituent, that substituent is at the 4-position;

vi) $C_{1-4}$alkylsulfonyl;

vii) $C_{3-7}$cycloalkylsulfonyl; or viii) trifluoromethylsulfonyl;

$R^2$ is i) phenyl optionally substituted with a substituent that is selected from the group consisting of $C_{1-4}$alkoxy and trifluoromethoxy;

ii) a heteroaryl selected from the group consisting of pyridinyl, pyrimidinyl, thiazolyl, triazolyl, and pyrazinyl; wherein said heteroaryl is optionally substituted with a substituent that is $C_{1-4}$alkyl, $C_{1-4}$alkoxy, trifluoromethoxy, or hydroxy;

iii) $C_{3-7}$cycloalkyl; or iv) $C_{3-7}$cycloalkyl-$(C_{1-2})$alkyl;

R³ is selected from the group consisting of hydrogen, chloro, and methyl;

G is G1, G2, or G3,

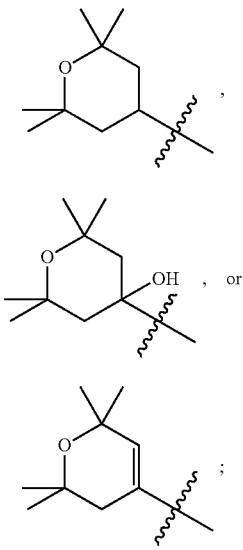

and enantiomers, diastereomers, solvates and pharmaceutically acceptable salts thereof The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a N-Type calcium channel-modulated disorder in a subject, including a human or other mammal in which the disease, syndrome, or condition is affected by the modulation of the N-Type calcium channel, such as pain and the diseases that lead to such pain, using a compound of Formula (I).

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g. $C_{1-8}$) refer independently to the number of carbon atoms in an alkyl moiety or to the alkyl portion of a larger alkyl-containing substituent. In substituent groups with multiple alkyl groups such as ($C_{1-6}$alkyl)$_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups.

When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term "aryl" refers to an unsaturated, aromatic monocyclic or bicyclic ring of 6 to 10 carbon members. Examples of aryl rings include phenyl and naphthalenyl.

The term "heteroaryl" refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term "halogen" or "halo" refers to fluorine, chlorine, bromine and iodine.

The term "formyl" refers to the group —C(=O)H.

The term "oxo" refers to the group (=O).

Whenever the term "alkyl" or "aryl" or either of their prefix roots appear in a name of a substituent (e.g., arylalkyl, alkylamino) the name is to be interpreted as including those limitations given above for "alkyl" and "aryl." Designated numbers of carbon atoms (e.g., $C_1$-$C_6$) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a "$C_1$-$C_6$ alkylcarbonyl" substituent refers to a group of the formula:

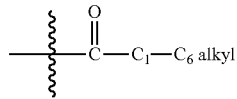

The term "R" at a stereocenter designates that the stereocenter is purely of the R-configuration as defined in the art; likewise, the term "S" means that the stereocenter is purely of the S-configuration. As used herein, the terms "*R" or "*S" at a stereocenter are used to designate that the stereocenter is of pure but unknown configuration. As used herein, the term "RS" refers to a stereocenter that exists as a mixture of the R- and S-configurations. Similarly, the terms "*RS" or "*SR" refer to a stereocenter that exists as a mixture of the R- and S-configurations and is of unknown configuration relative to another stereocenter within the molecule.

Compounds containing one stereocenter drawn without a stereo bond designation are a mixture of two enantiomers. Compounds containing two stereocenters both drawn without stereo bond designations are a mixture of 4 diastereomers. Compounds with 2 stereocenters both labeled "RS" and drawn with stereo bond designations are a 2-component mixture with relative stereochemistry as drawn. Compounds with 2 stereocenters both labeled "*RS" and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I) can be selected by one of ordinary skill in the art to provide compounds that are chemically stable and that can be readily synthesized by techniques known in the art as well as those methods set forth herein.

The term "subject" refers to an animal, preferably a mammal, most preferably a human, who has been the object of treatment, observation or experiment.

The term "therapeutically effective amount" refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term "composition" refers to a product that includes the specified ingredients in therapeutically effective amounts, as well as any product that results, directly, or indirectly, from combinations of the specified ingredients in the specified amounts.

The term "N-Type calcium channel blocker" is intended to encompass a compound that interacts with the N-Type calcium channel to substantially reduce or eliminate its functional activity, thereby decreasing the flow of calcium ions through the channel and the rise of intracellular calcium concentrations.

The term "N-Type calcium channel-modulated" is used to refer to the condition of being affected by the modulation of the N-Type calcium channel, including the condition of being affected by the inhibition of the N-Type calcium channel, such as, for example, pain, the diseases that lead to such pain and treatments that lead to the reduction of such pain.

As used herein, unless otherwise noted, the term "affect" or "affected" (when referring to a disease, syndrome, condition or disorder that is affected by the inhibition of N-Type calcium channel) shall include a reduction in the frequency and/or severity of one or more symptoms or manifestations of said disease, syndrome, condition or disorder and/or include the prevention of the development of one or more symptoms or manifestations of said disease, syndrome, condition or disorder or the development of the disease, condition, syndrome or disorder.

The compounds of Formula (I) are useful in methods for treating, ameliorating and/or preventing a disease, a syndrome, a condition or a disorder that is affected by the inhibition of N-Type calcium channel. Such methods comprise, consist of and/or consist essentially of administering to a subject, including an animal, a mammal, and a human in need of such treatment, amelioration and/or prevention, a therapeutically effective amount of a compound of Formula (I), or an enantiomer, diastereomer, solvate or pharmaceutically acceptable salt form thereof. In particular, the compounds of Formula (I) are useful for treating, ameliorating and/or preventing pain as well as diseases, syndromes, conditions or disorders causing such pain. More particularly, the compounds of Formula (I) are useful for treating, ameliorating and/or preventing acute pain, inflammatory pain and/or neuropathic pain, comprising administering to a subject in need thereof a therapeutically effective amount of a compound of Formula (I), as herein defined.

Acute pain, as used herein, refers to pain that comes on quickly, can be of varying severity but is self-limiting and of relatively short duration. Examples of acute pain include, but are not limited to, post-operative pain, post-surgical pain, toothache, burn, sunburn, insect/animal bites and stings, headache and/or any pain associated with acute trauma or injury.

Inflammatory pain refers to pain arising from an inflammatory disease, condition, syndrome or disorder, including but not limited to inflammatory bowel disease, irritable bowel syndrome, visceral pain, migraine, post-operative pain, osteoarthritis, rheumatoid arthritis, back pain, low back pain, joint pain, abdominal pain, chest pain, labor pain, musculoskeletal diseases, skin diseases, toothache, pyresis, burn, sunburn, snake bite, venomous snake bite, spider bite, insect sting, neurogenic or overactive bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache or arachnoiditis.

A further embodiment of the present invention is directed to a method for treating, ameliorating and/or preventing neuropathic pain. Neuropathic pain refers to a disease, syndrome, condition and/or disorder involving damage to the peripheral or central nervous system, including cancer pain, neurological disorders, spine and peripheral nerve surgery, brain tumor, traumatic brain injury (TBI), chemotherapy-induced pain, pain chronification, radicular pain, HIV pain, spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, post-herpetic neuralgia, causalgia, red neuralgia, Sluder's neuralgia, splenopalatine neuralgia, supraorbital neuralgia, trigeminal neuralgia, vulvodynia, or vidian neuralgia.

Embodiments of the present invention include a compound of Formula (I)

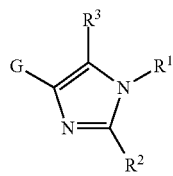

Formula (I)

wherein
a) $R^1$ is
  i) phenyl independently substituted with one to three substituents that are selected from the group consisting of chloro, fluoro, bromo, cyano, trifluoromethyl, $C_{1-4}$alkyl, difluoromethoxy, and $C_{1-4}$alkoxy; provided that when phenyl of group (i) is substituted with a single substituent, that substituent is at the 4-position;
  ii) a heteroaryl that is pyridinyl; wherein said pyridinyl is optionally independently substituted with one or two substituents that are chloro, fluoro, bromo, cyano, trifluoromethyl, $C_{1-4}$alkyl, or $C_{1-4}$alkoxy;
  iii) phenylmethyl, wherein the phenyl portion of phenylmethyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylmethyl of group (iii) is substituted with a single substituent, that substituent is at the 4-position;
  iv) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylsulfonyl of group (iv) is substituted with a single substituent, that substituent is at the 4-position;
  v) $C_{1-4}$alkylsulfonyl;
  or
  vi) trifluoromethylsulfonyl;
b) $R^1$ is
  i) phenyl independently substituted with one to three substituents that are selected from the group consisting of chloro, fluoro, bromo, cyano, trifluoromethyl, methyl, difluoromethoxy, and $C_{1-2}$alkoxy; provided that when phenyl of group (i) is substituted with a single substituent, that substituent is at the 4-position;
  or
  ii) a heteroaryl that is pyridinyl; wherein said pyridinyl is optionally independently substituted with one or two substituents that are chloro, fluoro, bromo, cyano, trifluoromethyl, or $C_{1-4}$alkyl;
c) $R^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;
d) $R^2$ is
  i) phenyl substituted with a substituent that is selected from the group consisting of $C_{1-4}$alkoxy and trifluoromethoxy;
  ii) a heteroaryl selected from the group consisting of pyridinyl, pyrimidinyl, and pyrazinyl; wherein said heteroaryl is optionally substituted with a substituent that is $C_{1-4}$alkoxy or trifluoromethoxy;
  iii) $C_{3-7}$cycloalkyl; or
  iv) $C_{3-7}$cycloalkyl-$(C_{1-2})$alkyl;
e) $R^2$ is
  i) phenyl substituted with $C_{1-4}$alkoxy;
  ii) a heteroaryl selected from the group consisting of pyridinyl and pyrazinyl; wherein said heteroaryl is optionally substituted with $C_{1-4}$alkoxy; or
  iii) $C_{3-7}$cycloalkyl-$(C_{1-2})$alkyl;
f) $R^2$ is
  i) phenyl substituted with $C_{1-4}$alkoxy; or
  ii) a heteroaryl selected from the group consisting of pyridinyl and pyrazinyl; wherein said heteroaryl is optionally substituted with $C_{1-4}$alkoxy;

g) R² is
   i) phenyl substituted with methoxy; or
   ii) a heteroaryl selected from the group consisting of pyridinyl and pyrazinyl; wherein said heteroaryl is optionally substituted with $C_{1-2}$alkoxy;
h) R³ is hydrogen;
i) G is G1 or G2:

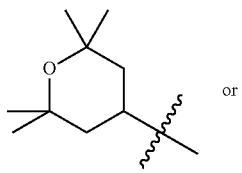
G1 or

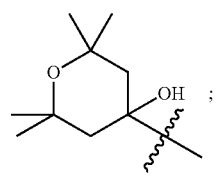
G2 j) G is G1;

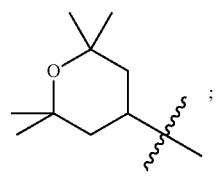
G1 k) G is G2;

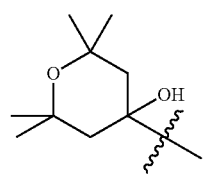
G2 and any combination of embodiments a) through k) above, provided that it is understood that combinations in which different embodiments of the same substituent would be combined are excluded;

and enantiomers, diastereomers, solvates and pharmaceutically acceptable salts thereof.

An embodiment of the present invention is directed to a compound of Formula (I)

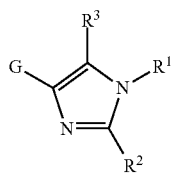
Formula (I)

wherein

R¹ is
  i) phenyl independently substituted with one to three substituents that are selected from the group consisting of chloro, fluoro, bromo, cyano, trifluoromethyl, $C_{1-4}$alkyl, difluoromethoxy, and $C_{1-4}$alkoxy; provided that when phenyl of group (i) is substituted with a single substituent, that substituent is at the 4-position;

ii) a heteroaryl that is pyridinyl; wherein said pyridinyl is optionally independently substituted with one or two substituents that are chloro, fluoro, bromo, cyano, trifluoromethyl, $C_{1-4}$alkyl, or $C_{1-4}$alkoxy;

iii) phenylmethyl, wherein the phenyl portion of phenylmethyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylmethyl of group (iii) is substituted with a single substituent, that substituent is at the 4-position;

iv) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$alkyl, and $C_{1-4}$alkoxy; provided that when phenylsulfonyl of group (iv) is substituted with a single substituent, that substituent is at the 4-position;

v) $C_{1-4}$alkylsulfonyl; or
  vi) trifluoromethylsulfonyl;

R² is
  i) phenyl substituted with a substituent that is selected from the group consisting of $C_{1-4}$alkoxy and trifluoromethoxy;
  ii) a heteroaryl selected from the group consisting of pyridinyl, pyrimidinyl, and pyrazinyl; wherein said heteroaryl is optionally substituted with a substituent that is $C_{1-4}$alkoxy or trifluoromethoxy;
  iii) $C_{3-7}$cycloalkyl; or
  iv) $C_{3-7}$cycloalkyl-$(C_{1-2})$alkyl;

R³ is hydrogen, chloro, or methyl;

G is G1 or G2;

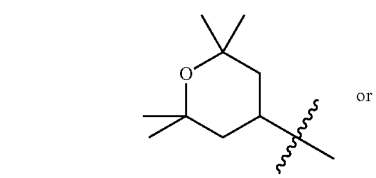
G1 or

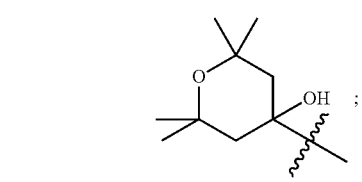
G2 and enantiomers, diastereomers, solvates, and pharmaceutically acceptable salt forms thereof.

An embodiment of the present invention is directed to a compound of Formula (I)

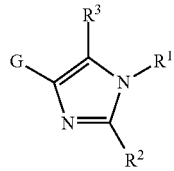

Formula (I)

wherein
R¹ is
i) phenyl independently substituted with one to three substituents that are selected from the group consisting of chloro, fluoro, bromo, cyano, trifluoromethyl, methyl, difluoromethoxy, and $C_{1-2}$alkoxy; provided that when phenyl of group (i) is substituted with a single substituent, that substituent is at the 4-position; or
ii) a heteroaryl that is pyridinyl; wherein said pyridinyl is optionally independently substituted with one or two substituents that are chloro, fluoro, bromo, cyano, trifluoromethyl, or $C_{1-4}$alkoxy;
R² is
i) phenyl substituted with $C_{1-4}$alkoxy;
ii) a heteroaryl selected from the group consisting of pyridinyl and pyrazinyl; wherein said heteroaryl is optionally substituted with $C_{1-4}$alkoxy; or
iii) $C_{3-7}$cycloalkyl-($C_{1-2}$)alkyl;
R³ is hydrogen;
G is G1 or G2;

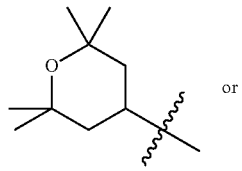

G1 or

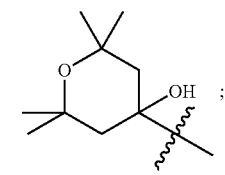

G2 and enantiomers, diastereomers, solvates, and pharmaceutically acceptable salt forms thereof.

An embodiment of the present invention is directed to a compound of Formula (I)

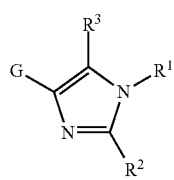

Formula (I)

wherein
R¹ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;
R² is
i) phenyl substituted with $C_{1-4}$alkoxy; or
ii) a heteroaryl selected from the group consisting of pyridinyl and pyrazinyl; wherein said heteroaryl is optionally substituted with $C_{1-4}$alkoxy;
R³ is hydrogen;
G is G1 or G2;

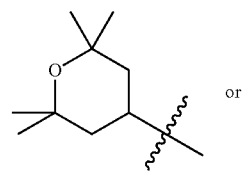

G1 or

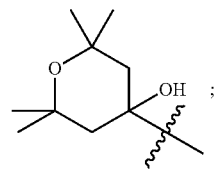

G2 and enantiomers, diastereomers, solvates, and pharmaceutically acceptable salt forms thereof.

An embodiment of the present invention is directed to a compound of Formula (I)

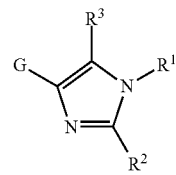

Formula (I)

wherein
R¹ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;
R² is
i) phenyl substituted with methoxy; or
ii) a heteroaryl selected from the group consisting of pyridinyl and pyrazinyl; wherein said heteroaryl is optionally substituted with $C_{1-2}$alkoxy;
R³ is hydrogen;
G is G1 or G2;

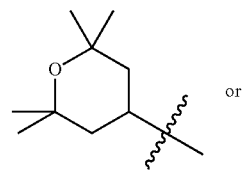

G1 or

-continued

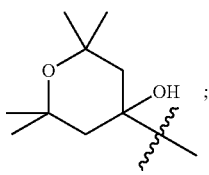

and enantiomers, diastereomers, solvates, and pharmaceutically acceptable salt forms thereof.

An embodiment of the present invention is directed to a compound of Formula (I)

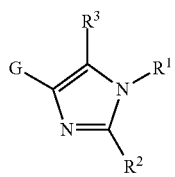

Formula (I)

wherein

R$^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

R$^2$ is
i) phenyl substituted with methoxy; or
ii) a heteroaryl selected from the group consisting of pyridinyl and pyrazinyl; wherein said heteroaryl is optionally substituted with C$_{1-2}$alkoxy;

R$^3$ is hydrogen;

G is G1;

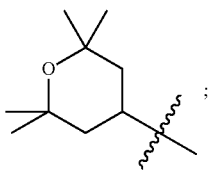

G1 and enantiomers, diastereomers, solvates, and pharmaceutically acceptable salt forms thereof.

An embodiment of the present invention is directed to a compound of Formula (I)

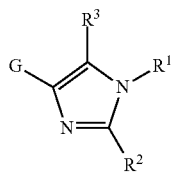

Formula (I)

wherein

R$^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

R$^2$ is
i) phenyl substituted with methoxy; or
ii) a heteroaryl selected from the group consisting of pyridinyl and pyrazinyl; wherein said heteroaryl is optionally substituted with C$_{1-2}$alkoxy;

R$^3$ is hydrogen;

G is G2;

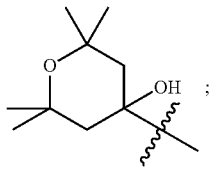

G2 and enantiomers, diastereomers, solvates, and pharmaceutically acceptable salt forms thereof.

Further embodiments of the present invention are directed to a compound of Formula (I)

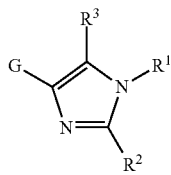

Formula (I)

selected from the group consisting of

Cpd 1, 4-[2-(2-Methoxyphenyl)-4-(2,2,6,6-tetramethyltetrahydro-2H-pyran-4-yl)-1H-imidazol-1-yl]benzonitrile;

Cpd 2, 4-[1-(4-Fluorophenyl)-4-(2,2,6,6-tetramethyltetrahydro-2H-pyran-4-yl)-1H-imidazol-2-yl]-3-methoxypyridine;

Cpd 3, 2-Ethoxy-5-[2-(3-methoxypyridin-4-yl)-4-(2,2,6,6-tetramethyltetrahydro-2H-pyran-4-yl)-1H-imidazol-1-yl]pyridine;

Cpd 4, 1-(4-Fluorophenyl)-2-(2-methoxyphenyl)-4-(2,2,6,6-tetramethyltetrahydro-2H-pyran-4-yl)-1H-imidazole;

Cpd 5, 5-[2-(2-Methoxyphenyl)-4-(2,2,6,6-tetramethyltetrahydro-2H-pyran-4-yl)-1H-imidazol-1-yl]-2-methylpyridine;

Cpd 6, 2-[2-(2-Methoxyphenyl)-4-(2,2,6,6-tetramethyltetrahydro-2H-pyran-4-yl)-1H-imidazol-1-yl]-5-methylpyridine;

Cpd 7, 2-(2-Methoxyphenyl)-1-(4-methoxyphenyl)-4-(2,2,6,6-tetramethyltetrahydro-2H-pyran-4-yl)-1H-imidazole;

Cpd 8, 5-[2-(2-Methoxyphenyl)-4-(2,2,6,6-tetramethyltetrahydro-2H-pyran-4-yl)-1H-imidazol-1-yl]-2-methylpyrimidine;

Cpd 9, 3-(1-(3-chlorobenzyl)-4-(2,2,6,6-tetramethyltetrahydro-2H-pyran-4-yl)-1H-imidazol-2-yl)-2-methoxypyridine;

Cpd 10, 3-[1-(4-Fluorophenyl)-4-(2,2,6,6-tetramethyltetrahydro-2H-pyran-4-yl)-1H-imidazol-2-yl]-2-methoxypyridine;

Cpd 11, 3-[1-(4-Chlorophenyl)-4-(2,2,6,6-tetramethyltetrahydro-2H-pyran-4-yl)-1H-imidazol-2-yl]-2-methoxypyridine;

Cpd 12, 4-[2-(3-Methoxypyridin-2-yl)-4-(2,2,6,6-tetramethyltetrahydro-2H-pyran-4-yl)-1H-imidazol-1-yl]benzonitrile;

Cpd 13, 4-[1-(4-Chloro-3-fluorophenyl)-4-(2,2,6,6-tetramethyltetrahydro-2H-pyran-4-yl)-1H-imidazol-2-yl]-3-methoxypyridine;

Cpd 14, 2-Chloro-5-[2-(2-methoxyphenyl)-4-(2,2,6,6-tetramethyltetrahydro-2H-pyran-4-yl)-1H-imidazol-1-yl]benzonitrile;

Cpd 15, 4-[2-(2-Methoxypyridin-3-yl)-4-(2,2,6,6-tetramethyltetrahydro-2H-pyran-4-yl)-1H-imidazol-1-yl]-2-methylbenzonitrile;

Cpd, 16, 2-methoxy-3-(4-(2,2,6,6-tetramethyltetrahydro-2H-pyran-4-yl)-1-(2,3,4-trifluorophenyl)-1H-imidazol-2-yl)pyridine;

Cpd 17, 2-[1-(3-Chloro-4-fluorophenyl)-4-(2,2,6,6-tetramethyltetrahydro-2H-pyran-4-yl)-1H-imidazol-2-yl]-3-methoxypyridine;

Cpd 18, 4-[1-(3-Chloro-4-fluorophenyl)-4-(2,2,6,6-tetramethyltetrahydro-2H-pyran-4-yl)-1H-imidazol-2-yl]-3-methoxypyridine;

Cpd 19, 2-[1-(4-Chloro-3-fluorophenyl)-4-(2,2,6,6-tetramethyltetrahydro-2H-pyran-4-yl)-1H-imidazol-2-yl]-3-methoxypyridine;

Cpd 20, 3-[1-(3-Chloro-4-fluorophenyl)-4-(2,2,6,6-tetramethyltetrahydro-2H-pyran-4-yl)-1H-imidazol-2-yl]-4-methoxypyridine;

Cpd 21, 4-[2-(2-Methoxyphenyl)-4-(2,2,6,6-tetramethyltetrahydro-2H-pyran-4-yl)-1H-imidazol-1-yl]-2-methylbenzonitrile;

Cpd 22, 5-[2-(2-Methoxyphenyl)-4-(2,2,6,6-tetramethyltetrahydro-2H-pyran-4-yl)-1H-imidazol-1-yl]-2-methylbenzonitrile;

Cpd 23, 3-[1-(3-Fluoro-4-methoxyphenyl)-4-(2,2,6,6-tetramethyltetrahydro-2H-pyran-4-yl)-1H-imidazol-2-yl]-2-methoxypyridine;

Cpd 24, 3-[1-(4-Fluoro-3-methoxyphenyl)-4-(2,2,6,6-tetramethyltetrahydro-2H-pyran-4-yl)-1H-imidazol-2-yl]-2-methoxypyridine;

Cpd 25, 5-[2-(2-Methoxypyridin-3-yl)-4-(2,2,6,6-tetramethyltetrahydro-2H-pyran-4-yl)-1H-imidazol-1-yl]-2-methylbenzonitrile;

Cpd 26, 3-[1-(4-Chlorophenyl)-4-(2,2,6,6-tetramethyltetrahydro-2H-pyran-4-yl)-1H-imidazol-2-yl]-4-methyl-4H-1,2,4-triazole;

Cpd 27, 3-[1-(2-Chlorobenzyl)-4-(2,2,6,6-tetramethyltetrahydro-2H-pyran-4-yl)-1H-imidazol-2-yl]-2-methoxypyridine;

Cpd 28, 3-[1-(4-Chlorobenzyl)-4-(2,2,6,6-tetramethyltetrahydro-2H-pyran-4-yl)-1H-imidazol-2-yl]-2-methoxypyridine;

Cpd 29, 4-(2-(2-methoxypyridin-3-yl)-4-(2,2,6,6-tetramethyltetrahydro-2H-pyran-4-yl)-1H-imidazol-1-yl)-2-(trifluoromethyl)benzonitrile;

Cpd 30, 3-[1-(2,4-Difluorophenyl)-4-(2,2,6,6-tetramethyltetrahydro-2H-pyran-4-yl)-1H-imidazol-2-yl]-2-methoxypyridine;

Cpd 31, 3-(1-(2,3-difluorophenyl)-4-(2,2,6,6-tetramethyltetrahydro-2H-pyran-4-yl)-1H-imidazol-2-yl)-2-methoxypyridine;

Cpd 32, 3-[2-(2-Methoxyphenyl)-4-(2,2,6,6-tetramethyltetrahydro-2H-pyran-4-yl)-1H-imidazol-1-yl]benzonitrile;

Cpd 33, 4-[1-(3,4-Difluorophenyl)-4-(2,2,6,6-tetramethyltetrahydro-2H-pyran-4-yl)-1H-imidazol-2-yl]-3-methoxypyridine;

Cpd 34, 2-Methoxy-4-[2-(2-methoxyphenyl)-4-(2,2,6,6-tetramethyltetrahydro-2H-pyran-4-yl)-1H-imidazol-1-yl]benzonitrile;

Cpd 35, 2-[1-(3,4-Difluorophenyl)-4-(2,2,6,6-tetramethyltetrahydro-2H-pyran-4-yl)-1H-imidazol-2-yl]-3-methoxypyridine;

Cpd 36, 3-Fluoro-4-[2-(2-methoxyphenyl)-4-(2,2,6,6-tetramethyltetrahydro-2H-pyran-4-yl)-1H-imidazol-1-yl]benzonitrile;

Cpd 37, 2-Methoxy-5-[2-(2-methoxyphenyl)-4-(2,2,6,6-tetramethyltetrahydro-2H-pyran-4-yl)-1H-imidazol-1-yl]benzonitrile;

Cpd 38, 1-(4-Chlorophenyl)-2-(2-methoxyphenyl)-4-(2,2,6,6-tetramethyltetrahydro-2H-pyran-4-yl)-1H-imidazole;

Cpd 39, 5-Chloro-2-[2-(2-methoxyphenyl)-4-(2,2,6,6-tetramethyltetrahydro-2H-pyran-4-yl)-1H-imidazol-1-yl]pyridine;

Cpd 40, 3-[1-(3,4-Difluorophenyl)-4-(2,2,6,6-tetramethyltetrahydro-2H-pyran-4-yl)-1H-imidazol-2-yl]-2-methoxypyridine;

Cpd 41, 1-(4-Chloro-3-fluorophenyl)-2-(2-methoxyphenyl)-4-(2,2,6,6-tetramethyltetrahydro-2H-pyran-4-yl)-1H-imidazole;

Cpd 42, 1-(3,4-Difluorophenyl)-2-(2-methoxyphenyl)-4-(2,2,6,6-tetramethyltetrahydro-2H-pyran-4-yl)-1H-imidazole;

Cpd 43, 4-[2-(2-Methoxypyridin-3-yl)-4-(2,2,6,6-tetramethyltetrahydro-2H-pyran-4-yl)-1H-imidazol-1-yl]benzonitrile;

Cpd 44, 3-[1-(4-Chloro-3-fluorophenyl)-4-(2,2,6,6-tetramethyltetrahydro-2H-pyran-4-yl)-1H-imidazol-2-yl]-2-methoxypyridine;

Cpd 45, 1-(3-Chloro-4-fluorophenyl)-2-(2-methoxyphenyl)-4-(2,2,6,6-tetramethyltetrahydro-2H-pyran-4-yl)-1H-imidazole;

Cpd 46, 3-[1-(3-Chloro-4-fluorophenyl)-4-(2,2,6,6-tetramethyltetrahydro-2H-pyran-4-yl)-1H-imidazol-2-yl]-2-methoxypyridine;

Cpd 47, 2-[1-(4-Fluorophenyl)-4-(2,2,6,6-tetramethyltetrahydro-2H-pyran-4-yl)-1H-imidazol-2-yl]-3-methoxypyrazine;

Cpd 48, 3-[2-(2-Methoxypyridin-3-yl)-4-(2,2,6,6-tetramethyltetrahydro-2H-pyran-4-yl)-1H-imidazol-1-yl]benzonitrile;

Cpd 49, 5-[1-(4-Chlorophenyl)-4-(2,2,6,6-tetramethyltetrahydro-2H-pyran-4-yl)-1H-imidazol-2-yl]-4-methoxypyrimidine;

Cpd 50, 2-[1-(4-Chlorophenyl)-4-(2,2,6,6-tetramethyltetrahydro-2H-pyran-4-yl)-1H-imidazol-2-yl]-3-methoxypyrazine;

Cpd 51, 3-[1-(4-Chlorophenyl)-4-(2,2,6,6-tetramethyltetrahydro-2H-pyran-4-yl)-1H-imidazol-2-yl]-2-ethoxypyridine;

Cpd 52, 3-[1-(3,4-Difluorophenyl)-4-(2,2,6,6-tetramethyltetrahydro-2H-pyran-4-yl)-1H-imidazol-2-yl]-2-ethoxypyridine;

Cpd 53, 5-[2-(2-Methoxyphenyl)-4-(2,2,6,6-tetramethyltetrahydro-2H-pyran-4-yl)-1H-imidazol-1-yl]-2-(trifluoromethyl)pyridine;

Cpd 54, 2-Methoxy-3-{4-(2,2,6,6-tetramethyltetrahydro-2H-pyran-4-yl)-1-[6-(trifluoromethyl)pyridin-3-yl]-1H-imidazol-2-yl}pyridine;

Cpd 55, 1-(4-Chlorophenyl)-2-(cyclopropylmethyl)-4-(2,2,6,6-tetramethyltetrahydro-2H-pyran-4-yl)-1H-imidazole;

Cpd 56, 1-(4-Chlorophenyl)-2-cyclopropyl-4-(2,2,6,6-tetramethyltetrahydro-2H-pyran-4-yl)-1H-imidazole;

Cpd 57, 4-[2-Cyclopropyl-4-(2,2,6,6-tetramethyltetrahydro-2H-pyran-4-yl)-1H-imidazol-1-yl]benzonitrile;

Cpd 58, 4-[2-(Cyclopropylmethyl)-4-(2,2,6,6-tetramethyltetrahydro-2H-pyran-4-yl)-1H-imidazol-1-yl]benzonitrile;

Cpd 59, 5-[2-(Cyclopropylmethyl)-4-(2,2,6,6-tetramethyltetrahydro-2H-pyran-4-yl)-1H-imidazol-1-yl]-2-(trifluoromethyl)pyridine;

Cpd 60, 2-[1-(4-Chlorophenyl)-4-(2,2,6,6-tetramethyltetrahydro-2H-pyran-4-yl)-1H-imidazol-2-yl]-3-ethoxypyrazine;

Cpd 61, 1-(4-(difluoromethoxy)phenyl)-2-(2-methoxyphenyl)-4-(2,2,6,6-tetramethyltetrahydro-2H-pyran-4-yl)-1H-imidazole;

Cpd 62, 1-(4-Bromo-3-fluorophenyl)-2-(2-methoxyphenyl)-4-(2,2,6,6-tetramethyltetrahydro-2H-pyran-4-yl)-1H-imidazole;

Cpd 63, 1-(3-Bromo-4-fluorophenyl)-2-(2-methoxyphenyl)-4-(2,2,6,6-tetramethyltetrahydro-2H-pyran-4-yl)-1H-imidazole;

Cpd 64, 3-[1-(3-Bromo-4-fluorophenyl)-4-(2,2,6,6-tetramethyltetrahydro-2H-pyran-4-yl)-1H-imidazol-2-yl]-2-methoxypyridine;

Cpd 65, 3-[1-(4-Bromo-3-fluorophenyl)-4-(2,2,6,6-tetramethyltetrahydro-2H-pyran-4-yl)-1H-imidazol-2-yl]-2-methoxypyridine;

Cpd 66, 4-(1-(4-chlorophenyl)-4-(2,2,6,6-tetramethyltetrahydro-2H-pyran-4-yl)-1H-imidazol-2-yl)-3-methoxypyridine;

Cpd 67, 2-(1-(4-chlorophenyl)-4-(2,2,6,6-tetramethyltetrahydro-2H-pyran-4-yl)-1H-imidazol-2-yl)-3-methoxypyridine;

Cpd 68, 3-(1-(4-chlorophenyl)-4-(2,2,6,6-tetramethyltetrahydro-2H-pyran-4-yl)-1H-imidazol-2-yl)-4-methoxypyridine;

Cpd 69, 3-(1-(4-fluorophenyl)-4-(2,2,6,6-tetramethyltetrahydro-2H-pyran-4-yl)-1H-imidazol-2-yl)-4-methoxypyridine;

Cpd 70, 2-(1-(4-fluorophenyl)-4-(2,2,6,6-tetramethyltetrahydro-2H-pyran-4-yl)-1H-imidazol-2-yl)-3-methoxypyridine;

Cpd 71, 3-(1-(2,5-difluorophenyl)-4-(2,2,6,6-tetramethyltetrahydro-2H-pyran-4-yl)-1H-imidazol-2-yl)-2-methoxypyridine;

Cpd 72, 3-(1-(3,5-difluorophenyl)-4-(2,2,6,6-tetramethyltetrahydro-2H-pyran-4-yl)-1H-imidazol-2-yl)-2-methoxypyridine;

Cpd 73, 3-fluoro-5-(2-(2-methoxypyridin-3-yl)-4-(2,2,6,6-tetramethyltetrahydro-2H-pyran-4-yl)-1H-imidazol-1-yl)benzonitrile;

Cpd 74, 2-Fluoro-5-[2-(2-methoxy-phenyl)-4-(2,2,6,6-tetramethyl-tetrahydro-pyran-4-yl)-imidazol-1-yl]-benzonitrile;

Cpd 75, 3-[1-(6-Ethoxypyridin-3-yl)-4-(2,2,6,6-tetramethyl-tetrahydro-2H-pyran-4-yl)-1H-imidazol-2-yl]-2-methoxypyridine;

Cpd 76, 3-Fluoro-4-[2-(2-methoxypyridin-3-yl)-4-(2,2,6,6-tetramethyltetrahydro-2H-pyran-4-yl)-1H-imidazol-1-yl]benzonitrile;

Cpd 77, 2-Methoxy-4-[2-(2-methoxypyridin-3-yl)-4-(2,2,6,6-tetramethyltetrahydro-2H-pyran-4-yl)-1H-imidazol-1-yl]benzonitrile;

Cpd 78, 2-Chloro-4-[2-(2-methoxypyridin-3-yl)-4-(2,2,6,6-tetramethyltetrahydro-2H-pyran-4-yl)-1H-imidazol-1-yl]benzonitrile;

Cpd 79, 2-Fluoro-5-[2-(2-methoxypyridin-3-yl)-4-(2,2,6,6-tetramethyltetrahydro-2H-pyran-4-yl)-1H-imidazol-1-yl]benzonitrile;

Cpd 80, 2-Fluoro-4-[2-(2-methoxypyridin-3-yl)-4-(2,2,6,6-tetramethyltetrahydro-2H-pyran-4-yl)-1H-imidazol-1-yl]benzonitrile;

Cpd 81, 2-Fluoro-4-[2-(2-methoxyphenyl)-4-(2,2,6,6-tetramethyltetrahydro-2H-pyran-4-yl)-1H-imidazol-1-yl]benzonitrile;

Cpd 82, 2,6-difluoro-4-(2-(2-methoxypyridin-3-yl)-4-(2,2,6,6-tetramethyltetrahydro-2H-pyran-4-yl)-1H-imidazol-1-yl)benzonitrile;

Cpd 83, 3,5-difluoro-4-(2-(2-methoxyphenyl)-4-(2,2,6,6-tetramethyltetrahydro-2H-pyran-4-yl)-1H-imidazol-1-yl)benzonitrile;

Cpd 84, 2-Chloro-5-[2-(2-methoxypyridin-3-yl)-4-(2,2,6,6-tetramethyltetrahydro-2H-pyran-4-yl)-1H-imidazol-1-yl]benzonitrile;

Cpd 85, 2-Methoxy-5-[2-(2-methoxypyridin-3-yl)-4-(2,2,6,6-tetramethyltetrahydro-2H-pyran-4-yl)-1H-imidazol-1-yl]benzonitrile;

Cpd 86, 4-[2-(4-Methoxypyrimidin-5-yl)-4-(2,2,6,6-tetramethyltetrahydro-2H-pyran-4-yl)-1H-imidazol-1-yl]benzonitrile;

Cpd 87, 4-[2-(3-Methoxypyrazin-2-yl)-4-(2,2,6,6-tetramethyltetrahydro-2H-pyran-4-yl)-1H-imidazol-1-yl]benzonitrile;

Cpd 88, 2-fluoro-4-(2-(3-methoxypyrazin-2-yl)-4-(2,2,6,6-tetramethyltetrahydro-2H-pyran-4-yl)-1H-imidazol-1-yl)benzonitrile;

Cpd 89, 4-(2-(2-ethoxypyridin-3-yl)-4-(2,2,6,6-tetramethyltetrahydro-2H-pyran-4-yl)-1H-imidazol-1-yl)-2-fluorobenzonitrile;

Cpd 90, 1-(4-chlorophenyl)-2-(2-methoxyphenyl)-5-methyl-4-(2,2,6,6-tetramethyltetrahydro-2H-pyran-4-yl)-1H-imidazole;

Cpd 91, 4-[5-Chloro-2-(2-methoxypyridin-3-yl)-4-(2,2,6,6-tetramethyltetrahydro-2H-pyran-4-yl)-1H-imidazol-1-yl]benzonitrile;

Cpd 92, 3-[5-Chloro-1-(4-fluorophenyl)-4-(2,2,6,6-tetramethyltetrahydro-2H-pyran-4-yl)-1H-imidazol-2-yl]-2-methoxypyridine;

Cpd 93, 3-[5-Chloro-1-(4-chlorophenyl)-4-(2,2,6,6-tetramethyltetrahydro-2H-pyran-4-yl)-1H-imidazol-2-yl]-2-methoxypyridine;

Cpd 94, 2-(2-Methoxyphenyl)-4-(2,2,6,6-tetramethyltetrahydro-2H-pyran-4-yl)-1-[(trifluoromethyl)sulfonyl]-1H-imidazole;

Cpd 95, 1-(Cyclopropylsulfonyl)-2-(2-methoxyphenyl)-4-(2,2,6,6-tetramethyltetrahydro-2H-pyran-4-yl)-1H-imidazole;

Cpd 96, 2-(2-Methoxyphenyl)-1-[(2-methylpropyl)sulfonyl]-4-(2,2,6,6-tetramethyltetrahydro-2H-pyran-4-yl)-1H-imidazole;

Cpd 97, 1-[(4-Chlorophenyl)sulfonyl]-2-(2-methoxyphenyl)-4-(2,2,6,6-tetramethyltetrahydro-2H-pyran-4-yl)-1H-imidazole;

Cpd 98, 1-[(4-Fluorophenyl)sulfonyl]-2-(2-methoxyphenyl)-4-(2,2,6,6-tetramethyltetrahydro-2H-pyran-4-yl)-1H-imidazole;

Cpd 99, 4-{[2-(2-Methoxyphenyl)-4-(2,2,6,6-tetramethyltetrahydro-2H-pyran-4-yl)-1H-imidazol-1-yl]methyl}benzonitrile;

Cpd 100, 5-{[2-(2-Methoxyphenyl)-4-(2,2,6,6-tetramethyltetrahydro-2H-pyran-4-yl)-1H-imidazol-1-yl]methyl}pyrimidine;

Cpd 101, 3-{[2-(2-Methoxyphenyl)-4-(2,2,6,6-tetramethyltetrahydro-2H-pyran-4-yl)-1H-imidazol-1-yl]methyl}benzonitrile;

Cpd 102, 4-[1-(4-Chlorophenyl)-2-(2-methoxyphenyl)-1H-imidazol-4-yl]-2,2,6,6-tetramethyltetrahydro-2H-pyran-4-ol;

Cpd 103, 4-[1-(4-Chlorophenyl)-2-(4-methoxypyridin-3-yl)-1H-imidazol-4-yl]-2,2,6,6-tetramethyltetrahydro-2H-pyran-4-ol;

Cpd 104, 4-[1-(4-Chlorophenyl)-2-(3-methoxypyridin-2-yl)-1H-imidazol-4-yl]-2,2,6,6-tetramethyltetrahydro-2H-pyran-4-ol;

Cpd 105, 4-[1-(4-Chlorophenyl)-2-(2-methoxypyridin-3-yl)-1H-imidazol-4-yl]-2,2,6,6-tetramethyltetrahydro-2H-pyran-4-ol;

Cpd 106, 4-[1-(3-Bromo-4-fluorophenyl)-2-(2-methoxyphenyl)-1H-imidazol-4-yl]-2,2,6,6-tetramethyltetrahydro-2H-pyran-4-ol;

Cpd 107, 4-[1-(3,4-Difluorophenyl)-2-(2-methoxyphenyl)-1H-imidazol-4-yl]-2,2,6,6-tetramethyltetrahydro-2H-pyran-4-ol;

Cpd 108, 4-[1-(3,4-Difluorophenyl)-2-(2-methoxypyridin-3-yl)-1H-imidazol-4-yl]-2,2,6,6-tetramethyltetrahydro-2H-pyran-4-ol;

Cpd 109, 4-{2-(2-Methoxyphenyl)-1-[6-(trifluoromethyl)pyridin-3-yl]-1H-imidazol-4-yl}-2,2,6,6-tetramethyltetrahydro-2H-pyran-4-ol;

Cpd 110, 4-[1-(3-Chloro-4-fluorophenyl)-2-(2-methoxypyridin-3-yl)-1H-imidazol-4-yl]-2,2,6,6-tetramethyltetrahydro-2H-pyran-4-ol;

Cpd 111, 4-[1-(3-Chloro-4-fluorophenyl)-2-(2-methoxyphenyl)-1H-imidazol-4-yl]-2,2,6,6-tetramethyltetrahydro-2H-pyran-4-ol;

Cpd 112, 4-[1-(4-Chloro-3-fluorophenyl)-2-(2-methoxyphenyl)-1H-imidazol-4-yl]-2,2,6,6-tetramethyltetrahydro-2H-pyran-4-ol;

Cpd 113, 4-[1-(4-Chloro-3-fluorophenyl)-2-(2-methoxypyridin-3-yl)-1H-imidazol-4-yl]-2,2,6,6-tetramethyltetrahydro-2H-pyran-4-ol;

Cpd 114, 4-[1-(4-Chlorophenyl)-2-(2-ethoxypyridin-3-yl)-1H-imidazol-4-yl]-2,2,6,6-tetramethyltetrahydro-2H-pyran-4-ol;

Cpd 115, 4-[4-(4-Hydroxy-2,2,6,6-tetramethyltetrahydro-2H-pyran-4-yl)-2-(2-methoxypyridin-3-yl)-1H-imidazol-1-yl]benzonitrile;

Cpd 116, 2-Fluoro-5-[4-(4-hydroxy-2,2,6,6-tetramethyltetrahydro-2H-pyran-4-yl)-2-(2-methoxypyridin-3-yl)-1H-imidazol-1-yl]benzonitrile;

Cpd 117, 2-Fluoro-5-[4-(4-hydroxy-2,2,6,6-tetramethyltetrahydro-2H-pyran-4-yl)-2-(2-methoxyphenyl)-1H-imidazol-1-yl]benzonitrile;

Cpd 118, 2-Fluoro-4-[4-(4-hydroxy-2,2,6,6-tetramethyltetrahydro-2H-pyran-4-yl)-2-(2-methoxyphenyl)-1H-imidazol-1-yl]benzonitrile;

Cpd 119, 2-Fluoro-4-[4-(4-hydroxy-2,2,6,6-tetramethyltetrahydro-2H-pyran-4-yl)-2-(2-methoxypyridin-3-yl)-1H-imidazol-1-yl]benzonitrile;

Cpd 120, 4-[1-(4-Chlorophenyl)-2-(3-methoxypyridin-4-yl)-1H-imidazol-4-yl]-2,2,6,6-tetramethyltetrahydro-2H-pyran-4-ol;

Cpd 121, 4-[2-(2-Methoxyphenyl)-4-(2,2,6,6-tetramethyltetrahydro-2H-pyran-4-yl)-1H-imidazol-1-yl]-2-(trifluoromethyl)benzonitrile;

Cpd 122, 3-[1-(4-Chlorophenyl)-4-(2,2,6,6-tetramethyltetrahydro-2H-pyran-4-yl)-1H-imidazol-2-yl]pyridin-2-ol;

Cpd 123, 2-Chloro-4-[2-(2-methoxyphenyl)-4-(2,2,6,6-tetramethyltetrahydro-2H-pyran-4-yl)-1H-imidazol-1-yl]benzonitrile;

Cpd 124, 1-(4-Chlorophenyl)-2-(2-methoxyphenyl)-4-(2,2,6,6-tetramethyl-3,6-dihydro-2H-pyran-4-yl)-1H-imidazole;

Cpd 125, 1-(4-Bromo-3-fluorophenyl)-2-(2-methoxyphenyl)-4-(2,2,6,6-tetramethyl-3,6-dihydro-2H-pyran-4-yl)-1H-imidazole;

Cpd 126, 2-Fluoro-4-[2-(2-methoxyphenyl)-4-(2,2,6,6-tetramethyl-3,6-dihydro-2H-pyran-4-yl)-1H-imidazol-1-yl]benzonitrile;

and pharmaceutically acceptable salt forms thereof.

For use in medicine, salts of compounds of Formula (I) refer to non-toxic "pharmaceutically acceptable salts." Other salts may, however, be useful in the preparation of compounds of Formula (I) or of their pharmaceutically acceptable salts thereof. Suitable pharmaceutically acceptable salts of compounds of Formula (I) include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I) carry an acidic moiety, suitable pharmaceutically acceptable salts thereof may include alkali metal salts, such as sodium or potassium salts; alkaline earth metal salts, such as calcium or magnesium salts; and salts formed with suitable organic ligands, such as quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glutamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+)\text{-enantiomer} = \frac{(\text{mass}(+)\text{-enantiomer})}{(\text{mass}(+)\text{-enantiomer}) + (\text{mass}(-)\text{-enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)\text{-enantiomer} = \frac{(\text{mass}(-)\text{-enatiomer})}{(\text{mass}(+)\text{-enantiomer}) + (\text{mass}(-)\text{-enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I) may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I) can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I) as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I) or a pharmaceutical composition thereof includes a dose range from about 0.1 mg to about 3000 mg, or any particular amount or range therein, in particular from about 1 mg to about 1000 mg, or any particular amount or range therein; or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I) will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I).

Advantageously, a compound of Formula (I) may be administered in a single daily dose, or the total daily dosage may be administered in divided doses of two, three and four times daily.

Optimal dosages of a compound of Formula (I) to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I) may be administered in any of the foregoing compositions and dosage regimens or by means of those compositions and dosage regimens established in the art whenever use of a compound of Formula (I) is required for a subject in need thereof.

As N-Type calcium channel blockers, the compounds of Formula (I) are useful in methods for treating and/or preventing a disease, a syndrome, a condition or a disorder in a subject, including an animal, a mammal and a human in which the disease, the syndrome, the condition or the disorder is affected by the modulation of the N-Type calcium channel. Such methods comprise, consist of and/or consist essentially of administering to a subject, including an animal, a mammal, and a human in need of such treatment or prevention a therapeutically effective amount of a compound, salt or solvate of Formula (I). In particular, the compounds of Formula (I) are useful for preventing or treating pain, such as inflammatory pain or neuropathic pain, or diseases, syndromes, conditions or disorders causing such pain.

GENERAL SYNTHETIC METHODS

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

The following solvents, reagents or scientific terminology may be referred to by their abbreviations:
TLC Thin Layer Chromatography
DCM Dichloromethane
DCE 1,2-Dichloroethane
THF Tetrahydrofuran
MeOH Methanol
EtOH Ethanol
IPA Isopropyl alcohol
n-BuOH n-Butanol
EtOAc Ethyl acetate
$Et_2O$ Diethyl ether
DMA N,N-Dimethylacetamide DMF N,N-Dimethylformamide
Et₃N Triethylamine
DMSO Dimethylsulfoxide
DIPEA Diisopropylethylamine (Hunig's base)
HEK Human embryonic kidney
MeI Methyliodide
NBS N-Bromosuccinimide
TFA Trifluoroacetic acid
PTSA p-Toluenesulfonic acid
AcOH Acetic acid
Boc tert-butoxycarbonyl
Cat Catalytic
mL milliliters
mol moles
mmol millimoles
h hour or hours
min minute or minutes
g grams
mg milligrams
μL Microliters
eq Equivalents
rt or RT Room temperature, ambient, about 27° C.
MS Mass spectrometry
NA Not available
NE No Effect
tmhd Dipivaloylmethanato Scheme A illustrates a route for the synthesis of certain compounds of the present invention wherein $R^2$ is an optionally substituted phenyl or an optionally substituted heteroaryl as defined herein.

A compound of formula a1 is either commercially available or may be prepared by methods known in the scientific literature. A compound of formula a1 may be reacted with a compound of formula a2 in the presence of an appropriate Lewis acid such as trimethylaluminum or the like, in an aprotic organic solvent such as toluene, at a temperature from about 0° C. to about 70° C., to afford a compound of formula a3. A compound of formula a3 may be treated with a compound of formula a4 in the presence of an appropriate inorganic base such as sodium bicarbonate, at about 100° C., to afford a compound of formula (I)-A. A compound of formula (I)-A may be treated with NCS to afford compound of formula (I)-A1.

Alternatively, an appropriately substituted carboxylic acid compound of formula a6 (commercially available or prepared by methods known in the scientific literature) may be converted to its corresponding acid chloride by the action of an appropriate chlorinating agent such as oxalyl chloride, thionyl chloride, or the like, in an organic solvent such as dichloromethane, at a temperature of about 0° C. to room temperature, to afford a compound of formula a7. A compound of formula a7 may be converted to an amide of formula a8 via treatment with an appropriately substituted amine of formula a2, in the presence of a non-nucleophilic tertiary amine base such as triethylamine, in an organic solvent such as dichloromethane, at a temperature of about 0° C. to room temperature. Conversion of a compound of formula a8 to a compound of formula a3 may be accomplished by treatment with a chlorinating reagent such as phosphorus pentachloride, in an organic solvent such as

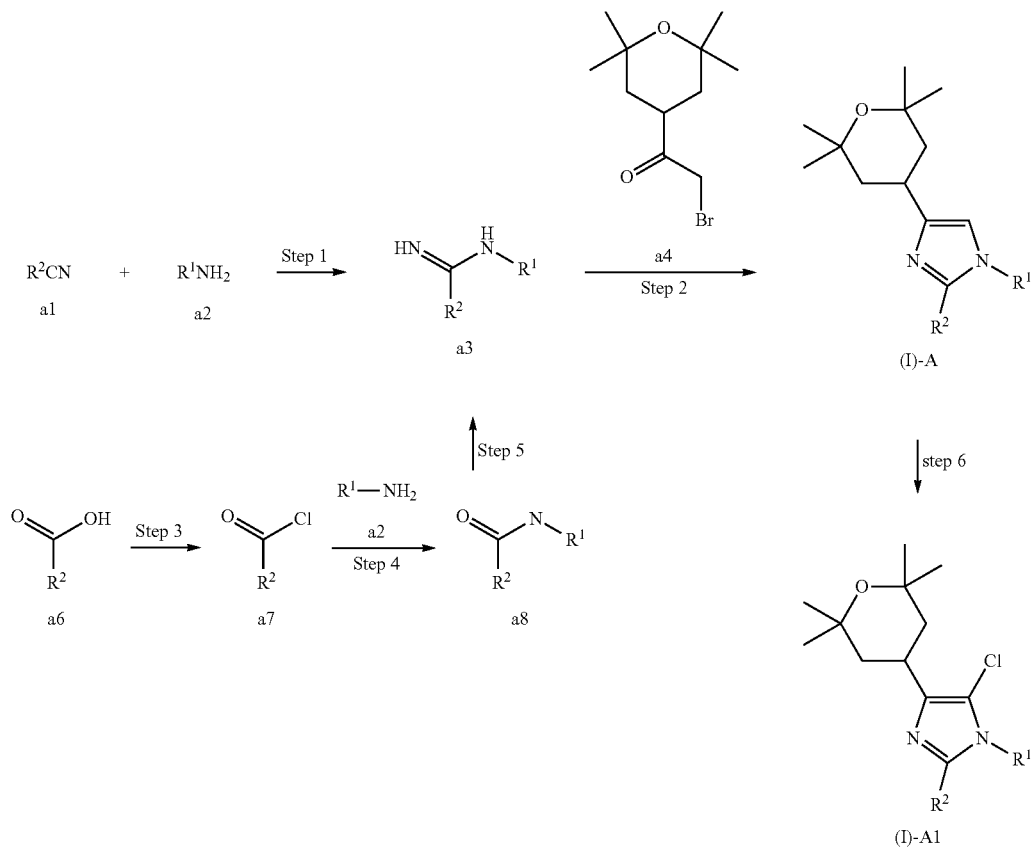

chloroform, at about room temperature, followed by reaction with ammonia gas at a temperature of about 0° C.

Scheme B illustrates a route for the synthesis of certain compounds of the present invention wherein $R^1$ is an optionally substituted phenyl as defined herein.

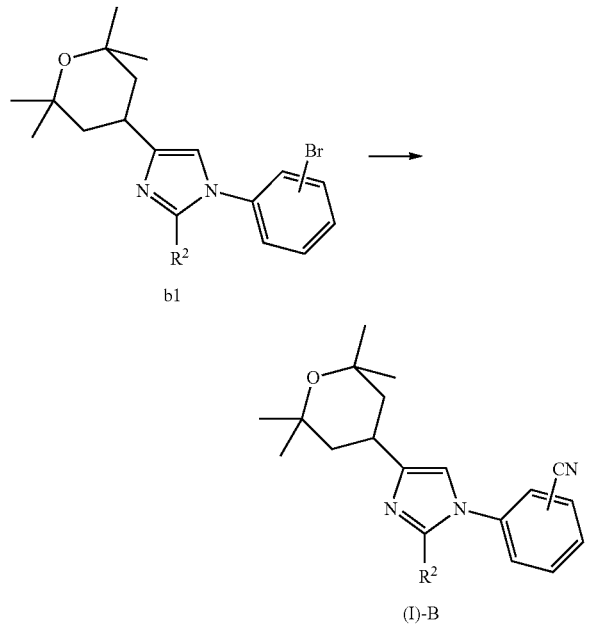

A compound of formula b1 may be converted to its corresponding phenyl cyanide in the presence of zinc cyanide, a transition metal catalyst, dimethylformamide, and suitable ligands, to afford compounds of Formula (I)-B wherein $R^1$ is a cyano-substituted phenyl ring.

Scheme C illustrates a route for the synthesis of certain compounds of the present invention wherein $R^1$ is an optionally substituted phenylsulfonyl or alkylsulfonyl as defined herein.

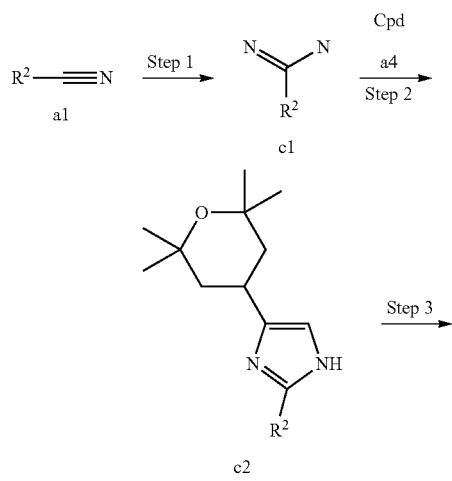

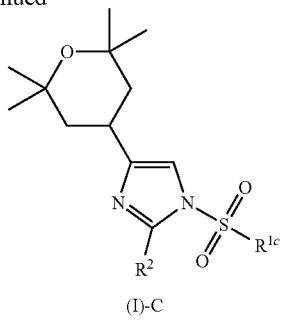

A compound of formula a1 may be reacted with ammonium chloride, in the presence of an appropriate Lewis acid such as trimethylaluminum or the like, in an aprotic organic solvent such as toluene, at a temperature from about 0° C. to about 70° C., to afford a compound of formula c1. A compound of formula c1 may be reacted with a compound of formula a4 in the presence of an appropriate inorganic base such as sodium bicarbonate, at about 100° C., to afford a compound of formula c2. A compound of formula c2 may be treated with an appropriately substituted sulfonyl chloride in the presence of a non-nucleophilic tertiary amine base such as triethylamine, in an organic solvent such as dichloromethane, at a temperature of about 0° C. to room temperature, to afford a compound of formula (I)-C.

Scheme D illustrates a route for the synthesis of certain compounds of the present invention wherein $R^{1d}$ is an optionally substituted phenylmethyl or heteroaryl-methyl group as defined by the scope of the invention.

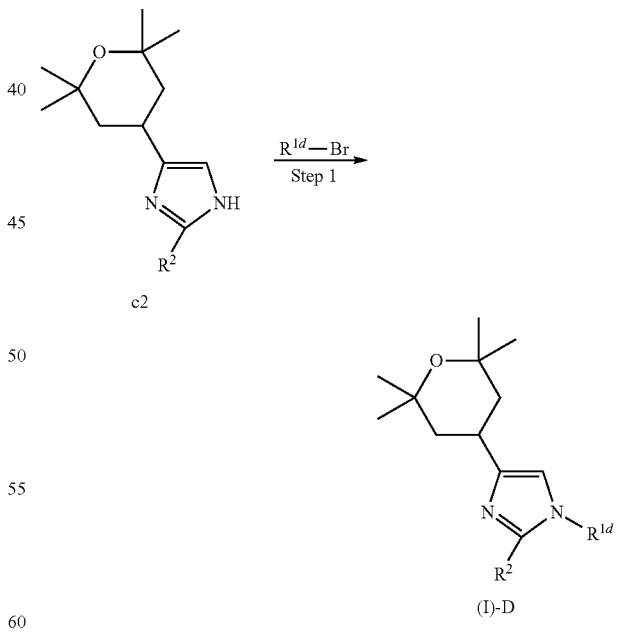

A compound of formula c2 may be reacted with an inorganic base such as NaH, $K_2CO_3$ or $Cs_2CO_3$, in the presence of an appropriate phenylmethyl-halide or heteroarylmethyl-halide to afford a compound of formula (I)-D.

Scheme E illustrates a route for the synthesis of certain compounds of the present invention wherein G is G2.

Scheme E

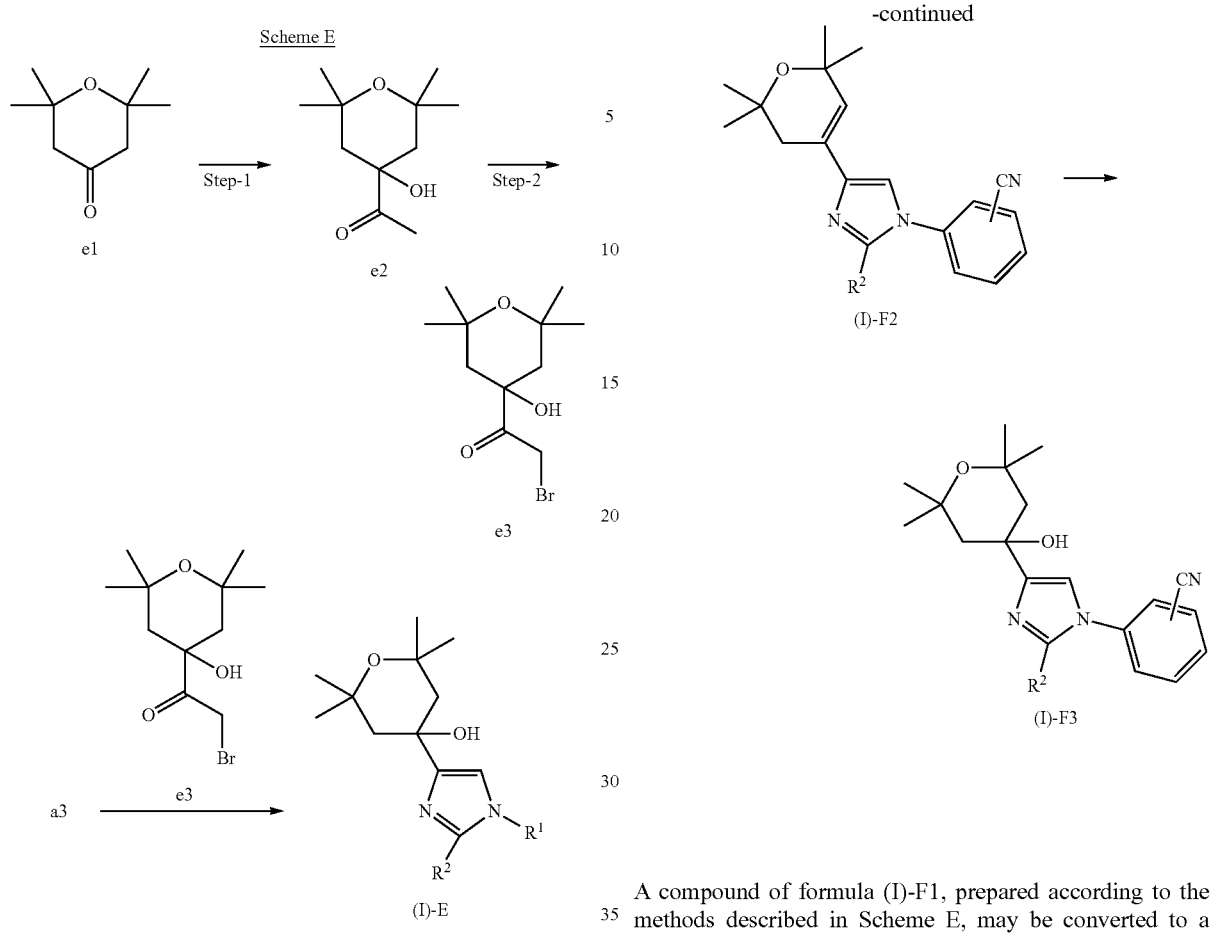

Commercially available ethoxy ethylene may be treated with a strong organic base such as an alkyllithium base, organomagnesium bromide, or the like, at 0° C., followed by addition of compound e1, to afford compound e2. Compound e2 may be treated with a brominating reagent such as hydrogen bromide in acetic acid, NBS, or the like, at 0° C. to room temperature, to afford compound e3. A compound of formula a3 may be treated with a compound of formula e3 in the presence of an appropriate inorganic base such as sodium bicarbonate, at about 100° C., to afford a compound of formula (I)-E.

Scheme F illustrates a route for the conversion of certain compounds of Formula (I)-F1, wherein G is G2, to compounds of Formulae (I)-F2 and (I)-F3.

Scheme F

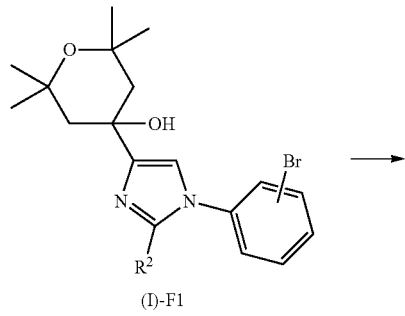

A compound of formula (I)-F1, prepared according to the methods described in Scheme E, may be converted to a compound of formula (I)-F2 (wherein G is G3) in the presence of zinc cyanide, a transition metal catalyst, dimethylformamide, and suitable ligands. Reaction of a compound of formula (I)-F2 may occur by the action of a hydride source such as triphenylsilane, or the like, in the presence of Mn(tmhd)$_3$, at a temperature of about 0° C. to room temperature in an oxygen atmosphere, to afford a compound of formula (I)-F3.

SPECIFIC EXAMPLES

Yields reported herein refer to purified products (unless specified) and are not optimized. Analytical TLC was performed on Merck silica gel 60 F254 aluminium-backed plates. Compounds were visualized by UV light and/or stained either with iodine, potassium permanganate or ninhydrin solution. Flash column chromatography was performed on silica gel (100-200 M) or flash chromatography. $^1$H-NMR spectra were recorded on a Bruker Avance-400 MHz spectrometer with a BBO (Broad Band Observe) and BBFO (Broad Band Fluorine Observe) probe. Chemical shifts (δ) are expressed in parts per million (ppm) downfield by reference to tetramethylsilane (TMS) as the internal standard. Splitting patterns are designated as s (singlet), d (doublet), t (triplet), q (quartet), m (multiplet) and br s (broad singlet). Coupling constants (J) are given in hertz (Hz). LC-MS analyses were performed using the Electrospray Ionization (ESI) technique.

A. Preparation of Chemical Intermediates

Example 1

Preparation of intermediate A1;
N-(4-cyanophenyl)-2-methoxybenzimidamide

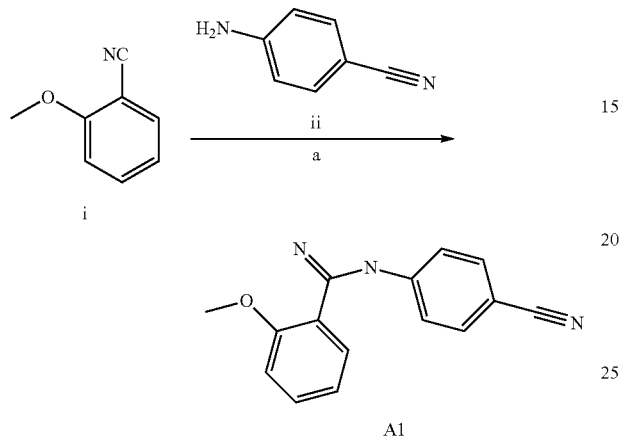

Reaction conditions: a) Me₃Al, toluene, 0-70° C.;

To a stirred solution of 2-methoxybenzonitrile (10 g, 0.075 mol) in toluene (200 ml) at 0° C. was added trimethylaluminum (90 mL, 0.09 mol) drop-wise over a period of 10 min. The reaction mixture was then stirred at room temperature for 3 h followed by addition of 4-aminobenzonitrile (8.6 g, 0.074 mol) in toluene 100 mL. The reaction mixture was heated to 70° C. for 16 h. After confirming the completion by LCMS the reaction mixture was quenched with ice-cold water; the aqueous layer was filtered through a pad of diatomaceous earth, and the resultant filtrate was washed with ethyl acetate. The aqueous layer was extracted with ethyl acetate (2×100 mL). The combined organic extracts were washed with brine, dried over anhydrous Na₂SO₄, filtered, and concentrated under reduced pressure to provide a residue. Purification by column chromatography on silica gel (100-200 mesh) using ethyl acetate in hexane afforded the title compound as a white solid. (12.8 g, 68%).

By using analogous protocols as described in the foregoing example the intermediates described in Table 1 have been prepared using appropriate starting materials TABLE 1-continued

| Intermediate No. | Structure |
|---|---|
| A11 | (2-methoxypyridin-3-yl)-N-(4-fluorophenyl)carboximidamide |
| A12 | (2-methoxypyridin-3-yl)-N-(4-chlorophenyl)carboximidamide |
| A13 | (2-methoxypyridin-3-yl)-N-(6-ethoxypyridin-3-yl)carboximidamide |
| A14 | (2-methoxypyridin-3-yl)-N-(2,4-difluorophenyl)carboximidamide |
| A15 | (4-methoxypyridin-3-yl)-N-(4-chlorophenyl)carboximidamide |
| A16 | (3-methoxypyridin-4-yl)-N-(3-fluoro-4-chlorophenyl)carboximidamide |
| A17 | (2-methoxyphenyl)-N-(3-cyano-4-chlorophenyl)carboximidamide |
| A18 | (2-methoxypyridin-3-yl)-N-(4-cyano-3-methylphenyl)carboximidamide |
| A19 | (2-methoxypyridin-3-yl)-N-(2,3,4-trifluorophenyl)carboximidamide |
| A20 | (2-methoxypyridin-3-yl)-N-(2,5-difluorophenyl)carboximidamide |
| A21 | (3-methoxypyridin-2-yl)-N-(3-chloro-4-fluorophenyl)carboximidamide |
| A22 | (3-methoxypyridin-4-yl)-N-(3-chloro-4-fluorophenyl)carboximidamide |
| A23 | (3-methoxypyridin-2-yl)-N-(3-fluoro-4-chlorophenyl)carboximidamide |
| A24 | (4-methoxypyridin-3-yl)-N-(3-fluoro-4-chlorophenyl)carboximidamide |
| A25 | (2-methoxyphenyl)-N-(4-cyano-3-methylphenyl)carboximidamide |
| A26 | (2-methoxyphenyl)-N-(3-cyano-4-methylphenyl)carboximidamide |

TABLE 1-continued

| Intermediate No. | Structure |
|---|---|
| A27 | (structure) |
| A28 | (structure) |
| A29 | (structure) |
| A30 | (structure) |
| A31 | (structure) |
| A32 | (structure) |
| A33 | (structure) |
| A34 | (structure) |
| A35 | (structure) |
| A36 | (structure) |
| A37 | (structure) |
| A38 | (structure) |
| A39 | (structure) |
| A40 | (structure) |
| A41 | (structure) |

TABLE 1-continued

| Intermediate No. | Structure |
|---|---|
| A42 | (2-methoxyphenyl)(N-(3,4-difluorophenyl))carboximidamide |
| A43 | (2-methoxypyridin-3-yl)(N-(4-cyanophenyl))carboximidamide |
| A44 | (2-methoxypyridin-3-yl)(N-(3-fluoro-4-chlorophenyl))carboximidamide |
| A45 | (2-methoxyphenyl)(N-(3-chloro-4-fluorophenyl))carboximidamide |
| A46 | (2-methoxypyridin-3-yl)(N-(3-chloro-4-fluorophenyl))carboximidamide |
| A47 | (3-methoxypyrazin-2-yl)(N-(4-fluorophenyl))carboximidamide |
| A48 | (2-methoxypyridin-3-yl)(N-(3-cyanophenyl))carboximidamide |
| A49 | (4-methoxypyrimidin-5-yl)(N-(4-chlorophenyl))carboximidamide |

TABLE 1-continued

| Intermediate No. | Structure |
|---|---|
| A50 | (3-methoxypyrazin-2-yl)(N-(4-chlorophenyl))carboximidamide |
| A51 | (2-ethoxypyridin-3-yl)(N-(4-chlorophenyl))carboximidamide |
| A52 | (2-ethoxypyridin-3-yl)(N-(3,4-difluorophenyl))carboximidamide |
| A53 | (3-ethoxypyrazin-2-yl)(N-(4-chlorophenyl))carboximidamide |
| A54 | (2-methoxyphenyl)(N-(4-(difluoromethoxy)phenyl))carboximidamide |
| A55 | (2-methoxyphenyl)(N-(3-fluoro-4-bromophenyl))carboximidamide |
| A56 | (2-methoxyphenyl)(N-(3-bromo-4-fluorophenyl))carboximidamide |
| A57 | (2-methoxypyridin-3-yl)(N-(3-bromo-4-fluorophenyl))carboximidamide |

TABLE 1-continued

| Intermediate No. | Structure |
|---|---|
| A58 | (2-methoxyphenyl)(N'-(2,6-difluoro-4-cyanophenyl))carboximidamide structure |
| A59 | (1-(4-chlorophenyl)-1H-1,2,4-triazol-5-yl)carboximidamide structure |
| A60 | N-(2-chlorobenzyl)-2-methoxynicotinimidamide structure |
| A61 | N-(3-chlorobenzyl)-2-methoxynicotinimidamide structure |
| A62 | N-(4-chlorobenzyl)-2-methoxynicotinimidamide structure |

Example 2

Preparation of intermediate A-63; 2-methoxy-N-(6-(trifluoromethyl)pyridin-3-yl)nicotinimidamide

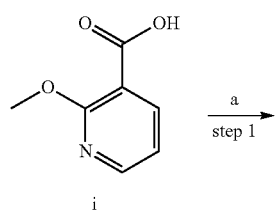

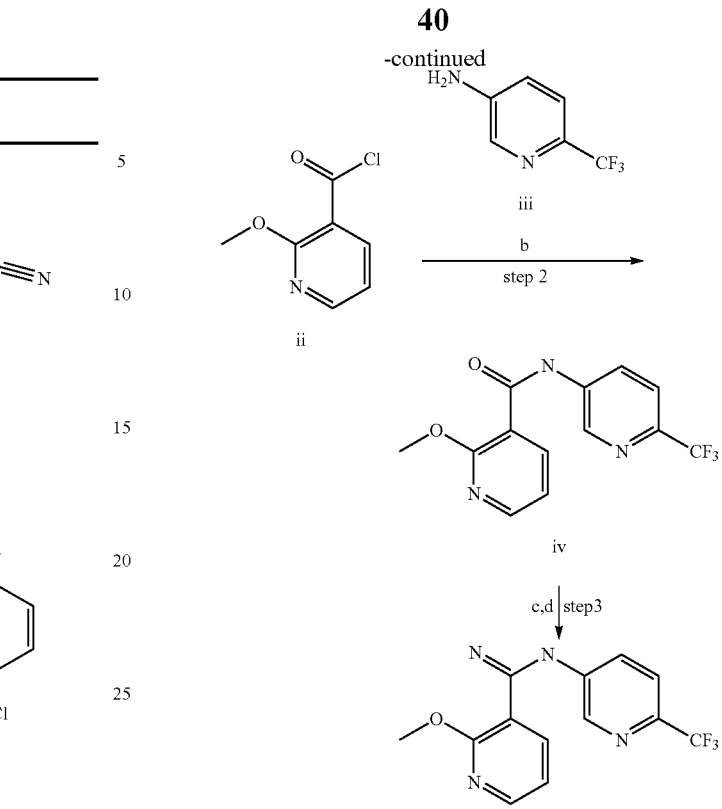

Reaction conditions: a) Oxalyl chloride, DCM, 0° C.-RT; b) DCM, Et₃N, 0° C.-RT; c) PCl₅, CHCl₃, RT; d) NH₃, 0° C.

Step 1. 2-Methoxy-nicotinoyl chloride

To a stirred solution of 2-methoxynicotinic acid (2 g, 0.013 mol) in DCM (20 mL) under a N₂ atmosphere was added oxalyl chloride (2 mL, 0.026 mol) drop-wise at 0° C. followed by the addition of a catalytic amount of DMF (2 drops). The reaction mixture was stirred at room temperature for 2 h. Upon completion of the reaction, the solvent was removed under reduced pressure in an inert atmosphere to provide title compound as a thick liquid (2.1 g, 98%).

Step 2. 2-Methoxy-N-(6-trifluoromethyl-pyridin-3-yl)-nicotinamide

To a stirred solution of 6-(trifluoromethyl)pyridin-3-amine (1.8 g, 0.0011 mol) in DCM (20 mL) under a N₂ atmosphere was added triethylamine (4.9 mL, 0.035 mol) at 0° C. followed by the drop-wise addition of 2-methoxy-nicotinoyl chloride (2 g, 0.0011 mol) in DCM (5 mL). The reaction mixture was stirred at room temperature for 2 h. Upon completion of the reaction, the solvent was evaporated and resultant residue was partitioned between DCM and water. The organic layer was separated and washed with brine, dried over anhydrous Na₂SO₄, filtered, and concentrated to afford the title compound as an off-white solid (2.02 g, 61.3%). LCMS: 298.1 [M+H]⁺.

Step 3. 2-methoxy-N-(6-(trifluoromethyl)pyridin-3-yl)nicotinimidamide

To a stirred solution of PCl₅ (0.17 g, 0.0084 mol) in chloroform (5 mL) at room temperature under a N₂ atmosphere was added 2-methoxy-N-(6-trifluoromethyl-pyridin-3-yl)-nicotinamide (0.5 g, 0.00168 mol). The reaction mixture was stirred at 61° C. for 30 min. The reaction mixture was cooled to 0° C. followed by bubbling of ammonia gas for 1 h. The reaction was quenched with $NaHCO_3$, partitioned between DCM and water. The organic layer was separated and washed with brine, dried over anhydrous $Na_2SO_4$, filtered, and concentrated to afford title compound as an off-white solid (0.25 g, 50.7%). LCMS—297.1 $[M+H]^+$. By using analogous protocols as described in the foregoing example the compounds described in FIG. 1 have been prepared using appropriate starting materials

FIG. 1

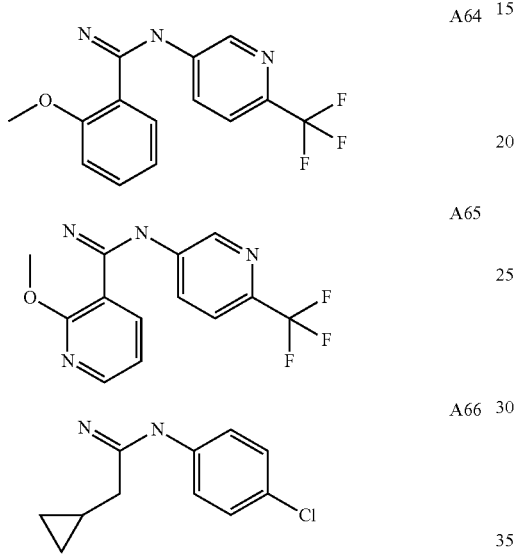

A64

A65

A66

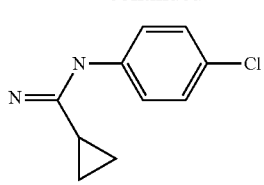

A67

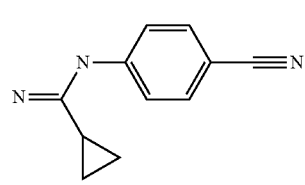

A68

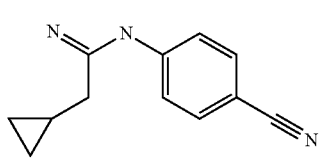

A69

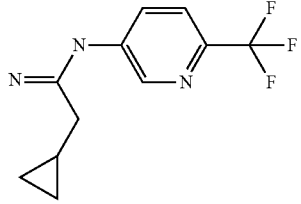

A70

Example 3

Preparation of intermediate A71; 2-bromo-1-(2,2,6,6-tetramethyltetrahydro-2H-pyran-yl)ethanone

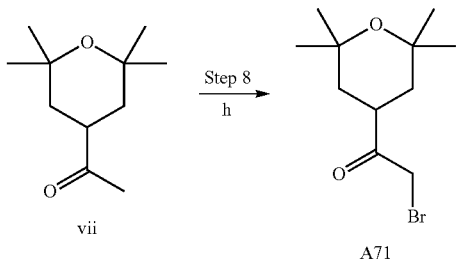

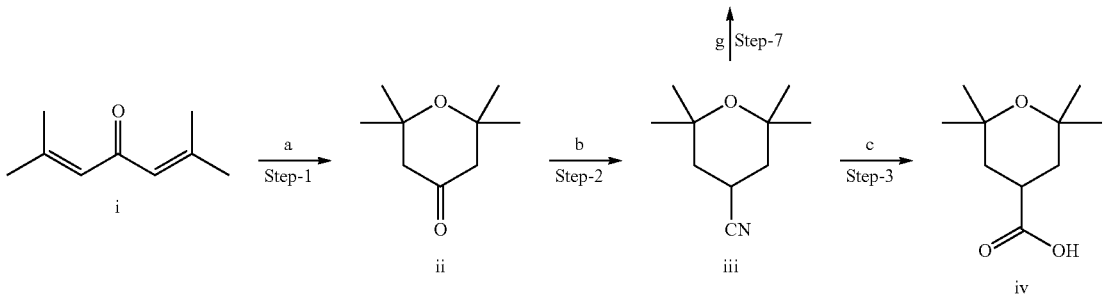

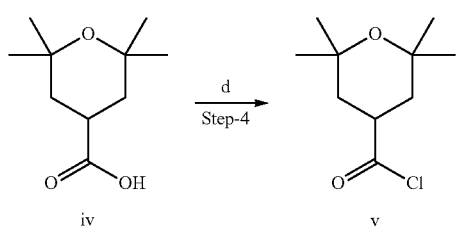 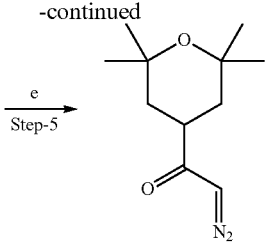 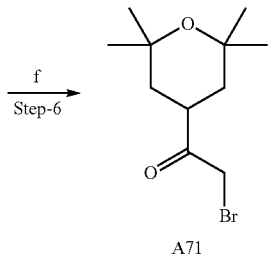

Reaction conditions: a) 6N HCl, 45° C., 7 days; b)Tosmic Cyanide, t-Butanol, DME, 0° C.-RT; c) 2M KOH Reflux d) Oxalyl chloride, DCM, 0° C.-RT; e) TMS-CHN₂, DCM, 0° C.-RT; f) Aq.HBr, Et₂O, 0° C.
g) MeMgBr, 0° C.-RT; h) Br₂, EtOH, 0° C.-RT

Step 1. 2,2,6,6-tetramethyldihydro-2H-pyran-4(3H)-one

To a stirred solution of 2,6-dimethylhepta-2,5-dien-4-one (100 g, 0.724 mol) was added 6N HCl (600 mL), then the reaction mixture was heated to 45° C. for 7 days. Upon completion, the reaction was quenched with ice cold water and extracted with ethyl acetate (4×150 mL). The combined organic extracts were washed with brine, dried over anhydrous Na₂SO₄, filtered, and concentrated under reduced pressure to provide a residue. Purification by column chromatography on silica gel (100-200 mesh) using ethyl acetate in hexane afforded the title compound as a yellow liquid. (yield 28 g, 25%)

Step 2. 2,2,6,6-tetramethyltetrahydro-2H-pyran-4-carbonitrile

To a stirred solution of 2,2,6,6-tetramethyldihydro-2H-pyran-4(3H)-one (30 g, 0.192 mol) in dimethoxyethane (400 mL) was added tosylmethyl isocyanide (48.7 g, 0.249 eq) followed by the addition of tert-butyl alcohol (24.1 g, 0.326) at room temperature. The reaction mixture was cooled to 0° C. followed by portion-wise addition of potassium tert-butoxide (53.8 g, 0.48 mol). It was stirred at room temperature for 12 h. The reaction mixture was filtered after dilution with diethyl ether at 0° C. and the residue was further washed with diethyl ether. The resultant filtrate was concentrated to provide the title compound as a yellow semisolid (22 g, 68%)

Step 3. 2,2,6,6-tetramethyltetrahydro-2H-pyran-4-carboxylic acid

To a stirred solution of 2,2,6,6-tetramethyltetrahydro-2H-pyran-4-carbonitrile (22 g, 0.131 mol) in water (400 mL) was added KOH (45 g, 0.815 mol) and the reaction mixture was allowed to reflux for 8 h. The completion of the reaction was confirmed by TLC. The reaction mixture was diluted with water and extracted with dichloromethane (3×100 mL). The aqueous layer was acidified with 1N HCl, extracted with dichloromethane. The combined organic extracts were washed with brine, dried over anhydrous Na₂SO₄, filtered, and concentrated under reduced pressure to provide a residue. Purification by column chromatography on silica gel (100-200 mesh) using ethyl acetate in hexane afforded the title compound as a pale yellow solid (13 g, 52%).

Step 4. 2,2,6,6-tetramethyltetrahydro-2H-pyran-4-carbonyl chloride

To a stirred solution of 2,2,6,6-tetramethyltetrahydro-2H-pyran-4-carboxylic acid (2.7 g, 0.0144 mol) in DCM (30 mL) was added oxalyl chloride (3.6 g, 0.0289 mol) at 0° C. The reaction mixture was allowed stirred for 3 h at room temperature and then concentrated to provide the title compound as a black thick liquid (2.6 g, crude). It was used in the next step without further purification.

Step 5. 2-diazo-1-(2,2,6,6-tetramethyltetrahydro-2H-pyran-4-yl)ethanone

To a stirred solution of 2,2,6,6-tetramethyltetrahydro-2H-pyran-4-carbonyl chloride (2.6 g, 0.012 mol) in dichloromethane (20 mL) was added trimethylsilyldiazomethane (2.9 g, 0.025 mol) at 0° C. after which it was stirred for 12 h at rt. The completion of the reaction was confirmed by TLC. The reaction mixture was concentrated under reduced pressure to provide a crude residue of the title compound as a black thick liquid which was used in the next step without further purification. (2.5 g, crude)

Step 6. 2-bromo-1-(2,2,6,6-tetramethyltetrahydro-2H-pyran-yl)ethanone

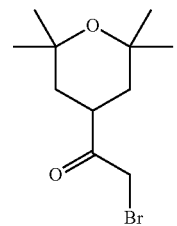

A71

To a stirred solution of 2-diazo-1-(2,2,6,6-tetramethyltetrahydro-2H-pyran-4-yl)ethanone. (2.5 g, 0.011 mol) in diethyl ether (20 mL) was added aqueous hydrobromic acid (8 mL) drop wise at 0° C. The stirring was continued for 3 h at 0° C. The completion of the reaction was confirmed by TLC. The reaction mixture was quenched with 10% NaHCO₃ aqueous solution (50 mL). The combined organic layers were dried over Na₂SO₄, filtered, and concentrated under reduced pressure to provide a crude residue of the title compound as a yellow liquid which was used in the next step without further purification. (2.4 g, crude).

Step 7. 1-(2,2,6,6-tetramethyltetrahydro-2H-pyran-4-yl)ethanone

To a stirred solution of 2,2,6,6-tetramethyltetrahydro-2H-pyran-4-carbonitrile (2 g, 0.012 mol) in THF (25 mL) was added MeMgBr (3M in Et₂O) (4.7 mL, 0.0036 mol) at −78° C. and the reaction was slowly allowed to reach room temperature and stirred for overnight. After completion of the reaction, the reaction was quenched with saturated NH₄Cl solution at 0° C. and extracted with EtOAc (2×75 mL). The combined organic extracts were washed with brine, dried over anhydrous Na₂SO₄, filtered, and concentrated under reduced pressure to provide a residue. Purification by column chromatography on silica gel (100-200 mesh) using ethyl acetate in hexane afforded the title compound as thick liquid. (1.54 g, 70%).

Step 8. 2-bromo-1-(2,2,6,6-tetramethyltetrahydro-2H-pyran-4-yl)ethanone

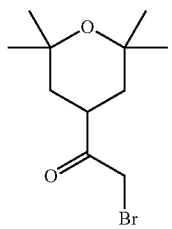

A71

To a stirred solution of 1-(2,2,6,6-tetramethyltetrahydro-2H-pyran-4-yl)ethanone (0.15 g, 0.0008 mol) in EtOH (3 mL) was added Br₂ solution (0.06 mL, 0.0012 mol) at 0° C. and the reaction was stirred for overnight. After completion of the reaction, the reaction was diluted with ice water and extracted with DCM (2×50 mL). The combined organic extracts were washed with NaHCO₃, brine, dried over anhydrous Na₂SO₄, filtered, and concentrated under reduced pressure to provide the crude title compound which was used in the subsequent stage without purification. Yield: 0.35 g (Crude).

Example 4

Preparation of intermediate A72; 2-bromo-1-(2,2,6,6-tetramethyltetrahydro-2H-pyran-4-yl)propan-1-one Step 1. 1-(2,2,6,6-tetramethyltetrahydro-2H-pyran-4-yl)propan-1-one To a stirred solution of 2,2,6,6-tetramethyltetrahydro-2H-pyran-4-carbonitrile (0.5 g, 0.003 mol) in THF (5 mL) was added EtMgBr (3M in Et₂O) (1.19 mL, 0.0036 mol) at −78° C. and the reaction was slowly allowed to reach room temperature and stirred for overnight. After completion of the reaction, the reaction was quenched with saturated NH₄Cl solution at 0° C. and extracted with EtOAc (2×10 mL). The combined organic extracts were washed with brine, dried over anhydrous Na₂SO₄, filtered, and concentrated under reduced pressure to provide a residue. Purification by column chromatography on silica gel (100-200 mesh) using ethyl acetate in hexane afforded the title compound as colorless solid. (0.25 g, 42.3%)

Step 2. 2-bromo-1-(2,2,6,6-tetramethyltetrahydro-2H-pyran-4-yl)propan-1-one

To a stirred solution of 1-(2,2,6,6-tetramethyltetrahydro-2H-pyran-4-yl)propan-1-one (0.2 g, 0.001 mol) in EtOH (5 mL) was added Br₂ solution (0.078 mL, 0.0015 mol) at 0° C. and the reaction was stirred for overnight. After completion of the reaction, the reaction was diluted with ice water and extracted with DCM (2×50 mL). The combined organic extracts were washed with brine, dried over anhydrous Na₂SO₄, filtered, and concentrated under reduced pressure to provide the crude title compound which was used in the subsequent stage without purification. Yield: 0.35 g (Crude).

Example 5

Preparation of intermediate A74: 2-(2-methoxyphenyl)-4-(2,2,6,6-tetramethyltetrahydro-2H-pyran-4-yl)-1H-imidazole

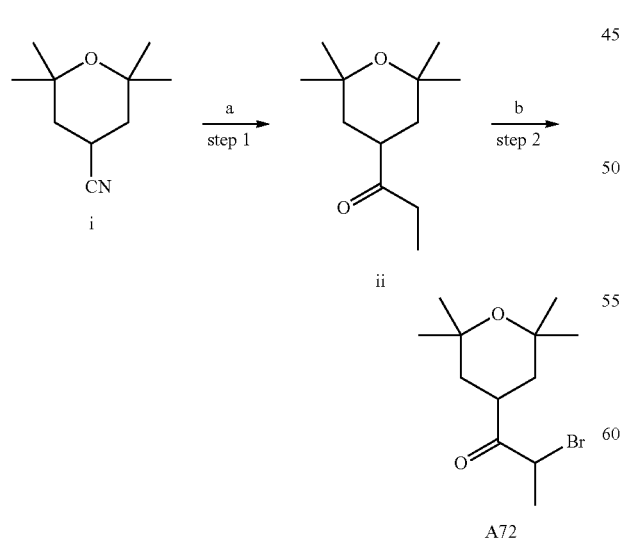

Reaction conditions: a) EtMgBr, 0° C.-RT; b) Br₂, EtOH, 0° C.-RT

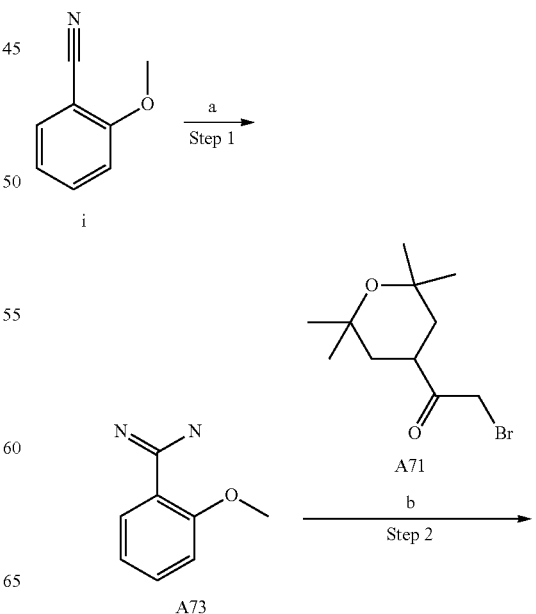

Step 2. 2-(2-methoxyphenyl)-4-(2,2,6,6-tetramethyl-tetrahydro-2H-pyran-4-yl)-1H-imidazole To a stirred solution of 2-methoxybenzimidamide A73 (0.6 g, 0.004 mol) in 1,4-dioxane (20 mL) was added 2-bromo-1-(2,2,6,6-tetramethyltetrahydro-2H-pyran-4-yl)ethanone A71 (1.04 g, 0.004 mol), followed by the addition of NaHCO$_3$ (1 g, 0.012 mol). The reaction mixture was refluxed for 5 h. The reaction was quenched with ice cold water after completion. The aqueous layer was extracted with ethyl acetate (3×25 mL). The combined organic extracts were washed with brine, dried over anhydrous Na$_2$SO$_4$, filtered, and concentrated under reduced pressure to provide a residue. Purification by column chromatography on silica gel (100-200 mesh) using ethyl acetate in hexane afforded the title compound as a white solid (0.5 g crude).

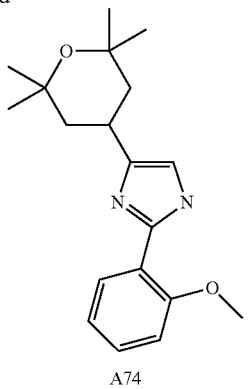

A74

Reaction conditions: a) Me$_3$Al, toluene, NH$_4$Cl, 0-70° C.; b) NaHCO$_3$, dixoane, 100° C.;

Step 1. 2-methoxybenzimidamide

To a stirred solution of ammonium chloride (6 g, 0.113 mol) in toluene (80 mL) at 0° C. was added trimethylaluminium (2.97 g, 0.041 mol) drop wise for a period of 10 min. The reaction mixture was stirred for 3 h at room temperature followed by addition of 2-methoxybenzonitrile (5 g, 0.037 mol) in toluene (10 mL). The reaction was then heated to 70° C. for 16 h. After completion, the reaction was quenched with ice cold water, filtered through diatomaceous earth, and washed with ethyl acetate. The aqueous layer was extracted with ethyl acetate (2×). The combined organic extracts were washed with brine, dried over anhydrous Na$_2$SO$_4$, filtered, and concentrated under reduced pressure to provide a residue. Purification by column chromatography on silica gel (100-200 mesh) using ethyl acetate in hexane afforded the title compound as a solid (4.5 g, 80%).

Example 6

Preparation of intermediate A75: 2-bromo-1-(4-hydroxy-2,2,6,6-tetramethyltetrahydro-2H-pyran-4-yl)ethanone

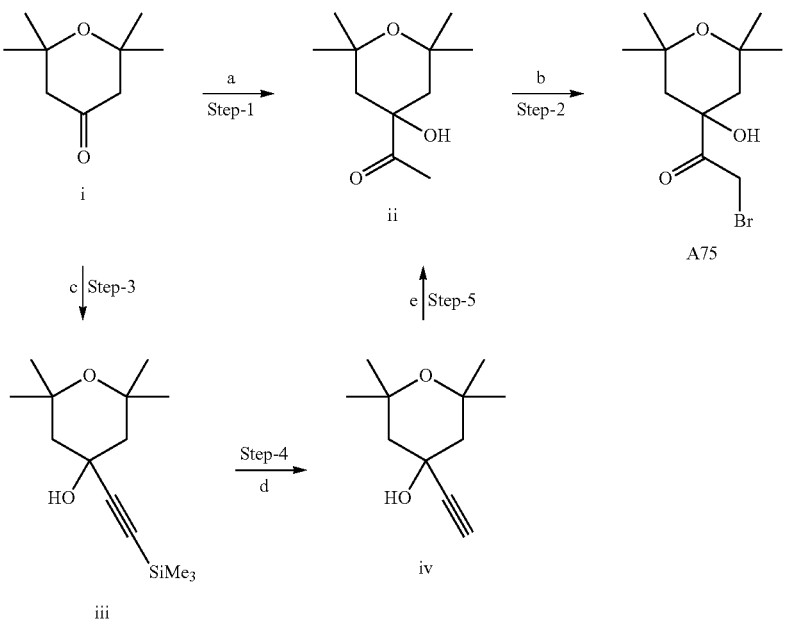

a) Ethoxy ethylene, $^t$BuLi, 0° C.-RT; b) HBr/AcOH, CHCl$_3$, 0° C.-RT; c) $^t$BuLi, TMS-acetylene, -78° C.-RT; d) K$_2$CO$_3$, MeOH, RT; e) HgO, H$_2$SO$_4$, Acetone/H$_2$O, 60° C.

Step 1. 1-(4-hydroxy-2,2,6,6-tetramethyltetrahydro-2H-pyran-4-yl)ethanone

To a stirred solution of ethoxyethene (1.84 g, 25.5 mmol) in THF (40 mL) was added $^t$BuLi (16 mL, 25.6 mmol) at −78° C. The reaction mixture was slowly allowed to warm to 10° C. followed by addition of 2,2,6,6-tetramethyldihydro-2H-pyran-4(3H)-one (2 g, 12.8 mmol). The mixture was stirred for 16 h at room temperature. The reaction was quenched by the addition of HCl (3 mL) in aqueous methanol (20 mL, MeOH:H₂O=1:1). The combined organic extracts were washed with brine, dried over anhydrous Na₂SO₄, filtered, and concentrated under reduced pressure to provide the crude title compound as an off-white solid (1.2 g) which was used in the next step without further purification.

Step 2. (See below)

Step 3. 2,2,6,6-Tetramethyl-4-trimethylsilanylethynyl-tetrahydro-pyran-4-ol

To a solution of ethynyl-trimethyl-silane (5.5 mL, 38.4 mmol) in dry THF (25 mL) was added n-BuLi (32 mL, 38.4 mmol) at −78° C. and the mixture was stirred at that temperature for 45 min followed by addition of 2,2,6,6-tetramethyl-tetrahydro-pyran-4-one (5.0 g, 32 mmol) in dry THF (25 mL) at −78° C. The mixture was stirred for 1 h and then quenched with saturated NH₄Cl solution and extracted with ethyl acetate (3×100 mL). The combined organic extract was washed with water and brine solution, dried over Na₂SO₄, filtered, and concentrated under reduced pressure to afford the product as sticky white solid. Crude product was forwarded for next stage without purification. Yield: 8.0 g, crude.

Step 4. 4-Ethynyl-2,2,6,6-tetramethyl-tetrahydro-pyran-4-ol

To a stirred solution of 2,2,6,6-tetramethyl-4-trimethylsilanylethynyl-tetrahydro-pyran-4-ol (8.0 g, 0.031 mol) in MeOH (120 mL) was added potassium carbonate (10.86 g, 0.078 mol) and the mixture was stirred at rt for 12 h. MeOH was evaporated to obtain a residue, to which water was added. The mixture was extracted with ethyl acetate (3×100 mL). The organic portion was washed with brine solution, dried over Na₂SO₄, filtered, and concentrated under reduced pressure to afford the crude product, which was triturated with n-pentane to afford the purified product as an off-white solid. (Yield: 3.5 g, 61%).

Step 5. 1-(4-hydroxy-2,2,6,6-tetramethyltetrahydro-2H-pyran-4-yl)ethanone

To a stirred solution of HgO (0.185 g, 0.085 mmol) in acetone/H₂O (30 mL/4 mL) was added H₂SO₄ (0.03 mL) and the mixture was heated to 60° C., followed by addition of 4-ethynyl-2,2,6,6-tetramethyl-tetrahydro-pyran-4-ol (3) (2.6 g, 1.42 mmol) in acetone (10 mL) drop wise at that temperature. After consumption of starting material (TLC), the reaction mixture was concentrated, diluted with cold water (50 mL) and extracted with EtOAc (3×50 mL). The combined organic extracts were washed with water and brine, dried over Na₂SO₄, filtered, and concentrated under reduced pressure to afford the crude product. Yield: 2.5 g (87%).

Step 2. 2-bromo-1-(4-hydroxy-2,2,6,6-tetramethyl-tetrahydro-2H-pyran-4-yl)ethanone

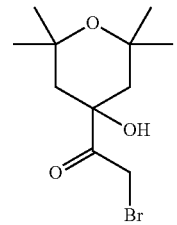

A75

To a stirred solution of 1-(4-hydroxy-2,2,6,6-tetramethyltetrahydro-2H-pyran-4-yl)ethanone (1.1 g, 0.0054 mol) in CHCl₃ (30 mL) was added two drops of HBr/AcOH at 0° C., followed by addition of Br₂ (0.3 mL, 0.006 mol) in CHCl₃ (2 mL). The temperature was gradually increased to room temperature and the reaction mixture was stirred for 4 h. After completion of the reaction, the reaction mixture was diluted with DCM (100 mL). The DCM solution was washed with NaHCO₃, brine, dried over anhydrous Na₂SO₄, filtered, and concentrated under reduced pressure to provide the crude title compound as a thick liquid which is used directly for the next stage without further purification. Yield: 1.2 g (Crude).

B. Preparation of Final Compounds

Example 7

Compound 1: 4-(2-(2-methoxyphenyl)-4-(2,2,6,6-tetramethyltetrahydro-2H-pyran-4-yl)-1H-imidazol-1-yl)benzonitrile

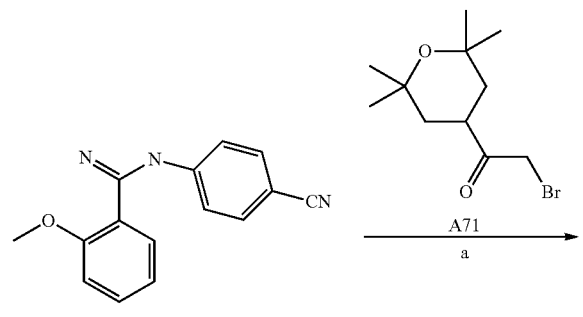

A1

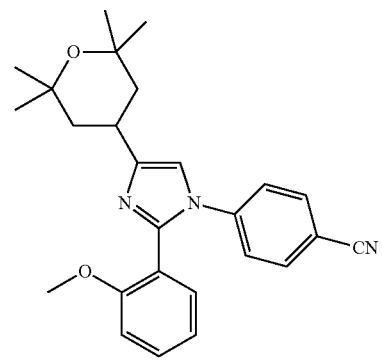

Reaction conditions: (a) NaHCO3, dixoane, 100° C.

To a stirred solution of N-(4-cyanophenyl)-2-methoxybenzimidamide A1 (2.5 g, 0.0099 mol) and 2-bromo-1-(2,2,6,6-tetramethyltetrahydro-2H-pyran-4-yl)ethanone A71 (3.24 g, 0.0123 mol) in dioxane (50 mL) was added NaHCO$_3$ (1.67 g, 0.0199 mol) and the reaction mixture was refluxed at 100° C. for 5 h. After completion of the reaction the mixture was concentrated under reduced pressure and quenched with ice cold water. The aqueous layer was extracted with ethyl acetate (2×150 mL). The combined organic extracts were washed with brine, dried over anhydrous Na$_2$SO$_4$, filtered, and concentrated under reduced pressure to provide a residue. The residue was purified by column chromatography on silica gel (100-200 mesh) using ethyl acetate in hexane to afford the title compound 1 as a white solid. $^1$H NMR (400 MHz, CDCl$_3$) δ 7.61-7.57 (m, 3H), 7.38-7.34 (m, 1H), 7.21 (d, J=8.4 Hz, 2H), 7.05 (t, J=6.8 Hz, 1H), 6.96 (s, 1H), 6.71 (d, J=8.4 Hz, 1H), 3.27 (s, 3H), 3.24-3.22 (m, 1H), 2.06-2.02 (m, 2H), 1.50-1.44 (m, 2H), 1.36 (s, 6H), 1.25 (s, 6H); LCMS: 416.3 (M+H)$^+$.

Using analogous protocols to those described in Example 7, the compounds described in Table 2 have been prepared using an appropriately substituted amidine intermediate.

TABLE 2

| Cpd No. | Structure | Compound Name | Analytical data |
|---|---|---|---|
| 2 | 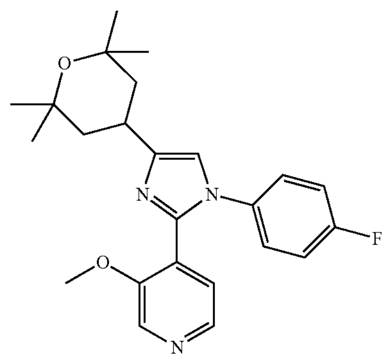 [SMILES: COc1cnccc1-c1nc(C2CC(C)(C)OC(C)(C)C2)cn1-c1ccc(F)cc1] | 4-(1-(4-fluorophenyl)-4-(2,2,6,6-tetramethyltetrahydro-2H-pyran-4-yl)-1H-imidazol-2-yl)-3-methoxypyridine | $^1$H NMR (400 MHz, DMSO-d$_6$) 8.29-8.26 (m, 2H), 7.50 (d, J = 4.4 Hz, 1H), 7.33 (s, 1H), 7.28-7.16 (m, 4H), 3.32 (s, 3H), 3.15-3.08 (m, 1H), 1.90 (d, J = 2.8 Hz, 2H), 1.40-1.39 (m, , 2H), 1.28 (s, 6H), 1.15 (s, 6 H). LCMS: 410.4 [M + H]$^+$ |
| 3 | 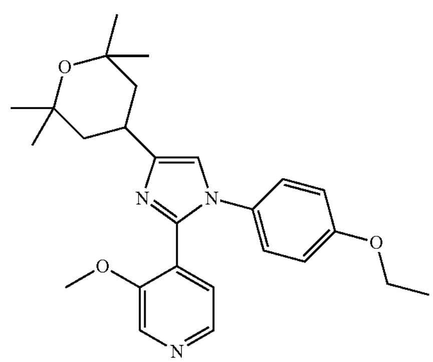 [SMILES: CCOc1ccc(-n2cc(C3CC(C)(C)OC(C)(C)C3)nc2-c2ccncc2OC)cc1] | 4-(1-(4-ethoxyphenyl)-4-(2,2,6,6-tetramethyltetrahydro-2H-pyran-4-yl)-1H-imidazol-2-yl)-3-methoxypyridine | $^1$H NMR (400 MHz, DMSO-d$_6$) δ = 8.28-8.29 (m, 2H), 7.94-7.93 (m, 1H), 7.53-7.45 (m, 2H), 7.33 (s, 1H), 6.80 (d, J = 8.8 Hz, 1H), 4.29-4.24 (q, 2H), 3.41 (s, 3H), 3.14-3.08 (m, 1H), 1.93-1.89 (m, 2H), 1.36-1.24 (m, 3H), 1.21-1.12 (m, 6H), 1.11-1.09 (m, 2H). LCMS: 436.2 [M + H]$^+$ |
| 4 | 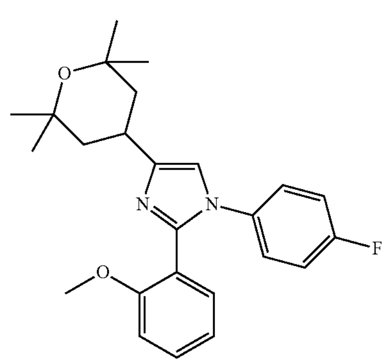 [SMILES: COc1ccccc1-c1nc(C2CC(C)(C)OC(C)(C)C2)cn1-c1ccc(F)cc1] | 1-(4-fluorophenyl)-2-(2-methoxyphenyl)-4-(2,2,6,6-tetramethyltetrahydro-2H-pyran-4-yl)-1H-imidazole | $^1$H NMR (400 MHz, DMSO-d$_6$) δ = 7.45 (d, J = 6.8 Hz, 1H), 7.36 (t, J = 6.8 Hz, 1H), 7.13-7.12 (m, 5H), 7.01 (J = 7.6 Hz, 1H), 6.87 (d, J = 8 Hz, 1H), 3.23 (s, 3H), 3.10 (d, J = 11.6 Hz, 1H), 1.91 (d, J = 11.6 Hz, 2H), 1.36 (t, J = 12.8 Hz, 2H), 1.28 (s, 6H), 1.15 (s, 6H). LCMS: 409.2 [M + H]$^+$ |

TABLE 2-continued

| Cpd No. | Structure | Compound Name | Analytical data |
|---|---|---|---|
| 5 | 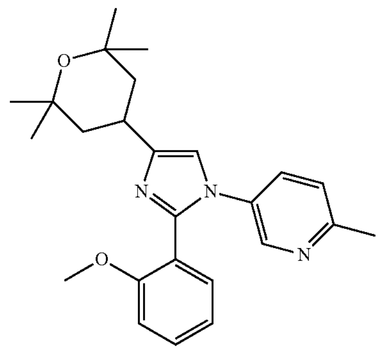 | 5-(2-(2-methoxyphenyl)-4-(2,2,6,6-tetramethyltetrahydro-2H-pyran-4-yl)-1H-imidazol-1-yl)-2-methylpyridine | $^1$H NMR (400 MHz, DMSO-$d_6$) δ = 8.18 (s, 1 H), 7.35-7.5 (m, 3 H), 7.28 (s, 1 H), 7.22 (d, J = 8.4 Hz, 1 H), 7.02 (t, J = 7.6 Hz, 1 H), 6.88 (d, J = 8.0 Hz 1 H), 3.23 (s, 3 H), 3.03-3.14 (m, 1 H), 2.43 (s, 3 H), 1.93 (t, J = 2.4 Hz, 2 H), 1.36 (t, J = 12.8 Hz, 2 H), 1.28 (s, 6 H), 1.15 (s, 6 H). LCMS: 406.5 [M + H]$^+$. |
| 6 | 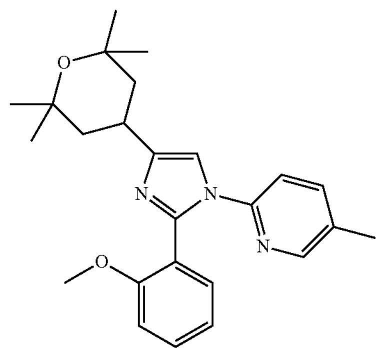 | 2-(2-(2-methoxyphenyl)-4-(2,2,6,6-tetramethyltetrahydro-2H-pyran-4-yl)-1H-imidazol-1-yl)-5-methylpyridine | $^1$H NMR (400 MHz, DMSO-$d_6$) δ = 8.20 (s, 1H), 7.60 (d, J = 8 Hz, 1H), 7.50 (d, J = 1.2 Hz, 1H), 7.35-7.39 (m, 2H), 7.03 (t, J = 7.6 Hz, 1H), 6.87-6.93 (m, 2H), 3.16 (s, 3H), 3.07-3.13 (m, 1H), 2.26 (s, 3H), 1.93 (d, J = 2.8 Hz, 2H), 1.39-1.33 (m, 2H), 1.29 (s, 6H), 1.15 (s, 6H). LCMS: 406.3 [M + H]$^+$ |
| 7 | 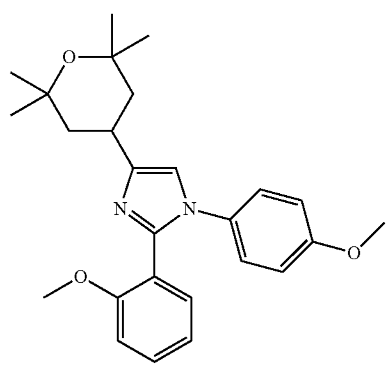 | 2-(2-methoxyphenyl)-1-(4-methoxyphenyl)-4-(2,2,6,6-tetramethyltetrahydro-2H-pyran-4-yl)-1H-imidazole | $^1$H NMR (400 MHz, DMSO-$d_6$) δ 7.40 (d, J = 7.6 Hz, 1H), 7.31 (t, J = 8 Hz, 1H), 7.12 (s, 1H), 6.99 (q, J = 8.8 Hz, J = 8.8 Hz, 1H), 6.87 (d, J = 8 Hz, 1H), 3.71 (s, 3H), 3.26 (s, 3H), 3.08 (t, J = 12.4 Hz, 1H), 1.90 (dd, J = 2.8 Hz, J = 12.8 Hz, 2H), 1.36 (t, J = 12.8 Hz, 2H), 1.28 (s, 6H), 1.15 (s, 6H). LCMS: 421.2 [M + H]$^+$ |
| 8 | 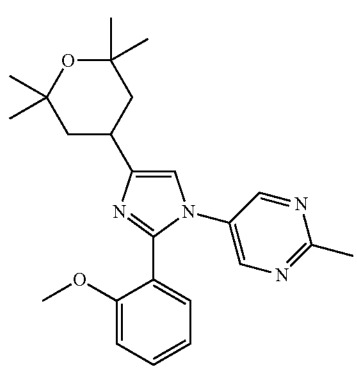 | 5-(2-(2-methoxyphenyl)-4-(2,2,6,6-tetramethyltetrahydro-2H-pyran-4-yl)-1H-imidazol-1-yl)-2-methylpyrimidine | $^1$H NMR (400 MHz, DMSO-$d_6$) δ 8.47 (s, 2 H), 7.51 (d, J = 1.6 Hz, 1 H), 7.43 (d, J = 1.2 Hz, 1 H), 7.39 (s, 1 H), 7.08-7.04 (m, 1 H), 6.90 (d, J = 8.4 Hz 1 H), 3.27 (s, 3 H), 3.14-3.03 (m, 1 H), 2.60 (s, 3 H), 1.94 (d, J = 2.8 Hz, 2 H), 1.42-1.36 (m, 2 H), 1.28 (s, 6 H), 1.15 (s, 6 H) LCMS: 407.5 [M + H]$^+$ |

TABLE 2-continued

| Cpd No. | Structure | Compound Name | Analytical data |
|---|---|---|---|
| 9 | 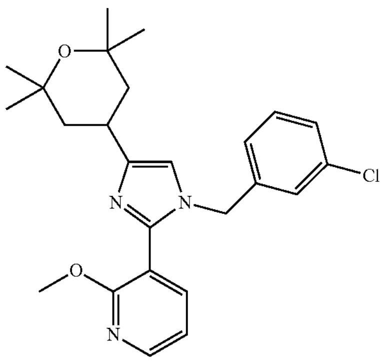 [SMILES: COc1ncccc1-c1nc(C2CC(C)(C)OC(C)(C)C2)cn1Cc1cccc(Cl)c1] | 3-(1-(3-chlorobenzyl)-4-(2,2,6,6-tetramethyltetrahydro-2H-pyran-4-yl)-1H-imidazol-2-yl)-2-methoxypyridine | $^1$H NMR (400 MHz, DMSO-$d_6$) δ = 8.25 (d, J = 4 Hz, 1H), 7.67 (d, J = 8 Hz, 1H), 7.30 (t, J = 5.2 Hz, 2H), 7.05 (t, J = 11.2 Hz, 3H), 6.90 (s, 1H), 4.99 (s, 2H), 3.78 (s, 3H), 3.08-3.01 (m, 1H), 1.86 (q, J = 2.8 & 2.9 Hz, 2H), 1.32-1.40 (m, 2H), 1.26 (s, 6H), 1.12 (s, 6H). LCMS: 440.2 [M + H]$^+$ |
| 10 | 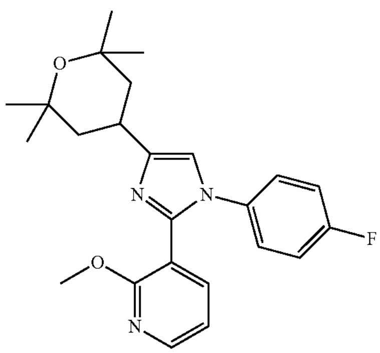 [SMILES: COc1ncccc1-c1nc(C2CC(C)(C)OC(C)(C)C2)cn1-c1ccc(F)cc1] | 3-(1-(4-fluorophenyl)-4-(2,2,6,6-tetramethyltetrahydro-2H-pyran-4-yl)-1H-imidazol-2-yl)-2-methoxypyridine | $^1$H NMR (400 MHz, DMSO-$d_6$) δ = 8.17 (d, J = 4.8 Hz, 1H), 7.90 (d, J = 7.6 Hz, 1H), 7.27 (s, 1H), 7.1-7.26 (m, 4H), 7.07 (d, J = 5.2 Hz, 1H), 3.1 (s, 1H), 1.89 (t, J = 15.6 Hz, 2H), 1.36 (t, J = 12.8 Hz, 2H), 1.28 (s, 6H), 1.14 (s, 6H). LCMS: 410.5 [M + H]$^+$ |
| 11 | 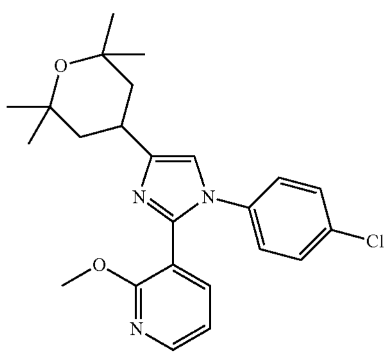 [SMILES: COc1ncccc1-c1nc(C2CC(C)(C)OC(C)(C)C2)cn1-c1ccc(Cl)cc1] | 3-(1-(4-chlorophenyl)-4-(2,2,6,6-tetramethyltetrahydro-2H-pyran-4-yl)-1H-imidazol-2-yl)-2-methoxypyridine | $^1$H NMR: (400 MHz, CDCl$_3$) δ 8.16 (d, J = 3.2 Hz, 1H), 7.88 (d, J = 6.4 Hz, 1H), 7.30-7.27 (m, 2H), 7.04 (d, J = 8.4 Hz, 2H), 6.97-6.93 (m, 2H), 3.48 (s, 3H), 3.25-3.19 (m, 1H), 2.03 (d, J = 10.8 Hz, 2H), 1.51-1.44 (m, 2H), 1.36 (s, 6H), 1.25 (s, 2H). LCMS 426.2 (M + H)$^+$ |
| 12 | 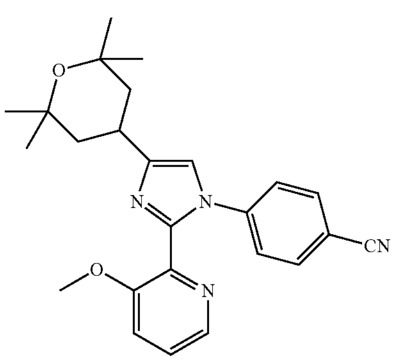 [SMILES: COc1cccnc1-c1nc(C2CC(C)(C)OC(C)(C)C2)cn1-c1ccc(C#N)cc1] | 4-(2-(3-methoxypyridin-2-yl)-4-(2,2,6,6-tetramethyltetrahydro-2H-pyran-4-yl)-1H-imidazol-1-yl)benzonitrile | $^1$H NMR (400 MHz, DMSO-$d_6$) δ = 8.19 (s, 1H), 7.75-7.85 (m, 2H), 7.40-7.50 (m, 3H), 7.26 (d, J = 8 Hz, 2H), 3.45 (s, 3H), 3.05-3.20 (m, 1H), 1.92 (d, J = 11.6 Hz, 2H), 1.30-1.40 (m, 2H), 1.29 (s, 6H), 1.16 (s, 6H). LCMS: 417.5 [M + H]$^+$ |

TABLE 2-continued

| Cpd No. | Structure | Compound Name | Analytical data |
|---|---|---|---|
| 13 | 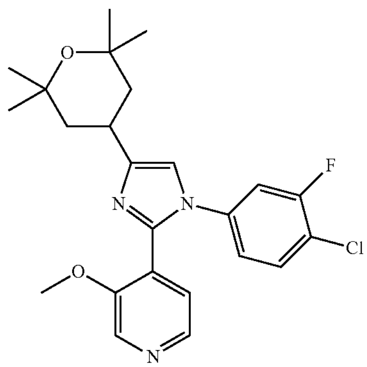 [SMILES: COc1cnccc1-c1nc(C2CC(C)(C)OC(C)(C)C2)cn1-c1ccc(Cl)c(F)c1] | 4-(1-(4-chloro-3-fluorophenyl)-4-(2,2,6,6-tetramethyltetrahydro-2H-pyran-4-yl)-1H-imidazol-2-yl)-3-methoxypyridine | $^1$H NMR (CDCl$_3$, 400 MHz) δ 8.35 (d, J = 4.8 Hz, 1H), 8.18 (s, 1H), 7.53 (d, J = 4.8 Hz, 1H), 7.36-7.32 (m, 1H), 6.99-6.96 (m, 2H), 6.82 (d, J = 8.4 Hz, 1H), 3.47 (s, 3H), 3.25-3.19 (m, 1H), 2.02-1.99 (m, 2H), 1.50-1.43 (m, 2H), 1.35 (s, 6H), 1.28 (s, 6H). LCMS: 444.4 [M + H]$^+$ |
| 14 | 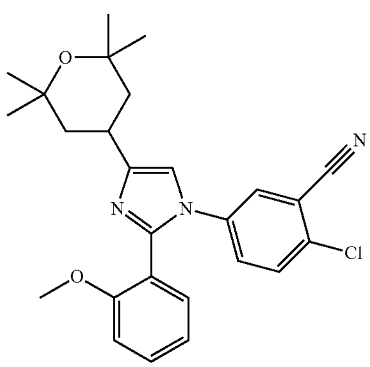 [SMILES: COc1ccccc1-c1nc(C2CC(C)(C)OC(C)(C)C2)cn1-c1ccc(Cl)c(C#N)c1] | 2-chloro-5-(2-(2-methoxyphenyl)-4-(2,2,6,6-tetramethyltetrahydro-2H-pyran-4-yl)-1H-imidazol-1-yl)benzonitrile | $^1$H NMR (CDCl$_3$, 400 MHz) δ 7.57-7.55 (m, 1H), 7.47-7.46 (m, 1H), 7.42-7.35 (m, 1H), 7.26 (s, 1H), 7.06-7.03 (m, 1H), 6.92 (s, 1H), 6.74 (d, J = 8.4 Hz, 1H), 3.37 (s, 3H), 3.26-3.19 (m, 1H), 2.04-2.01 (m, 2H), 1.50-1.43 (m, 2H), 1.35 (s, 6H), 1.29 (s, 6H). LCMS: 450.5 [M + H]$^+$ |
| 15 | 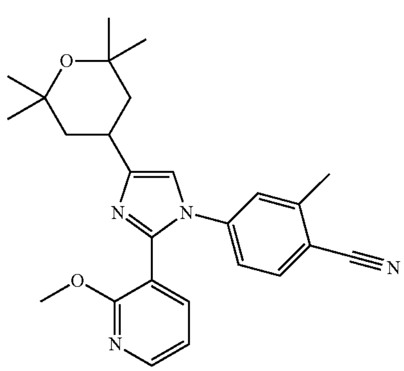 | 4-(2-(2-methoxypyridin-3-yl)-4-(2,2,6,6-tetramethyltetrahydro-2H-pyran-4-yl)-1H-imidazol-1-yl)-2-methylbenzonitrile | $^1$H NMR (CDCl$_3$, 400 MHz) δ 8.20-8.18 (m, 1H), 7.94-7.91 (m, 1H), 7.55-7.53 (m, 1H), 7.11 (s, 1H), 7.01-6.97 (m, 3H), 3.44 (s, 3H), 3.26-3.19 (m, 1H), 2.50 (s, 3H), 2.04-2.00 (m, 2H), 1.50-1.42 (m, 2H), 1.35 (s, 6H), 1.26 (s, 6H). LCMS: 431.5 [M + H]$^+$ |
| 16 | 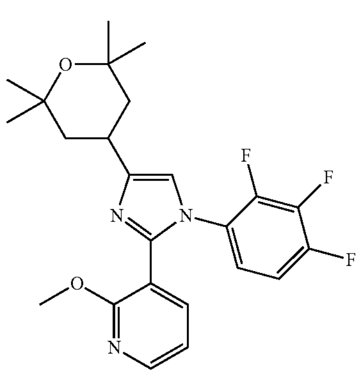 [SMILES: COc1ncccc1-c1nc(C2CC(C)(C)OC(C)(C)C2)cn1-c1ccc(F)c(F)c1F] | 2-methoxy-3-(4-(2,2,6,6-tetramethyltetrahydro-2H-pyran-4-yl)-1-(2,3,4-trifluorophenyl)-1H-imidazol-2-yl)pyridine | $^1$H NMR (400 MHz, DMSO-d$_6$): 8.20-8.18 (m, 1H), 7.94-7.91 (m, 1H), 7.29-7.35 (m, 2H), 7.10-7.07 (m, 2H), 3.45 (s, 3H), 3.16-3.10 (m, 1H), 1.93-1.89 (m, 2H), 1.39-1.33 (m, 2H), 1.29 (s, 6H), 1.15 (s, 6H). LCMS: 446.4 [M + H]$^+$ |

TABLE 2-continued

| Cpd No. | Structure | Compound Name | Analytical data |
|---|---|---|---|
| 17 | 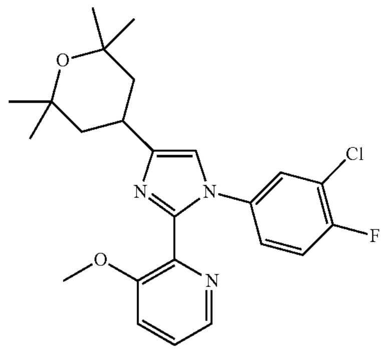 [SMILES: COc1cccnc1-c1nc(C2CC(C)(C)OC(C)(C)C2)cn1-c1ccc(F)c(Cl)c1] | 2-(1-(3-chloro-4-fluorophenyl)-4-(2,2,6,6-tetramethyltetrahydro-2H-pyran-4-yl)-1H-imidazol-2-yl)-3-methoxypyridine | $^1$H NMR (400 MHz, DMSO-$d_6$) 8.18-8.17 (m, 1H), 7.47-7.35 (m, 5H), 7.02-7.00 (m, 1H), 3.51 (s, 3H), 3.13-3.07 (m, 1H), 1.92 (d, J = 11.6 Hz, 2H), 1.37 (d, J = 13.2 Hz, 2H), 1.29 (s, 6H), 1.15 (s, 6H). LCMS: 444.4 [M + H]$^+$ |
| 18 | 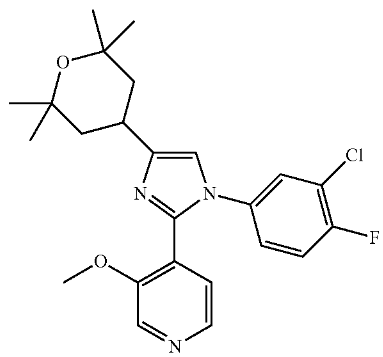 [SMILES: COc1cnccc1-c1nc(C2CC(C)(C)OC(C)(C)C2)cn1-c1ccc(F)c(Cl)c1] | 4-(1-(3-chloro-4-fluorophenyl)-4-(2,2,6,6-tetramethyltetrahydro-2H-pyran-4-yl)-1H-imidazol-2-yl)-3-methoxypyridine | $^1$H NMR (400 MHz, DMSO-$d_6$) 8.31-8.28 (m, 2H), 7.55-7.51 (m, 2H), 7.44-7.39 (m, 2H), 7.12-7.08 (m, 1H), 3.37 (s, 3H), 3.14-3.07 (m, 1H), 1.93-1.89 (m, 2H), 1.39-1.32 (m, 2H), 1.28 (s, 6H), 1.15 (s, 6H). LCMS: 444.4 [M + H]$^+$ |
| 19 | 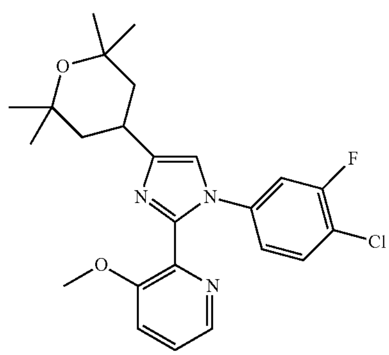 [SMILES: COc1cccnc1-c1nc(C2CC(C)(C)OC(C)(C)C2)cn1-c1ccc(Cl)c(F)c1] | 2-(1-(4-chloro-3-fluorophenyl)-4-(2,2,6,6-tetramethyltetrahydro-2H-pyran-4-yl)-1H-imidazol-2-yl)-3-methoxypyridine | $^1$H NMR (400 MHz, DMSO-$d_6$) 8.19-8.17 (s, 1H), 7.55-7.51 (m, 1H), 7.48-7.42 (m, 2H), 7.37 (s, 1H), 7.29-7.26 (m, 1H), 6.87-6.85 (m, 1H), 3.51 (s, 3H), 3.14-3.07 (m, 1H), 1.93-1.89 (m, 2H), 1.39-1.33 (m, 2H), 1.29 (s, 6H), 1.15 (s, 6H). LCMS: 444.4 [M + H]$^+$ |
| 20 | 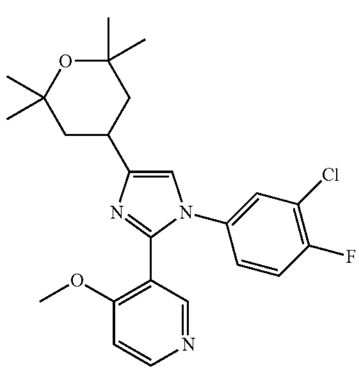 [SMILES: COc1ccncc1-c1nc(C2CC(C)(C)OC(C)(C)C2)cn1-c1ccc(F)c(Cl)c1] | 3-(1-(3-chloro-4-fluorophenyl)-4-(2,2,6,6-tetramethyltetrahydro-2H-pyran-4-yl)-1H-imidazol-2-yl)-4-methoxypyridine | $^1$H NMR (400 MHz, DMSO-$d_6$) 8.51 (s, 1H), 8.48-8.47 (m, 1H), 7.54-7.52 (m, 1H), 7.43-7.38 (m, 2H), 7.15-7.11 (m, 1H), 6.98-6.97 (m, 1H) 3.40 (s, 3H), 3.05-3.15 (m, 1H), 1.94-1.90 (m, 2H), 1.39-1.32 (m, 2H), 1.29 (s, 6H), 1.15 (s, 6H). LCMS: 444.4 [M + H]$^+$ |

TABLE 2-continued

| Cpd No. | Structure | Compound Name | Analytical data |
|---|---|---|---|
| 21 | 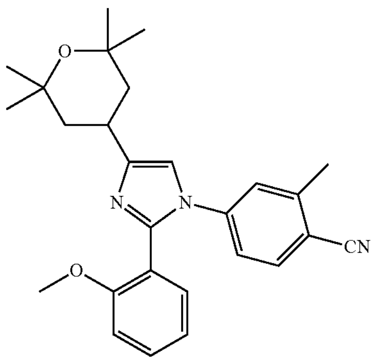 [SMILES: COc1ccccc1-c1nc(C2CC(C)(C)OC(C)(C)C2)cn1-c1ccc(C#N)c(C)c1] | 4-(2-(2-methoxyphenyl)-4-(2,2,6,6-tetramethyltetrahydro-2H-pyran-4-yl)-1H-imidazol-1-yl)-2-methylbenzonitrile | $^1$H NMR (400 MHz, DMSO-$d_6$) 7.70 (d, J = 8 Hz, 1H), 7.49 (d, J = 7.6 Hz, 1H), 7.41 (t, 1H), 7.34-7.33 (m, 2H), 7.05 (t, 1H), 6.98-6.96 (m, 1H), 6.89 (d, J = 8 Hz, 1H), 3.18 (s, 3H), 3.13-3.06 (m, 1H), 2.42 (s, 3H), 1.94-1.90 (m, 2H), 1.39-1.32 (m, 2H), 1.29 (s, 6H), 1.15 (s, 6H). LCMS: 430.5 [M + H]$^+$ |
| 22 | 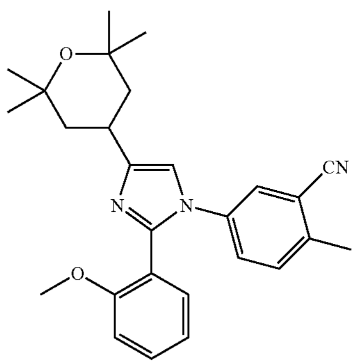 | 5-(2-(2-methoxyphenyl)-4-(2,2,6,6-tetramethyltetrahydro-2H-pyran-4-yl)-1H-imidazol-1-yl)-2-methylbenzonitrile | $^1$H NMR (400 MHz, DMSO-$d_6$) 7.58 (s, 1H), 7.47 (d, J = 6.8 Hz, 1H), 7.38 (d, J = 7.6 Hz, 2H), 7.31 (s, 1H), 7.25 (d, J = 7.2 Hz, 1H), 7.04 (t, 1H), 6.89 (d, J = 8.4 Hz, 1H), 3.22 (s, 3H), 3.12-2.98 (m, 1H), 2.44 (s, 3H), 1.92 (d, J = 12.8 Hz, 2H), 1.44-1.35 (m, 2H), 1.29 (s, 6H), 1.15 (s, 6H). LCMS: 430.3 [M + H]$^+$ |
| 23 | 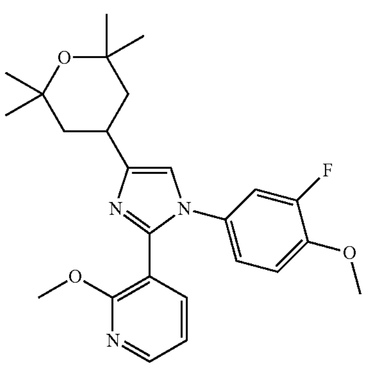 | 3-(1-(3-fluoro-4-methoxyphenyl)-4-(2,2,6,6-tetramethyltetrahydro-2H-pyran-4-yl)-1H-imidazol-2-yl)-2-methoxypyridine | $^1$H NMR (400 MHz, DMSO-$d_6$) 8.20-8.18 (m, 1H), 7.89-7.87 (m, 1H), 7.25 (s, 1H), 7.16-7.06 (m, 3H), 6.85 (d, J = 7.6 Hz, 1H), 3.81 (s, 3H), 3.41 (s, 3H), 3.12-3.05 (m, 1H), 1.93-1.89 (m, 2H), 1.39-1.32 (m, 2H), 1.28 (s, 6H), 1.15 (s, 6H). LCMS: 440.5 [M + H]$^+$ |
| 24 | 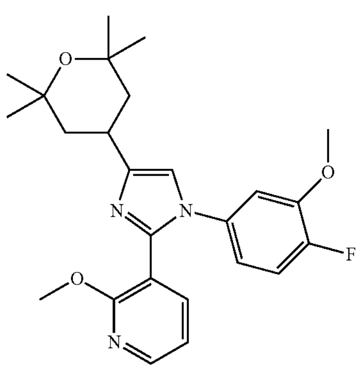 [SMILES: COc1cc(-n2cc(C3CC(C)(C)OC(C)(C)C3)nc2-c2cccnc2OC)ccc1F] | 3-(1-(4-fluoro-3-methoxyphenyl)-4-(2,2,6,6-tetramethyltetrahydro-2H-pyran-4-yl)-1H-imidazol-2-yl)-2-methoxypyridine | $^1$H NMR (400 MHz, DMSO-$d_6$) 8.20-8.18 (m, 1H), 7.91-7.88 (m, 1H), 7.32 (s, 1H), 7.20-7.15 (m, 1H), 7.10-7.07 (m, 1H), 7.00-6.98 (m, 1H), 6.63-6.60 (m, 1H), 3.70 (s, 3H), 3.39 (s, 3H), 3.13-3.07 (m, 1H), 1.94-1.90 (m, 2H), 1.40-1.34 (m, 2H), 1.29 (s, 6H), 1.15 (s, 6H). LCMS: 440.5 [M + H]$^+$ |

TABLE 2-continued

| Cpd No. | Structure | Compound Name | Analytical data |
|---|---|---|---|
| 25 | 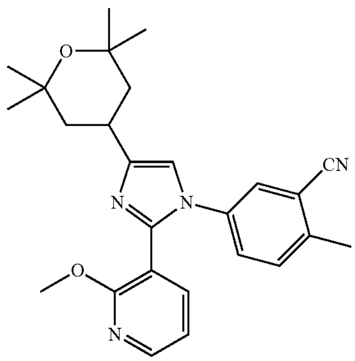 | 5-(2-(2-methoxypyridin-3-yl)-4-(2,2,6,6-tetramethyltetrahydro-2H-pyran-4-yl)-1H-imidazol-1-yl)-2-methylbenzonitrile | $^1$H NMR (400 MHz, DMSO-d$_6$) 8.20 (d, J = 2.4 Hz, 1H), 7.92 (d, J = 3.6 Hz, 1H), 7.66 (s, 1H), 7.42 (d, J = 8.4 Hz, 1H), 7.37 (s, 1H), 7.29 (d, J = 2 Hz, 1H), 7.11 (d, J = 4.8 Hz, 1H), 3.32 (s, 3H), 3.13-.307 (m, 1H), 2.46 (s, 3H), 1.92 (d, J = 13.2 Hz, 2H), 1.37 (d, J = 12.8 Hz, 2H), 1.29 (s, 6H), 1.15 (s, 6H). LCMS: 431.5 [M + H]$^+$ |
| 26 | 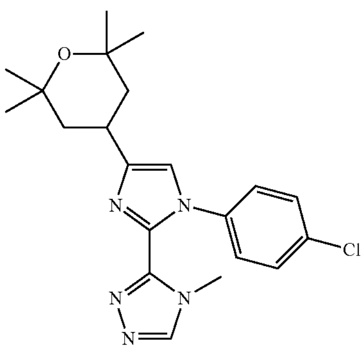 [SMILES: Cn1cnnc1-c1nc(C2CC(C)(C)OC(C)(C)C2)cn1-c1ccc(Cl)cc1] | 3-(1-(4-chlorophenyl)-4-(2,2,6,6-tetramethyltetrahydro-2H-pyran-4-yl)-1H-imidazol-2-yl)-4-methyl-4H-1,2,4-triazole | $^1$H NMR: $^1$HNMR (400 MHz, DMSO-d$_6$) δ 8.41 (bs, 1H), 7.46 (d, J = 6.8 Hz, 2H), 7.29 (t, J = 14 Hz, 3H), 3.83 (s, 3H), 1.88 (d, J = 11.6 Hz, 2H), 1.38 (d, J = 12.4 Hz, 2H), 1.28 (s, 6H), 1.15 (s, 6H). LCMS 400.46 [M + H]$^+$ |
| 27 | 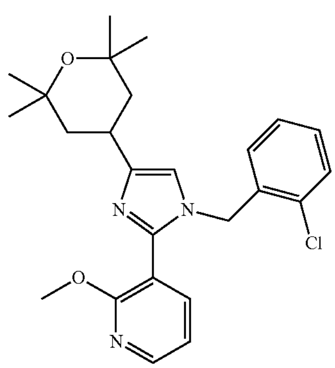 [SMILES: COc1ncccc1-c1nc(C2CC(C)(C)OC(C)(C)C2)cn1Cc1ccccc1Cl] | 3-(1-(2-chlorobenzyl)-4-(2,2,6,6-tetramethyltetrahydro-2H-pyran-4-yl)-1H-imidazol-2-yl)-2-methoxypyridine | $^1$H NMR (CDCl$_3$, 400 MHz) δ 8.27 (s, 1 H), 7.7-7.84 (m, 1H), 7.35 (d J = 7.2 Hz, 1 H), 7.18-7.28 (m, 2 H), 7.08 (s, 1 H), 6.9-7.0 (m, 1 H), 6.68 (s, 1 H), 5.13 (s, 1 H), 5.05 (s, 1 H), 3.79 (s, 3 H), 2.68-2.80 (m, 1 H), 2.0-2.10 (m, 1 H), 1.75-1.86 (m, 1 H), 1.4-1.5 (m, 3 H), 1.16 (s, 6 H), 1.03 (s, 3 H), 0.89 (s, 3 H). LCMS: 440.4 [M + H]$^+$ |
| 28 | 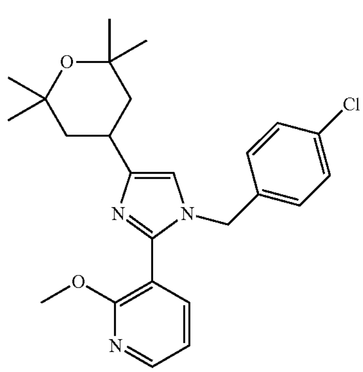 [SMILES: COc1ncccc1-c1nc(C2CC(C)(C)OC(C)(C)C2)cn1Cc1ccc(Cl)cc1] | 3-(1-(4-chlorobenzyl)-4-(2,2,6,6-tetramethyltetrahydro-2H-pyran-4-yl)-1H-imidazol-2-yl)-2-methoxypyridine | $^1$H NMR (400 MHz, DMSO-d$_6$) 8.25 (d, J = 3.2 Hz, 1 H), 7.6-7.7 (m, 1 H), 7.33 (d, J = 8.4 Hz, 2 H), 7.06-7.03 (m, 1 H), 6.98 (d, J = 6.8 Hz, 3 H), 4.97 (s, 2 H), 3.78 (s, 3 H), 3.05-2.99 (m, 1 H), 1.86-1.82 (m, 2 H), 1.35-1.30 (m, 1 H), 1.25 (s, 7 H), 1.12 (s, 6 H). LCMS: 440.2 [M + H]$^+$ |

TABLE 2-continued

| Cpd No. | Structure | Compound Name | Analytical data |
|---|---|---|---|
| 29 | 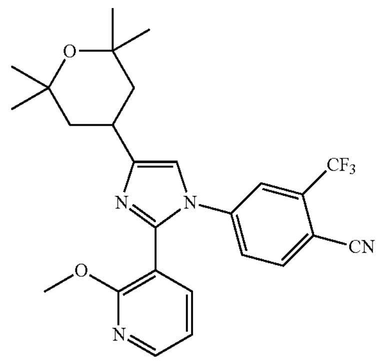 [SMILES: COc1ncccc1-c1nc(C2CC(C)(C)OC(C)(C)C2)cn1-c1ccc(C#N)c(C(F)(F)F)c1] | 4-(2-(2-methoxypyridin-3-yl)-4-(2,2,6,6-tetramethyltetrahydro-2H-pyran-4-yl)-1H-imidazol-1-yl)-2-(trifluoromethyl)benzonitrile | $^1$H NMR (CDCl$_3$, 400 MHz) δ 8.2-8.3 (m, 1 H), 7.99-7.97 (m, 1 H), 7.78 (d, J = 7 Hz, 1 H), 7.62 (s, 1 H), 7.3-7.4 (m, 1 H), 7.05-7.01 (m, 2 H), 3.4 (s, 3 H), 3.26-3.20 (m, 1 H), 2.04-2.00 (m, 2H), 1.51-1.45 (m, 2 H), 1.35 (s, 6 H), 1.26 (s, 6 H). LCMS: 485.5 [M + H]$^+$ |
| 30 | 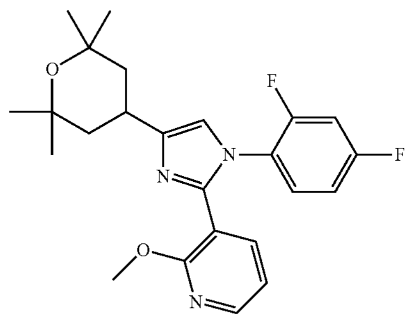 [SMILES: COc1ncccc1-c1nc(C2CC(C)(C)OC(C)(C)C2)cn1-c1ccc(F)cc1F] | 3-(1-(2,4-difluorophenyl)-4-(2,2,6,6-tetramethyltetrahydro-2H-pyran-4-yl)-1H-imidazol-2-yl)-2-methoxypyridine | $^1$H NMR (400 MHz, DMSO-d$_6$) δ 8.21 (s, 1 H), 7.92 (d, J = 7.2 Hz, 1 H), 7.46-7.1 (m, 1 H), 7.3-7.44 (m, 2 H), 7.09 (m, 2 H), 3.6 (s, 3 H), 3.1-3.2 (m, 1 H), 1.92 (d, J = 12.8 Hz, 2 H), 1.38 (d, J = 13.2 Hz, 2 H), 1.29 (s, 6 H), 1.15 (s, 6 H). LCMS: 428.5 [M + H]$^+$ |
| 31 | 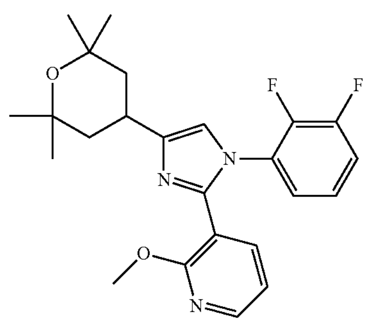 [SMILES: COc1ncccc1-c1nc(C2CC(C)(C)OC(C)(C)C2)cn1-c1cccc(F)c1F] | 3-(1-(2,3-difluorophenyl)-4-(2,2,6,6-tetramethyltetrahydro-2H-pyran-4-yl)-1H-imidazol-2-yl)-2-methoxypyridine | $^1$H NMR (400 MHz, DMSO-d$_6$) δ 8.28 (t, J = 3.6 Hz, 1 H), 8.01 (t, J = 5.6 Hz, 1 H), 7.68 (s, 1 H), 7.55-7.63 (m, 1 H), 7.22-7.27 (m, 1 H), 7.11-7.19 (m, 2 H), 3.48 (s, 3 H), 3.29-3.23 (m, 1 H), 1.98-1.93 (m, 2 H), 1.44-1.38 (m, 2 H), 1.30 (s, 6 H), 1.17 (s, 6 H). LCMS: 428.5 [M + H]$^+$ |
| 32 | 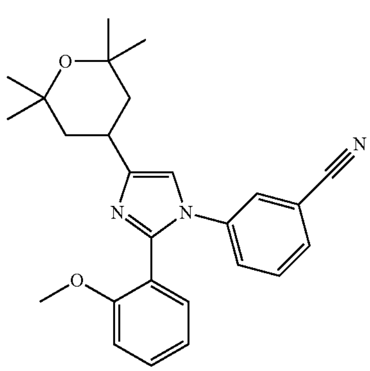 [SMILES: COc1ccccc1-c1nc(C2CC(C)(C)OC(C)(C)C2)cn1-c1cccc(C#N)c1] | 3-(2-(2-methoxyphenyl)-4-(2,2,6,6-tetramethyltetrahydro-2H-pyran-4-yl)-1H-imidazol-1-yl)benzonitrile | $^1$H NMR (400 MHz, DMSO-d$_6$) δ 7.75 (d, J = 7.2 Hz, 1H), 7.67 (s, 1H), 7.53-7.50 (m, 2H), 7.42-7.37 (m, 3H), 7.05 (t, J = 7.6 Hz, 1H), 6.68 (d, J = 8 Hz, 1H), 3.18 (s, 3H), 3.10 (m, 1H), 1.93 (d, J = 14.4 Hz, 2 H), 1.38 (d, J = 12.8 Hz, 2H), 1.32 (s, 6H), 1.15 s, 6H). LCMS: 416.5 [M + H]$^+$ |

TABLE 2-continued

| Cpd No. | Structure | Compound Name | Analytical data |
|---|---|---|---|
| 33 | 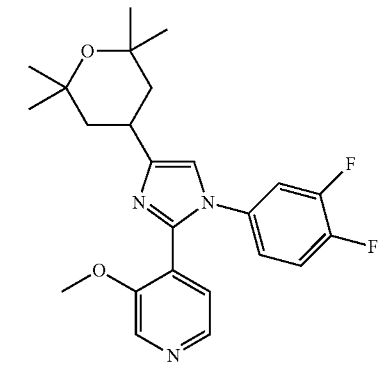 [SMILES: COc1cnccc1-c1nc(C2CC(C)(C)OC(C)(C)C2)cn1-c1ccc(F)c(F)c1] | 4-(1-(3,4-difluorophenyl)-4-(2,2,6,6-tetramethyltetrahydro-2H-pyran-4-yl)-1H-imidazol-2-yl)-3-methoxypyridine | ¹H NMR (CDCl₃, 400 MHz) δ 8.35 (d, J = 4.8 Hz, 1H), 8.1 (s, 1H), 7.52 (d, J = 4.8 Hz, 1H), 7.15-7.10 (m, 1H), 7.03-6.99 (m, 1H), 6.95 (s, 1H), 6.84 (d, J = 9.6 1H), 3.49 (s, 3H), 3.25-3.19 (m, 1H), 2.03 (d, J = 10 Hz, 2H), 1.50-1.43 (m, 2H), 1.36 (s, 6H), 1.26 (s, 6H). LCMS: 428.2 [M + H]⁺ |
| 34 | 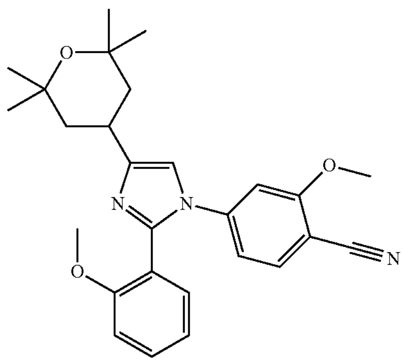 [SMILES: COc1cc(-n2cc(C3CC(C)(C)OC(C)(C)C3)nc2-c2ccccc2OC)ccc1C#N] | 2-methoxy-4-(2-(2-methoxyphenyl)-4-(2,2,6,6-tetramethyltetrahydro-2H-pyran-4-yl)-1H-imidazol-1-yl)benzonitrile | ¹H NMR (CDCl₃, 400 MHz) δ 7.60-7.59 (d, J = 1.2 Hz, 1H), 7.52-7.50 (d, J = 8.4 Hz, 1H), 7.39-7.35 (m, 1H), 7.07 (t, J = 7.6 Hz, 1H), 6.98 (s, 1H), 6.85 (d, J = 2.0 Hz, 1H), 6.75 (d, J = 10.4 Hz, 1H), 6.60 (s, 1H), 3.60 (s, 3H), 3.26 (s, 3H), 3.26-3.20 (m, 1H), 2.06-2.02 (m, 2H), 1.51-1.45 (m, 2H), 1.36 (s, 6H), 1.26 (s, 6H). LCMS: 446.5 [M + H]⁺ |
| 35 | 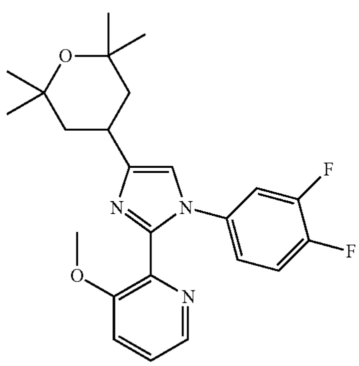 [SMILES: COc1cccnc1-c1nc(C2CC(C)(C)OC(C)(C)C2)cn1-c1ccc(F)c(F)c1] | 2-(1-(3,4-difluorophenyl)-4-(2,2,6,6-tetramethyltetrahydro-2H-pyran-4-yl)-1H-imidazol-2-yl)-3-methoxypyridine | ¹H NMR (400 MHz, DMSO-d₆) δ = 8.18-8.16 (m, 1H), 7.49-7.38 (m, 3H), 7.37-7.28 (m, 2H), 6.87-6.85 (m, 1H), 3.51 (s, 3H), 3.14-3.17 (m, 1H), 1.92 (dd, J = 2.8 Hz, J = 12.8 Hz, 2H), 1.39-1.33 (m, 2H), 1.29 (s, 6H), 1.15 (s, 6H). LCMS: 428.23 [M + H]⁺ |
| 36 | 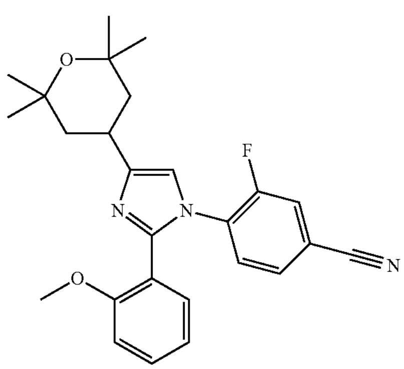 [SMILES: COc1ccccc1-c1nc(C2CC(C)(C)OC(C)(C)C2)cn1-c1ccc(C#N)cc1F] | 3-fluoro-4-(2-(2-methoxyphenyl)-4-(2,2,6,6-tetramethyltetrahydro-2H-pyran-4-yl)-1H-imidazol-1-yl)benzonitrile | ¹H NMR (400 MHz, DMSO-d₆) δ 8.07 (d, J = 10.4 Hz, 1H), 7.66 (d, J = 9.2 Hz, 1H), 7.51 (d, J = 7.2 Hz, 1H), 7.39-7.35 (m, 1H), 7.34-7.27 (m, 2H), 7.06-7.00 (m, 1H), 6.86 (d, J = 8.4 Hz, 1H), 3.22 (s, 3H), 3.16-3.12 (m, 1H), 1.94-1.88 (m, 2H), 1.41-1.33 (m, 2H), 1.29 (s, 6H), 1.15 (s, 6H). LCMS: 434.48 [M + H]⁺ |

TABLE 2-continued

| Cpd No. | Structure | Compound Name | Analytical data |
|---|---|---|---|
| 37 | 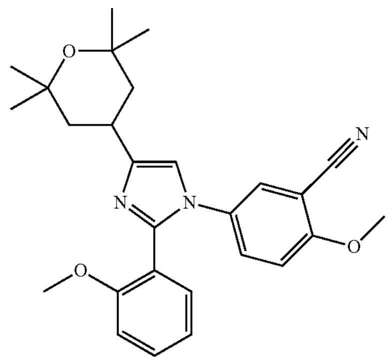 | 2-methoxy-5-(2-(2-methoxyphenyl)-4-(2,2,6,6-tetramethyltetrahydro-2H-pyran-4-yl)-1H-imidazol-1-yl)benzonitrile | $^1$H NMR (400 MHz, DMSO-$d_6$) δ = 7.57 (d, J = 2.4 Hz, 1H), 7.46 (dd, J = 2 Hz, J = 7.6 Hz, 1H), 7.41-7.36 (m, 1H), 7.34-7.31 (m, 1H), 7.26 (s, 1H), 7.18-7.16 (m, 1H), 7.04-6.98 (m, 1H), 6.90-6.88 (m, 1H), 3.88 (s, 3H), 3.28 (s, 3H), 3.11-3.05 (m, 1H), 1.91 (dd, J = 2.8 Hz, J = 12.8 Hz, 2H), 1.38-1.32 (m, 2H), 1.28 (s, 6H), 1.15 (s, 6H). LCMS: 446.30 [M + H]$^+$ |
| 38 | 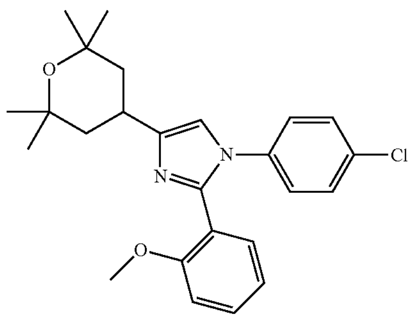 [SMILES: COc1ccccc1-c1nc(C2CC(C)(C)OC(C)(C)C2)cn1-c1ccc(Cl)cc1] | 1-(4-chlorophenyl)-2-(2-methoxyphenyl)-4-(2,2,6,6-tetramethyltetrahydro-2H-pyran-4-yl)-1H-imidazole | $^1$H NMR (CDCl$_3$, 400 MHz) δ 7.55 (d, J = 6.4 Hz, 1H), 7.32 (t, J = 7.2 Hz, 1H), 7.55-7.23 (m, 2H), 7.05-6.98 (m, 3H), 6.91 (s, 1H), 6.71 (d, J = 8.4 Hz, 1H), 3.23 (s, 3H), 3.26-3.20 (m, 1H), 2.06-2.03 (m, 2H), 1.51-1.44 (m, 2H), 1.35 (s, 6H), 1.25 (s, 6H). LCMS: 425.3 [M + H]$^+$ |
| 39 | 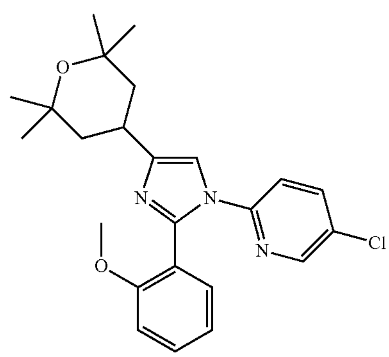 [SMILES: COc1ccccc1-c1nc(C2CC(C)(C)OC(C)(C)C2)cn1-c1ccc(Cl)cn1] | 5-chloro-2-(2-(2-methoxyphenyl)-4-(2,2,6,6-tetramethyltetrahydro-2H-pyran-4-yl)-1H-imidazol-1-yl)pyridine | $^1$H NMR (CDCl$_3$, 400 MHz) δ 8.41 (d, J = 2.4 Hz, 1H), 7.63-7.60 (m, 1H), 7.50-7.47 (m, 1H), 7.39-7.33 (m, 2H), 7.05 (t, 7.6 Hz, 1H), 6.81-6.75 (m, 2H), 3.35 (s, 3H), 3.25-3.19 (m, 1H), 2.06-2.07 (m, 2H), 1.49-1.46 (m, 2H), 1.35 (s, 6H), 1.25 (s, 6H). LCMS: 426.2 [M + H]$^+$ |
| 40 | 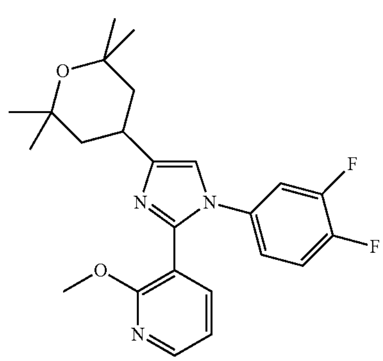 [SMILES: COc1ncccc1-c1nc(C2CC(C)(C)OC(C)(C)C2)cn1-c1ccc(F)c(F)c1] | 3-(1-(3,4-difluorophenyl)-4-(2,2,6,6-tetramethyltetrahydro-2H-pyran-4-yl)-1H-imidazol-2-yl)-2-methoxypyridine | $^1$H NMR (400 MHz, DMSO-$d_6$) δ 8.19 (dd, J = 6.4 Hz, 1.6 Hz, 1H), 7.90 (dd, J = 8.8 Hz, 1.6 Hz 1H), 7.45-7.36 (m, 2H), 7.31 (s, 1H), 7.10-7.07 (m, 1H), 6.93 (d, 8 Hz, 1H), 3.388 (s, 3H), 3.086 (m, 1H), 1.92-1.881 (m, 2H), 1.38-1.318 (m, 2H), 1.139 (s, 6H), 1.127 (s, 6H); LCMS: 428.3 [M + H]$^+$ |

TABLE 2-continued

| Cpd No. | Structure | Compound Name | Analytical data |
|---|---|---|---|
| 41 | 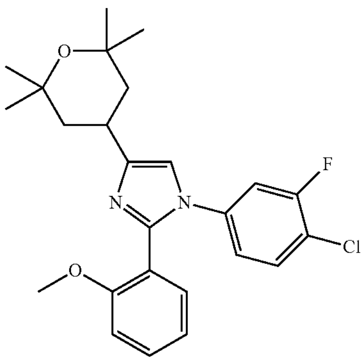 [SMILES: COc1ccccc1-c1nc(C2CC(C)(C)OC(C)(C)C2)cn1-c1ccc(Cl)c(F)c1] | 1-(4-chloro-3-fluorophenyl)-2-(2-methoxyphenyl)-4-(2,2,6,6-tetramethyltetrahydro-2H-pyran-4-yl)-1H-imidazole | $^1$H NMR (CDCl$_3$, 400 MHz) δ 7.56-7.53 (dd, J = 7.2 Hz, 1.2 Hz, 1H), 7.37-7.31 (m, 1H), 7.27 (t, J = 8 Hz, 1H), 7.02 (t, J = 7.6 Hz, 1H), 6.97-6.94 (dd, J = 9.6 Hz, 2.4 Hz, 1H), 6.91 (s, 1H), 6.85 (d, J = 8.4 Hz, 1H), 6.73 (d, J = 8.4 Hz, 1H), 3.37 (s, 3H), 3.23-3.22 (m, 1H), 2.06-2.02 (dd, J = 12.8 Hz, 2.8 Hz, 2H), 1.47 (t, J = 12.8 Hz, 2H), 1.35 (s, 6H), 1.25 (s, 6H). LCMS: 443.2 [M + H]$^+$ |
| 42 | 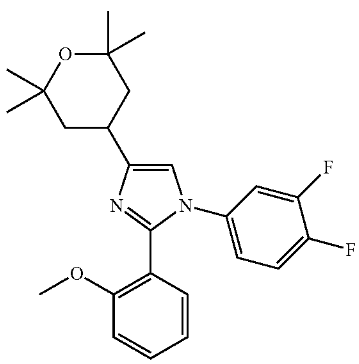 [SMILES: COc1ccccc1-c1nc(C2CC(C)(C)OC(C)(C)C2)cn1-c1ccc(F)c(F)c1] | 1-(3,4-difluorophenyl)-2-(2-methoxyphenyl)-4-(2,2,6,6-tetramethyltetrahydro-2H-pyran-4-yl)-1H-imidazole | $^1$H NMR (400 MHz, DMSO-d$_6$) δ 7.45 (dd, J = 1.6 Hz, 6.0 Hz, 1H), 7.39 (m, 2H), 7.30 (m, 2H), 7.01 (t, J = 2.8 Hz, 1H), 3.07 (m, 1H), 1.90 (dd, J = 3.2 Hz, 10.0 Hz, 2H), 1.34 (t, J = 12.8 Hz, 1H), 1.27 (s, 6H), 1.13 (s, 6H); LCMS: 427.3 [M + H]$^+$ |
| 43 | 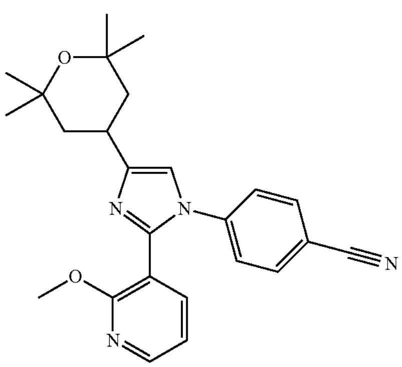 [SMILES: COc1ncccc1-c1nc(C2CC(C)(C)OC(C)(C)C2)cn1-c1ccc(C#N)cc1] | 4-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.21-8.19 (m, 1H), 7.96-7.94 (m, 1H), 7.85 (d, J = 8.8 Hz, 2H), 7.39 (s, 1H), 7.32 (d, J = 8.4 Hz, 2H), 7.12-7.09 (m, 1H), 3.12-3.08 (m, 1H), 1.92-1.88 (m, 2H), 1.39-1.33 (m, 2H), 1.27 (s, 6H), 1.14 (s, 6H). LCMS: 417.3 [M + H]$^+$ |
| 44 | 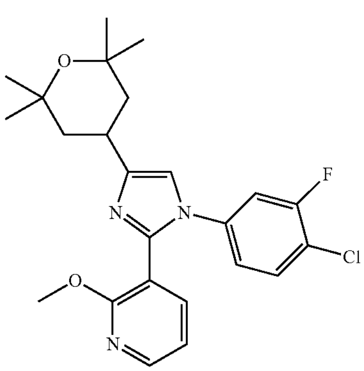 | 3-(1-(4-chloro-3-fluorophenyl)-4-(2,2,6,6-tetramethyltetrahydro-2H-pyran-4-yl)-1H-imidazol-2-yl)-2-methoxypyridine | $^1$H NMR (400 MHz, DMSO-d$_6$) δ 8.20 (m, 1H), 7.91 (dd, J = 8 Hz, 1H), 7.56 (t, J = 8 Hz, 1H), 7.35 (m, 1H), 7.1 (m, 1H), 6.94 (dd, J = 12 Hz, 8 Hz, 1H), 3.30 (s, 3H), 3.0 (m, 1H), 1.91 (dd, J = 4 Hz, 12 Hz, 2H), 1.36 (t, J = 16 Hz, 2H), 1.2 (s, 6H), 1.1 (s, 6H), LCMS: 444.2 [M + H]$^+$ |

TABLE 2-continued

| Cpd No. | Structure | Compound Name | Analytical data |
|---|---|---|---|
| 45 | 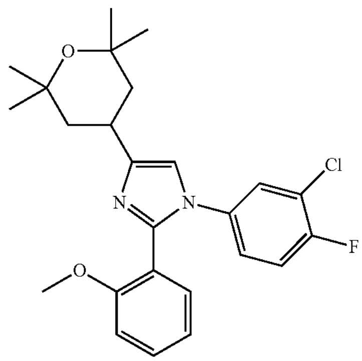 | 1-(3-chloro-4-fluorophenyl)-2-(2-methoxyphenyl)-4-(2,2,6,6-tetramethyltetrahydro-2H-pyran-4-yl)-1H-imidazole | $^1$H NMR (400 MHz, DMSO-d$_6$) δ 7.53 (dd, , J = 8 Hz, 8 Hz, 1H), 7.33 (m, 1H), 7.23 (t, J = 7.6 Hz, 1H), 7.01 (m, 2H), 6.94 (m, 1H), 6.8 (s, 1H), 6.72 (d, J = 12 Hz, 1H), 3.30 (s, 3H), 3.22 (m, 1H), 2.04 (d, J = 7.6 Hz, 2H), 1.46 (t, J = 12 Hz, 2H), 1.35 (s, 6H), 1.25 (s, 6H). LCMS: 443.2 [M + H]$^+$ |
| 46 | 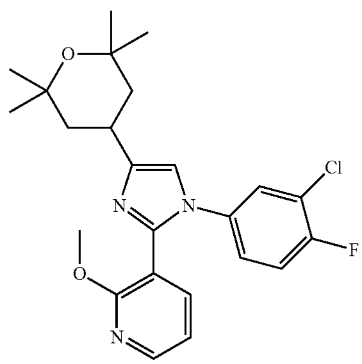 [SMILES: COc1ncccc1-c1nc(C2CC(C)(C)OC(C)(C)C2)cn1-c1ccc(F)c(Cl)c1] | 3-(1-(3-chloro-4-fluorophenyl)-4-(2,2,6,6-tetramethyltetrahydro-2H-pyran-4-yl)-1H-imidazol-2-yl)-2-methoxypyridine | $^1$H NMR (CDCl$_3$, 400 MHz) δ 8.17 (m, 1H), 7.88 (m, 1H), 7.27 (m, 1H), 7.06 (m, 1H), 6.95 (m, 2H), 6.92 (s, 2H), 3.54 (s, J = 12.8 Hz, 3H), 3.219 (m, 1H), 2.02 (m, 2H), 1.46 (m, 2H) 1.35 (s, 6H) 1.25 (s, 6H); LCMS: 444.2 [M + H]$^+$ |
| 47 | 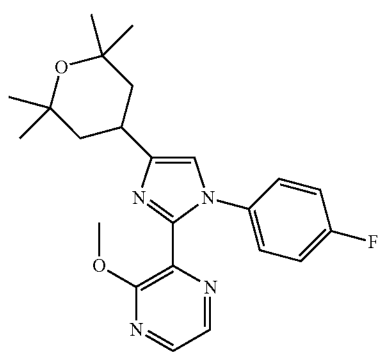 [SMILES: COc1nccnc1-c1nc(C2CC(C)(C)OC(C)(C)C2)cn1-c1ccc(F)cc1] | 2-(1-(4-fluorophenyl)-4-(2,2,6,6-tetramethyltetrahydro-2H-pyran-4-yl)-1H-imidazol-2-yl)-3-methoxypyrazine | $^1$H NMR (CDCl$_3$, 400 MHz) δ 8.20 (d, J = 2.4 Hz, 1H), 8.07 (d, J = 4 Hz, 1H), 7.11 (t, J = 8 Hz, 2H), 7.0 (t, J = 8 Hz, 2H), 6.96 (s, 1H), 3.6 (s, 3H), 2.05 (d, J = 4 Hz, 2H), 1.52 (d, J = 16 Hz, 2H), 1.35 (s, 6H), 1.25 (s, 6H). LCMS: 411.2 [M + H]$^+$ |
| 48 | 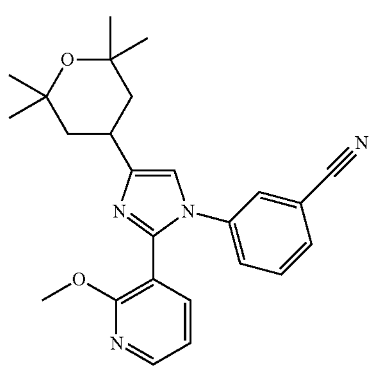 [SMILES: COc1ncccc1-c1nc(C2CC(C)(C)OC(C)(C)C2)cn1-c1cccc(C#N)c1] | 3-(2-(2-methoxypyridin-3-yl)-4-(2,2,6,6-tetramethyltetrahydro-2H-pyran-4-yl)-1H-imidazol-1-yl)benzonitrile | $^1$H NMR (CDCl$_3$, 400 MHz) δ 8.18 (t, J = 2 Hz, 1H), 7.94 (d, J = 7.6 Hz, 1H), 7.58 (d, J = 8 Hz, 1H), 7.44 (t, J = 10.4 Hz, 2H), 7.33 (d, J = 8 Hz, 1H), 7.01-6.96 (m, 2H), 3.44 (s, 3H), 3.23 (t, J = 12.4 Hz, 1H), 2.04-2.01 (dd, J = 12.8 Hz, 2.4 Hz, 2H), 1.48 (t, J = 12.8 Hz, 2H), 1.36 (s, 6H), 1.26 (s, 6H). LCMS: 417.3 [M + H]$^+$ |

TABLE 2-continued

| Cpd No. | Structure | Compound Name | Analytical data |
|---|---|---|---|
| 49 | 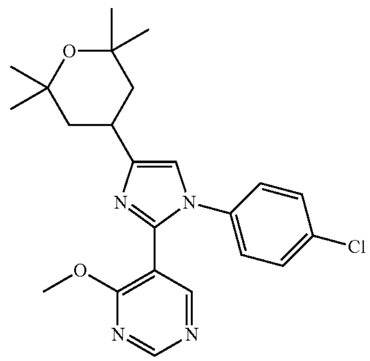 [SMILES: COc1ncncc1-c1nc(C2CC(C)(C)OC(C)(C)C2)cn1-c1ccc(Cl)cc1] | 5-(1-(4-chlorophenyl)-4-(2,2,6,6-tetramethyltetrahydro-2H-pyran-4-yl)-1H-imidazol-2-yl)-4-methoxypyrimidine | $^1$H NMR (CDCl$_3$, 400 MHz) δ 8.75 (s, 1H), 8.71 (s, 1H), 7.32 (d, J = 8 Hz, 2H), 7.06 (d, J = 8.80 Hz, 2H), 6.97 (s, 1H), 3.6 (s, 3H), 3.20-3.26 (m, 1H), 2.0-2.04 (dd, J = 12.8 hz, 3.2 Hz, 2H), 1.48 (t, J = 12.8 Hz, 2H), 1.36 (s, 6H), 1.26 (s, 6H). LCMS: 427.4 [M + H]$^+$ |
| 50 | 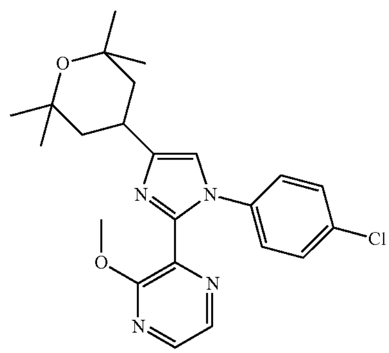 [SMILES: COc1nccnc1-c1nc(C2CC(C)(C)OC(C)(C)C2)cn1-c1ccc(Cl)cc1] | 2-(1-(4-chlorophenyl)-4-(2,2,6,6-tetramethyltetrahydro-2H-pyran-4-yl)-1H-imidazol-2-yl)-3-methoxypyrazine | $^1$H NMR (CDCl$_3$, 400 MHz) δ 8.21 (d, J = 2.8 Hz, 1H), 8.09 (d, J = 2 Hz, 1H), 7.28 (t, J = 8.4 Hz, 2H), 7.06 (d, J = 8.4 Hz, 2H), 6.96 (s, 1H), 3.62 (s, 3H), 3.28 (m, 1H), 2.05 (dd, J = 12.8 Hz, 12.8 Hz, 2H), 1.49 (t, J = 13.2 Hz, 2H), 1.35 (s, 6H), 1.25 (s, 6H). LCMS: 427.2 [M + H]$^+$ |
| 51 | 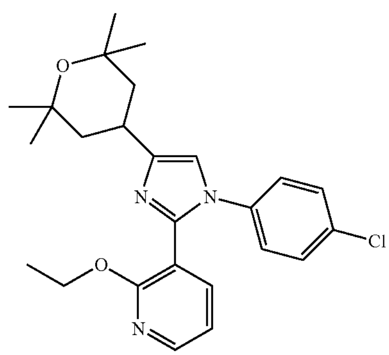 [SMILES: CCOc1ncccc1-c1nc(C2CC(C)(C)OC(C)(C)C2)cn1-c1ccc(Cl)cc1] | 3-(1-(4-chlorophenyl)-4-(2,2,6,6-tetramethyltetrahydro-2H-pyran-4-yl)-1H-imidazol-2-yl)-2-ethoxypyridine | $^1$H NMR (CDCl$_3$, 400 MHz) δ 8.15-8.14 (m, 1H), 7.92-7.91 (m, 1H), 7.29-7.27 (m, 2H), 7.05 (d, J = 8.4 Hz, 2H), 6.96-6.93 (m, 2H), 3.97 (dd, J = 14, 6.8 Hz, 2H), 3.29-3.21 (m, 1H), 2.04-2.01 (m, 2H), 1.51-1.44 (m, 2H), 1.36 (s, 6H), 1.26 (s, 6H), 0.94 (t, J = 6.8 Hz, 3H). LCMS: 440.3 [M + H]$^+$ |
| 52 | 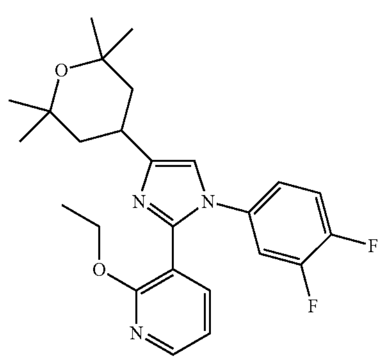 [SMILES: CCOc1ncccc1-c1nc(C2CC(C)(C)OC(C)(C)C2)cn1-c1ccc(F)c(F)c1] | 3-(1-(3,4-difluorophenyl)-4-(2,2,6,6-tetramethyltetrahydro-2H-pyran-4-yl)-1H-imidazol-2-yl)-2-ethoxypyridine | $^1$H NMR (400 MHz, DMSO-d$_6$) δ 8.17 (t, J = 3.2 Hz, 1H), 7.94-7.92 (dd, J = 6.8 Hz, 1.2 Hz, 1H), 7.46-7.35 (m, 2H), 7.32 (s, 1H), 7.09-7.06 (m, 1H), 6.94 (d, J = 8.4 Hz, 1H), 3.90 (q, J = 7.2 Hz, 2H), 3.08 (t, J = 12.4 Hz, 1H), 1.92-1.89 (dd, J = 12.8 hz, 2 Hz, 2H), 1.35 (t, J = 12.8 Hz, 2H), 1.27 (s, 6H), 1.14 (s, 6H), 0.84 (t, J = 7.2 Hz, 3H). LCMS: 442.3 [M + H]$^+$ |

TABLE 2-continued

| Cpd No. | Structure | Compound Name | Analytical data |
|---|---|---|---|
| 53 | 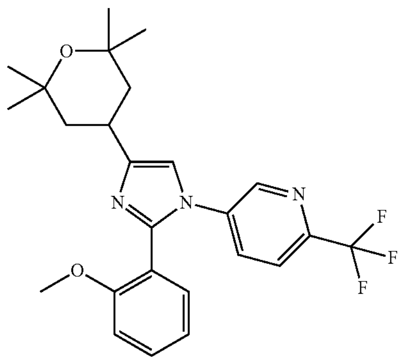 [SMILES: COc1ccccc1-c1nc(C2CC(C)(C)OC(C)(C)C2)cn1-c1ccc(C(F)(F)F)nc1] | 5-(2-(2-methoxyphenyl)-4-(2,2,6,6-tetramethyltetrahydro-2H-pyran-4-yl)-1H-imidazol-1-yl)-2-(trifluoromethyl)pyridine | $^1$H NMR (CDCl$_3$, 400 MHz) δ 8.592 (s, 1H), 7.61 (m, 2H), 7.55 (m, 1H), 7.393-7.354 (m, 1H), 7.260 (s, 1H), 7.07-7.04 (m, 1H), 6.989 (s, 1H), 6.7195 (d, 8.4 Hz, 1H), 3.28 (s, 3H), 3.23 (m, 1H), 2.05 (m, 2H), 1.51 (m, 2H) 1.36 (s, 6H), 1.26 (s, 6H); LCMS: 460.3 [M + H]$^+$ |
| 54 | 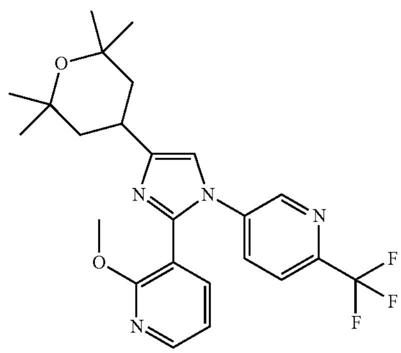 [SMILES: COc1ncccc1-c1nc(C2CC(C)(C)OC(C)(C)C2)cn1-c1ccc(C(F)(F)F)nc1] | 2-methoxy-3-(4-(2,2,6,6-tetramethyltetrahydro-2H-pyran-4-yl)-1-(6-(trifluoromethyl)pyridin-3-yl)-1H-imidazol-2-yl)pyridine | $^1$H NMR (CDCl$_3$, 400 MHz) δ 8.595 (d, 2.4 Hz, 1H), 8.20 (dd J = 6.8 Hz, 1.6 Hz, 1H), 7.99 (dd, J = 9.2 Hz, 2 Hz 1H), 7.66 (m, 1H), 7.55 (m, 1H), 7.01 (m, 2H), 3.435 (s, 3H), 3.24 (m, 1H), 2.03 (m, 2H), 1.5 (m, 2H), 1.369 (s, 6H), 1.270 (s, 6H); LCMS: 461.2 [M + H]$^+$ |
| 55 | 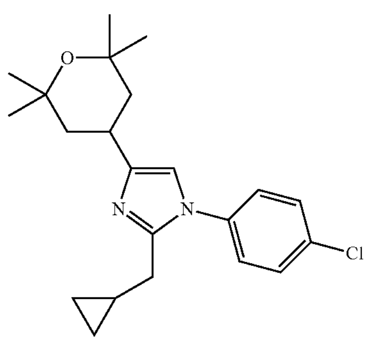 [SMILES: CC1(C)CC(c2cn(-c3ccc(Cl)cc3)c(CC3CC3)n2)CC(C)(C)O1] | 1-(4-chlorophenyl)-2-(cyclopropylmethyl)-4-(2,2,6,6-tetramethyltetrahydro-2H-pyran-4-yl)-1H-imidazole | $^1$H NMR (400 MHz, DMSO-d$_6$) 7.75 (d, J = 8.4 Hz, 2H), 7.42 (d, J = 8.4 Hz, 2H), 6.93 (s, 1H), 2.99 (s, 1H), 2.51 (s, 2H), 1.86-1.82 (dd, J = 12.8 Hz, 2.8 Hz, 2H), 1.31-1.25 (m, 8H), 1.11 (s, 6H), 0.85 (m, 1H), 0.32 (d, J = 6.4 Hz, 2H), −0.047 (d, J = 4.4 Hz, 2H). LCMS: 373.3 [M + H]$^+$ |
| 56 | 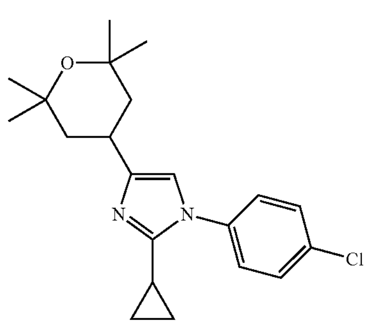 [SMILES: CC1(C)CC(c2cn(-c3ccc(Cl)cc3)c(C3CC3)n2)CC(C)(C)O1] | 1-(4-chlorophenyl)-2-cyclopropyl-4-(2,2,6,6-tetramethyltetrahydro-2H-pyran-4-yl)-1H-imidazole | $^1$H NMR (CDCl$_3$, 400 MHz) δ 7.44 (d, J = 8.8 Hz, 2H), 7.34 (d, J = 8.8 Hz, 2H), 6.67 (s, 1H), 5.29 (s, 1H), 3.0 (m, 1H), 1.93 (dd, J = 12.8 Hz, 13.2 Hz, 2H), 1.34 (m, 1H), 1.70 (m, 1H), 1.25 (m, 1H), 1.33 (s, 6H), 1.22 (s, 6H), 1.05 (m, 2H), 0.87 (m, 2H). LCMS: 359.3 [M + H]$^+$ |

TABLE 2-continued

| Cpd No. | Structure | Compound Name | Analytical data |
|---|---|---|---|
| 57 | 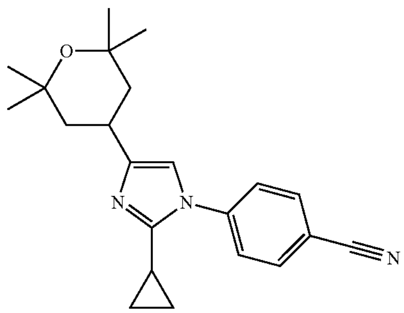 [SMILES: CC1(C)CC(c2cn(-c3ccc(C#N)cc3)c(C3CC3)n2)CC(C)(C)O1] | 4-(2-cyclopropyl-4-(2,2,6,6-tetramethyltetrahydro-2H-pyran-4-yl)-1H-imidazol-1-yl)benzonitrile | $^1$H NMR (400 MHz, DMSO-d$_6$) δ 7.95 (d, J = 8 Hz, 2H), 7.71 (d, J = 7.6 Hz, 2H), 7.08 (s, 1H), 2.94 (t, J = 12.8 Hz, 1H), 1.80 (t, J = 7.2 Hz, 3H), 1.27-1.21 (s, 8H), 1.10 (s, 6H), 0.88-0.85 (m, 4H). LCMS: 350.3 [M + H]$^+$ |
| 58 | 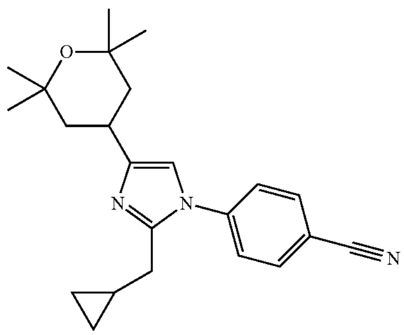 [SMILES: CC1(C)CC(c2cn(-c3ccc(C#N)cc3)c(CC3CC3)n2)CC(C)(C)O1] | 4-(2-(cyclopropylmethyl)-4-(2,2,6,6-tetramethyltetrahydro-2H-pyran-4-yl)-1H-imidazol-1-yl)benzonitrile | $^1$H NMR (400 MHz, DMSO-d$_6$) δ = 7.99-7.99 (2H, d, J = 0.06 Hz), 7.64-7.62 (2H, d, J = 1.44 Hz), 7.08 (1H, s), 3.0 (3H, s), 2.59-2.57 (2H, d, J = 0.96 Hz), 1.87-1.83 (2H, dd, J = 2.4 Hz), 1.31-1.25 (2H, d, J = 3.48 Hz), 1.25 (6 H, s), 1.12 (6H, s). LCMS: 364 [M + H]$^+$ |
| 59 | 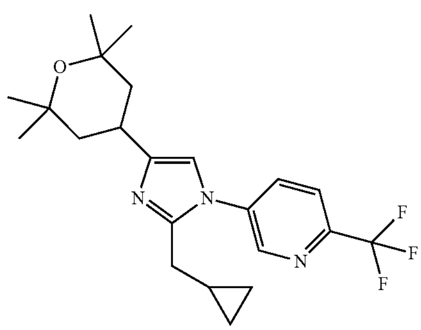 [SMILES: CC1(C)CC(c2cn(-c3ccc(C(F)(F)F)nc3)c(CC3CC3)n2)CC(C)(C)O1] | 5-(2-(cyclopropylmethyl)-4-(2,2,6,6-tetramethyltetrahydro-2H-pyran-4-yl)-1H-imidazol-1-yl)-2-(trifluoromethyl)pyridine | $^1$H NMR (400 MHz, DMSO-d$_6$) δ 8.87 (s, 1H), 8.19 (d, J = 8.4 Hz, 1H), 8.06 (d, J = 8.4 Hz, 1H), 7.15 (s, 1H), 2.61 (t, J = 6.4 Hz, 1H), 2.06 (d, J = 6.4 Hz, 2H), 1.88-1.84 (dd. J = 12.8 Hz, 2.8 Hz, 2H), 1.31 (d, J = 12.8 Hz, 2H), 1.26 (s, 6H), 1.26 (s, 6H), 0.89 (m, 1H), 0.35-0.32 (dd. J = 7.6 Hz, 4.4 Hz, 2H), −0.04-−0.04 (dd. J = 10 Hz, 5.2 Hz, 2H). LCMS: 408.5 [M + H]$^+$ |
| 60 | 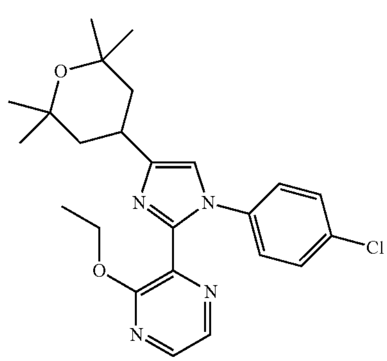 [SMILES: CCOc1nccnc1-c1nc(C2CC(C)(C)OC(C)(C)C2)cn1-c1ccc(Cl)cc1] | 2-(1-(4-chlorophenyl)-4-(2,2,6,6-tetramethyltetrahydro-2H-pyran-4-yl)-1H-imidazol-2-yl)-3-ethoxypyrazine | $^1$H NMR (CDCl$_3$, 400 MHz) δ 8.23 (d, J = 2.4 Hz, 1H), 8.08 (d, J = 2.8 Hz, 1H), 7.29 (d, = 8.8 Hz, 2H), 7.06 (d, J = 8.8 Hz, 2H), 6.96 (s, 1H), 4.08-4.02 (q, J = 7.2 Hz, 2H), 3.31-3.24 (m, 1H), 2.07-2.03 (dd, J = 13.2 Hz, 3.2 Hz, 2H), 1.50 (t, J = 13.6 Hz, 2H), 1.35 (s, 6H), 1.25 (s, 6H), 1.02 (t, J = 6.8 Hz, 3H). LCMS: 441.4 [M + H]$^+$ |

TABLE 2-continued

| Cpd No. | Structure | Compound Name | Analytical data |
|---|---|---|---|
| 61 | 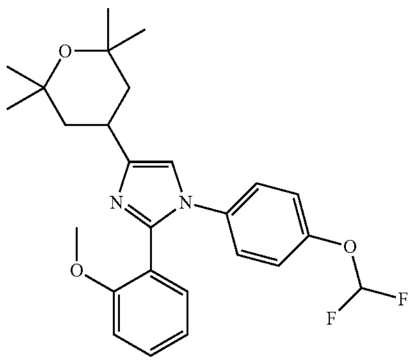 [SMILES: COc1ccccc1-c1nc(C2CC(C)(C)OC(C)(C)C2)cn1-c1ccc(OC(F)F)cc1] | 1-(4-(difluoromethoxy)phenyl)-2-(2-methoxyphenyl)-4-(2,2,6,6-tetramethyltetrahydro-2H-pyran-4-yl)-1H-imidazole | $^1$H NMR (400 MHz, DMSO-d$_6$) δ 7.45-7.43 (dd, J = 7.6 Hz, 1.6 Hz, 1H), 7.38-7.33 (m, 1H), 7.20 (s, 1H), 7.13 (s, 1H), 7.00 (t, J = 5.2 Hz, 1H), 6.86 (d, J = 8.4 Hz, 1H), 3.21 (s, 3H) 3.08 (t, J = 12.8 Hz, 1H), 1.92-1.88 (dd, J = 13.2 Hz, 3.2 Hz, 2H), 1.35 (t, J = 12.8 Hz, 2H), 1.27 (s, 6h), 1.14 (s, 6H). LCMS: 457.6 [M + H]$^+$ |
| 62 | 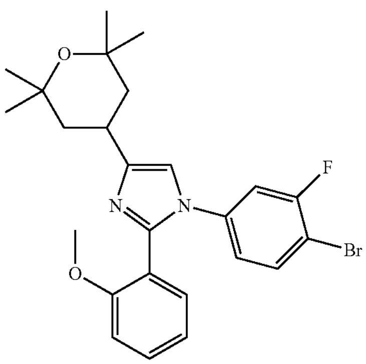 [SMILES: COc1ccccc1-c1nc(C2CC(C)(C)OC(C)(C)C2)cn1-c1ccc(Br)c(F)c1] | 1-(4-bromo-3-fluorophenyl)-2-(2-methoxyphenyl)-4-(2,2,6,6-tetramethyltetrahydro-2H-pyran-4-yl)-1H-imidazole | $^1$H NMR (CDCl$_3$, 400 MHz) δ 7.56-7.53 (dd, J = 7.6 Hz, 2 Hz, 1H), 7.44 (t, J = 8.0 Hz, 1H), 7.37-7.33 (m, 1H), 7.02 (t, J = 7.6 Hz, 1H), 6.94-6.91 (m, 2H), 6.08-6.78 (m, 1H), 6.74 (d, J = 8.4 Hz, 1H), 3.36 (s, 3H), 3.22 (t, J = 12.8 Hz, 1H), 2.02 (d, J = 2.8 Hz, 2H), 1.47 (t, J = 12.8 Hz, 2H), 1.35 (s, 6H), 1.25 (s, 6H). LCMS: 487.2 [M + H]$^+$ |
| 63 | 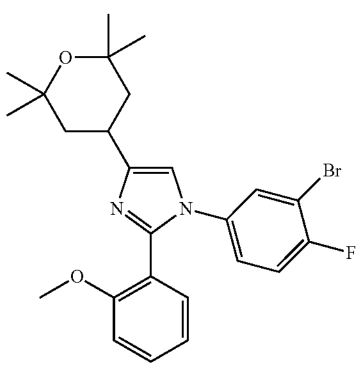 | 1-(3-bromo-4-fluorophenyl)-2-(2-methoxyphenyl)-4-(2,2,6,6-tetramethyltetrahydro-2H-pyran-4-yl)-1H-imidazole | $^1$H NMR (400 MHz, DMSO-d$_6$) δ 7.49-7.51 (dd, J = 5.6 Hz, 2.4 Hz, 1H), 7.45 (d, J = 7.6 Hz, 1H), 7.37 (t, J = 6.8 Hz, 1H), 7.32 (t, J = 8.8 Hz, 1H), 7.27 (s, 1H), 7.06-7.10 (m, 1H), 7.01 (t, J = 7.2 Hz, 1H), 6.88 (d, J = 8.4 Hz, 1H), 3.26 (s, 3H), 3.04-3.10 (m, 1H), 1.88-1.92 (dd, J = 13.2 Hz, 3.2 Hz, 2H), 1.34 (t, J = 12.8 Hz, 2H), 1.27 (s, 6H), 1.14 (s, 6H). LCMS: 487.2 [M + H]$^+$ |
| 64 | 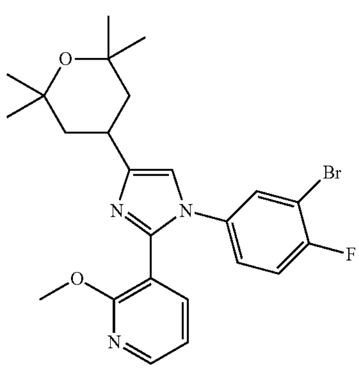 | 3-(1-(3-bromo-4-fluorophenyl)-4-(2,2,6,6-tetramethyltetrahydro-2H-pyran-4-yl)-1H-imidazol-2-yl)-2-methoxypyridine | $^1$H NMR (CDCl$_3$, 400 MHz) δ 8.18-8.16 (dd, J = 4.8 Hz, 2H, 1H), 7.89-7.87 (dd, J = 7.2 Hz, 1.6 Hz, 1H), 7.44-7.42 (dd, J = 6.4 Hz, 2.8 Hz, 1H), 7.06 (m, 3H), 6.92 (s, 1H), 3.53 (s, 3H), 3.25-3.18 (m, 1H), 2.04-2.00 (dd, J = 12.8 Hz, 3.2 Hz, 2H), 1.47 (t, J = 12.8 Hz, 2H), 1.35 (s, 6H), 1.25 (s, 6H). LCMS: 488.2 [M + H]$^+$ |

TABLE 2-continued

| Cpd No. | Structure | Compound Name | Analytical data |
|---|---|---|---|
| 65 | 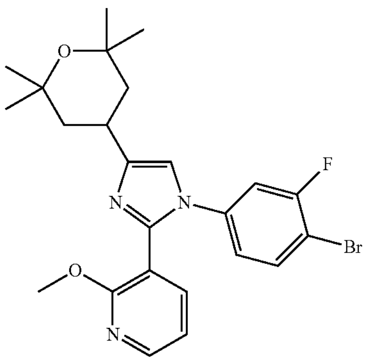 [SMILES: COc1ncccc1-c1nc(C2CC(C)(C)OC(C)(C)C2)cn1-c1ccc(Br)c(F)c1] | 3-(1-(4-bromo-3-fluorophenyl)-4-(2,2,6,6-tetramethyltetrahydro-2H-pyran-4-yl)-1H-imidazol-2-yl)-2-methoxypyridine | $^1$H NMR (CDCl$_3$, 400 MHz) δ 8.19-8.17 (dd, J = 7.2 Hz, 2H, 1H), 7.90-7.88 (dd, J = 7.6 Hz, 1.6 Hz, 1H), 7.51-7.46 (m, 1H), 6.99-6.93 (m, 3H), 6.79 (d, J = 8.4 Hz, 1H), 3.52 (s, 3H), 3.28-3.22 (m, 1H), 2.04-2.00 (dd, J = 12.8 Hz, 2.8 Hz, 2H), 1.54-1.44 (m, 2H), 1.35 (s, 6H), 1.26 (s, 6H). LCMS: 488.2 [M + H]$^+$ |
| 66 | 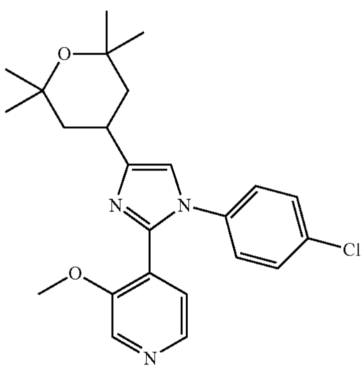 [SMILES: COc1cnccc1-c1nc(C2CC(C)(C)OC(C)(C)C2)cn1-c1ccc(Cl)cc1] | 4-(1-(4-chlorophenyl)-4-(2,2,6,6-tetramethyltetrahydro-2H-pyran-4-yl)-1H-imidazol-2-yl)-3-methoxpyridine | $^1$H NMR (400 MHz, DMSO-d$_6$) δ 8.30 (d, J = 4.8 Hz, 1H), 8.28 (s, 1H), 7.51 (d, J = 4.8 Hz, 1H), 7.44 (d, J = 8.44 Hz, 2H), 7.36 (s, 1H), 7.16 (d, J = 8.8 Hz, 2H), 3.33 (s, 3H), 3.11 (t, J = 13.2 Hz, 1H), 1.92-1.89 (m, 2H), 1.36 (t, J = 12.4 Hz, 2H), 1.28 (s, 6H), 1.15 (s, 6H). LCMS 426.36 [M + H]$^+$ |
| 67 | 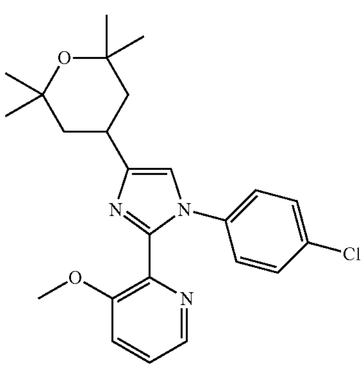 [SMILES: COc1cccnc1-c1nc(C2CC(C)(C)OC(C)(C)C2)cn1-c1ccc(Cl)cc1] | 2-(1-(4-chlorophenyl)-4-(2,2,6,6-tetramethyltetrahydro-2H-pyran-4-yl)-1H-imidazol-2-yl)-3-methoxypyridine | $^1$H NMR (400 MHz, DMSO-d$_6$) δ 8.16 (d, J = 3.2 Hz, 1H), 7.45-7.37 (m, 4H), 7.30 (s, 1H), 7.09 (d, J = 8.4 Hz, 2H), 3.47 (s, 3H), 1.93-1.89 (m, 2H), 1.40-1.33 (m, 2H), 1.29 (s, 6H), 1.15 (s, 6H). LCMS 426.36 [M + H]$^+$ |
| 68 | 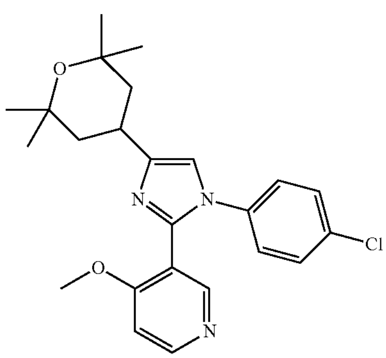 [SMILES: COc1ccncc1-c1nc(C2CC(C)(C)OC(C)(C)C2)cn1-c1ccc(Cl)cc1] | 3-(1-(4-chlorophenyl)-4-(2,2,6,6-tetramethyltetrahydro-2H-pyran-4-yl)-1H-imidazol-2-yl)-4-methoxypyridine | $^1$H NMR (400 MHz, DMSO-d$_6$) δ 8.50 (s, 1H), 8.66 (d, J = 5.6 Hz, 1H), 7.43 (d, J = 8.8 Hz, 2H), 7.33 (s, 1H), 7.17 (d, J = 6.0 Hz, 1H), 3.36 (s, 3H), 3.14-3.08 (m, 1H), 1.94-1.89 (m, 2H), 1.4-1.33 (m, 2H), 1.29 (s, 6H), 1.15 (s, 6H). LCMS 426.36 [M + H]$^+$ |

TABLE 2-continued

| Cpd No. | Structure | Compound Name | Analytical data |
|---|---|---|---|
| 69 | 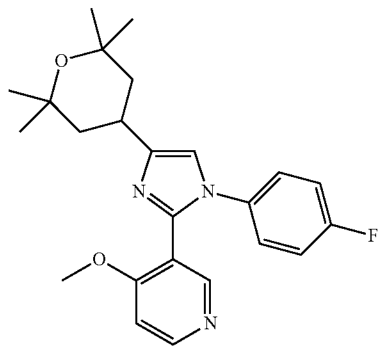 [SMILES: COc1ccncc1-c1nc(C2CC(C)(C)OC(C)(C)C2)cn1-c1ccc(F)cc1] | 3-(1-(4-fluorophenyl)-4-(2,2,6,6-tetramethyltetrahydro-2H-pyran-4-yl)-1H-imidazol-2-yl)-4-methoxypyridine | $^1$H NMR (400 MHz, DMSO-d$_6$) δ 8.49 (s, 1H), 8.53 (d, J = 5.6 Hz, 1H), 7.3 (s, 1H), 7.20 (d, J = 6.0 Hz, 4H), 6.95 (d, J = 5.2 Hz, 1H), 3.37 (s, 3H), 3.11-3.08 (m, 1H), 1.93-1.85 (m, 2H), 1.40-1.37 (m, 2H), 1.29 (s, 6H), 1.15 (s, 6H). LCMS 410.23 [M + H]$^+$ |
| 70 | 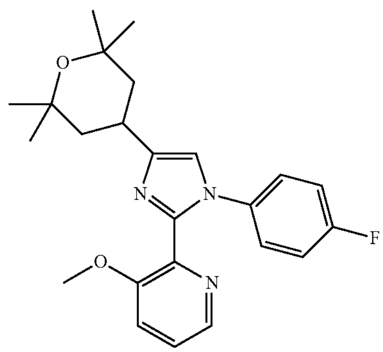 [SMILES: COc1cccnc1-c1nc(C2CC(C)(C)OC(C)(C)C2)cn1-c1ccc(F)cc1] | 2-(1-(4-fluorophenyl)-4-(2,2,6,6-tetramethyltetrahydro-2H-pyran-4-yl)-1H-imidazol-2-yl)-3-methoxypyridine | $^1$H NMR (400 MHz, DMSO-d$_6$) δ 8.12-8.16 (m, 1H), 7.44-7.38 (m, 1H), 7.26 (s, 1H), 7.19-7.09 (m, 4H), 3.47 (s, 3H), 3.14-3.07 (m, 1H), 1.94-1.91 (m, 2H), 1.40-1.37 (m, 2H), 1.34 (s, 6H), 1.15 (s, 6H). LCMS 410.47 [M + H]$^+$ |
| 71 | 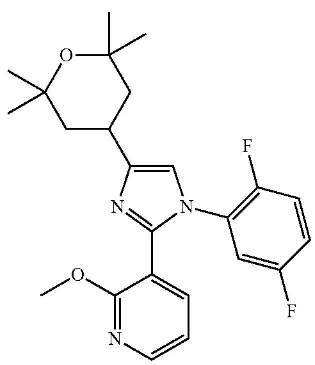 [SMILES: COc1ncccc1-c1nc(C2CC(C)(C)OC(C)(C)C2)cn1-c1cc(F)ccc1F] | 3-(1-(2,5-difluorophenyl)-4-(2,2,6,6-tetramethyltetrahydro-pyran-4-yl)-1H-imidazol-2-yl)-2-methoxypyridine | $^1$H NMR (400 MHz, DMSO-d$_6$) δ 8.18 (d, J = 3.2 Hz, 1H), 7.91 (d, J = 5.6 Hz, 1H), 7.43-7.40 (m, 1H), 7.29 (br s, 2H), 7.26-7.22 (m, 1H), 7.10-7.07 (m, 1H), 3.40 (s, 3H), 3.12 (m, 1H), 1.91 (d, J = 12.8 1H), 1.36 (dd, J = 12.8 & 12.8 Hz, 1H), 1.29 (s, 6H), 1.15 (s, 6H). LCMS: 428.62 [M + H]$^+$ |
| 72 | 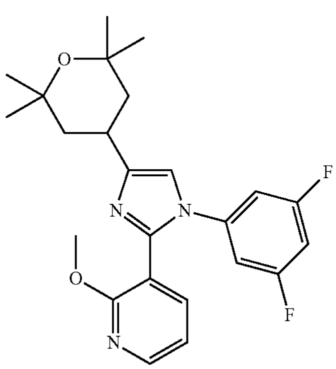 [SMILES: COc1ncccc1-c1nc(C2CC(C)(C)OC(C)(C)C2)cn1-c1cc(F)cc(F)c1] | 3-(1-(3,5-difluorophenyl)-4-(2,2,6,6-tetramethyltetrahydro-2H-pyran-4-yl)-1H-imidazol-2-yl)-2-methoxypyridine | $^1$H NMR (400 MHz, DMSO-d$_6$) δ 8.20 (dd, J = 1.6 & 5.2 Hz, 1H), 7.91 (dd, J = 1.6 & 5.6 Hz, 1H), 6.99 (dd, J = 5.2 & 7.2 Hz, 1H), 6.95 (s, 1H), 6.75 (dd, J = 8.4 & 8.4 Hz, 1H), 6.68 (d, J = 5.6 Hz, 2H), 3.50 (s, 3H), 3.21 (m, 1H), 2.02-2.00 (m, 2H), 1.50-1.43 (m, 2H), 1.35 (s, 6H), 1.20 (s, 6H). LCMS 428.51 [M + H]$^+$ |

TABLE 2-continued

| Cpd No. | Structure | Compound Name | Analytical data |
|---|---|---|---|
| 73 | 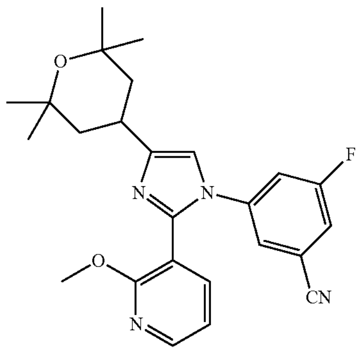 [SMILES: COc1ncccc1-c1nc(C2CC(C)(C)OC(C)(C)C2)cn1-c1cc(F)cc(C#N)c1] | 3-fluoro-5-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-$d_6$) δ 8.22 (dd, J = 1.6 & 5.2 Hz, 1H), 7.96 (dd, J = 1.6 & 5.6 Hz, 1H), 7.31 (d, J = 7.2 Hz, 1H), 7.23 (d, J = 4.4 Hz, 1H), 7.12 (d, J = 9.2 Hz, 1H), 7.02 (dd, J = 5.2 & 7.2 Hz, 1H), 6.96 (s, 1H), 3.50 (s, 3H), 3.22 (m, 1H), 2.02 (dd, J = 2.8 & 13.2 Hz, 2H), 1.50-1.43 (m, 2H), 1.36 (s, 6H), 1.20 (s, 6H). LCMS 435.36 [M + H]$^+$ |
| 75 | 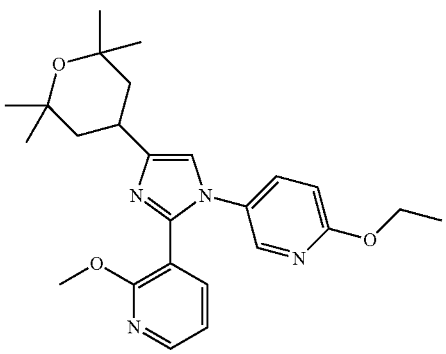 [SMILES: CCOc1ccc(-n2cc(C3CC(C)(C)OC(C)(C)C3)nc2-c2cccnc2OC)cn1] | 3-(1-(6-ethoxypyridin-3-yl)-4-(2,2,6,6-tetramethyltetrahydro-2H-pyran-4-yl)-1H-imidazol-2-yl)-2-methoxypyridine | $^1$H NMR (400 MHz, DMSO-$d_6$) δ 8.18-8.19 (m, 1H), 7.94 (d, J = 2.8 Hz, 1H), 7.88-7.91 (m, 1H), 7.51-7.54 (m, 1H), 7.27 (s, 1H), 7.07-7.10 (m, 1H), 6.79 (d, J = 9.2 Hz, 1H), 4.23-4.28 (q, 2H), 3.42 (s, 3H), 3.10 (t, J = 13.2 Hz, 1H), 1.89-1.93 (m, 2H), 1.36-1.39 (m, 2H), 1.28-1.33 (m, 9H), 1.15 (m, 6H) LCMS 437.5 [M + H]$^+$ |
| 121 | 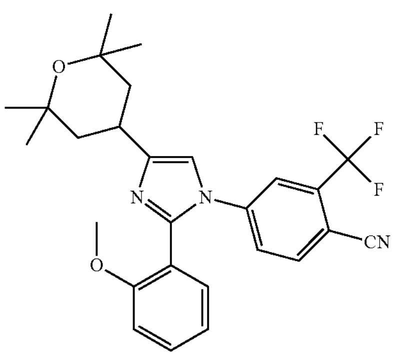 | 4-(2-(2-methoxyphenyl)-4-(2,2,6,6-tetramethyltetrahydro-2H-pyran-4-yl)-1H-imidazol-1-yl)-2-(trifluoromethyl)benzonitrile | $^1$H NMR (400 MHz, DMSO-$d_6$) δ 8.13 (d, J = 8.4 Hz, 1H), 7.69 (s, 1H), 7.53-7.58 (m, 3H), 7.42 (t, J = 7.6 Hz, 1H), 7.07 (t, J = 7.6 Hz, 1H), 6.88 (d, J = 8.4 Hz, 1H), 3.16 (s, 3H), 3.09-3.13 (m, 1H), 1.90-1.94 (m, 2H), 1.32-1.39 (m, 2H), 1.28 (s, 6H), 1.14 (s, 6H). LCMS 453.2 [M + H]$^+$ |
| 123 | 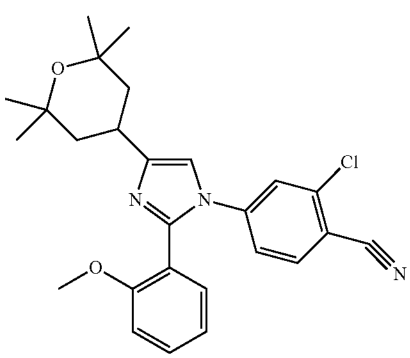 [SMILES: COc1ccccc1-c1nc(C2CC(C)(C)OC(C)(C)C2)cn1-c1ccc(C#N)c(Cl)c1] | 2-chloro-4-(2-(2-methoxyphenyl)-4-(2,2,6,6-tetramethyltetrahydro-2H-pyran-4-yl)-1H-imidazol-1-yl)benzonitrile | $^1$H NMR (DMSO-$d_6$, 400 MHz) δ 7.59 (d, J = 7.6 Hz, 1H), 7.55 (d, J = 7.6 Hz, 1H), 7.39 (t, J = 6.4 Hz, 1H), 7.34 (d, J = 2.0 Hz, 1H), 7.08-7.05 (m, 2H), 6.96 (s, 1H), 6.75 (d, J = 8.4 Hz, 1H), 3.34 (s, 3H), 3.22 (m, 1H), 2.03 (dd, J = 2.4 & 12.8 Hz, 2H), 1.50-1.40 (m, 2H), 1.35 (s, 6H), 1.26 (s, 6H). LCMS 450.50 [M + H]$^+$ |

TABLE 2-continued

| Cpd No. | Structure | Compound Name | Analytical data |
|---|---|---|---|
| 124* | 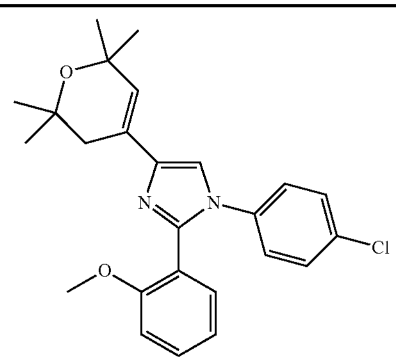 | 1-(4-chlorophenyl)-2-(2-methoxyphenyl)-4-(2,2,6,6-tetramethyl-3,6-dihydro-2H-pyran-4-yl)-1H-imidazole | $^1$H NMR (400 MHz, CDCl$_3$) δ 7.62-7.60 (dd, J = 7.6, 1.6 Hz, 1H), 7.36-7.32 (m, 1H), 7.26-7.24 (m, 2H), 7.10 (s, 1H), 7.06-7.00 (m, 3H), 6.71 (d, J = 8.4 Hz, 1H), 6.53 (s, 1H), 3.33 (s, 3H), 2.31 (s, 2H), 1.33 (d, J = 6.0 Hz, 12H). LCMS 423.2 [M + H]$^+$ |
| 125* | 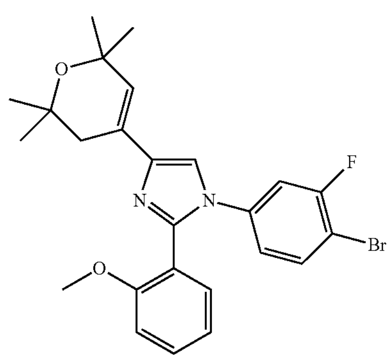 [SMILES: COc1ccccc1-c1nc(C2=CC(C)(C)OC(C)(C)C2)cn1-c1ccc(Br)c(F)c1] | 1-(4-bromo-3-fluorophenyl)-2-(2-methoxyphenyl)-4-(2,2,6,6-tetramethyl-3,6-dihydro-2H-pyran-4-yl)-1H-imidazole | $^1$H NMR: (400 MHz, DMSO-d$_6$) δ 7.66 (t, J = 8.4 Hz, 1H), 7.58 (s, 1H), 7.51-7.49 (m, 1H), 7.43-7.39 (m, 1H), 7.26-7.23 (dd, J = 10 Hz, 2 Hz, 1H), 7.04 (t, J = 7.6 Hz, 1H), 6.93-6.87 (m, 2H), 6.33 (s, 1H), 3.28 (d, J = 10 Hz, 3H), 2.24 (s, 2H), 1.22 (d, J = 6.8 Hz, 12H) LCMS 485.2 [M + H]$^+$ |

Compounds 124 and 125 were side products obtained while synthesizing compound 38 and 62 respectively

Example 8

Compound 74: 2-Fluoro-5-[2-(2-methoxy-phenyl)-4-(2,2,6,6-tetramethyl-tetrahydro-pyran-4-yl)-imidazol-1-yl]-benzonitrile

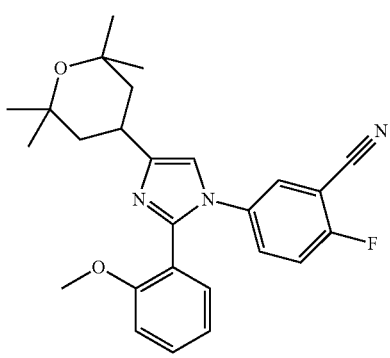 [SMILES: COc1ccccc1-c1nc(C2CC(C)(C)OC(C)(C)C2)cn1-c1ccc(F)c(C#N)c1]

To a solution of (3-bromo-4-fluoro-phenyl)-2-(2-methoxy-phenyl)-4-(2,2,6,6-tetramethyl-tetrahydro-pyran-4-yl)-1H-imidazole 63 (0.17 g, 0.00034 mol) in DMF (10 mL) was added Zn(CN)$_2$ (0.08 g, 0.00068 mol) under N$_2$. The reaction mixture was further purged with N$_2$ for 30 min and then stirred for 1 h at 160° C. The reaction was then quenched with ice cold water and extracted with ethyl acetate (50 mL×3). The combined organic extracts were washed with brine, dried over anhydrous Na$_2$SO$_4$, filtered, and concentrated under reduced pressure to provide a residue. Purification by column chromatography on silica gel (100-200 mesh) using ethyl acetate in hexane afforded the title compound 74 as a pale yellow solid. Yield: 0.11 g (72.8%). $^1$H NMR (CDCl$_3$, 400 MHz) δ 7.54-7.57 (dd, J=5.2 Hz, 2.8 Hz, 1H), 7.41-7.43 (dd, J=5.2 Hz, 2.8 Hz, 1H), 7.31-7.38 (m, 2H), 7.13 (t, J=8.4 Hz, 1H), 7.04 (t, J=7.6 Hz, 1H), 6.90 (s, 1H), 6.73 (d, J=8.4 Hz, 1H), 3.38 (s, 3H), 3.23 (m, 1H), 2.01-2.05 (dd, J=12.8 Hz, 3.2 Hz, 2H), 1.43-1.50 (m, 2H), 1.36 (s, 6H), 1.26 (s, 6H). LCMS: 487.2 [M+H]$^+$.

Using analogous protocols to those described in Example 8, the compounds described in Table 3 have been prepared using and appropriately substituted bromide intermediate.

TABLE 3

| Cpd No. | Structure | Compound name | Analytical data |
|---|---|---|---|
| 76 | 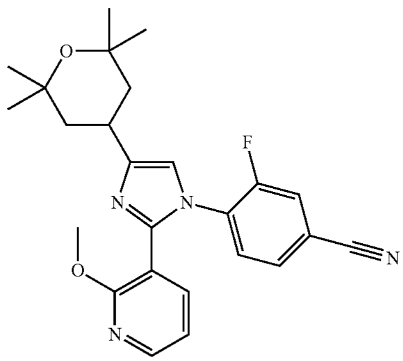 [SMILES: COc1ncccc1-c1nc(C2CC(C)(C)OC(C)(C)C2)cn1-c1ccc(C#N)cc1F] | 3-fluoro-4-(2-(2-methoxypyridin-3-yl)-4-(2,2,6,6-tetramethyltetrahydro-2H-pyran-4-yl)-1H-imidazol-1-yl)benzonitrile | $^1$H NMR (CDCl$_3$, 400 MHz) δ 8.16 (dd, J = 4.8 Hz, 4.8 Hz, 2H), 7.96 (dd, J = 1.6 Hz, 7.6 Hz, 1H), 7.49 (d, J = 4 Hz, 1H), 7.38 (d, J = 8 Hz, 1H), 7.17 (t, J = 8 Hz, 1H), 6.9 (m, 2H), 3.4 (s, 3H), 3.2 (m, 1H), 2.02 (dd, J = 12 Hz, 9.6 Hz, 2H), 1.48 (t, J = 12 Hz, 2H), 1.36 (s, 6H), 1.26 (s, 6H). LCMS: 435.3 [M + H]$^+$ |
| 77 | 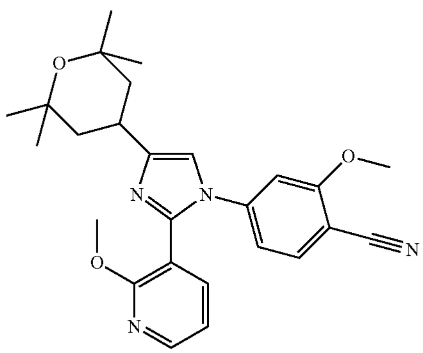 [SMILES: COc1cc(-n2cc(C3CC(C)(C)OC(C)(C)C3)nc2-c2cccnc2OC)ccc1C#N] | 2-methoxy-4-(2-(2-methoxypyridin-3-yl)-4-(2,2,6,6-tetramethyltetrahydro-2H-pyran-4-yl)-1H-imidazol-1-yl)benzonitrile | $^1$H NMR (CDCl$_3$, 400 MHz) δ 8.2 (d, J = 1.6 Hz, 1H), 7.92 (d, J = 6.8 Hz, 1H), 7.52 (d, J = 8.4 Hz, 1H), 6.99 (s, 2H), 6.81 (d, J = 1.6 Hz, 1H), 6.65 (s, 1H), 3.70 (m, 2H), 3.4 (s, 3H), 3.23 (m, 1H), 2.02 (d, J = 10.4 Hz, 2H), 1.48 (t, J = 12.8 Hz, 2H), 1.36 (s, 6H), 1.26 (s, 6H). LCMS: 447.3 [M + H]$^+$ |
| 78 | 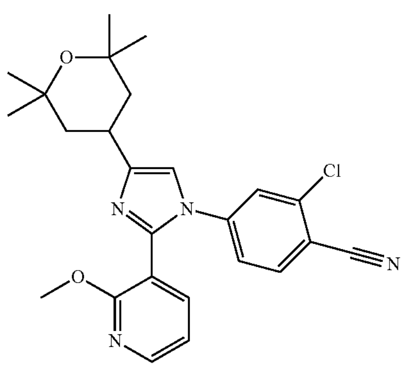 [SMILES: COc1ncccc1-c1nc(C2CC(C)(C)OC(C)(C)C2)cn1-c1ccc(C#N)c(Cl)c1] | 2-chloro-4-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) 8.23-8.22 (dd, J = 4.8 Hz, 1.6 Hz, 1H), 7.98-7.94 (m, J = 2.6 Hz, 1H), 7.48 (s, 1H), 7.25-7.12 (dd, J = 8.4 Hz, 2.4 Hz, 1H), 7.14-7.11 (dd, J = 6.8 Hz, 4.8 Hz, 1H), 3.34 (s, 3H) 3.08 (m, 1H), 1.93-1.89 (dd, J = 12.8 Hz, 2.8 Hz, 2H), 1.35 (t, J = 12.8 Hz, 2H), 1.27 (s, 6H). LCMS: 451.2 [M + H]$^+$ |
| 79 | 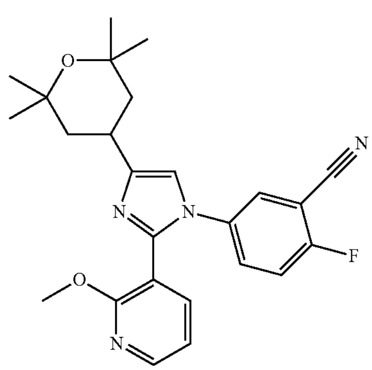 [SMILES: COc1ncccc1-c1nc(C2CC(C)(C)OC(C)(C)C2)cn1-c1ccc(F)c(C#N)c1] | 2-fluoro-5-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.19 (d, J = 4.8 Hz, 1H), 7.91 (t, J = 6 Hz, 1H), 7.45-7.43 (m, 1H), 7.36-7.32 (m, 1H), 7.18 (t, J = 8.4 Hz, 1H), 7.01-6.98 (m, 1H), 6.92 (s, 1H), 3.52 (s, 3H), 3.22 (bs, 1H), 2.03-1.99 (m, 2H), 1.47 (t, J = 12.8 Hz, 3H), 1.36 (s, 6H), 1.26 (s, 6H). LCMS: 435.3 [M + H]$^+$ |

TABLE 3-continued

| Cpd No. | Structure | Compound name | Analytical data |
|---|---|---|---|
| 80 | 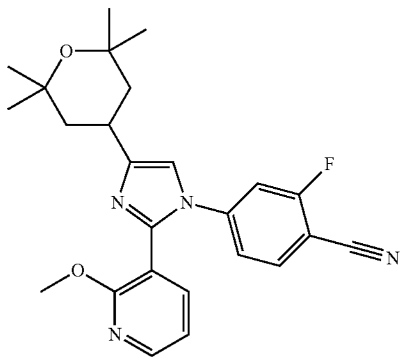 [SMILES: COc1ncccc1-c1nc(C2CC(C)(C)OC(C)(C)C2)cn1-c1ccc(C#N)c(F)c1] | 2-fluoro-4-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.22-8.21 (dd, J = 4.8 Hz, 1.6 Hz, 1H), 7.96-7.94 (dd, J = 7.6 Hz, 2 Hz, 1H), 7.58 (t, J = 8 Hz, 1H), 7.04-6.97 (m, 4H), 3.49 (s, 3H), 3.25-3.18 (m, 1H), 2.03-1.99 (dd, J = 13.2 Hz, 3.2 Hz, 2H), 1.47 (t, J = 12.8 Hz, 2H), 1.36 (s, 6H), 1.26 (s, 7H). LCMS: 435 [M + H]$^+$ |
| 81 | 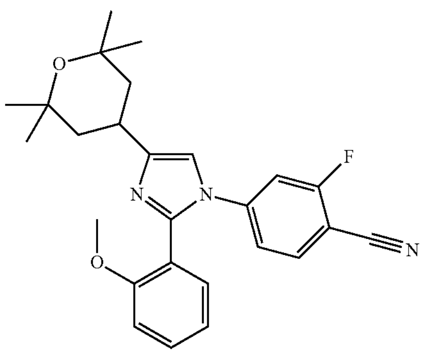 [SMILES: COc1ccccc1-c1nc(C2CC(C)(C)OC(C)(C)C2)cn1-c1ccc(C#N)c(F)c1] | 2-fluoro-4-(2-(2-methoxyphenyl)-4-(2,2,6,6-tetramethyltetrahydro-2H-pyran-4-yl)-1H-imidazol-1-yl)benzonitrile | $^1$H NMR (400 MHz, DMSO-d$_6$) δ 7.06-7.58 (dd, J = 7.2 Hz, 1.6 Hz, 1H), 7.53 (t, J = 8 Hz, 1H), 7.41-7.37 (m, 1H), 7.067 (t, J = 7.6 Hz, 1H), 7.00 (d, J = 8.4 Hz, 2H), 6.95 (s, 1H), 6.75 (d, J = 8.4 Hz, 1H), 3.34 (s, 3H), 3.26-3.19 (m, 1H), 2.05-2.01 (dd, J = 13.6 Hz, 3.2 Hz, 2H), 1.47 (t, J = 12.8 Hz, 2H), 1.35 (s, 6H), 1.25 (s, 6H). LCMS: 434.3 [M + H]$^+$ |
| 82 | 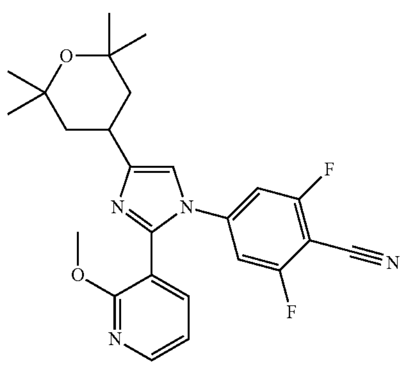 [SMILES: COc1ncccc1-c1nc(C2CC(C)(C)OC(C)(C)C2)cn1-c1cc(F)c(C#N)c(F)c1] | 2,6-difluoro-4-(2-(2-methoxypyridin-3-yl)-4-(2,2,6,6-tetramethyltetrahydro-2H-pyran-4-yl)-1H-imidazol-1-yl)benzonitrile | $^1$H NMR (CDCl$_3$, 400 MHz) δ 8.25 (d, J = 3.6 Hz, 1H), 7.96 (d, J = 5.6 Hz, 1H), 7.05-7.03 (m, 1H), 6.96 (s, 1H), 6.84 (d, J = 8.0 Hz, 2H), 3.56 (s, 3H), 3.24-3.18 (m, 1H), 2.02-1.981 (m, 2H), 1.46 (t, J = 12.8 Hz, 2H), 1.35 (s, 6H), 1.26 (s, 6H). LCMS: 453.3 [M + H]$^+$ |
| 83 | 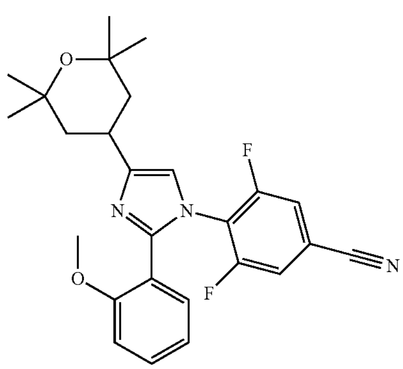 [SMILES: COc1ccccc1-c1nc(C2CC(C)(C)OC(C)(C)C2)cn1-c1c(F)cc(C#N)cc1F] | 3,5-difluoro-4-(2-(2-methoxyphenyl)-4-(2,2,6,6-tetramethyltetrahydro-2H-pyran-4-yl)-1H-imidazol-1-yl)benzonitrile | $^1$H NMR (400 MHz, DMSO-d$_6$) δ ppm 7.93 (d, J = 7.6 Hz, 2H), 7.45 (d, J = 7.2 Hz, 1H), 7.35 (t, J = 7.2 Hz, 1H), 7.26 (s, 1H), 7.00 (t, J = 7.6 Hz, 1H), 6.86 (d, J = 8.4 Hz, 1H), 3.31 (s, 3H), 1.91 (d, J = 12.8 Hz, 2H), 1.36 (d, J = 12.8 Hz, 2H), 1.28 (s, 6H), 1.14 (s, 6H); LCMS: 452.3 [M + H]$^+$ |

TABLE 3-continued

| Cpd No. | Structure | Compound name | Analytical data |
|---|---|---|---|
| 84 | 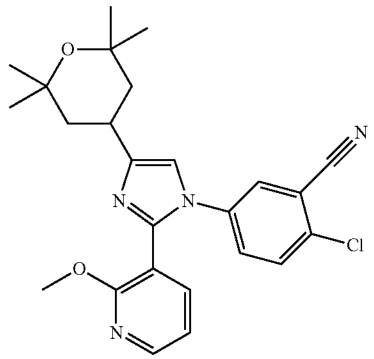 | 2-chloro-5-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.21 (dd, J = 1.2 Hz, 5.2 Hz, 1H), 7.94 (dd, J = 8.8 Hz, 9.6 Hz, 2H), 7.71 (d, J = 8.8 Hz, 1H), 7.41 (m, 2H), 7.12 (m, 1H), 3.35 (s, 3H), 3.12 (m, 1H), 1.89 (d, J = 2.8 Hz, 2H), 1.34 (m, 2H), 1.27 (s, 6H), 1.14 (s, 6H). LCMS: 452.1 [M + H]$^+$ |
| 85 | 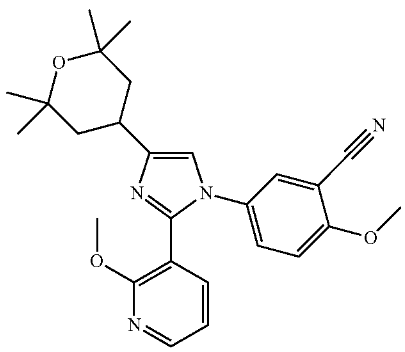 | 2-methoxy-5-(2-(2-methoxypyridin-3-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.19-8.17 (dd, J = 4.8 Hz, J2 = 1.6 Hz, 1H), 7.93-7.88 (m, 1H), 7.63 (d, J = 2.4 Hz, 1H), 7.37-7.34 (dd, J = 8.8 Hz, 2.8 Hz, 1H), 7.29 (s, 1H), 7.18 (d, J = 9.2 Hz, 1H), 7.09-7.06 (m, 1H), 3.88 (s, 3H), 3.39 (s, 3H), 3.08 (t, J = 12.8 Hz, 1H), 1.92-1.88 (dd, J = 12.8 Hz, 2.8 Hz, 2H), 1.34 (t, J = 12.8 Hz, 2H), 1.27 (s, 6H), 1.14 (s, 6H). LCMS: 447.3 [M + H]$^+$ |
| 86 | 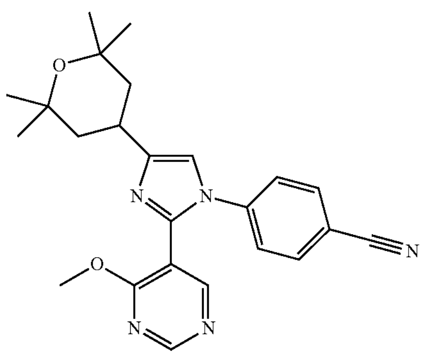 [SMILES: COc1ncncc1-c1nc(C2CC(C)(C)OC(C)(C)C2)cn1-c1ccc(C#N)cc1] | 4-(2-(4-methoxypyrimidin-5-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.81 (s, 1H), 8.74 (s, 1H), 7.87 (d, J = 8.4 Hz, 2H), 7.48 (s, 1H), 7.41 (d, J = 8.4 Hz, 2H), 3.40 (s, 3H), 3.09-3.15 (m, 1H), 1.89-1.93 (dd, J = 12.8 Hz, 2.4 Hz, 2H), 1.36 (t, J = 12.8 Hz, 2H), 1.27 (s, 6H), 1.14 (s, 6H). LCMS: 418.3 [M + H]$^+$ |
| 87 | 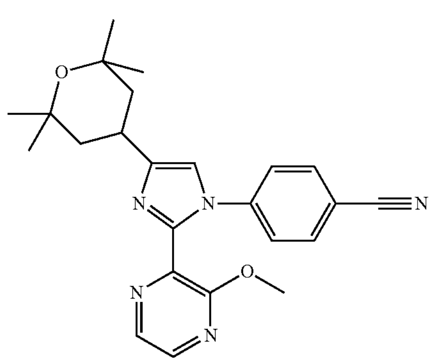 [SMILES: COc1nccnc1-c1nc(C2CC(C)(C)OC(C)(C)C2)cn1-c1ccc(C#N)cc1] | 4-(2-(3-methoxypyridazin-2-yl)-4-(2,2,6,6-tetramethyltetrahydro-2H-pyran-4-yl)-1H-imidazol-1-yl)benzonitrile | $^1$H NMR (400 MHz, DMSO-d$_6$) δ 8.27-8.22 (dd, J = 18 Hz, 2.8 Hz, 2H), 7.84 (d, J = 8.4 Hz, 2H), 7.48 (s, 1H), 7.30 (d, J = 8.8 Hz, 2H), 3.59 (s, 3H), 3.13 (t, J = 12.4 Hz, 1H), 1.93-1.89 (dd, J = 13.6 Hz, 3.2 Hz, 2H), 1.40-1.31 (m, 2H), 1.28 (s, 6H), 1.23 (t, J = 4 Hz, 1H), 1.14 (s, 6H). LCMS: 418.3 [M + H]$^+$ |

TABLE 3-continued

| Cpd No. | Structure | Compound name | Analytical data |
|---|---|---|---|
| 88 | 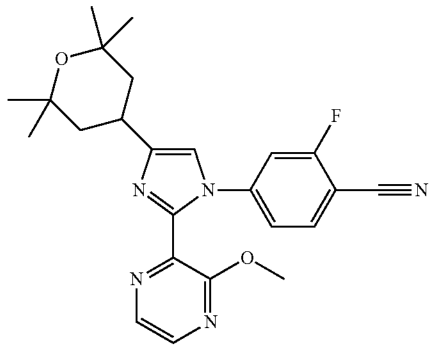 [SMILES: COc1nccnc1-c1nc(C2CC(C)(C)OC(C)(C)C2)cn1-c1ccc(C#N)c(F)c1] | 2-fluoro-4-(2-(3-methoxypyrazin-2-yl)-4-(2,2,6,6-tetramethyltetrahydro-2H-pyran-4-yl)-1H-imidazol-1-yl)benzonitrile | ¹H NMR (CDCl₃, 400 MHz) δ 8.20 (d, J = 2.4 Hz, 1H), 8.13 (d, J = 2.0 Hz, 1H), 7.59 (t, J = 7.2 Hz, 1H), 7.03 (q, J = 10 Hz, 3H), 3.72 (s, 3H), 3.28 (t, J = 12.8 Hz, 1H), 2.05-2.02 (m, 2H), 1.54-1.45 (m, 2H), 1.35 (s, 6H), 1.25 (s, 6H). LCMS: 436.2 [M + H]⁺ |
| 89 | 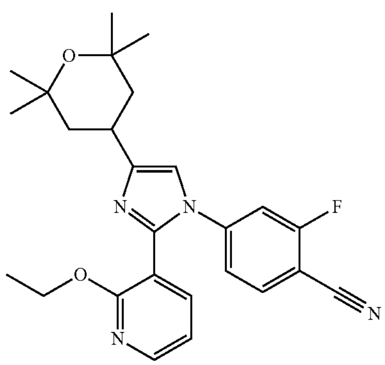 [SMILES: CCOc1ncccc1-c1nc(C2CC(C)(C)OC(C)(C)C2)cn1-c1ccc(C#N)c(F)c1] | 4-(2-(2-ethoxypyridin-3-yl)-4-(2,2,6,6-tetramethyltetrahydro-2H-pyran-4-yl)-1H-imidazol-1-yl)-2-fluorobenzonitrile | ¹H NMR (CDCl₃, 400 MHz) δ 8.18 (d, J = 4.8 Hz, 1H), 7.94 (d, J = 6.8 Hz, 1H), 7.45 (d, J = 3.2 Hz, 1H), 7.36-7.33 (m, 1H), 7.17 (t, J = 8.4 Hz, 1H), 6.99 (t, J = 5.2 Hz, 1H), 6.93 (s, 1H), 4.01 (q, J = 6.8 Hz, 2H), 3.22 (t, J = 12.4 Hz, 1H), 2.02 (d, J = 13.2 Hz, 2H), 1.51-1.42 (m, 2H), 1.36 (s, 6H), 1.26 (s, 6H), 0.98 (t, J = 6.8 Hz, 3H). LCMS: 449.3 [M + H]⁺ |

Example 9

Compound 90: 1-(4-chlorophenyl)-2-(2-methoxyphenyl)-5-methyl-4-(2,2,6,6-tetra methyl tetrahydro-2H-pyran-4-yl)-1H-imidazole

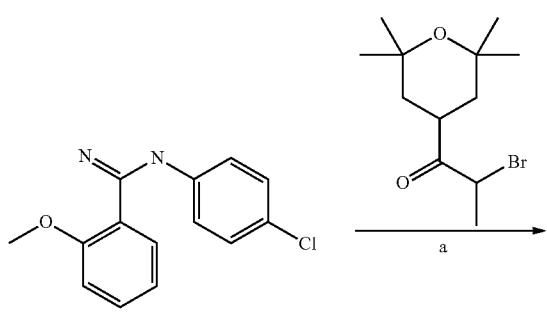

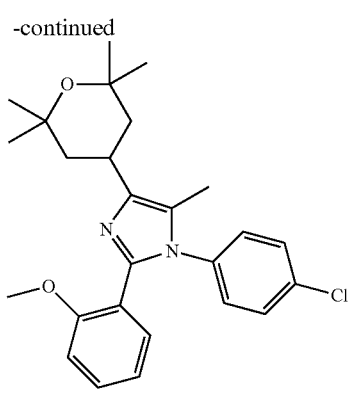

Reaction conditions: a) NaHCO3, dixoane, 100° C.;

To a stirred solution of N-(4-chlorophenyl)-2-methoxybenzimidamide A 38, (0.2 g, 0.07 mmol) and 2-bromo-1-(2,2,6,6-tetramethyltetrahydro-2H-pyran-4-yl)propan-1-one A72 (0.3 g, 0.108 mmol) in dioxane (10 mL) was added NaHCO₃ (0.13 g, 0.15 mmol). The reaction mixture was refluxed at 100° C. for 12 h. After completion of the reaction it was filtered through a pad of diatomaceous earth. The resultant filtrate was concentrated under reduced pressure to provide a crude mixture. Purification by column chromatography on silica gel (100-200 mesh) using ethyl acetate in hexane afforded the title compound as an off-white solid. Yield: 0.055 g, 17%. ¹H NMR (400 MHz, DMSO-$d_6$) 7.45 (d, J=7.2 Hz, 1H), 7.28-7.23 (m, 3H), 7.00 (d, J=8.4 Hz, 2H), 6.93 (t, J=8.0 Hz, 1H), 6.64 (d, J=7.6 Hz, 1H), 3.37 (s, 3H), 3.16-3.18 (m, 1H), 2.11 (s, 3H), 1.87 (t, J=12.8 Hz, 2H), 1.75-1.72 (m, 2H), 1.36 (s, 6H), 1.26 (s, 6H); LCMS: 439.3 [M+H]⁺.

Example 10

Compound 91: 4-(5-chloro-2-(2-methoxypyridin-3-yl)-4-(2,2,6,6-tetramethyltetrahydro-2H-pyran-4-yl)-1H-imidazol-1-yl)benzonitrile

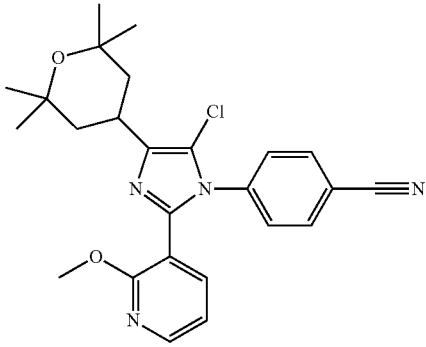 [SMILES: COc1ncccc1-c1nc(C2CC(C)(C)OC(C)(C)C2)c(Cl)n1-c1ccc(C#N)cc1]

To a solution of 4-(2-(2-methoxypyridin-3-yl)-4-(2,2,6,6-tetramethyltetrahydro-2H-pyran-4-yl)-1H-imidazol-1-yl)benzonitrile, Cpd 43, (0.055 g, 0.012 mmol) in acetonitrile (3 mL) was added NCS (0.017 g, 0.013 mmol) at 0° C. The reaction mixture was then heated at 80° C. for 5 h. After completion of the reaction, it was quenched with water and extracted with DCM (2×50 mL). The combined organic extracts were washed with brine, dried over anhydrous $Na_2SO_4$, filtered, and concentrated under reduced pressure to provide a residue. Purification by column chromatography on silica gel (100-200 mesh) using ethyl acetate in hexane afforded the title compound as a white solid. Yield: 0.02 g, 34%. ¹H NMR (CDCl₃, 400 MHz) δ 8.16-8.14 (m, 1H), 7.89-7.86 (m, 1H), 7.67 (d, J=8.4 Hz, 2H), 7.27-7.25 (m, 1H), 6.97-6.94 (m, 1H), 3.45 (s, 3H), 3.34-3.26 (m, 1H), 1.82-1.76 (m, 4H), 1.37 (s, 6H), 1.27 (s, 6H); LCMS: 451.2 [M+H]⁺.

Example 11

Compound 92: 3-(5-chloro-1-(4-fluorophenyl)-4-(2,2,6,6-tetramethyltetrahydro-2H-pyran-4-yl)-1H-imidazol-2-yl)-2-methoxypyridine

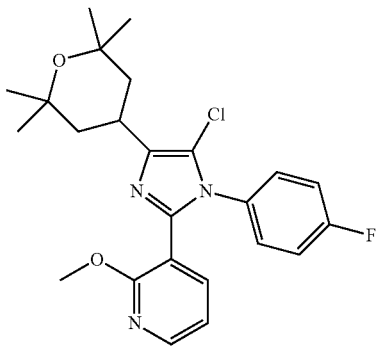 [SMILES: COc1ncccc1-c1nc(C2CC(C)(C)OC(C)(C)C2)c(Cl)n1-c1ccc(F)cc1]

Compound 92 was prepared using the procedure described Example 10 for the synthesis of Compound 91. ¹H NMR (DMSO, 400 MHz) 8.17 (dd, J=1.6 & 4.8 Hz, 1H), 7.88 (dd, J=1.6 & 3.6 Hz, 1H), 7.28-7.24 (m, 4H), 7.07-7.04 (m, 1H), 3.46 (s, 3H), 3.18 (m, 1H), 1.75-1.70 (m, 2H), 1.64-1.57 (m, 2H), 1.30 (s, 6H), 1.16 (s, 6H); LCMS 444.46 [M+H]⁺.

Example 12

Compound 93: 3-(5-chloro-1-(4-chlorophenyl)-4-(2,2,6,6-tetramethyltetrahydro-2H-pyran-4-yl)-1H-imidazol-2-yl)-2-methoxypyridine

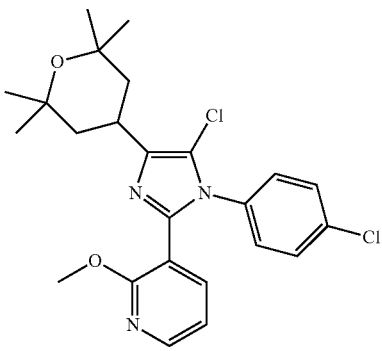 [SMILES: COc1ncccc1-c1nc(C2CC(C)(C)OC(C)(C)C2)c(Cl)n1-c1ccc(Cl)cc1]

Compound 93 was prepared using the procedure described Example 10 for the synthesis of Compound 91. ¹H NMR (DMSO, 400 MHz): 8.12 (d, J=4.8 Hz, 1H), 7.81 (dd, J=1.6 & 5.2 Hz, 1H), 7.33 (d, J=8.4 Hz, 2H), 7.07 (d, J=8.4 Hz, 2H), 6.93 (dd, J=5.2 & 7.2 Hz, 1H), 3.51 (s, 3H), 3.32-3.20 (m, 1H), 1.90-1.80 (m, 4H), 1.37 (s, 6H), 1.26 (s, 6H); LCMS 460.44 [M+H]⁺

Example 13

Compound 94: 2-(2-methoxyphenyl)-4-(2,2,6,6-tetramethyltetrahydro-2H-pyran-4-yl)1((trifluoromethyl)sulfonyl)-1H-imidazole

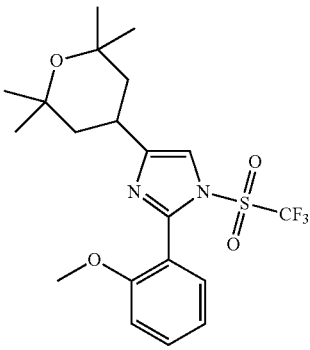 [SMILES: COc1ccccc1-c1nc(C2CC(C)(C)OC(C)(C)C2)cn1S(=O)(=O)C(F)(F)F]

To a stirred solution of 2-(2-methoxyphenyl)-4-(2,2,6,6-tetramethyltetrahydro-2H-pyran-4-yl)-1H-imidazole (0.2 g, 0.0006 mol) in DCM (10 mL) at 0° C. was added triethylamine (0.129 g, 0.0012 mol) dropwise over a period of 1 min. The reaction mixture was stirred at 0° C. followed by the addition of trifluoromethanesulfonic anhydride (0.36 g, 0.0012 mol) and stirred to room temperature for 12 h. After completion, the reaction was quenched with ice cold water, then extracted with ethyl acetate (3×25 mL). The combined organic extracts were washed with brine, dried over anhydrous $Na_2SO_4$, filtered, and concentrated under reduced pressure to provide a residue. Purification by column chromatography on silica gel (100-200 mesh) using ethyl acetate in hexane afforded the title compound as a white solid. Yield: 37 mg, 24%. $^1$H NMR (400 MHz, DMSO-$d_6$) 7.67 (s, 1H), 7.50-7.55 (m, 1H), 7.31 (d, J=7.6 Hz, 1H), 7.12 (d, J=8.4 Hz, 1H), 7.03 (t, J=7.2 Hz, 1H), 3.74 (s, 3H), 3.16 (s, 1H), 1.87 (dd, J=2.8 Hz, J=12.8 Hz, 2H), 1.34 (t, J=12.4 Hz, 2H), 1.26 (s, 6H), 1.14 (s, 6H); LCMS: 447.4 [M+H]$^+$.

Example 14

Compound 95: 1-(cyclopropylsulfonyl)-2-(2-methoxyphenyl)-4-(2,2,6,6-tetramethyltetrahydro-2H-pyran-4-yl)-1H-imidazole

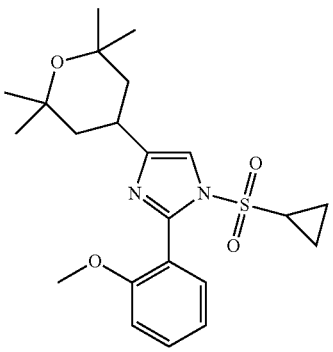 [SMILES: COc1ccccc1-c1nc(C2CC(C)(C)OC(C)(C)C2)cn1S(=O)(=O)C1CC1]

To a stirred solution of 2-(2-methoxyphenyl)-4-(2,2,6,6-tetramethyltetrahydro-2H-pyran-4-yl)-1H-imidazole (0.1 g 0.00031 mol), in THF (3 mL) was added NaH (0.031 g, 0.00079 mol) portion-wise at 0° C. under a $N_2$ atmosphere. The reaction mixture was stirred for 15 min followed by the addition of cyclopropylsulfonyl chloride (0.053 g 0.00038 mol) and then the reaction was stirred at rt for 16 h. The reaction mixture was cooled and quenched with water, extracted with ethyl acetate (2×20 mL). The combined organic extracts were washed with brine, dried over anhydrous $Na_2SO_4$, filtered, and concentrated under reduced pressure to provide a residue. Purification by column chromatography on silica gel (100-200 mesh) using ethyl acetate in hexane afforded the title compound as a white solid. Yield: 0.012 g, 10%. $^1$H NMR (400 MHz, DMSO-$d_6$) δ 7.42 (t, J=7.6 Hz, 1H), 7.20 (d, J=7.2 Hz, 1H), 7.03 (d, 2H), 6.95 (t, J=7.6 Hz, 1H), 3.70 (s, 3H), 3.27 (s, 1H), 1.89 (s, 2H), 1.25-1.15 (m, 19H); LCMS 419.2 [M+H]$^+$.

By using analogous protocols to those described in the foregoing example, the compounds described in Table 4 have been prepared, using appropriately substituted aryl or alkyl sulfonyl chlorides or of sulfonic anhydrides.

TABLE 4

| Cpd No. | Structure | Compound name | Analytical data |
|---|---|---|---|
| 96 | 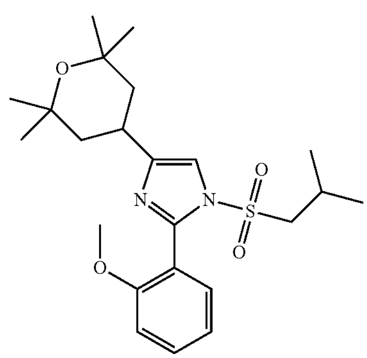 [SMILES: COc1ccccc1-c1nc(C2CC(C)(C)OC(C)(C)C2)cn1S(=O)(=O)CC(C)C] | 1-(isobutylsulfonyl)-2-(2-methoxyphenyl)-4-(2,2,6,6-tetramethyltetrahydro-2H-pyran-4-yl)-1H-imidazole | $^1$H NMR (CDCl$_3$, 400 MHz) δ 7.46-7.42 (m, 1H), 7.35-7.33 (m, 1H), 7.14 (s, 1H), 7.02 (t, J = 7.6 Hz, 1H), 6.94 (d, J = 8.4 Hz, 1H), 3.80 (s, 3H), 3.19-3.12 (m, 3H), 2.20-2.14 (m, 1H), 2.01-1.97 (m, 2H), 1.45-1.39 (m, 2H), 1.33 (s, 6H), 1.25 (s, 6H), 1.02 (d, J = 6.4 Hz, 6H). LCMS: 435.3 [M + H]$^+$ |
| 97 | 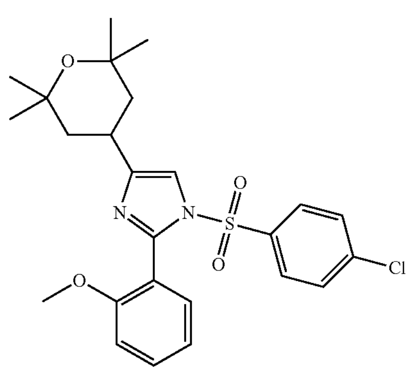 [SMILES: COc1ccccc1-c1nc(C2CC(C)(C)OC(C)(C)C2)cn1S(=O)(=O)c1ccc(Cl)cc1] | 1-((4-chlorophenyl)sulfonyl)-2-(2-methoxyphenyl)-4-(2,2,6,6-tetramethyltetrahydro-2H-pyran-4-yl)-1H-imidazole | $^1$H NMR (400 MHz, DMSO-$d_6$) δ 7.6 (d, J = 8.8 Hz, 2H), 7.50 (s, 1H), 6.59 (s, 1H), 7.40 (t, J = 7.2 Hz, 1H), 7.05-6.94 (m, 3H), 3.45 (s, 3H), 1.03 (t, J = 12.0 Hz, 1H), 1.84 (dd, J = 2.8 Hz, 2.4 Hz, 2H), 1.29 (d, J = 12 Hz, 2H) 1.23 (s, 6H), 1.12 (s, 6H): LCMS: 489.2 [M + H]$^+$ |

TABLE 4-continued

| Cpd No. | Structure | Compound name | Analytical data |
|---|---|---|---|
| 98 | 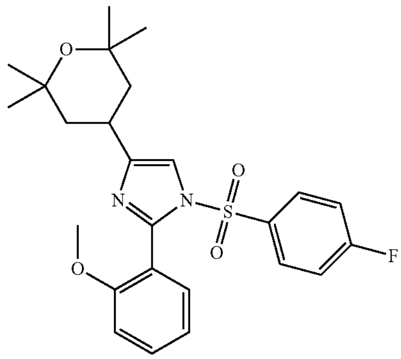 [SMILES: COc1ccccc1-c1nc(C2CC(C)(C)OC(C)(C)C2)cn1S(=O)(=O)c1ccc(F)cc1] | 1-((4-fluorophenyl)sulfonyl)-2-(2-methoxyphenyl)-4-(2,2,6,6-tetramethyltetrahydro-2H-pyran-4-yl)-1H-imidazole | $^1$H NMR (CDCl$_3$, 400 MHz) δ 7.69-7.66 (m, 2H), 7.50 (s, 1H), 7.49-7.42 (m, 3H), 7.04 (m, 3H), 7.05-6.94 (m, 3H), 3.47 (s, 3H), 3.02 (s, 1H), 1.84 (dd, J = 2.8 Hz, 2.4 Hz, 2H), 1.30-1.23 (m, 9H), 1.10 (s, 6H): LCMS: 473.3 [M + H]$^+$ |

Example 15

Compound 99: 4-((2-(2-methoxyphenyl)-4-(2,2,6,6-tetramethyltetrahydro-2H-pyran-4-yl)-1H-imidazol-1-yl)methyl)benzonitrile

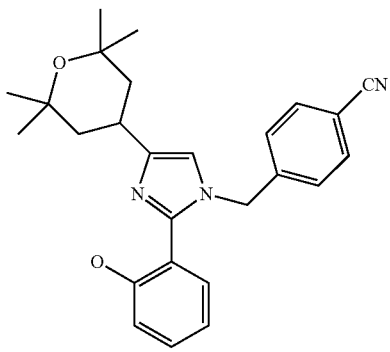 [SMILES: CC1(C)CC(c2cn(Cc3ccc(C#N)cc3)c(-c3ccccc3O)n2)CC(C)(C)O1]

To a stirred solution of 2-(2-methoxyphenyl)-4-(2,2,6,6-tetramethyltetrahydro-2H-pyran-4-yl)-1H-imidazole (0.1 g, 0.00031 mol), in THF was added NaH (0.031 g, 0.000791 mol) portion-wise at 0° C. under a N$_2$ atmosphere. The reaction mixture was stirred for 15 min followed by the addition of 4-cyanobenzyl bromide (0.074 g, 0.00034 mol). The reaction was then stirred at rt for 16 h. The reaction mixture was cooled and quenched with water, and extracted with ethyl acetate (2×20 mL). The combined organic extracts were washed with brine, dried over anhydrous Na$_2$SO$_4$, filtered, and concentrated under reduced pressure to provide a residue. Purification by column chromatography on silica gel (100-200 mesh) using ethyl acetate in hexane afforded the title compound as white solid. (0.081 g, 59.5%). $^1$H NMR (CDCl$_3$, 400 MHz) δ 7.59 (d, J=8.4 Hz, 2H), 7.41-7.36 (m, 2H), 7.14 (d, J=8.0 Hz, 2H), 7.01 (t, J=7.6 Hz, 1H), 6.85 (d, J=8.4 Hz, 1H), 6.60 (s, 1H), 4.90 (s, 2H), 3.60 (s, 3H), 3.10 (t, J=12.8 Hz, 1H), 2.0 (dd, J=2.4 Hz, 2.0 Hz, 2H), 1.23 (s, 6H), 1.13 (s, 6H); LCMS: 430.5 [M+H]$^+$.

By using analogous protocols to those described in the foregoing example the compounds described in Table 5 have been prepared using appropriately substituted bromide compounds.

TABLE 5

| Cpd No. | Structure | Compound name | Analytical data |
|---|---|---|---|
| 100 | 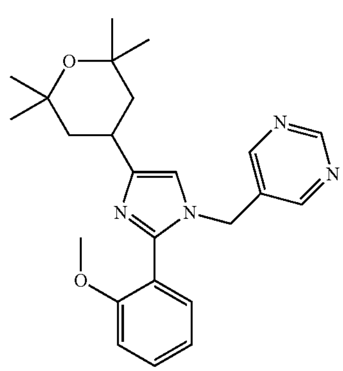 [SMILES: COc1ccccc1-c1nc(C2CC(C)(C)OC(C)(C)C2)cn1Cc1cncnc1] | 5-((2-(2-methoxyphenyl)-4-(2,2,6,6-tetramethyltetrahydro-2H-pyran-4-yl)-1H-imidazol-1-yl)methyl)pyrimidine | $^1$H NMR (CDCl$_3$, 400 MHz) δ 9.13 (s, 1H), 8.4 (s 2H), 7.51-7.39 (m, 2H), 7.03 (t, J = 15.2 Hz, 1H), 6.93 (d, J = 8.4 Hz, 1H), 6.65 (s, 1H), 3.6 (s, 3H), 3.10 (t, J = 12.8 Hz, 1H) 1.98 (dd, J = 12.8 Hz, 2H) 1.40 (t, 2H), 1.30 (s, 6H), 1.23 (s, 6H): LCMS: 407.2 [M + H]$^+$ |

TABLE 5-continued

| Cpd No. | Structure | Compound name | Analytical data |
|---|---|---|---|
| 101 | 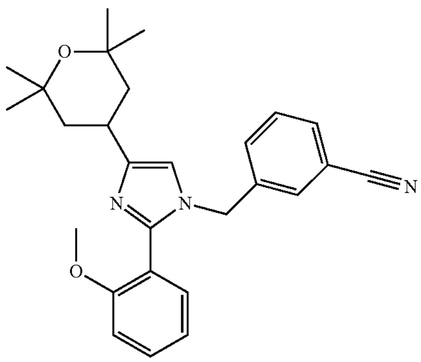 [SMILES: COc1ccccc1-c1nc(C2CC(C)(C)OC(C)(C)C2)cn1Cc1cccc(C#N)c1] | 3-((2-(2-methoxyphenyl)-4-(2,2,6,6-tetramethyltetrahydro-2H-pyran-4-yl)-1H-imidazol-1-yl)methyl)benzonitrile | $^{1}$H NMR (CDCl$_3$, 400 MHz) δ 7.56 (d, J = 8.0 Hz, 1H), 7.43-7.25 (m, 5H), 7.01 (t, J = 7.6 Hz, 1H), 6.92 (d, J = 8.8 Hz, 1H), 6.60 (s, 1H), 6.60 (s, 1H), 4.90 (s, 2H), 3.60 (s, 3H), 3.1 (t, J = 12.8 Hz, 1H), 2.0 (dd, J = 2.4 Hz, 2.0 Hz, 2H), 1.53-1.37 (m, 2H), 1.3 (s, 6H), 1.23 (s, 6H): LCMS: 430.5 [M + H]$^+$ |

Example 16

Compound 102: 4-(1-(4-chlorophenyl)-2-(2-methoxyphenyl)-1H-imidazol-4-yl)-2,2,6,6-tetramethyltetrahydro-2H-pyran-4-ol

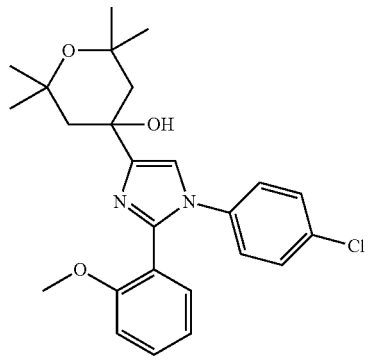 [SMILES: COc1ccccc1-c1nc(C2(O)CC(C)(C)OC(C)(C)C2)cn1-c1ccc(Cl)cc1]

To a stirred solution of N-(4-chlorophenyl)-2-methoxybenzimidamide A 39 (0.37 g, 0.0014 mol) in dioxane (15 mL) was added 2-bromo-1-(4-hydroxy-2,2,6,6-tetramethyltetrahydro-pyran-4-yl)-ethanone A 75 (0.4 g, 0.0014 mol) and NaHCO$_3$ (0.24 g, 0.00286 mol) and the mixture was stirred for 5 h at 85° C. The solvent was evaporated and the resultant crude residue was partitioned between ethyl acetate and water. The combined organic extracts were washed with brine, dried over anhydrous Na$_2$SO$_4$, filtered, and concentrated under reduced pressure to provide a residue. Purification by column chromatography on silica gel (100-200 mesh) using ethyl acetate in hexane afforded the title compound as a pale yellow solid. Yield: 0.12 g, 20%. $^{1}$H NMR (400 MHz, DMSO-d$_6$) 7.47-7.45 (m, 1H), 7.40-7.35 (m, 3H), 7.26 (s, 1H), 7.09 (d, J=8.8 Hz, 2H), 7.01 (t, J=7.6 Hz, 1H), 6.87 (d, J=8.4 Hz, 1H), 4.82 (s, 1H), 3.21 (s, 3H), 1.87-1.76 (m, 4H), 1.44 (s, H), 1.10 (s, 6H); LCMS: 441.2 [M+H]$^+$.

By using analogous protocols to those described in the foregoing example the compounds described in Table 6 have been prepared using an appropriately substituted amidine intermediate.

TABLE 6

| Cpd No. | Structure | Compound name | Analytical data |
|---|---|---|---|
| 103 | 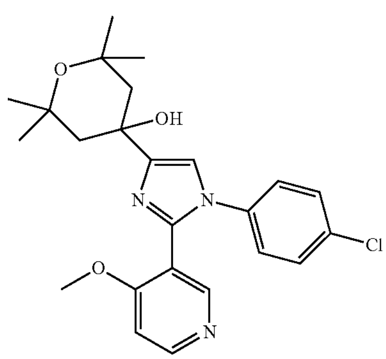 [SMILES: COc1ccncc1-c1nc(C2(O)CC(C)(C)OC(C)(C)C2)cn1-c1ccc(Cl)cc1] | 4-(1-(4-chlorophenyl)-2-(4-methoxypyridin-3-yl)-1H-imidazol-4-yl)-2,2,6,6-tetramethyltetrahydro-2H-pyran-4-ol | $^{1}$H NMR (400 MHz, DMSO-d$_6$) δ = 8.51 (s, 1H), 8.47 (d, J = 5.6 Hz, 1H), 7.44 (d, J = 8.4 Hz, 2H), 7.36 (s, 1H), 7.17 (d, J = 8.4 Hz, 2H), 6.96 (d, J = 5.6 Hz, 1H), 4.92 (s, 1H), 3.35 (s, 3H), 1.86 (d, J = 13.2 Hz, 2H), 1.80 (d, J = 13.2 Hz, 2H), 1.46 (s, 6H), 1.12 (s, 6H). LCMS: 442.44 [M + H]$^+$ |

TABLE 6-continued

| Cpd No. | Structure | Compound name | Analytical data |
|---|---|---|---|
| 104 | 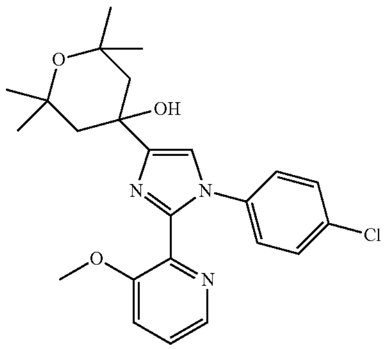 [SMILES: COc1cccnc1-c1nc(C2(O)CC(C)(C)OC(C)(C)C2)cn1-c1ccc(Cl)cc1] | 4-(1-(4-chlorophenyl)-2-(3-methoxypyridin-2-yl)-1H-imidazol-4-yl)-2,2,6,6-tetramethyltetrahydro-2H-pyran-4-ol | $^1$H NMR (400 MHz, DMSO-$d_6$) δ = 8.19 (s, 1H), 7.38-7.44 (m, 4H), 7.32 (s, 1H), 7.08 (d, J = 7.6 Hz, 2H), 4.94 (s, 1H), 3.44 (s, 3H), 1.77-1.87 (m, 4H), 1.46 (s, 6H), 1.11 (s, 6H). LCMS: 442.48 [M + H]$^+$ |
| 105 | 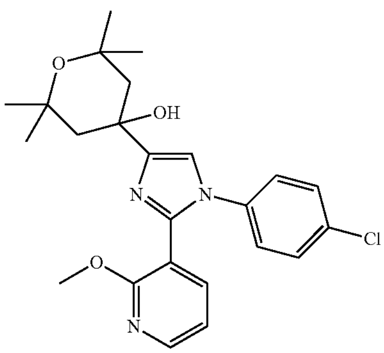 [SMILES: COc1ncccc1-c1nc(C2(O)CC(C)(C)OC(C)(C)C2)cn1-c1ccc(Cl)cc1] | 4-(1-(4-chlorophenyl)-2-(2-methoxypyridin-3-yl)-1H-imidazol-4-yl)-2,2,6,6-tetramethyltetrahydro-2H-pyran-4-ol | $^1$H NMR (400 MHz, DMSO-$d_6$) δ = 8.20 (d, J = 8 Hz, 1H), 7.93 (d, J = 7.2 Hz, 1H), 7.45 (d, J = 8.4 Hz, 2H), 7.34 (s, 1H), 7.15 (d, J = 8.4 Hz, 2H), 7.10 (t, J = 6.8 Hz, 1H), 4.93 (s, 1H), 3.34 (s, 3H), 1.77-1.87 (m, 4H), 1.46 (s, 6H), 1.11 (s, 6H). LCMS: 442.44 [M + H]$^+$ |
| 106 | 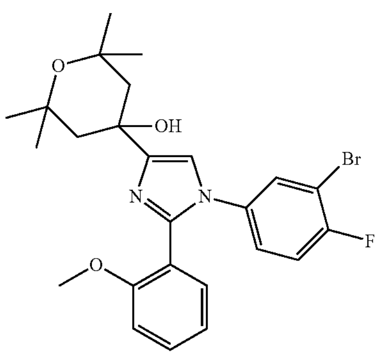 | 4-(1-(3-bromo-4-fluorophenyl)-2-(2-methoxyphenyl)-1H-imidazol-4-yl)-2,2,6,6-tetramethyltetrahydro-2H-pyran-4-ol | $^1$H NMR (400 MHz, DMSO-$d_6$) δ 7.46 (d, J = 8.0 Hz, 2H), 7.34-7.40 (m, 2H), 7.31 (s, 1H), 7.08-7.12 (m, 1H), 7.02 (t, J = 7.2 Hz, 1H), 6.80 (d, J = 8.4 Hz, 1H), 4.80 (s, 1H), 3.25 (s, 3H), 1.80-1.82 (m, 4H), 1.44 (s, 6H), 1.22 (s, 6H). LCMS: 453.2 [M + H]$^+$ |
| 107 | 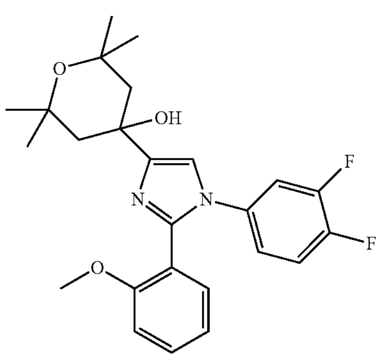 [SMILES: COc1ccccc1-c1nc(C2(O)CC(C)(C)OC(C)(C)C2)cn1-c1ccc(F)c(F)c1] | 4-(1-(3,4-difluorophenyl)-2-(2-methoxyphenyl)-1H-imidazol-4-yl)-2,2,6,6-tetramethyltetrahydro-2H-pyran-4-ol | $^1$H NMR (400 MHz, DMSO-$d_6$) δ 7.47 (m, 1H), 7.48 (m, 2H), 7.26 (m, 2H), 7.02 (t, J = 8 Hz, 1H), 6.89 (m, 2H), 4.8 (s, 1H), 3.2 (s, 3H), 1.81 (m, 4H), 1.44 (s, 6H), 1.10 (s, 6H). LCMS: 443.3 [M + H]$^+$ |

TABLE 6-continued

| Cpd No. | Structure | Compound name | Analytical data |
|---|---|---|---|
| 108 | 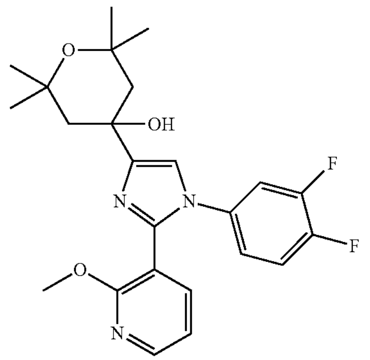 [SMILES: COc1ncccc1-c1nc(C2(O)CC(C)(C)OC(C)(C)C2)cn1-c1ccc(F)c(F)c1] | 4-(1-(3,4-difluorophenyl)-2-(2-methoxypyridin-3-yl)-1H-imidazol-4-yl)-2,2,6,6-tetramethyltetrahydro-2H-pyran-4-ol | $^1$H NMR (400 MHz, DMSO-$d_6$) δ 7.48 (d, J = 7.6 Hz, 1H), 7.39 (t, J = 8 Hz, 1H), 7.34 (s, 1H), 7.2 (dd, J = 8 Hz, 10.4 Hz, 1H), 7.04 (t, J = 7.6 Hz, 1H), 6.92 (t, J = 12 Hz, 1H), 4.8 (s, 1H), 3.2 (s, 3H), 1.81 (m, 4H), 1.1 (s, 6H), 1.4 (s, 6H). LCMS: 444.2 [M + H]$^+$ |
| 109 | 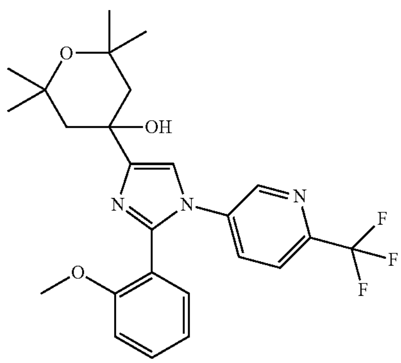 [SMILES: COc1ccccc1-c1nc(C2(O)CC(C)(C)OC(C)(C)C2)cn1-c1ccc(C(F)(F)F)nc1] | 4-(2-(2-methoxyphenyl)-1-(6-(trifluoromethyl)pyridin-3-yl)-1H-imidazol-4-yl)-2,2,6,6-tetramethyltetrahydro-2H-pyran-4-ol | $^1$H NMR (400 MHz, DMSO-$d_6$) δ 8.574 (s, 1H), 7.93 (d, J = 8.4 Hz, 1H), 7.804 (d, J = 10.4 Hz, 1H), 7.57 (d, J = 6 Hz, 1H), 7.516 (s, 1H), 7.430 (m, 1H), 7.101 (m, 1H), 6.898 (d, J = 8.4 Hz, 1H), 4.937 (s, 1H), 3.16 (s, 3H), 1.85 (m, 4H), 1.47 (s, 6H), 1.13 (s, 6H); LCMS: 476.3 [M + H]$^+$ |
| 110 | 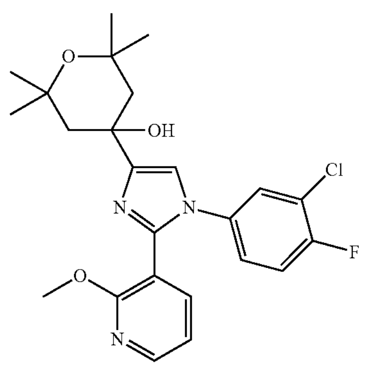 [SMILES: COc1ncccc1-c1nc(C2(O)CC(C)(C)OC(C)(C)C2)cn1-c1ccc(F)c(Cl)c1] | 4-(1-(3-chloro-4-fluorophenyl)-2-(2-methoxypyridin-3-yl)-1H-imidazol-4-yl)-2,2,6,6-tetramethyltetrahydro-2H-pyran-4-ol | $^1$H NMR (400 MHz, DMSO-$d_6$) δ 8.19 (t, J = 7.2 Hz, 2H), 7.91 (m, 1H), 7.46 (m, 1H), 7.42 (d, J = 8.0 Hz, 1H), 7.36 (s, 1H), 7.11 (m, 2H), 4.85 (s, 1H), 3.37 (s, 3H), 1.81 (dd, J = 13.6 Hz, 5.2 Hz, 4H), 1.44 (s, 6H), 1.10 (s, 6H): LCMS: 460.2 [M + H]$^+$ |
| 111 | 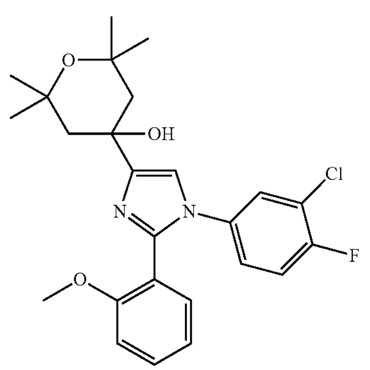 [SMILES: COc1ccccc1-c1nc(C2(O)CC(C)(C)OC(C)(C)C2)cn1-c1ccc(F)c(Cl)c1] | 4-(1-(3-chloro-4-fluorophenyl)-2-(2-methoxyphenyl)-1H-imidazol-4-yl)-2,2,6,6-tetramethyltetrahydro-2H-pyan-4-ol | $^1$H NMR (400 MHz, DMSO-$d_6$) δ 7.5 (d, J = 6 Hz, 1H), 7.40-7.39 (m, 3H), 6.20 (s, 1H), 7.09-7.01 (m, 2H), 6.80 (d, J = 8.4 Hz, 1H), 4.80 (s, 1H), 3.25 (s, 3H), 1.86-1.77 (m, 4H), 1.44 (s, 6H), 1.10 (s, 6H): LCMS: 459.2 [M + H]$^+$ |

TABLE 6-continued

| Cpd No. | Structure | Compound name | Analytical data |
|---|---|---|---|
| 112 | 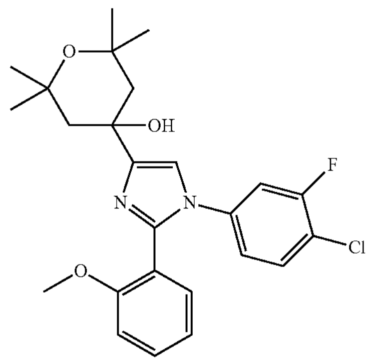 [SMILES: COc1ccccc1-c1nc(C2(O)CC(C)(C)OC(C)(C)C2)cn1-c1ccc(Cl)c(F)c1] | 4-(1-(4-chloro-3-fluorophenyl)-2-(2-methoxyphenyl)-1H-imidazol-4-yl)-2,2,6,6-tetramethyltetrahydro-2H-pyan-4-ol | $^1$H NMR (400 MHz, DMSO-$d_6$) δ 7.53 (t, J = 12 Hz, 1H), 7.48 (d, J = 7.6 Hz, 1H), 7.40 (t, J = 8 Hz, 1H), 7.34 (s, 1H), 7.2 (dd, J = 10 Hz, 10.4 Hz, 1H), 7.01 (t, J = 8 Hz, 1H), 6.90 (t, J = 8 Hz, 2H), 4.8 (s, 1H), 3.2 (s, 3H), 1.81 (m, 4H), 1.44 (s, 6H), 1.10 (s, 6H). LCMS: 459.2 [M + H]$^+$ |
| 113 | 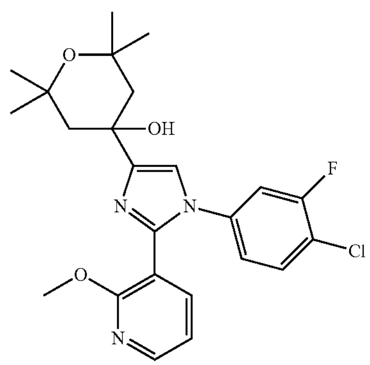 [SMILES: COc1ncccc1-c1nc(C2(O)CC(C)(C)OC(C)(C)C2)cn1-c1ccc(Cl)c(F)c1] | 4-(1-(4-chloro-3-fluorophenyl)-2-(2-methoxypyridin-3-yl)-1H-imidazol-4-yl)-2,2,6,6-tetramethyltetrahydro-2H-pyran-4-ol | $^1$H NMR (400 MHz, DMSO-$d_6$) δ 8.20 (t, J = 4Hz, 1H), 7.93 (dd, J = 8 Hz, 8 Hz, 1H), 7.58 (t, J = 8 Hz, 1H), 7.38 (s, 1H), 7.31 (d, J = 1.6 Hz, 1H), 7.10 (m, 1H), 6.96 (d, J = 8 Hz, 1H), 4.8 (s, 1H), 3.3 (s, 3H), 1.81 (m, 4H), 1.44 (s, 6H), 1.10 (s, 6H). LCMS: 460.2 [M + H]$^+$ |
| 114 | 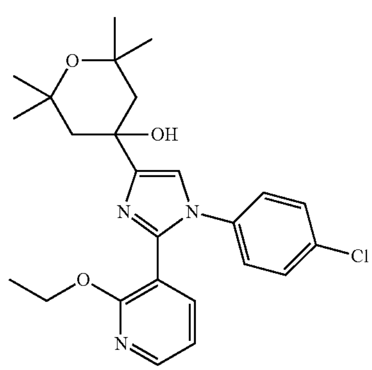 [SMILES: CCOc1ncccc1-c1nc(C2(O)CC(C)(C)OC(C)(C)C2)cn1-c1ccc(Cl)cc1] | 4-(1-(4-chlorophenyl)-2-(2-ethoxypyridin-3-yl)-1H-imidazol-4-yl)-2,2,6,6-tetramethyltetrahydro-2H-pyran-4-ol | $^1$H NMR (400 MHz, DMSO-$d_6$): 8.17 (d, J = 3.2 Hz, 1H), 7.93 (d, J = 5.6 Hz, 1H), 7.43 (d, J = 8.4 Hz, 2H), 7.33 (s, 1H), 7.15 (d, J = 8.8 Hz, 2H), 7.07 (m, 1H), 4.86 (s, 1H), 3.86 (q, J = 2.8 Hz, 2H), 1.82 (q, J = 12.8 Hz, 4H), 1.44 (s, 6H), 1.26 (s, 2H), 1.15 (s, 6H), 0.80 (q, J = 5.6 Hz, 3H). LCMS: 456.3 [M + H]$^+$ |

TABLE 6-continued

| Cpd No. | Structure | Compound name | Analytical data |
|---|---|---|---|
| 115 | 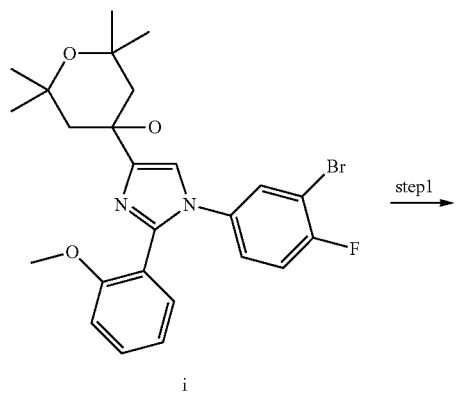 | 4-(4-(4-hydroxy-2,2,6,6-tetramethyltetrahydro-2H-pyran-4-yl)-2-(2-methoxypyridin-3-yl)-1H-imidazol-1-yl)benzonitrile | $^1$H NMR (400 MHz, DMSO-$d_6$): 8.21-8.19 (m, 1H), 7.98-7.95 (m, 1H), 7.86 (d, J = 8.4 Hz, 2H), 7.42 (s, 1H), 7.32 (d, J = 8.8 Hz, 2H), 7.13-7.10 (m, 1H), 4.90 (s, 1H), 1.89-1.77 (m, 4H), 1.45 (s, 6H), 1.10 (s, 6H). LCMS: 433.3 [M + H]$^+$ |

Example 17

Compound 116: 2-Fluoro-5-[4-(4-hydroxy-2,2,6,6-tetramethyl-tetrahydro-pyran-4-yl)-2-(2-methoxy-phenyl)-imidazol-1-yl]-benzonitrile

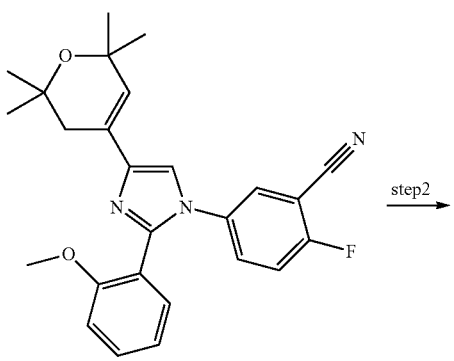

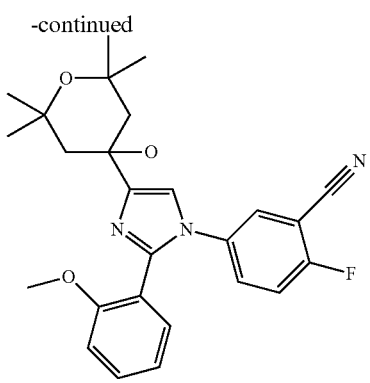

Step 1. Compound 126. 2-Fluoro-5-(2-(2-methoxy-phenyl)-4-(2,2,6,6-tetramethyl-3,6-dihydro-2H-pyran-4-yl)-1H-imidazol-1-yl)benzonitrile To a stirred solution of 4-[1-(3-bromo-4-fluoro-phenyl)-2-(2-methoxy-phenyl)-1H-imidazol-4-yl]-2,2,6,6-tetramethyl-tetrahydro-pyran-4-ol, (0.16 g, 0.000635 mol) in DMF (5 mL) under an $N_2$ atmosphere was added $Zn(CN)_2$ (0.075 g, 0.00212 mol) and tetrakis-triphenylphosphine palladium (0.184 g, 0.00015 mol), purging with nitrogen for 15 min before each addition. The reaction mixture was further purged for 5 min and stirred for 1.5 h at 160° C. The reaction mixture was quenched with ice cold water and extracted with ethyl acetate (50 mL×3). The combined organic extracts were washed with brine, dried over anhydrous $Na_2SO_4$, filtered, and concentrated under reduced pressure to provide a residue. Purification by column chromatography on silica gel (100-200 mesh) using ethyl acetate in hexane afforded the title compound as a white solid. (0.09 g, 63.3%), LCMS: 432.3 [M+H]$^+$.

Step 2. Compound 116: 2-Fluoro-5-[4-(4-hydroxy-2,2,6,6-tetramethyl-tetrahydro-pyran-4-yl)-2-(2-methoxy-phenyl)-imidazol-1-yl]-benzonitrile To a stirred solution of 2-fluoro-5-[2-(2-methoxy-phenyl)-4-(2,2,6,6-tetramethyl-3,6-dihydro-2H-pyran-4-yl)-imidazol-1-yl]-benzonitrile (0.09 g, 0.000208 mol), and Mn(tmhd)$_3$ (0.025 g, 0.0004172 mol) in i-PrOH (7 mL) and DCM (1 mL) at 0° C., phenylsilane (0.045 g, 0.000417 mol) was added and the reaction mixture was stirred for 3 h from 0° C. to rt under an oxygen atmosphere. Saturated $Na_2S_2O_3$ solution (2 mL) was added and the mixture was stirred for 2 h. The reaction mixture was further diluted with brine (10 mL) and extracted with ethyl acetate (10 mL×3). The combined organic extracts were dried over anhydrous $Na_2SO_4$, filtered, and concentrated under reduced pressure to provide a residue. Purification by column chromatography on silica gel (100-200 mesh) using ethyl acetate in hexane afforded the title compound as an off white solid (0.05 g, 56%). $^1$H NMR (CDCl$_3$, 400 MHz) δ 7.54-7.56 (dd, J=7.6 Hz, 1.2 Hz, 1H), 7.38-7.43 (m, 2H), 7.31-7.36 (m, 2H), 7.14 (t, J=8.8 Hz, 1H), 7.05 (t, J=8.0 Hz, 1H), 7.02 (s, 1H), 6.74 (d, J=8.4 Hz, 1H), 3.38 (s, 3H), 2.06 (d, J=13.2 Hz, 2H), 1.90 (d, J=13.6 Hz, 2H), 1.56 (s, 6H), 1.26 (s, 6H). LCMS: 450.3.2 [M+H]$^+$ By using analogous protocols to those described in the foregoing example the compounds described in Table 7 have been prepared using appropriately substituted bromide intermediate.

TABLE 7

| Cpd No. | Structure | Compound name | Analytical data |
|---|---|---|---|
| 117 | 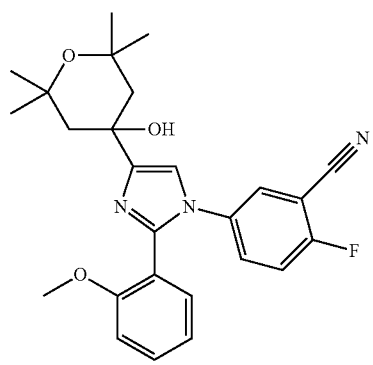 [SMILES: COc1ccccc1-c1nc(C2(O)CC(C)(C)OC(C)(C)C2)cn1-c1ccc(F)c(C#N)c1] | 2-fluoro-5-(4-(4-hydroxy-2,2,6,6-tetramethyltetrahydro-2H-pyran-4-yl)-2-(2-methoxyphenyl)-1H-imidazol-1-yl)benzonitrile | $^1$H NMR (CDCl$_3$, 400 MHz) δ 7.54-7.56 (dd, J = 7.6 Hz, 1.2 Hz, 1H), 7.38-7.43 (m, 2H), 7.31-7.36 (m, 2H), 7.14 (t, J = 8.8 Hz, 1H), 7.05 (t, J = 8.0 Hz, 1H), 7.02 (s, 1H), 6.74 (d, J = 8.4 Hz, 1H), 3.38 (s, 3H), 2.06 (d, J = 13.2 Hz, 2H), 1.90 (d, J = 13.6 Hz, 2H), 1.56 (s, 6H), 1.26 (s, 6H). LCMS: 450.3 [M + H]$^+$ |
| 118 | 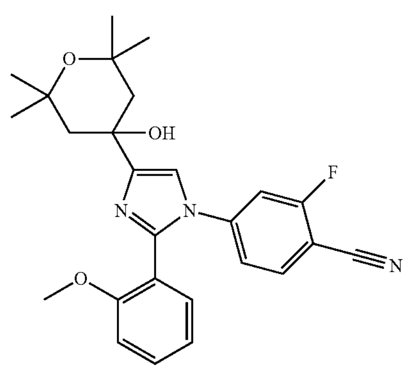 [SMILES: COc1ccccc1-c1nc(C2(O)CC(C)(C)OC(C)(C)C2)cn1-c1ccc(C#N)c(F)c1] | 2-fluoro-4-(4-(4-hydroxy-2,2,6,6-tetramethyltetrahydro-2H-pyran-4-yl)-2-(2-methoxyphenyl)-1H-imidazol-1-yl)benzonitrile | $^1$H NMR: (400 MHz, DMSO-d$_6$): δ 7.89 (t, J = 8.0 Hz, 1H), 7.52 (d, J = 7.2 Hz, 1H), 7.43-7.40 (m, 2H), 7.35 (d, J = 10 Hz, 1H), 7.07 (t, J = 7.6 Hz, 2H), 6.90 (d, J = 8.4 Hz, 1H), 4.88 (s, 1H), 3.22 (s, 3H), 1.85-1.77 (m, 4H), 1.44 (s, 6H), 1.10 (s, 6H). LCMS: 450.3 [M + H]$^+$ |
| 119 | 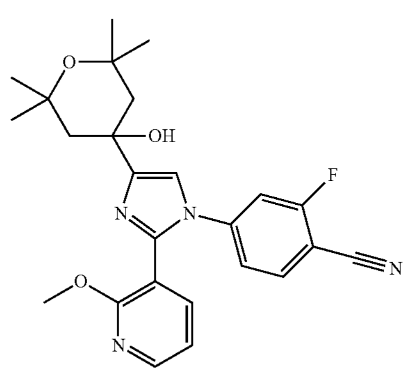 [SMILES: COc1ncccc1-c1nc(C2(O)CC(C)(C)OC(C)(C)C2)cn1-c1ccc(C#N)c(F)c1] | 2-fluoro-4-(4-(4-hydroxy-2,2,6,6-tetramethyltetrahydro-2H-pyran-4-yl)-2-(2-methoxypyridin-3-yl)-1H-imidazol-1-yl)benzonitrile | $^1$H NMR: (400 MHz, DMSO-d$_6$): δ 8.24-8.22 (dd, J = 4.8 hz, 1.6 Hz, 1H), 7.99-7.97 (dd, J = 7.2 Hz, 1.6 Hz, 1H), 7.93 (t, J = 8 Hz, 1H), 7.48 (s, 1H), 7.44 (d, J = 1.6 Hz, 1H), 7.34 (bs, 1H), 7.15-7.12 (m, 2H), 4.92 (s, 1H), 3.33 (s, 3H), 1.85-1.77 (m, 4H), 1.45 (s, 6H), 1.10 (s, 6H). LCMS: 451.3 [M + H]$^+$ |

TABLE 7-continued

| Cpd No. | Structure | Compound name | Analytical data |
|---|---|---|---|
| 120 | 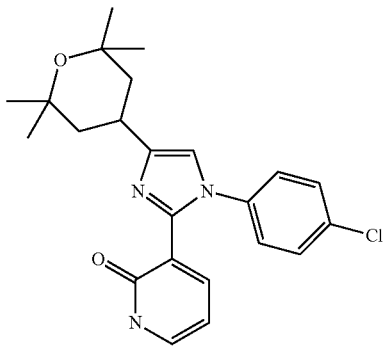 | 4-(1-(4-chlorophenyl)-2-(3-methoxypyridin-4-yl)-1H-imidazol-4-yl)-2,2,6,6-tetramethyltetrahydro-2H-pyran-4-ol | $^1$H NMR (DMSO-d$_6$, 400 MHz): 8.31-8.27 (m, 2H), 7.52 (d, J = 4.4 Hz, 1H), 7.44 (d, J = 18.4 Hz, 2H), 7.38 (s, 1H), 7.16 (d, J = 8.8 Hz, 2H), 3.32 (s, 3H) 4.95 (s, 1H), 1.87-1.84 (m, 4H), 1.46 (s, 6H), 1.11 (s, 6H). MS: ESI-MS, m/z 442.19 (M + 1). |

Example 18

Compound 122: 3-(1-(4-chlorophenyl)-4-(2,2,6,6-tetramethyltetrahydro-2H-pyran-4-yl)-1H-imidazol-2-yl)pyridin-2(1H)-one To a stirred solution of 3-(1-(4-chlorophenyl)-4-(2,2,6,6-tetramethyltetrahydro-2H-pyran-4-yl)-1H-imidazol-2-yl)-2-methoxypyridine (320 mg) was added aqueous HBr (47%) 2 mL at 0-5° C., and the mixture was stirred at rt for 16 h. The reaction was quenched with 10% NaHCO$_3$ solution (30 ml), extracted with 10% MeOH in DCM (2×50 mL). The combined organic extracts were dried over anhydrous Na$_2$SO$_4$, filtered, and concentrated under reduced pressure to provide a residue. Purification by column chromatography on silica gel (100-200 mesh) using a mixture of MeOH and DCM afforded the title compound as an off white solid. Yield: 0.015 g (48.5%); LCMS 412.2 [M+H]$^+$ The compounds of Table 8, exemplified hereinbelow, were prepared according to the schemes and specific examples described herein.

TABLE 8

Compounds of Formula (I)

| Cpd No. | Structure |
|---|---|
| 1 | 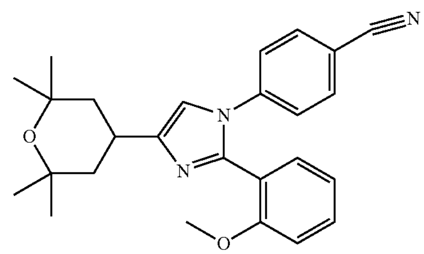 [SMILES: COc1ccccc1-c1nc(C2CC(C)(C)OC(C)(C)C2)cn1-c1ccc(C#N)cc1] |
| 2 | 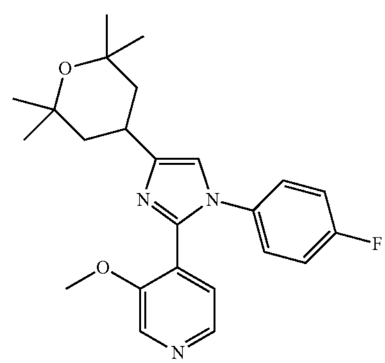 [SMILES: COc1cnccc1-c1nc(C2CC(C)(C)OC(C)(C)C2)cn1-c1ccc(F)cc1] |
| 3 | 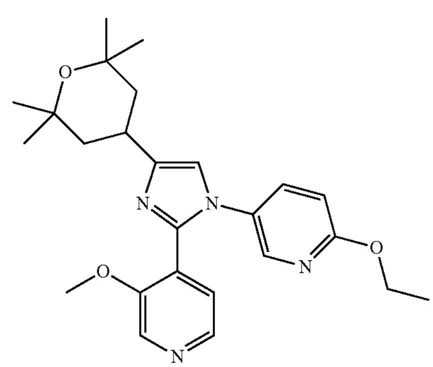 [SMILES: CCOc1ccc(-n2cc(C3CC(C)(C)OC(C)(C)C3)nc2-c2ccncc2OC)cn1] |

TABLE 8-continued
Compounds of Formula (I)
| Cpd No. | Structure |
| --- | --- |
| 4 | 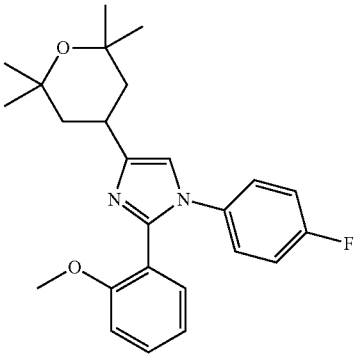 [SMILES: COc1ccccc1-c1nc(C2CC(C)(C)OC(C)(C)C2)cn1-c1ccc(F)cc1] |
| 5 | 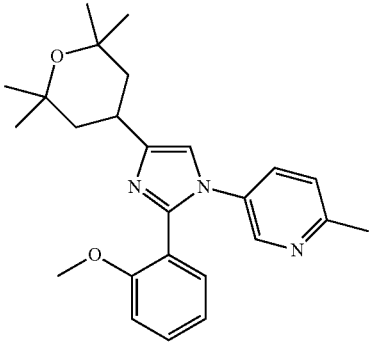 |
| 6 | 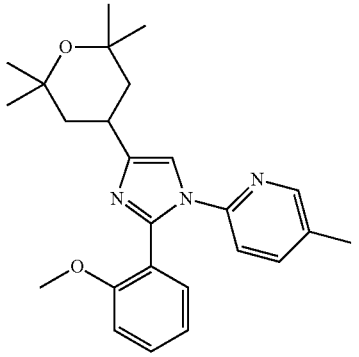 |
| 7 | 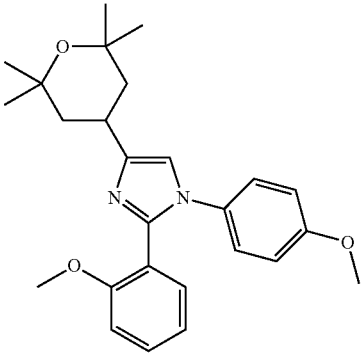 |
| 8 | 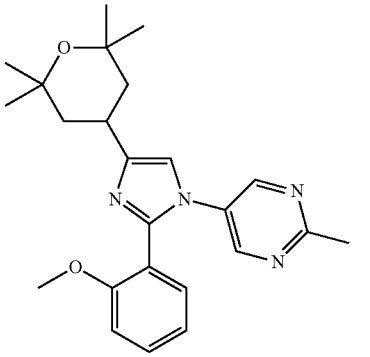 |
| 9 | 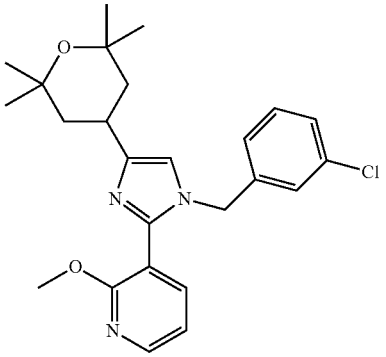 [SMILES: COc1ncccc1-c1nc(C2CC(C)(C)OC(C)(C)C2)cn1Cc1cccc(Cl)c1] |
| 10 | 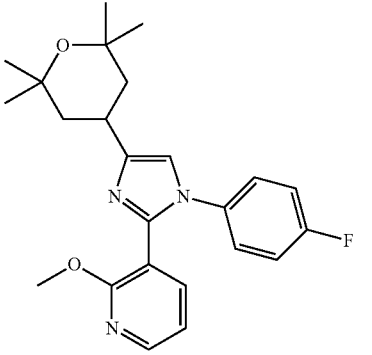 [SMILES: COc1ncccc1-c1nc(C2CC(C)(C)OC(C)(C)C2)cn1-c1ccc(F)cc1] |
| 11 | 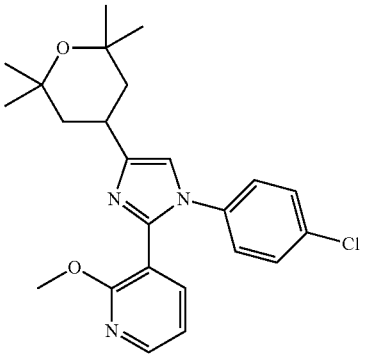 [SMILES: COc1ncccc1-c1nc(C2CC(C)(C)OC(C)(C)C2)cn1-c1ccc(Cl)cc1] |

TABLE 8-continued

Compounds of Formula (I)

| Cpd No. | Structure |
|---|---|
| 12 | (structure) |
| 13 | (structure) |
| 14 | (structure) |
| 15 | (structure) |
| 16 | (structure) |
| 17 | (structure) |
| 18 | (structure) |
| 19 | (structure) |

TABLE 8-continued
Compounds of Formula (I)
| Cpd No. | Structure |
|---|---|
| 20 | 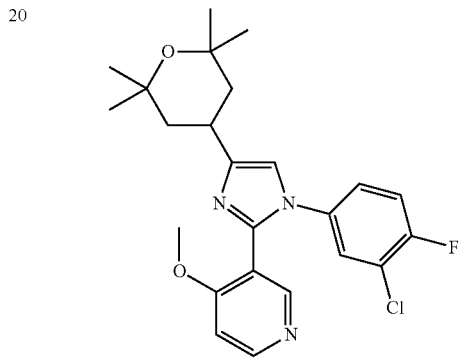 |
| 21 | 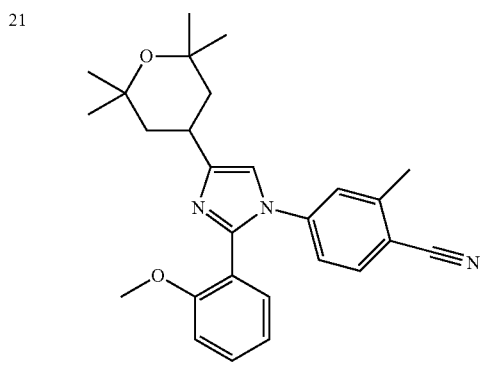 |
| 22 | 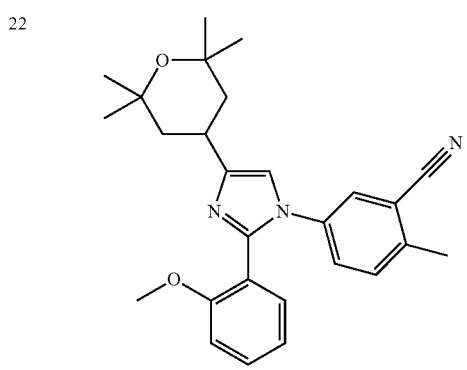 |
| 23 | 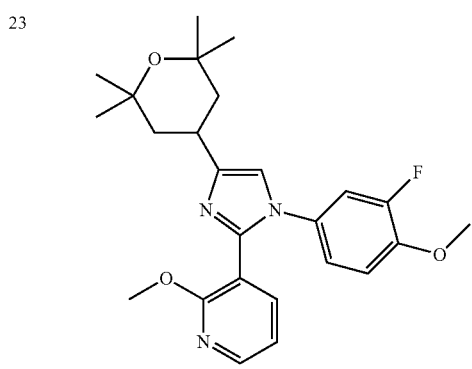 |
| 24 | 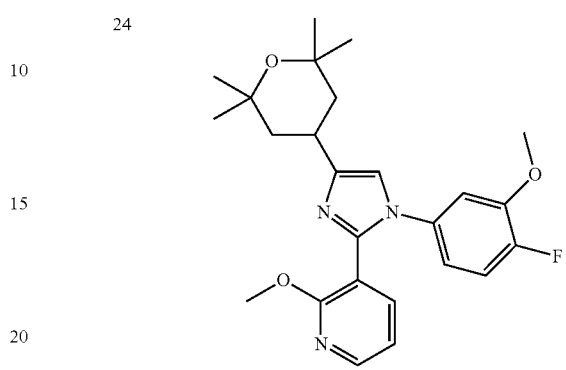 |
| 25 | 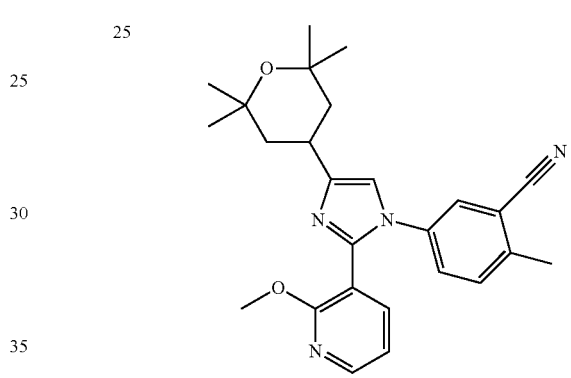 |
| 26 | 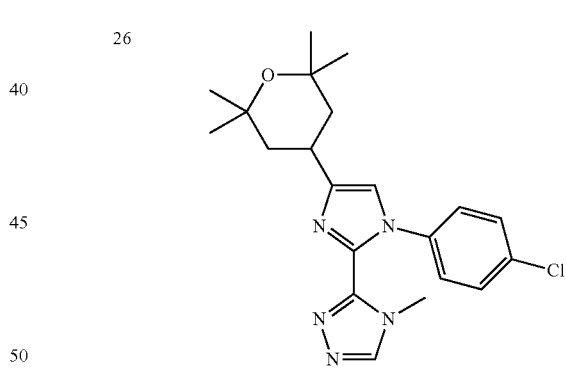 |
| 27 | 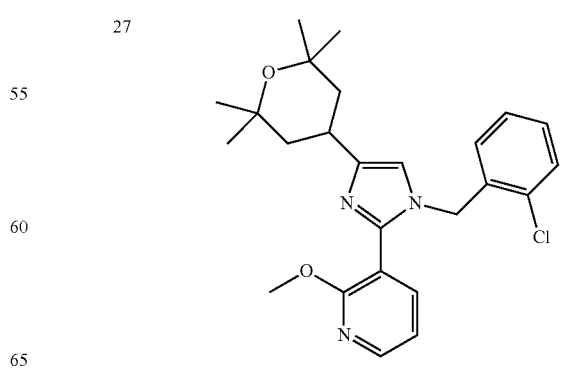 |

TABLE 8-continued

Compounds of Formula (I)

| Cpd No. | Structure |
|---|---|
| 28 | 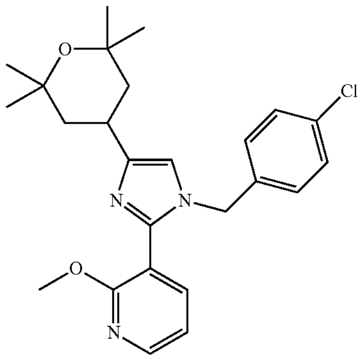 [SMILES: COc1ncccc1-c1nc(C2CC(C)(C)OC(C)(C)C2)cn1Cc1ccc(Cl)cc1] |
| 29 | 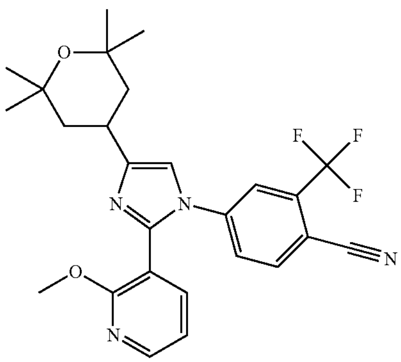 [SMILES: COc1ncccc1-c1nc(C2CC(C)(C)OC(C)(C)C2)cn1-c1ccc(C#N)c(C(F)(F)F)c1] |
| 30 | 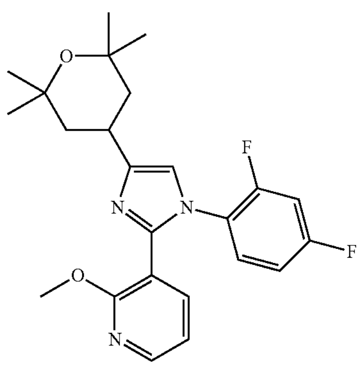 [SMILES: COc1ncccc1-c1nc(C2CC(C)(C)OC(C)(C)C2)cn1-c1ccc(F)cc1F] |
| 31 | 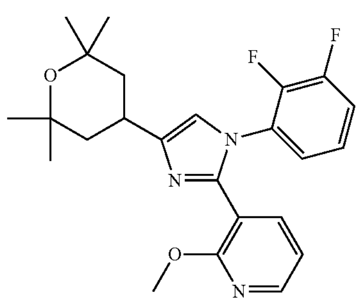 [SMILES: COc1ncccc1-c1nc(C2CC(C)(C)OC(C)(C)C2)cn1-c1cccc(F)c1F] |
| 32 | |
| 33 | |
| 34 | |
| 35 | |

TABLE 8-continued

Compounds of Formula (I)

| Cpd No. | Structure |
|---|---|
| 36 | 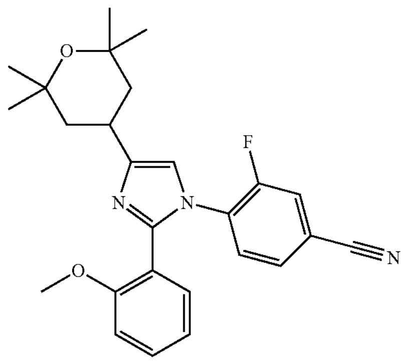 [SMILES: COc1ccccc1-c1nc(C2CC(C)(C)OC(C)(C)C2)cn1-c1ccc(C#N)cc1F] |
| 37 | 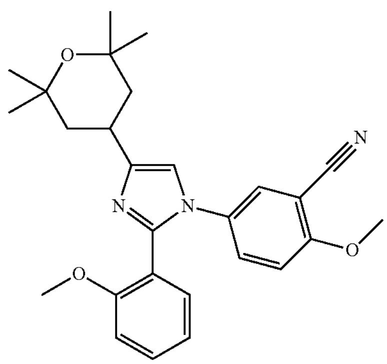 |
| 38 | 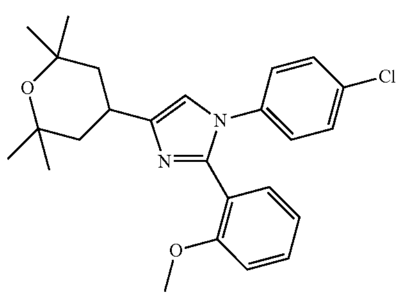 [SMILES: COc1ccccc1-c1nc(C2CC(C)(C)OC(C)(C)C2)cn1-c1ccc(Cl)cc1] |
| 39 | 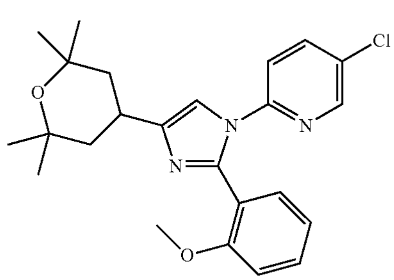 [SMILES: COc1ccccc1-c1nc(C2CC(C)(C)OC(C)(C)C2)cn1-c1ccc(Cl)cn1] |
| 40 | |
| 41 | |
| 42 | |
| 43 | |

TABLE 8-continued
Compounds of Formula (I)
| Cpd No. | Structure |
|---|---|
| 44 | 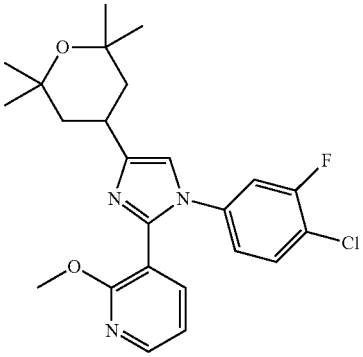 |
| 45 | 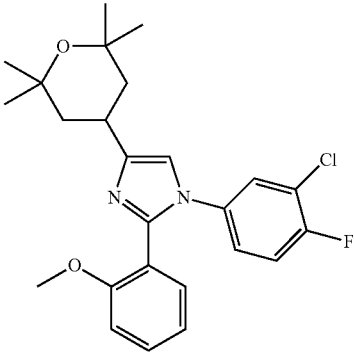 [SMILES: COc1ccccc1-c1nc(C2CC(C)(C)OC(C)(C)C2)cn1-c1ccc(F)c(F)c1] |
| 46 | 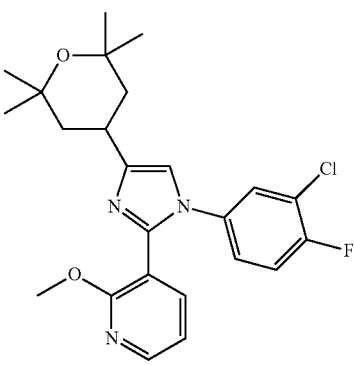 [SMILES: COc1ncccc1-c1nc(C2CC(C)(C)OC(C)(C)C2)cn1-c1ccc(F)c(Cl)c1] |
| 47 | 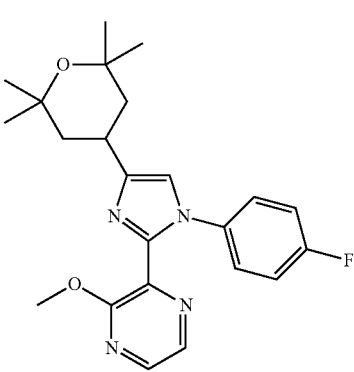 [SMILES: COc1nccnc1-c1nc(C2CC(C)(C)OC(C)(C)C2)cn1-c1ccc(F)cc1] |
| 48 | 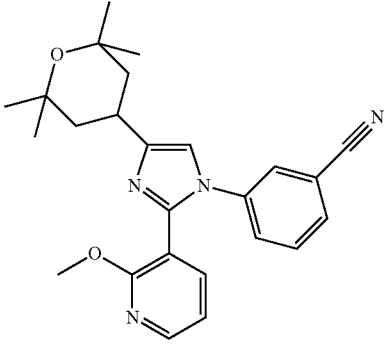 [SMILES: COc1ncccc1-c1nc(C2CC(C)(C)OC(C)(C)C2)cn1-c1cccc(C#N)c1] |
| 49 | 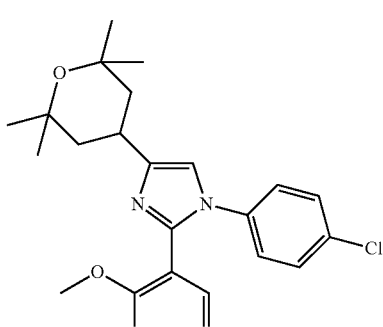 |
| 50 | 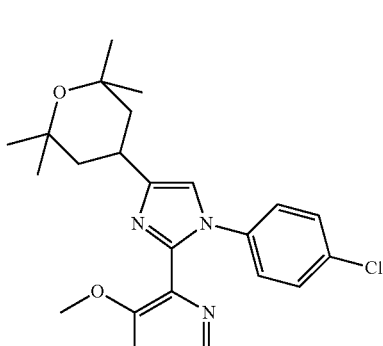 |
| 51 | 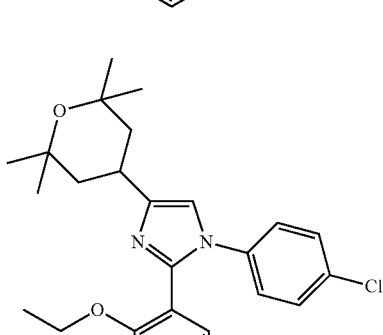 |

TABLE 8-continued
Compounds of Formula (I)
| Cpd No. | Structure |
|---|---|
| 52 | 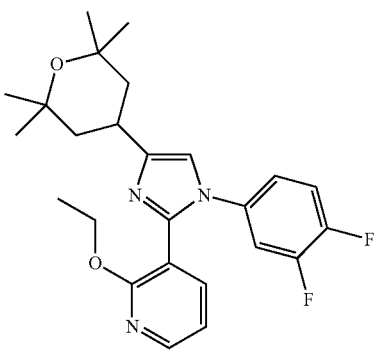 [SMILES: CCOc1ncccc1-c1nc(C2CC(C)(C)OC(C)(C)C2)cn1-c1ccc(F)c(F)c1] |
| 53 | 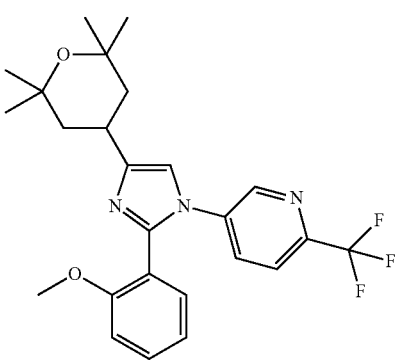 [SMILES: COc1ccccc1-c1nc(C2CC(C)(C)OC(C)(C)C2)cn1-c1ccc(C(F)(F)F)nc1] |
| 54 | 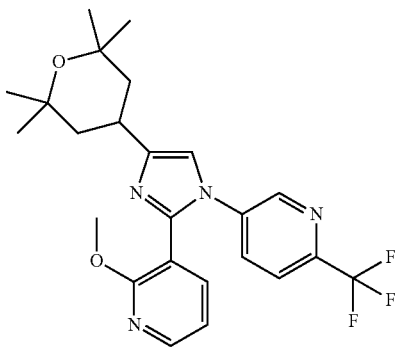 [SMILES: COc1ncccc1-c1nc(C2CC(C)(C)OC(C)(C)C2)cn1-c1ccc(C(F)(F)F)nc1] |
| 55 | 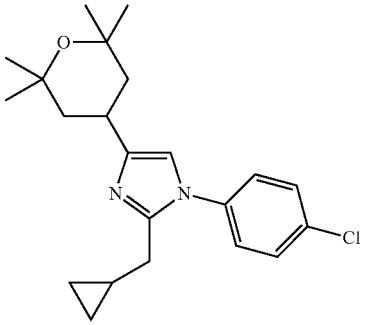 [SMILES: CC1(C)CC(c2cn(-c3ccc(Cl)cc3)c(CC3CC3)n2)CC(C)(C)O1] |
| 56 | 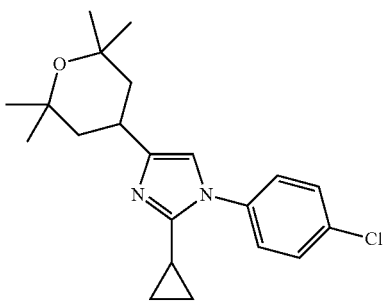 [SMILES: CC1(C)CC(c2cn(-c3ccc(Cl)cc3)c(C3CC3)n2)CC(C)(C)O1] |
| 57 | 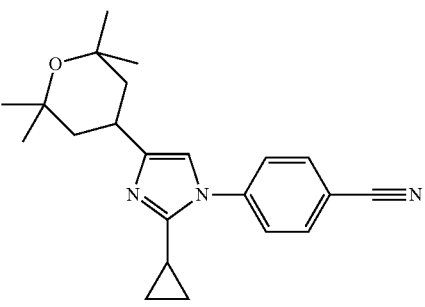 [SMILES: CC1(C)CC(c2cn(-c3ccc(C#N)cc3)c(C3CC3)n2)CC(C)(C)O1] |
| 58 | 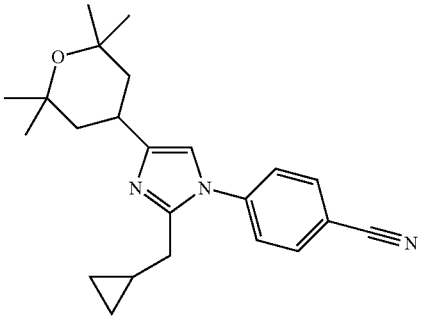 [SMILES: CC1(C)CC(c2cn(-c3ccc(C#N)cc3)c(CC3CC3)n2)CC(C)(C)O1] |
| 59 | 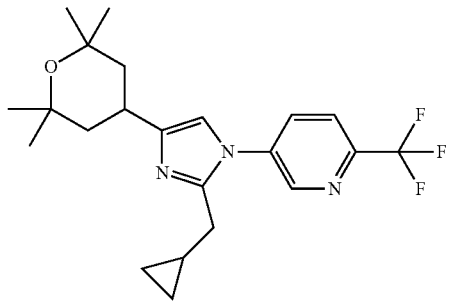 [SMILES: CC1(C)CC(c2cn(-c3ccc(C(F)(F)F)nc3)c(CC3CC3)n2)CC(C)(C)O1] |

TABLE 8-continued
Compounds of Formula (I)
| Cpd No. | Structure |
|---|---|
| 60 | 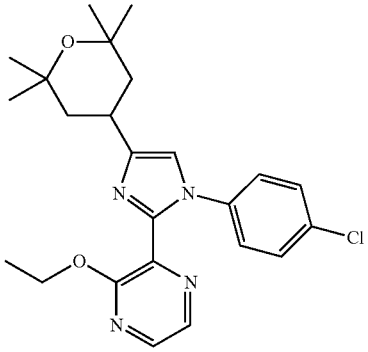 [SMILES: CCOc1nccnc1-c1nc(C2CC(C)(C)OC(C)(C)C2)cn1-c1ccc(Cl)cc1] |
| 61 | 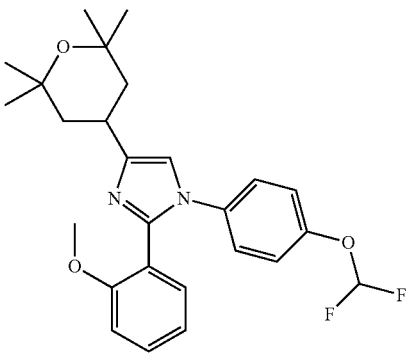 [SMILES: COc1ccccc1-c1nc(C2CC(C)(C)OC(C)(C)C2)cn1-c1ccc(OC(F)F)cc1] |
| 62 | 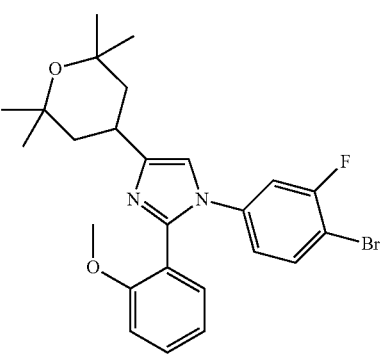 [SMILES: COc1ccccc1-c1nc(C2CC(C)(C)OC(C)(C)C2)cn1-c1ccc(Br)c(F)c1] |
| 63 | 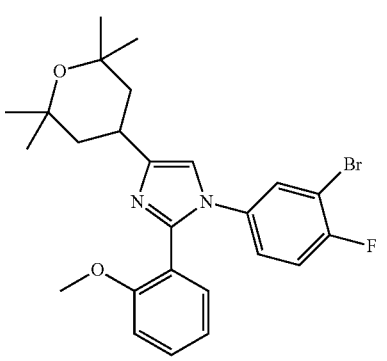 [SMILES: COc1ccccc1-c1nc(C2CC(C)(C)OC(C)(C)C2)cn1-c1ccc(F)c(Br)c1] |
| 64 | 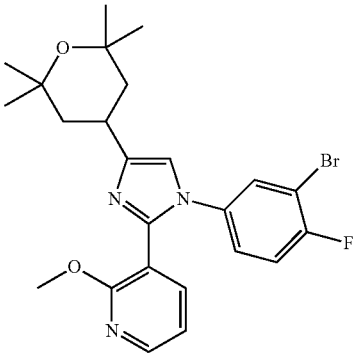 [SMILES: COc1ncccc1-c1nc(C2CC(C)(C)OC(C)(C)C2)cn1-c1ccc(F)c(Br)c1] |
| 65 | 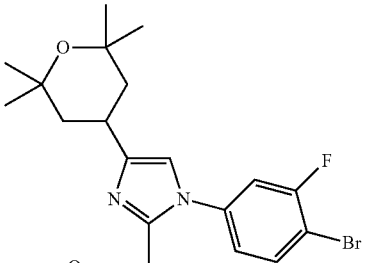 |
| 66 | 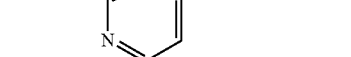 |
| 67 |  |

TABLE 8-continued
Compounds of Formula (I)
| Cpd No. | Structure |
|---|---|
| 68 | 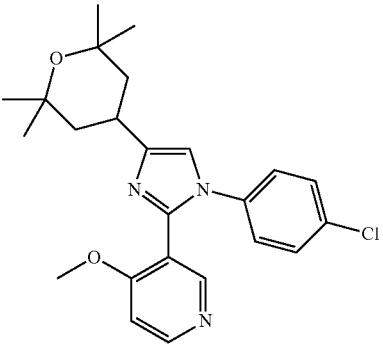 [SMILES: COc1ccncc1-c1nc(C2CC(C)(C)OC(C)(C)C2)cn1-c1ccc(Cl)cc1] |
| 69 | 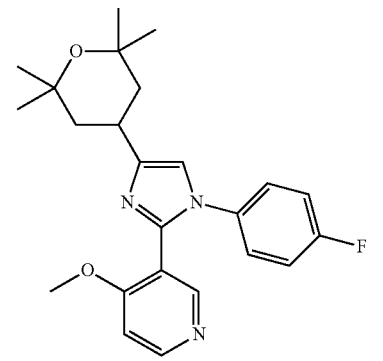 [SMILES: COc1ccncc1-c1nc(C2CC(C)(C)OC(C)(C)C2)cn1-c1ccc(F)cc1] |
| 70 | 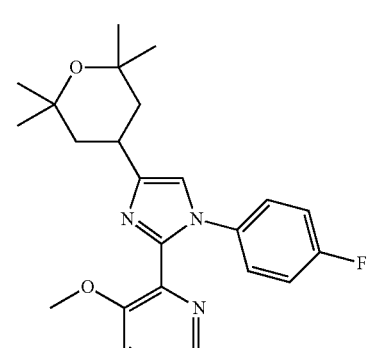 |
| 71 | 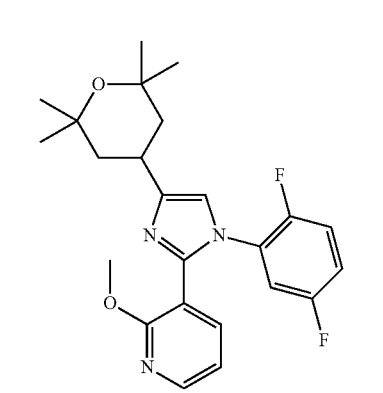 [SMILES: COc1ncccc1-c1nc(C2CC(C)(C)OC(C)(C)C2)cn1-c1cc(F)ccc1F] |
| 72 | 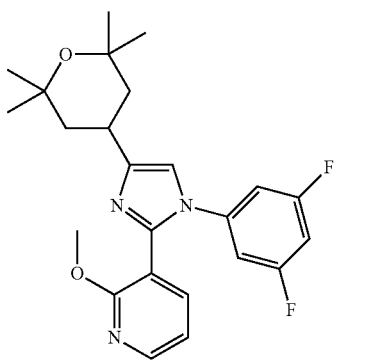 [SMILES: COc1ncccc1-c1nc(C2CC(C)(C)OC(C)(C)C2)cn1-c1cc(F)cc(F)c1] |
| 73 | 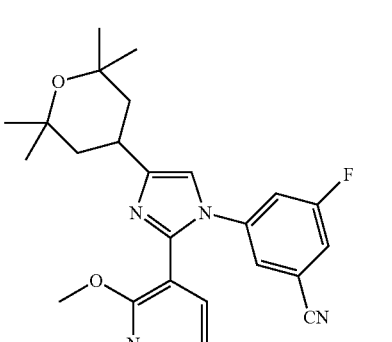 |
| 74 | 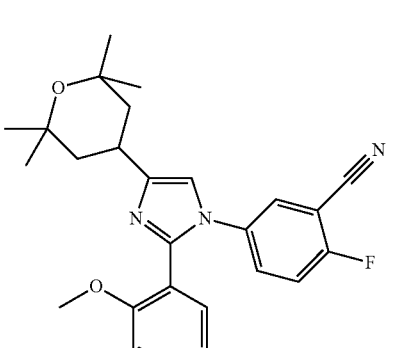 |
| 75 | 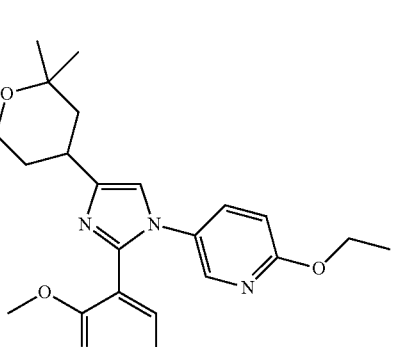 |

TABLE 8-continued
Compounds of Formula (I)
| Cpd No. | Structure |
|---|---|
| 76 | 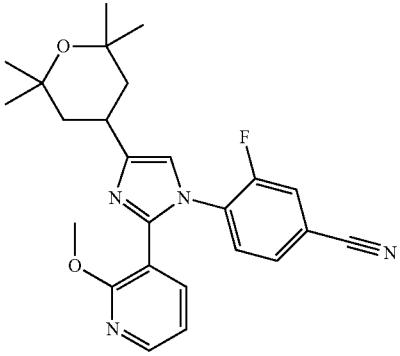 [SMILES: COc1ncccc1-c1nc(C2CC(C)(C)OC(C)(C)C2)cn1-c1ccc(C#N)cc1F] |
| 77 | 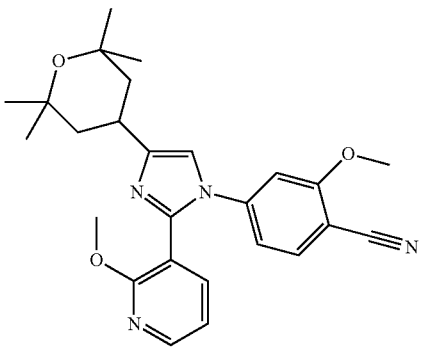 [SMILES: COc1cc(-n2cc(C3CC(C)(C)OC(C)(C)C3)nc2-c2cccnc2OC)ccc1C#N] |
| 78 | 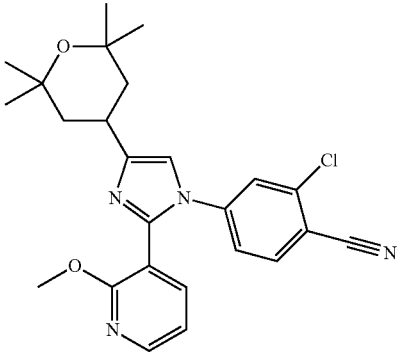 [SMILES: COc1ncccc1-c1nc(C2CC(C)(C)OC(C)(C)C2)cn1-c1ccc(C#N)c(Cl)c1] |
| 79 | 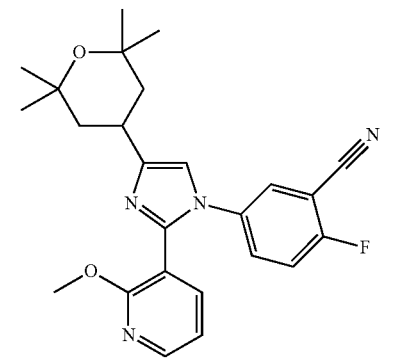 [SMILES: COc1ncccc1-c1nc(C2CC(C)(C)OC(C)(C)C2)cn1-c1ccc(F)c(C#N)c1] |
| 80 | 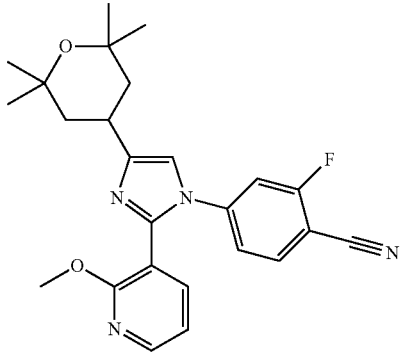 [SMILES: COc1ncccc1-c1nc(C2CC(C)(C)OC(C)(C)C2)cn1-c1ccc(C#N)c(F)c1] |
| 81 | 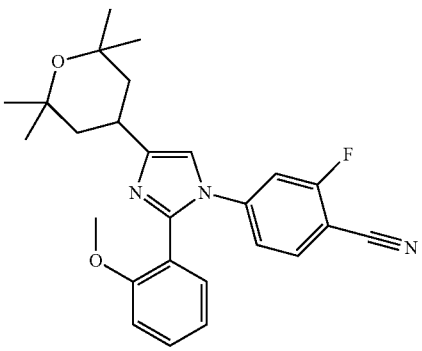 [SMILES: COc1ccccc1-c1nc(C2CC(C)(C)OC(C)(C)C2)cn1-c1ccc(C#N)c(F)c1] |
| 82 | 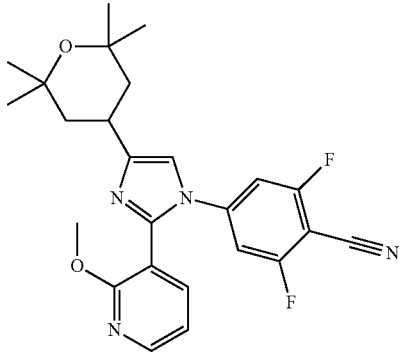 [SMILES: COc1ncccc1-c1nc(C2CC(C)(C)OC(C)(C)C2)cn1-c1cc(F)c(C#N)c(F)c1] |
| 83 | 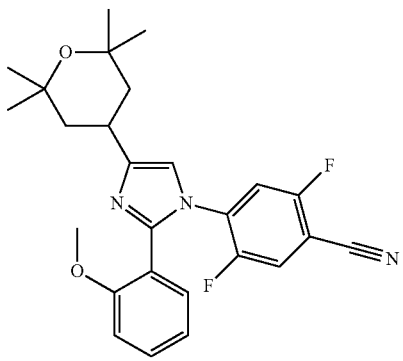 [SMILES: COc1ccccc1-c1nc(C2CC(C)(C)OC(C)(C)C2)cn1-c1cc(F)c(C#N)cc1F] |

TABLE 8-continued
Compounds of Formula (I)
| Cpd No. | Structure |
|---|---|
| 84 | 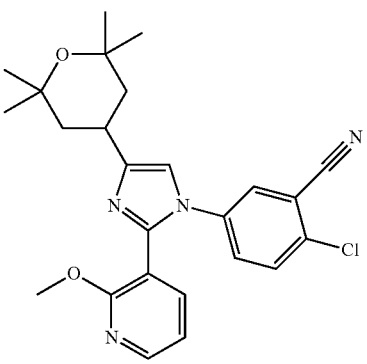 [SMILES: COc1ncccc1-c1nc(C2CC(C)(C)OC(C)(C)C2)cn1-c1ccc(Cl)c(C#N)c1] |
| 85 | 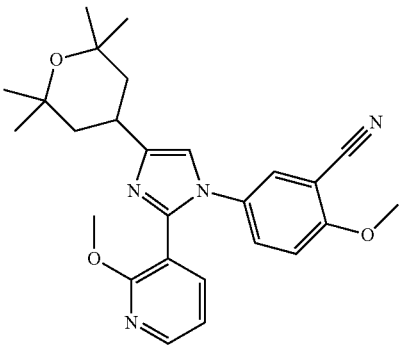 |
| 86 | 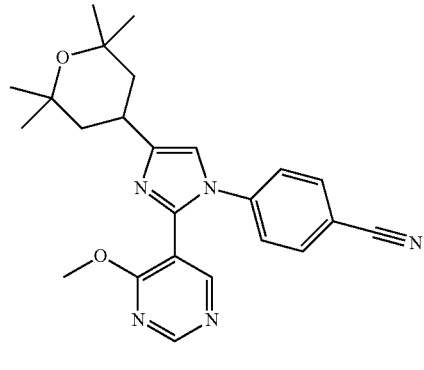 [SMILES: COc1ncncc1-c1nc(C2CC(C)(C)OC(C)(C)C2)cn1-c1ccc(C#N)cc1] |
| 87 | 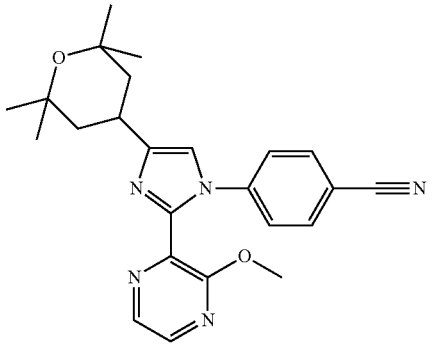 [SMILES: COc1nccnc1-c1nc(C2CC(C)(C)OC(C)(C)C2)cn1-c1ccc(C#N)cc1] |
| 88 | 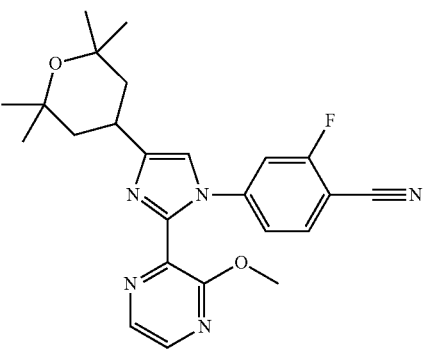 [SMILES: COc1nccnc1-c1nc(C2CC(C)(C)OC(C)(C)C2)cn1-c1ccc(C#N)c(F)c1] |
| 89 | 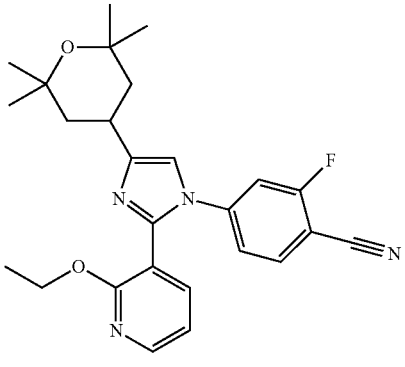 [SMILES: CCOc1ncccc1-c1nc(C2CC(C)(C)OC(C)(C)C2)cn1-c1ccc(C#N)c(F)c1] |
| 90 | 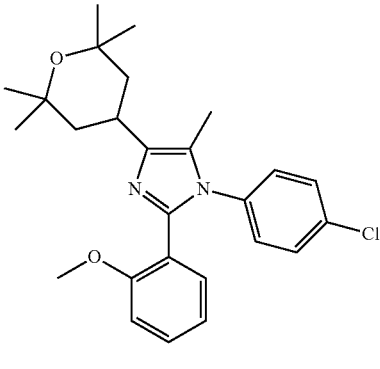 [SMILES: COc1ccccc1-c1nc(C2CC(C)(C)OC(C)(C)C2)c(C)n1-c1ccc(Cl)cc1] |
| 91 | 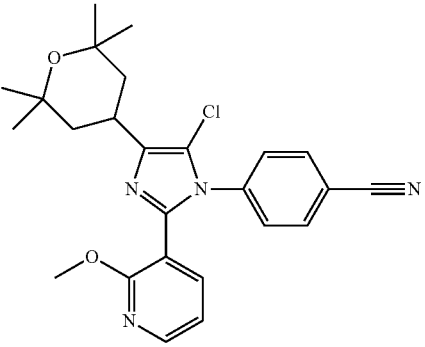 [SMILES: COc1ncccc1-c1nc(C2CC(C)(C)OC(C)(C)C2)c(Cl)n1-c1ccc(C#N)cc1] |

TABLE 8-continued

Compounds of Formula (I)

| Cpd No. | Structure |
|---------|-----------|
| 92 | 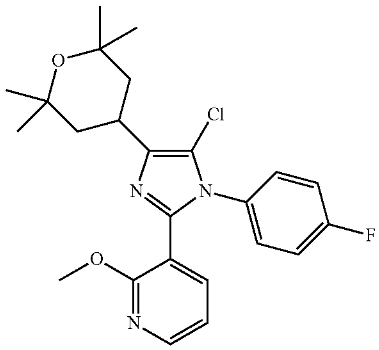 [SMILES: COc1ncccc1-c1nc(C2CC(C)(C)OC(C)(C)C2)c(Cl)n1-c1ccc(F)cc1] |
| 93 | 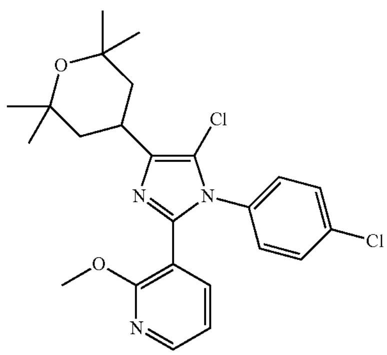 [SMILES: COc1ncccc1-c1nc(C2CC(C)(C)OC(C)(C)C2)c(Cl)n1-c1ccc(Cl)cc1] |
| 94 | 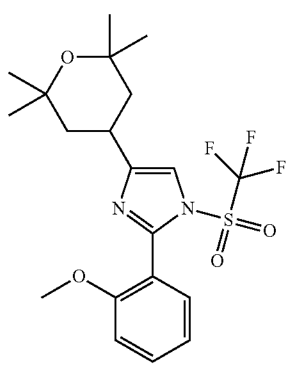 [SMILES: COc1ccccc1-c1nc(C2CC(C)(C)OC(C)(C)C2)cn1S(=O)(=O)C(F)(F)F] |
| 95 | 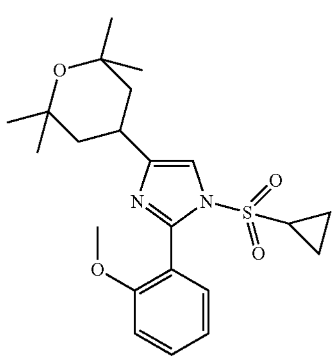 [SMILES: COc1ccccc1-c1nc(C2CC(C)(C)OC(C)(C)C2)cn1S(=O)(=O)C1CC1] |
| 96 | |
| 97 | |
| 98 | |
| 99 | |

TABLE 8-continued
Compounds of Formula (I)
| Cpd No. | Structure |
|---|---|
| 100 | 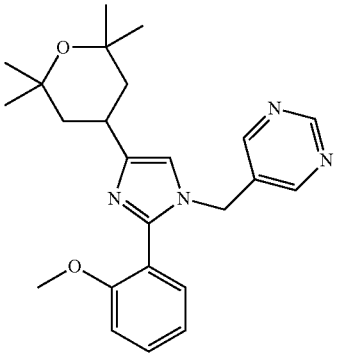 [SMILES: COc1ccccc1-c1nc(C2CC(C)(C)OC(C)(C)C2)cn1Cc1cncnc1] |
| 101 | 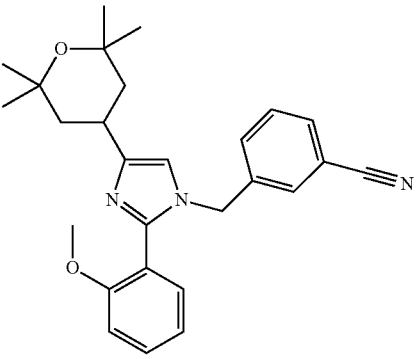 [SMILES: COc1ccccc1-c1nc(C2CC(C)(C)OC(C)(C)C2)cn1Cc1cccc(C#N)c1] |
| 102 | 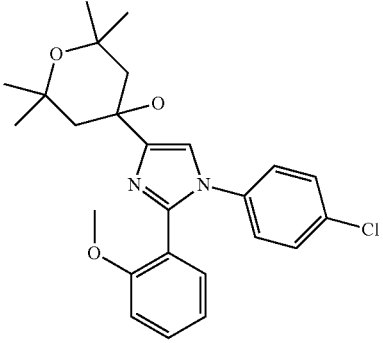 [SMILES: COc1ccccc1-c1nc(C2(O)CC(C)(C)OC(C)(C)C2)cn1-c1ccc(Cl)cc1] |
| 103 | 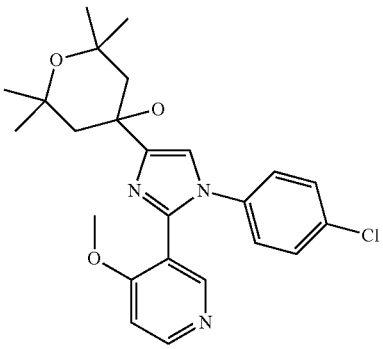 [SMILES: COc1ccncc1-c1nc(C2(O)CC(C)(C)OC(C)(C)C2)cn1-c1ccc(Cl)cc1] |
| 104 | 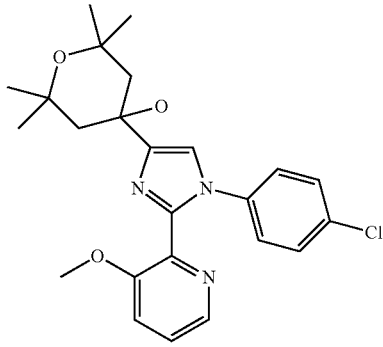 [SMILES: COc1cccnc1-c1nc(C2(O)CC(C)(C)OC(C)(C)C2)cn1-c1ccc(Cl)cc1] |
| 105 | 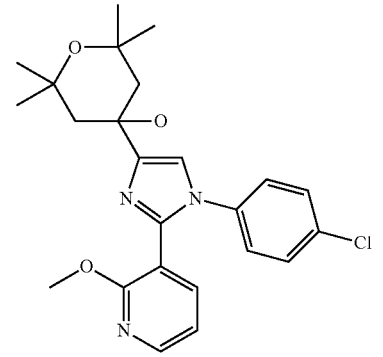 [SMILES: COc1ncccc1-c1nc(C2(O)CC(C)(C)OC(C)(C)C2)cn1-c1ccc(Cl)cc1] |
| 106 | 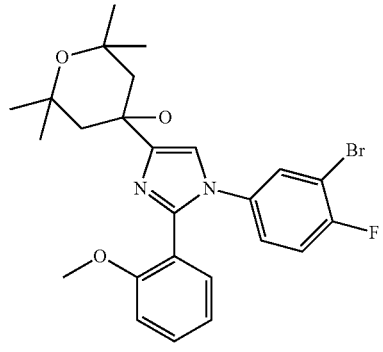 [SMILES: COc1ccccc1-c1nc(C2(O)CC(C)(C)OC(C)(C)C2)cn1-c1ccc(F)c(Br)c1] |
| 107 | 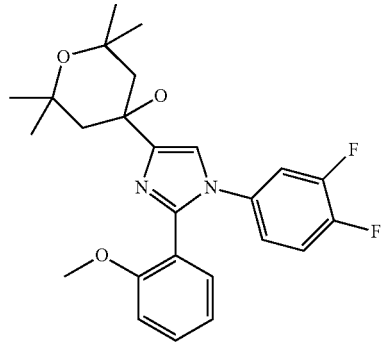 [SMILES: COc1ccccc1-c1nc(C2(O)CC(C)(C)OC(C)(C)C2)cn1-c1ccc(F)c(F)c1] |

TABLE 8-continued

Compounds of Formula (I)

| Cpd No. | Structure |
|---------|-----------|
| 108 | 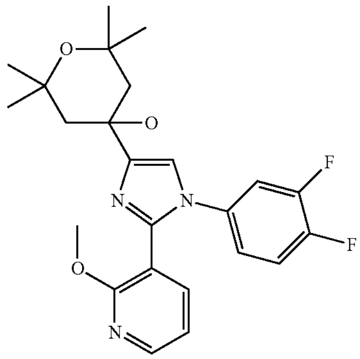 [SMILES: COc1ncccc1-c1nc(C2(O)CC(C)(C)OC(C)(C)C2)cn1-c1ccc(F)c(F)c1] |
| 109 | 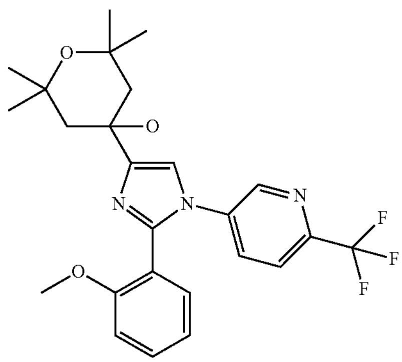 [SMILES: COc1ccccc1-c1nc(C2(O)CC(C)(C)OC(C)(C)C2)cn1-c1ccc(C(F)(F)F)nc1] |
| 110 | 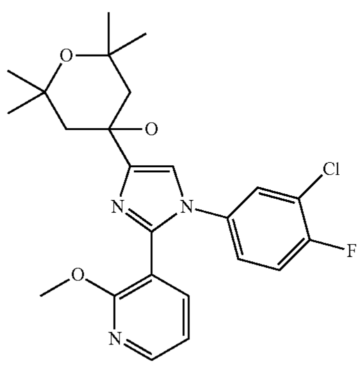 [SMILES: COc1ncccc1-c1nc(C2(O)CC(C)(C)OC(C)(C)C2)cn1-c1ccc(F)c(Cl)c1] |
| 111 | 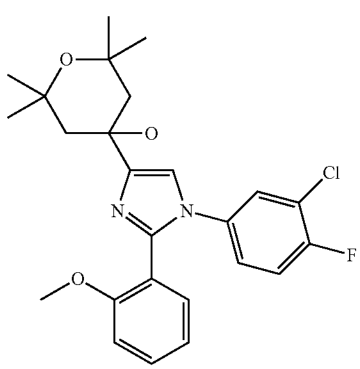 |
| 112 | |
| 113 | |
| 114 | |
| 115 | |

TABLE 8-continued
Compounds of Formula (I)
| Cpd No. | Structure |
|---|---|
| 116 | 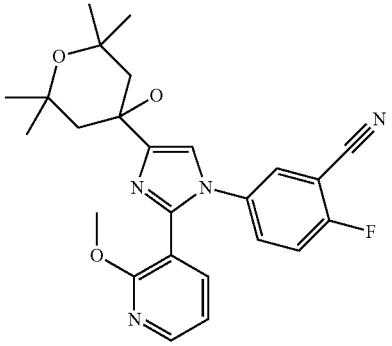 [SMILES: COc1ncccc1-c1nc(C2(O)CC(C)(C)OC(C)(C)C2)cn1-c1ccc(F)c(C#N)c1] |
| 117 | 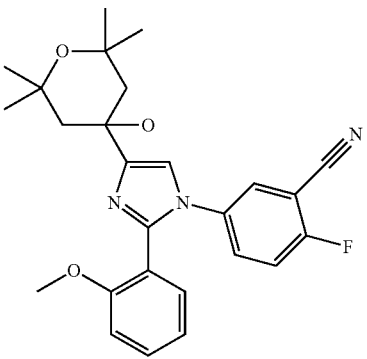 [SMILES: COc1ccccc1-c1nc(C2(O)CC(C)(C)OC(C)(C)C2)cn1-c1ccc(F)c(C#N)c1] |
| 118 | 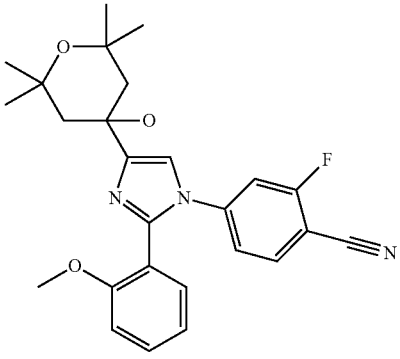 [SMILES: COc1ccccc1-c1nc(C2(O)CC(C)(C)OC(C)(C)C2)cn1-c1ccc(C#N)c(F)c1] |
| 119 | 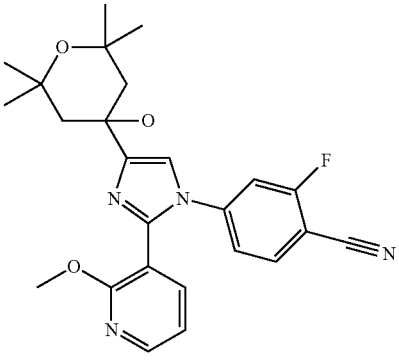 [SMILES: COc1ncccc1-c1nc(C2(O)CC(C)(C)OC(C)(C)C2)cn1-c1ccc(C#N)c(F)c1] |
| 120 | 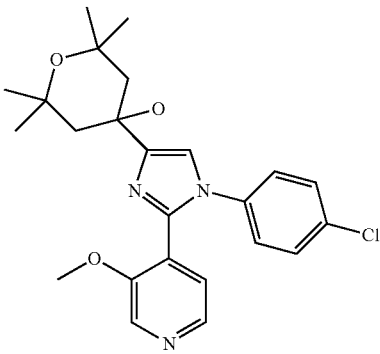 [SMILES: COc1cnccc1-c1nc(C2(O)CC(C)(C)OC(C)(C)C2)cn1-c1ccc(Cl)cc1] |
| 121 | 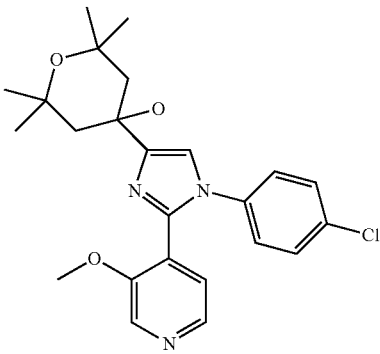 [SMILES: COc1cnccc1-c1nc(C2(O)CC(C)(C)OC(C)(C)C2)cn1-c1ccc(Cl)cc1] |
| 122 | 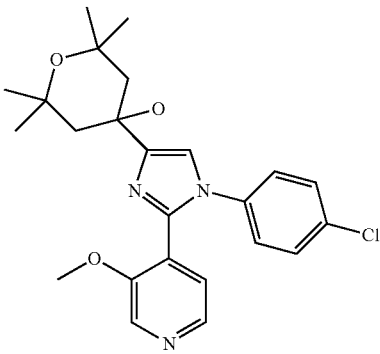 [SMILES: COc1cnccc1-c1nc(C2(O)CC(C)(C)OC(C)(C)C2)cn1-c1ccc(Cl)cc1] |
| 123 | 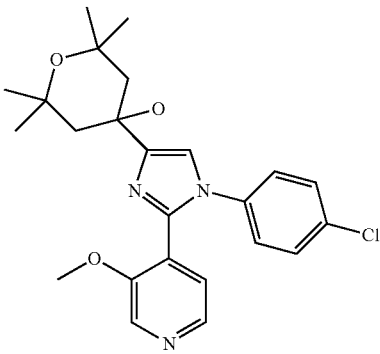 [SMILES: COc1cnccc1-c1nc(C2(O)CC(C)(C)OC(C)(C)C2)cn1-c1ccc(Cl)cc1] |

TABLE 8-continued

Compounds of Formula (I)

| Cpd No. | Structure |
|---|---|
| 124 | (structure: 2,2-dimethyl-dihydropyran connected to imidazole with 4-chlorophenyl and 2-methoxyphenyl substituents) |
| 125 | (structure: 2,2-dimethyl-dihydropyran connected to imidazole with 3-fluoro-4-bromophenyl and 2-methoxyphenyl substituents) |
| 126 | (structure: 2,2-dimethyl-dihydropyran connected to imidazole with 3-fluoro-4-cyanophenyl and 2-methoxyphenyl substituents) |

Biological Examples

In Vitro Assays

Example 1

Functional Assay

Calcium Influx Assay

A Ca flux assay using Functional Drug Screening System (FDSS, Hamamatsu) was utilized to identify novel N-type Ca channel antagonists (Dai et al 2008, Beladredetti et al 2009). All cell culture reagents were procured from HyClone and other reagents were from Fisher. Recombinant HEK 293 cells expressing human N-type Ca channel (Millipore) were maintained in DMEM F12 containing 10% FBS and selection antibiotics at 37° C. in 5% $CO_2$.

When CaV2.2 cells were 75%-85% confluent in their culture flask, they were removed from the flask, counted, and plated at 13,000-15,000 cells (50 μL) per well in black-wall clear-bottom 384-well assay plates. Cells were incubated at 30° C. in 5% $CO_2$ overnight. The medium was removed and cells were loaded with Fluo8 dye (AAT Bioquest) at 37° C. and 30° C., 30 min each in darkness. Cells were washed four times with wash buffer (16 mM Herep pH 7.2, 2 mM $CaCl_2$, 1 mM $MgCl_2$, 5 mM glucose, 140 mM choline chloride and 2 mM KCl) leaving 15 μL buffer after the last wash. Compounds of Formula (I), serially diluted, were added to the cell plate. The plates were incubated in darkness for 15 min. Cells were depolarized with 100 mM KCl and Ca influx was measured. Data was plotted as percent inhibition vs concentration of the compound and $IC_{50}$ values were generated using Graphpad Prism non-linear regression analysis. Resultant data are shown in Table 9.

Example 2

Measurement of Electrophysiological Response

The recombinant cell line described above was used in the measurement of electrophysiological properties with QPatch (Sophion). Cells were maintained in culture as mentioned above. Prior to the experiment, the flasks were moved to 30° C. and incubated for 48-72 hrs. On the day of assaying, cells were detached and harvested. The cell pellet was re-suspended in SMF4HEK (HyClone)/25 mM HEPS at 2-5 million/mL and placed on the QStirrer of the QPatch for 30-60 min prior to the start of the assay. The Intracellular Buffer contained 97.9 mM CsCl, 27 mM CsF, 8.2 mM EGTA, 10 mM HEPES, 2 mM NaCl, 0.3 mM GTP, 3 mM Mg-ATP pH ~7.3 adjusted with CsOH and ~280 mOsm. Extracellular buffer contained 132 mM NaCl, 5.4 mM KCl, 1.8 mM $CaCl_2$, 0.8 mM $MgCl_2$, 10 mM HEPES, 10 mM glucose pH ~7.4 adjusted with NaOH/HCl and ~300 mOsm. Microtiter-Plate/Reference Buffer contained 140 mM TEA-Cl, 10 mM $BaCl_2$, 0.8 mM $MgCl_2$, 10 mM HEPES pH ~7.4 adjusted with TEA-OH/HCl, and ~300 mOsm. Cells were transferred to a QPatch 48 plate and gigaseal was formed. The plate was perfused with intracellular and extracellular buffer. Compounds diluted in reference buffer were applied to the extracellular site and tested following the voltage protocol as described by Finley et al (2010). In brief, cells were depolarized from resting potential of −80 mV to +20 mV and current was recorded. Data was plotted as percent inhibition vs concentration of the compound and $IC_{50}$ values were generated using Graphpad Prism non-linear regression analysis. Resultant data is reported in Table 9. Concentration ranges for each compound are included with its Q patch value.

TABLE 9

FDSS and Q patch Assay Data

| Cpd No. | N Type $IC_{50}$ Data (μM) | | |
|---|---|---|---|
| | FDSS | Qpatch Pulse = 1 | Qpatch Pulse = 15 |
| 1 | 0.041 | 0.365 (0.01-1 μM) | >1 (0.01-1 μM) |
| 2 | 0.128 | NE (10 μM) | 6.2 (0.3-10 μM) |
| 3 | 0.376 | 0.830 (0.01-1 μM) | NE (0.01-1 μM) |
| 4 | 0.017 | 10 (0.3-10 μM) | 1.06 (0.3-10 μM) |
| 5 | 0.191 | 5.9 (0.3-10 μM) | 10 (0.3-10 μM) |
| 6 | 0.739 | 10 (0.3-10 μM) | 10 (0.3-10 μM) |
| 7 | 0.113 | 1.17 (0.3-10 μM) | 0.68 (0.3-10 μM) |
| 8 | >10 | 0.508 (0.01-1 μM) | >1 (0.01-1 μM) |
| 9 | 0.793 | 46% (0.01-1 μM) | 37% (0.01-1 μM) |
| 10 | 0.401 | 5.92 (0.3-10 μM) | 1.47 (0.3-10 μM) |

TABLE 9-continued

FDSS and Q patch Assay Data

| Cpd No. | FDSS | Qpatch Pulse = 1 | Qpatch Pulse = 15 |
|---|---|---|---|
| 11 | 0.082 | 63% (10 µM) | 21% (10 µM) |
| 12 | 0.63 | 28% (10 µM) | NE (10 µM) |
| 13 | 0.2 | >1 (0.01-1 uM) | NE (0.01-1 µM) |
| 14 | 2.7 | 0.266 (0.01-1 µM) | >1 (0.01-1 µM) |
| 15 | 0.256 | poor fit(0.01-0.3 µM) | poor fit(0.01-0.3 µM) |
| 16 | 0.359 | poor fit(0.01-0.3 µM) | poor fit(0.01-0.3 µM) |
| 17 | 0.591 | 4.4 (0.3-10 µM) | 5.2 (0.3-10 µM) |
| 18 | 0.108 | 0.694 (0.01-1 µM) | 0.376 (0.01- 1 µM) |
| 19 | 0.263 | 0.966 (0.01-1 µM) | 28% (1 µM) |
| 20 | 1.06 | >1 (0.01-1 µM) | NE (0.01-1 µM) |
| 21 | 0.119 | 0.639 (0.01-1 µM) | 39% (0.01-1 µM) |
| 22 | 0.075 | 0.590 (0.01-1 µM) | 0.847 (0.01-1 µM) |
| 23 | 0.31 | 21% (0.01-1 µM) | NE (0.01-1 µM) |
| 24 | 7.15 | 29% (0.01-1 µM) | NE (0.01-1 µM) |
| 25 | 0.818 | >1 (0.01-1 µM) | NE (0.01-1 µM) |
| 26 | 5.76 | >1 (0.01-1 µM) | >1 (0.01-1 µM) |
| 27 | 6.4 | poor fit(0.01-0.3 µM) | 1.9(0.01-1 µM) |
| 28 | 1.64 | poor fit(0.01-0.3 µM) | poor fit(0.01-0.3 µM) |
| 29 | 0.492 | poor fit(0.01-0.3 µM) | poor fit(0.01-0.3 µM) |
| 30 | 0.321 | 67% (10 µM) | 35% (10 µM) |
| 31 | 0.769 | 1.58(0.01-0.3 µM) | poor fit(0.01-0.3 µM) |
| 32 | 0.278 | >1 (0.01-1 µM) | NE (0.01-1 µM) |
| 33 | 0.459 | >1 (0.01-1 µM) | NE (0.01-1 µM) |
| 34 | 1.62 | 38% (0.01-1 µM) | NE (0.01-1 µM) |
| 35 | 0.838 | NA | NA |
| 36 | 0.04 | 0.376 (0.01-1 µM) | NE (0.01-1 µM) |
| 37 | 0.424 | NE (0.01-1 µM) | NE (0.01-1 µM) |
| 38 | 0.372 | 2.4 (0.3-10 µM) | 0.769 (0.3-10 µM) |
| 39 | 0.163 | 1.7 (0.3-10 µM) | 1.9 (0.3-10 µM) |
| 40 | 0.822 | 52% (10 µM) | 1.94 (0.3-10 µM) |
| 41 | 0.131 | 71% (10 µM) | 0.602 (0.3-10 µM) |
| 42 | 0.194 | 2.6 (0.3-10 µM) | 1.08 (0.3-10 µM) |
| 43 | 0.291 | 34% (10 µM) | 7.5 (0.3-10 µM) |
| 44 | 0.142 | 2.9 (0.3-10 µM) | 3.08 (0.3-10 µM) |
| 45 | 0.149 | 2.2 (0.3-10 µM) | 0.671 (0.3-10 µM) |
| 46 | 0.255 | 10 (0.3-10 µM) | 2.5 (0.3-10 µM) |
| 47 | 1.54 | >1 (0.01-1 µM) | NE (0.01-1 µM) |
| 48 | 5.41 | 0.222(0.01-1 µM) | 0.843 (0.01-1 µM) |
| 49 | 0.123 | >1 (0.01-1 µM) | NE (0.01-1 µM) |
| 50 | 0.215 | >1 (0.01-1 µM) | 0.971 (0.01-1 µM) |
| 51 | 0.029 | 0.179 (0.01-1 µM) | 0.701 (0.01-1 µM) |
| 52 | 0.115 | 0.721 (0.01-1 µM) | NE (0.01-1 µM) |
| 53 | 0.096 | 6.5 (0.3-10 µM) | 2.01 (0.3-10 µM) |
| 54 | 1.96 | 0.302 (0.01-1 µM) Poor fit(0.01-1 µM) | 0.237 (0.01-1 µM) Poor fit(0.01-1 µM) |
| 55 | 0.384 | 48% (0.01-1 µM) | 0.780 (0.01-1 µM) |
| 56 | 1.67 | NE (0.01-1 µM) | NE (0.01-1 µM) |
| 57 | 10 | NE (0.01-1 µM) | NE (0.01-1 µM) |
| 58 | 4.81 | NE (0.01-1 µM) | NE (0.01-1 µM) |
| 59 | 4.4 | poor fit(0.01-0.3 µM) | poor fit(0.01-0.3 µM) |
| 60 | 0.321 | 0.247(0.01-0.3 uM) | poor fit(0.01-0.3 µM) |
| 61 | 0.037 | 0.751(0.01-0.3 µM) | 1.05 (0.01-0.3 µM) |
| 62 | 0.177 | 81% (10 µM) | 0.413 (0.3-10 µM) |
| 63 | 0.213 | 53% (10 µM) | 3.5 (0.3-10 µM) |
| 64 | 0.36 | 4.06 (0.3-10 µM) | 1.72 (0.3-10 µM) |
| 65 | 0.225 | 58% (10 µM) | 8.6 (0.3-10 µM) |
| 66 | 0.049 | 10 (0.3-10 µM) | 1.3 (0.3-10 µM) |
| 67 | 0.166 | NE (10 µM) | NE (10 µM) |
| 68 | 0.109 | 10 (0.3-10 µM) | 4.6 (0.3-10 µM) |
| 69 | 1.43 | 53% (10 µM) | 29% (10 µM) |
| 70 | 0.871 | 41% (10 µM) | NE (10 µM) |
| 71 | 0.422 | 5.83 (0.01-1 µM) | poor fit(0.01-1 µM) |
| 72 | 2.4 | poor fit(0.01-1 µM) | poor fit(0.01-1 µM) |
| 73 | 8.16 | poor fit(0.01-1 µM) | poor fit(0.01-1 µM) |
| 74 | 0.488 | 36% (10 µM) | 44% (10 µM) |
| 75 | 2.060 | 9.8 (0.3-10 µM) | 4.2 (0.3-10 µM) |
| 76 | 0.151 | >1 (0.01-1 µM) | NE (0.01-1 µM) |
| 77 | 10 | >1 (0.01-1 µM) | NE (0.01-1 µM) |
| 78 | 0.234 | 58% (10 µM) | NE (0.01-1 µM) |
| 79 | 1.33 | 29% (10 µM) | 3.6 (0.3-10 µM) |
| 80 | 0.333 | NE (10 µM) | 28% (10 µM) |
| 81 | 0.201 | 6.7 (0.3-10 µM) | 2.8 (0.3-10 µM) |
| 82 | 3.26 | poor fit(0.01-0.3 µM) | poor fit(0.01-0.3 µM) |
| 83 | 0.049 | poor fit(0.01-0.3 µM) | poor fit(0.01-0.3 µM) |
| 84 | 0.362 | 39% (0.01-1 µM) | NE (0.01-1 µM) |
| 85 | 6.48 | 45% (0.01-1 µM) | NE (0.01-1 µM) |
| 86 | 1.3 | 28% (0.01-1 µM) | NE (0.01-1 µM) |
| 87 | 6.2 | poor fit(0.01-0.3 µM) | poor fit(0.01-0.3 µM) |
| 88 | 2.17 | 0.349 (0.01-0.3 µM) | poor fit(0.01-0.3 µM) |
| 89 | 0.205 | 0.517 (0.01-0.3 µM) | poor fit(0.01-0.3 µM) |
| 90 | 0.12 | poor fit(0.01-0.3 µM) | poor fit(0.01-0.3 µM) |
| 91 | 1.43 | 58% (10 µM) | 62% (10 µM) |
| 92 | 0.041 | 0.253 (0.01-1 µM) | 0.269 (0.01-1 µM) |
| 93 | 0.15 | 6.5 (0.3-10 µM) | 1.8 (0.3-10 µM) |
| 94 | 0.551 | NE (0.01-1 µM) | NE (0.01-1 µM) |
| 95 | 10 | NE (0.01-1 µM) | NE (0.01-1 µM) |
| 96 | 0.768 | 10 (0.3-10 µM) | 5.4 (0.3-10 µM) |
| 97 | 0.515 | NE (10 µM) | 3.08 (0.3-10 µM) |
| 98 | 0.692 | 9.02 (0.3-10 µM) | 3.6 (0.3-10 µM) |
| 99 | 10.9 | NE (0.01-1 µM) | NE (0.01-1 µM) |
| 100 | 10 | 10 (0.3-10 µM) | 10 (0.3-10 µM) |
| 101 | 3.58 | >1 (0.01-1 µM) | NE (0.01-1 µM) |
| 102 | 0.037 | 48% (10 µM) | 1.74 (0.3-10 µM) |
| 103 | 0.367 | 4.3 (0.3-10 µM) | 31% (10 µM) |
| 104 | 0.464 | NE (10 µM) | NE (10 µM) |
| 105 | 0.3 | 8.3 (0.3-10 µM) 0.964(0.01-1 µM) | 3.82 (0.3-10 µM) NE (0.01-1 µM) |
| 106 | 0.148 | 71% (10 µM) | 5.03 (0.3-10 µM) |
| 107 | 0.43 | 3.53(0.3-10 µM) | 2.42 (0.3-10 µM) |
| 108 | 0.394 | 5.8 (0.3-10 µM) | 7.4 (0.3-10 µM) |
| 109 | 0.322 | 4.5 (0.3-10 µM) | 7.9 (0.3-10 µM) |
| 110 | 0.385 | 44% (10 µM) | 30% (10 µM) |
| 111 | 0.257 | 62% (10 uM) | 2.5 (0.3-10 µM) |
| 112 | 0.041 | 2.5 (0.3-10 µM) | 3 (0.3-10 µM) |
| 113 | 0.083 | 4.4 (0.3-10 µM) | 7.8 (0.3-10 µM) |
| 114 | 0.607 | 0.668 (0.01-1 µM) | >1 (0.01-1 µM) |
| 115 | 0.731 | NE (10 µM) | NE (10 µM) |
| 116 | 1.37 | >1 (0.01-1 µM) | >1 (0.01-1 µM) |
| 117 | 1.44 | 40% (10 µM) | 25% (10 µM) |
| 118 | 0.15 | 8.1 (0.3-10 µM) | 10 (0.3-10 µM) |
| 119 | 1.29 | 28% (10 µM) | NE (10 µM) |
| 120 | 0.108 | 1.6 (0.3-10 µM) | 9.1 (0.3-10 µM) |
| 121 | 0.233 | 6.6 (0.3-10 µM) | 3.3 (0.3-10 µM) |
| 122 | 3.010 | NE (0.01-1 µM) | NE (0.01-1 µM) |
| 123 | 0.129 | 0.468 (0.01-1 µM) | >1 (0.01-1 µM) |
| 124 | 0.103 | 2.5 (0.3-10 µM) | 1.6 (0.3-10 µM) |
| 125 | 0.313 | 2.1 (0.3-10 µM) | 2.3 (0.3-10 µM) |
| 126 | 0.234 | 29% (10 µM) | 1.9 (0.3-10 µM) |

In Vivo Assays

Example 3

Complete Freud's Adjuvant (CFA) Induced Mechanical Allodynia

Animals arrived and were acclimatized for 1-2 weeks in a temperature-controlled room with a 12 h light/dark cycle and allowed free access to standard laboratory chow and water.

CFA (Sigma) was injected intra-plantar (75 µg/150 µL) from a concentration of 1:1 (diluted 1 mg/mL of CFA in 1 mL of PBS). CFA-induced mechanical allodynia was quantified by a Von frey test on day 2 (48 h post injection of CFA) and animals were randomized based on iPWT response (Dixon 1980). Animals exhibiting a PWT of <5.0 g were selected for testing. Animals were administered a compound of Formula (I) through appropriate route based on their pharmacokinetic properties. Responses were measured with a Von-Frey filament. The maximum possible effect (% MPE) was determined as 100% if sensitivity in ipsilateral paw neared that of the contralateral paw. Values from the vehicle-treated animals were considered 0%. The compound effect was determined based on these values. Resultant data are reported in Table 10, hereinbelow.

Example 4

Sciatic Nerve Ligation Model of Neuropathic Pain

Left L5 and L6 spinal nerves are isolated adjacent to the vertebral column and were ligated with 5-0 silk suture distal to the dorsal root ganglion, as described by Kim and Chung discovery of small-molecule N-type voltage-gated calcium channel antagonists". *Assay and Drug Development Technologies*, 2010; 8(6), 685-694.

Kim, S H and Chung, J M., "An Experimental Model For Peripheral Neuropathy Produced By Segmental Spinal Nerve Ligation In The Rat". *Pain,* 1992, 50, 355-363.

Nielsen C K, Lewis R J, Alewood D, Drinkwater R, Palant E, Patterson M, Yaksh T L, McCumber D and Smith M T. "Anti-allodynic efficacy of the c-conopeptide, Xen2174, in rats with neuropathic pain". *Pain,* 2005, 1-13.

TABLE 10

CFA and SNL In Vivo Data

| Dose | CFA (% Reversal) | | SNL(% MPE) | | | |
|---|---|---|---|---|---|---|
| (mg/kg) | Cpd 1 | Cpd 11 | Cpd 1 | Cpd 11 | Cpd 10 | Cpd 38 |
| 3 | NA | 20.97 ± 7.88 | NA | 28.29 ± 10.84 | 12.17 ± 11.24 | NA |
| 10 | NA | 41.12 ± 5.14 | NA | 49.01 ± 9.93 | 40.53 ± 13.64 | NA |
| 12.5 | 19.73 ± 8.25 | NA | 22.21 ± 7.61 | NA | NA | NA |
| 25 | 37.62 ± 7.17 | NA | 40.9 ± 20.29 | NA | NA | NA |
| 30 | NA | 55.8 ± 11.32 | NA | 70.69 ± 10.3 | 54.59 ± 13.37 | NA |
| 50 | 58.8 ± 10.22 | NA | 64.07 ± 12.31 | NA | NA | 87.01 ± 9.25 |
| 60 | NA | 76.4 ± 3.78 | NA | 96.18 ± 3.22 | NA | NA |
| 100 | 75.26 ± 8.96 | NA | 75 ± 13.01 | NA | 85.45 ± 8.44 | NA |

(1992). The incision was closed with the help of GLUture topical tissue adhesive. At 14 days post-surgery (one day prior to test compound administration), mechanical allodynia was quantified using eight von Frey filaments, calibrated in the range 0.4-15.1 g (Nielsen et al 2005). Rats were placed into individual plastic containers on top of a suspended wire mesh grid and acclimated to the test chambers for at least 15 min. Filaments were applied perpendicular to the mid-plantar paw surface, with enough force to cause slight buckling, and held in place for 6-8 sec until a response was noted as a sharp paw withdrawal, flinching, licking and/or biting immediately upon removal of the filament (Nielsen et al 2005). Rats exhibiting increased mechanical sensitivity (ipsilateral paw withdrawal test cut-off of <4.0 g) were selected and randomized. Test compounds of Formula (I) were administered and a response was measured at Tmax. The maximum possible effect (% MPE) was determined to be 100% if the sensitivity in the ipsilateral paw neared that of the contralateral paw. Values from vehicle-treated animals were considered 0%. The compound effect was determined based on these values. Resultant data are reported in Table 10, hereinbelow.

REFERENCES

Dai, G, Haedo R J, Warren V A, Ratliff K S, Bugianesi R M, Rush A, et al: A high-throughput assay for evaluating state-dependence and subtype selectivity of CaV2 calcium channel inhibitors. *Assay Drug Dev Technol,* 2008, 6, 195-212.

Beladredetti F, Tringham E, Eduljee C, Jiang X, Dong H, Hendricson A, et al. "A fluorescence-based high throughput screening assay for the identification of T-type calcium channel blockers". *Assay and Drug Development Technologies,* 2009, 7, 266-280.

Dixon, W J, "Efficient analysis of experimental observations". *Ann. Rev. Pharmacol. Toxicol.,* 1980, 20, 441-462.

Finley F A, Lubin M L, Neeper M P, Beck E, Liu Y, Flores C M, Qin N. "An integrated multiassay approach to the While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:
1. A compound of Formula (I)

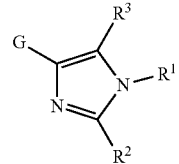

Formula (I)

wherein
R$^1$ is
i) phenyl optionally independently substituted with one to three substituents that are selected from the group consisting of chloro, fluoro, bromo, cyano, trifluoromethyl, C$_{1-4}$ alkyl, difluoromethoxy, and C$_{1-4}$ alkoxy; provided that when phenyl of group (i) is substituted with a single substituent, that substituent is at the 4-position;
ii) a heteroaryl selected from the group consisting of pyridinyl, pyrimidinyl, pyridazinyl, and pyrazinyl; wherein said heteroaryl is optionally independently substituted with one or two substituents that are chloro, fluoro, bromo, cyano, trifluoromethyl, C$_{1-4}$ alkyl, or C$_{1-4}$ alkoxy;
iii) pyrimidin-5-ylmethyl;
iv) phenylmethyl, wherein the phenyl portion of phenylmethyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylmethyl of group (iv) is substituted with a single substituent, that substituent is at the 4-position;
v) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylsulfonyl of group (v) is substituted with a single substituent, that substituent is at the 4-position;
vi) $C_{1-4}$ alkylsulfonyl;
vii) $C_{3-7}$cycloalkylsulfonyl; or
viii) trifluoromethylsulfonyl;
$R^2$ is
i) phenyl optionally substituted with a substituent that is selected from the group consisting of $C_{1-4}$alkoxy and trifluoromethoxy;
ii) a heteroaryl selected from the group consisting of pyridinyl, pyrimidinyl, thiazolyl, triazolyl, and pyrazinyl; wherein said heteroaryl is optionally substituted with a substituent that is $C_{1-4}$ alkyl, $C_{1-4}$ alkoxy, trifluoromethoxy, or hydroxy;
iii) $C_{3-7}$ cycloalkyl; or
iv) $C_{3-7}$ cycloalkyl-$(C_{1-2})$alkyl;
$R^3$ is selected from the group consisting of hydrogen, chloro, or methyl;
G is G1, G2, or G3,

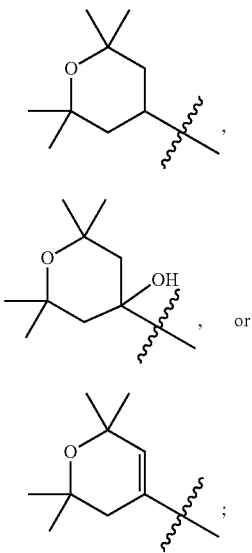

and enantiomers, diastereomers, and pharmaceutically acceptable salts thereof.

2. The compound of claim 1 wherein $R^1$ is
i) phenyl independently substituted with one to three substituents that are selected from the group consisting of chloro, fluoro, bromo, cyano, trifluoromethyl, $C_{1-4}$ alkyl, difluoromethoxy, and $C_{1-4}$ alkoxy; provided that when phenyl of group (i) is substituted with a single substituent, that substituent is at the 4-position;
ii) a heteroaryl that is pyridinyl; wherein said pyridinyl is optionally independently substituted with one or two substituents that are chloro, fluoro, bromo, cyano, trifluoromethyl, $C_{1-4}$ alkyl, or $C_{1-4}$ alkoxy;
iii) phenylmethyl, wherein the phenyl portion of phenylmethyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylmethyl of group (iii) is substituted with a single substituent, that substituent is at the 4-position;
iv) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylsulfonyl of group (iv) is substituted with a single substituent, that substituent is at the 4-position;
v) $C_{1-4}$ alkylsulfonyl; or
vi) trifluoromethylsulfonyl.

3. The compound of claim 2 wherein $R^1$ is
i) phenyl independently substituted with one to three substituents that are selected from the group consisting of chloro, fluoro, bromo, cyano, trifluoromethyl, methyl, difluoromethoxy, and $C_{1-2}$ alkoxy; provided that when phenyl of group (i) is substituted with a single substituent, that substituent is at the 4-position; or
ii) a heteroaryl that is pyridinyl; wherein said pyridinyl is optionally independently substituted with one or two substituents that are chloro, fluoro, bromo, cyano, trifluoromethyl, or $C_{1-4}$ alkoxy.

4. The compound of claim 3 wherein $R^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position.

5. The compound of claim 1 wherein $R^2$ is
i) phenyl substituted with a substituent that is selected from the group consisting of $C_{1-4}$ alkoxy and trifluoromethoxy;
ii) a heteroaryl selected from the group consisting of pyridinyl, pyrimidinyl, and pyrazinyl; wherein said heteroaryl is optionally substituted with a substituent that is $C_{1-4}$alkoxy or trifluoromethoxy;
iii) $C_{3-7}$cycloalkyl; or
iv) $C_{3-7}$cycloalkyl-$(C_{1-2})$alkyl.

6. The compound of claim 5 wherein $R^2$ is
i) phenyl substituted with $C_{1-4}$alkoxy;
ii) a heteroaryl selected from the group consisting of pyridinyl and pyrazinyl; wherein said heteroaryl is optionally substituted with $C_{1-4}$alkoxy; or
iii) $C_{3-7}$cycloalkyl-$(C_{1-2})$alkyl.

7. The compound of claim 6 wherein $R^2$ is
i) phenyl substituted with $C_{1-4}$alkoxy; or
ii) a heteroaryl selected from the group consisting of pyridinyl and pyrazinyl; wherein said heteroaryl is optionally substituted with $C_{1-4}$alkoxy.

8. The compound of claim 7 wherein $R^2$ is
i) phenyl substituted with methoxy; or
ii) a heteroaryl selected from the group consisting of pyridinyl and pyrazinyl; wherein said heteroaryl is optionally substituted with $C_{1-2}$ alkoxy.

9. The compound of claim 1 wherein $R^3$ is hydrogen.
10. The compound of claim 1 wherein G is G1 or G2;

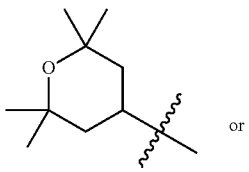

11. The compound of claim 10 wherein G is G1;

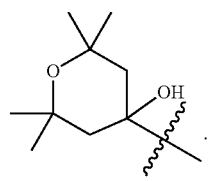

12. The compound of claim 11 wherein G is G2;

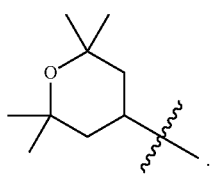

13. A compound of Formula (I)

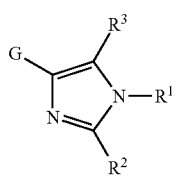

wherein
$R^1$ is
i) phenyl independently substituted with one to three substituents that are selected from the group consisting of chloro, fluoro, bromo, cyano, trifluoromethyl, $C_{1-4}$ alkyl, difluoromethoxy, and $C_{1-4}$ alkoxy; provided that when phenyl of group (i) is substituted with a single substituent, that substituent is at the 4-position;
ii) a heteroaryl that is pyridinyl; wherein said pyridinyl is optionally independently substituted with one or two substituents that are chloro, fluoro, bromo, cyano, trifluoromethyl, $C_{1-4}$ alkyl, or $C_{1-4}$ alkoxy;
iii) phenylmethyl, wherein the phenyl portion of phenylmethyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylmethyl of group (iii) is substituted with a single substituent, that substituent is at the 4-position;
iv) phenylsulfonyl, wherein the phenyl portion of phenylsulfonyl is optionally independently substituted with one or two substituents that are selected from the group consisting of chloro, fluoro, bromo, cyano, trifluoromethyl, $C_{1-4}$ alkyl, and $C_{1-4}$ alkoxy; provided that when phenylsulfonyl of group (iv) is substituted with a single substituent, that substituent is at the 4-position;
v) $C_{1-4}$ alkylsulfonyl; or
vi) trifluoromethylsulfonyl;
$R^2$ is
i) phenyl substituted with a substituent that is selected from the group consisting of $C_{1-4}$ alkoxy and trifluoromethoxy;
ii) a heteroaryl selected from the group consisting of pyridinyl, pyrimidinyl, and pyrazinyl; wherein said heteroaryl is optionally substituted with a substituent that is $C_{1-4}$ alkoxy or trifluoromethoxy;
iii) $C_{3-7}$ cycloalkyl; or
iv) $C_{3-7}$ cycloalkyl-$(C_{1-2})$alkyl;
$R^3$ is selected from the group consisting of hydrogen, chloro, or methyl;
G is G1 or G2;

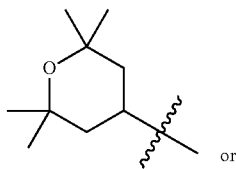
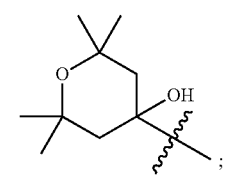

and enantiomers, diastereomers, and pharmaceutically acceptable salt forms thereof.
14. A compound of Formula (I)

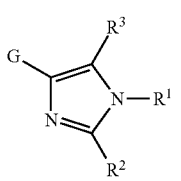

wherein
$R^1$ is
i) phenyl independently substituted with one to three substituents that are selected from the group consisting of chloro, fluoro, bromo, cyano, trifluoromethyl, methyl, difluoromethoxy, and $C_{1-2}$ alkoxy; provided that when phenyl of group (i) is substituted with a single substituent, that substituent is at the 4-position; or ii) a heteroaryl that is pyridinyl; wherein said pyridinyl is optionally independently substituted with one or two substituents that are chloro, fluoro, bromo, cyano, trifluoromethyl, or $C_{1-4}$ alkoxy;

$R^2$ is i) phenyl substituted with $C_{1-4}$ alkoxy;

ii) a heteroaryl selected from the group consisting of pyridinyl and pyrazinyl; wherein said heteroaryl is optionally substituted with $C_{1-4}$ alkoxy; or iii) $C_{3-7}$ cycloalkyl-$(C_{1-2})$alkyl;

$R^3$ is hydrogen;

G is G1 or G2;

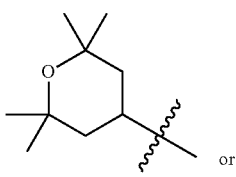

or

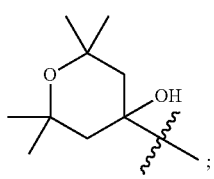

;

and enantiomers, diastereomers, and pharmaceutically acceptable salt forms thereof.

15. A compound of Formula (I)

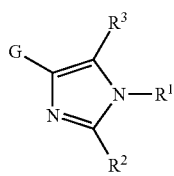

Formula (I)

wherein $R^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

$R^2$ is i) phenyl substituted with $C_{1-4}$ alkoxy; or ii) a heteroaryl selected from the group consisting of pyridinyl and pyrazinyl; wherein said heteroaryl is optionally substituted with $C_{1-4}$ alkoxy;

$R^3$ is hydrogen;

G is G1 or G2;

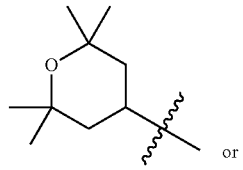

or

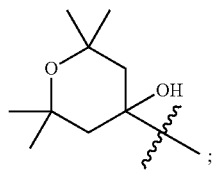

;

and enantiomers, diastereomers, and pharmaceutically acceptable salt forms thereof.

16. A compound of Formula (I)

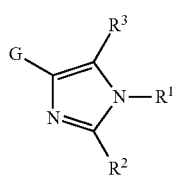

Formula (I)

wherein $R^1$ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

$R^2$ is i) phenyl substituted with methoxy; or ii) a heteroaryl selected from the group consisting of pyridinyl and pyrazinyl; wherein said heteroaryl is optionally substituted with $C_{1-2}$ alkoxy;

$R^3$ is hydrogen;

G is G1 or G2;

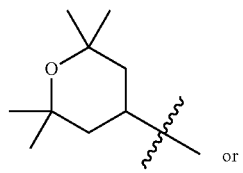

or

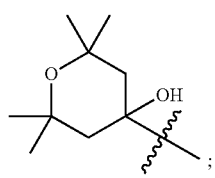

;

and enantiomers, diastereomers, and pharmaceutically acceptable salt forms thereof.

17. A compound of Formula (I)

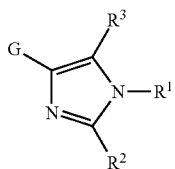

Formula (I)

wherein

R¹ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

R² is i) phenyl substituted with methoxy; or ii) a heteroaryl selected from the group consisting of pyridinyl and pyrazinyl; wherein said heteroaryl is optionally substituted with $C_{1-2}$ alkoxy;

R³ is hydrogen;

G is G1;

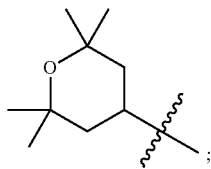

G1 and enantiomers, diastereomers, and pharmaceutically acceptable salt forms thereof.

18. A compound of Formula (I)

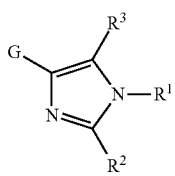

Formula (I)

wherein

R¹ is phenyl independently substituted with one to three substituents that are selected from the group consisting of chloro, fluoro, cyano, trifluoromethyl, difluoromethoxy, and methyl; provided that when phenyl is substituted with a single substituent, that substituent is at the 4-position;

R² is i) phenyl substituted with methoxy; or ii) a heteroaryl selected from the group consisting of pyridinyl and pyrazinyl; wherein said heteroaryl is optionally substituted with $C_{1-2}$alkoxy;

R³ is hydrogen;

G is G2;

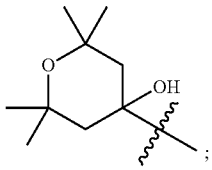

G2 and enantiomers, diastereomers, and pharmaceutically acceptable salt forms thereof.

19. A compound of Formula (I)

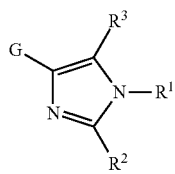

Formula (I)

selected from the group consisting of

Cpd 1, 4-[2-(2-Methoxyphenyl)-4-(2,2,6,6-tetramethyltetrahydro-2H-pyran-4-yl)-1H-imidazol-1-yl]benzonitrile;

Cpd 2, 4-[1-(4-Fluorophenyl)-4-(2,2,6,6-tetramethyltetrahydro-2H-pyran-4-yl)-1H-imidazol-2-yl]-3-methoxypyridine;

Cpd 3, 2-Ethoxy-5-[2-(3-methoxypyridin-4-yl)-4-(2,2,6,6-tetramethyltetrahydro-2H-pyran-4-yl)-1H-imidazol-1-yl]pyridine;

Cpd 4, 1-(4-Fluorophenyl)-2-(2-methoxyphenyl)-4-(2,2,6,6-tetramethyltetrahydro-2H-pyran-4-yl)-1H-imidazole;

Cpd 5, 5-[2-(2-Methoxyphenyl)-4-(2,2,6,6-tetramethyltetrahydro-2H-pyran-4-yl)-1H-imidazol-1-yl]-2-methylpyridine;

Cpd 6, 2-[2-(2-Methoxyphenyl)-4-(2,2,6,6-tetramethyltetrahydro-2H-pyran-4-yl)-1H-imidazol-1-yl]-5-methylpyridine;

Cpd 7, 2-(2-Methoxyphenyl)-1-(4-methoxyphenyl)-4-(2,2,6,6-tetramethyltetrahydro-2H-pyran-4-yl)-1H-imidazole;

Cpd 8, 5-[2-(2-Methoxyphenyl)-4-(2,2,6,6-tetramethyltetrahydro-2H-pyran-4-yl)-1H-imidazol-1-yl]-2-methylpyrimidine;

Cpd 9, 3-(1-(3-chlorobenzyl)-4-(2,2,6,6-tetramethyltetrahydro-2H-pyran-4-yl)-1H-imidazol-2-yl)-2-methoxypyridine;

Cpd 10, 3-[1-(4-Fluorophenyl)-4-(2,2,6,6-tetramethyltetrahydro-2H-pyran-4-yl)-1H-imidazol-2-yl]-2-methoxypyridine;

Cpd 11, 3-[1-(4-Chlorophenyl)-4-(2,2,6,6-tetramethyltetrahydro-2H-pyran-4-yl)-1H-imidazol-2-yl]-2-methoxypyridine;

Cpd 12, 4-[2-(3-Methoxypyridin-2-yl)-4-(2,2,6,6-tetramethyltetrahydro-2H-pyran-4-yl)-1H-imidazol-1-yl]benzonitrile;

Cpd 13, 4-[1-(4-Chloro-3-fluorophenyl)-4-(2,2,6,6-tetramethyltetrahydro-2H-pyran-4-yl)-1H-imidazol-2-yl]-3-methoxypyridine;

Cpd 14, 2-Chloro-5-[2-(2-methoxyphenyl)-4-(2,2,6,6-tetramethyltetrahydro-2H-pyran-4-yl)-1H-imidazol-1-yl]benzonitrile;

Cpd 15, 4-[2-(2-Methoxypyridin-3-yl)-4-(2,2,6,6-tetramethyltetrahydro-2H-pyran-4-yl)-1H-imidazol-1-yl]-2-methylbenzonitrile;

Cpd, 16, 2-methoxy-3-(4-(2,2,6,6-tetramethyltetrahydro-2H-pyran-4-yl)-1-(2,3,4-trifluorophenyl)-1H-imidazol-2-yl)pyridine;

Cpd 17, 2-[1-(3-Chloro-4-fluorophenyl)-4-(2,2,6,6-tetramethyltetrahydro-2H-pyran-4-yl)-1H-imidazol-2-yl]-3-methoxypyridine;

Cpd 18, 4-[1-(3-Chloro-4-fluorophenyl)-4-(2,2,6,6-tetramethyltetrahydro-2H-pyran-4-yl)-1H-imidazol-2-yl]-3-methoxypyridine;

Cpd 19, 2-[1-(4-Chloro-3-fluorophenyl)-4-(2,2,6,6-tetramethyltetrahydro-2H-pyran-4-yl)-1H-imidazol-2-yl]-3-methoxypyridine;

Cpd 20, 3-[1-(3-Chloro-4-fluorophenyl)-4-(2,2,6,6-tetramethyltetrahydro-2H-pyran-4-yl)-1H-imidazol-2-yl]-4-methoxypyridine;

Cpd 21, 4-[2-(2-Methoxyphenyl)-4-(2,2,6,6-tetramethyltetrahydro-2H-pyran-4-yl)-1H-imidazol-1-yl]-2-methylbenzonitrile;

Cpd 22, 5-[2-(2-Methoxyphenyl)-4-(2,2,6,6-tetramethyltetrahydro-2H-pyran-4-yl)-1H-imidazol-1-yl]-2-methylbenzonitrile;

Cpd 23, 3-[1-(3-Fluoro-4-methoxyphenyl)-4-(2,2,6,6-tetramethyltetrahydro-2H-pyran-4-yl)-1H-imidazol-2-yl]-2-methoxypyridine;

Cpd 24, 3-[1-(4-Fluoro-3-methoxyphenyl)-4-(2,2,6,6-tetramethyltetrahydro-2H-pyran-4-yl)-1H-imidazol-2-yl]-2-methoxypyridine;

Cpd 25, 5-[2-(2-Methoxypyridin-3-yl)-4-(2,2,6,6-tetramethyltetrahydro-2H-pyran-4-yl)-1H-imidazol-1-yl]-2-methylbenzonitrile;

Cpd 26, 3-[1-(4-Chlorophenyl)-4-(2,2,6,6-tetramethyltetrahydro-2H-pyran-4-yl)-1H-imidazol-2-yl]-4-methyl-4H-1,2,4-triazole;

Cpd 27, 3-[1-(2-Chlorobenzyl)-4-(2,2,6,6-tetramethyltetrahydro-2H-pyran-4-yl)-1H-imidazol-2-yl]-2-methoxypyridine;

Cpd 28, 3-[1-(4-Chlorobenzyl)-4-(2,2,6,6-tetramethyltetrahydro-2H-pyran-4-yl)-1H-imidazol-2-yl]-2-methoxypyridine;

Cpd 29, 4-(2-(2-methoxypyridin-3-yl)-4-(2,2,6,6-tetramethyltetrahydro-2H-pyran-4-yl)-1H-imidazol-1-yl)-2-(trifluoromethyl)benzonitrile;

Cpd 30, 3-[1-(2,4-Difluorophenyl)-4-(2,2,6,6-tetramethyltetrahydro-2H-pyran-4-yl)-1H-imidazol-2-yl]-2-methoxypyridine;

Cpd 31, 3-(1-(2,3-difluorophenyl)-4-(2,2,6,6-tetramethyltetrahydro-2H-pyran-4-yl)-1H-imidazol-2-yl)-2-methoxypyridine;

Cpd 32, 3-[2-(2-Methoxyphenyl)-4-(2,2,6,6-tetramethyltetrahydro-2H-pyran-4-yl)-1H-imidazol-1-yl]benzonitrile;

Cpd 33, 4-[1-(3,4-Difluorophenyl)-4-(2,2,6,6-tetramethyltetrahydro-2H-pyran-4-yl)-1H-imidazol-2-yl]-3-methoxypyridine;

Cpd 34, 2-Methoxy-4-[2-(2-methoxyphenyl)-4-(2,2,6,6-tetramethyltetrahydro-2H-pyran-4-yl)-1H-imidazol-1-yl]benzonitrile;

Cpd 35, 2-[1-(3,4-Difluorophenyl)-4-(2,2,6,6-tetramethyltetrahydro-2H-pyran-4-yl)-1H-imidazol-2-yl]-3-methoxypyridine;

Cpd 36, 3-Fluoro-4-[2-(2-methoxyphenyl)-4-(2,2,6,6-tetramethyltetrahydro-2H-pyran-4-yl)-1H-imidazol-1-yl]benzonitrile;

Cpd 37, 2-Methoxy-5-[2-(2-methoxyphenyl)-4-(2,2,6,6-tetramethyltetrahydro-2H-pyran-4-yl)-1H-imidazol-1-yl]benzonitrile;

Cpd 38, 1-(4-Chlorophenyl)-2-(2-methoxyphenyl)-4-(2,2,6,6-tetramethyltetrahydro-2H-pyran-4-yl)-1H-imidazole;

Cpd 39, 5-Chloro-2-[2-(2-methoxyphenyl)-4-(2,2,6,6-tetramethyltetrahydro-2H-pyran-4-yl)-1H-imidazol-1-yl]pyridine;

Cpd 40, 3-[1-(3,4-Difluorophenyl)-4-(2,2,6,6-tetramethyltetrahydro-2H-pyran-4-yl)-1H-imidazol-2-yl]-2-methoxypyridine;

Cpd 41, 1-(4-Chloro-3-fluorophenyl)-2-(2-methoxyphenyl)-4-(2,2,6,6-tetramethyltetrahydro-2H-pyran-4-yl)-1H-imidazole;

Cpd 42, 1-(3,4-Difluorophenyl)-2-(2-methoxyphenyl)-4-(2,2,6,6-tetramethyltetrahydro-2H-pyran-4-yl)-1H-imidazole;

Cpd 43, 4-[2-(2-Methoxypyridin-3-yl)-4-(2,2,6,6-tetramethyltetrahydro-2H-pyran-4-yl)-1H-imidazol-1-yl]benzonitrile;

Cpd 44, 3-[1-(4-Chloro-3-fluorophenyl)-4-(2,2,6,6-tetramethyltetrahydro-2H-pyran-4-yl)-1H-imidazol-2-yl]-2-methoxypyridine;

Cpd 45, 1-(3-Chloro-4-fluorophenyl)-2-(2-methoxyphenyl)-4-(2,2,6,6-tetramethyltetrahydro-2H-pyran-4-yl)-1H-imidazole;

Cpd 46, 3-[1-(3-Chloro-4-fluorophenyl)-4-(2,2,6,6-tetramethyltetrahydro-2H-pyran-4-yl)-1H-imidazol-2-yl]-2-methoxypyridine;

Cpd 47, 2-[1-(4-Fluorophenyl)-4-(2,2,6,6-tetramethyltetrahydro-2H-pyran-4-yl)-1H-imidazol-2-yl]-3-methoxypyrazine;

Cpd 48, 3-[2-(2-Methoxypyridin-3-yl)-4-(2,2,6,6-tetramethyltetrahydro-2H-pyran-4-yl)-1H-imidazol-1-yl]benzonitrile;

Cpd 49, 5-[1-(4-Chlorophenyl)-4-(2,2,6,6-tetramethyltetrahydro-2H-pyran-4-yl)-1H-imidazol-2-yl]-4-methoxypyrimidine;

Cpd 50, 2-[1-(4-Chlorophenyl)-4-(2,2,6,6-tetramethyltetrahydro-2H-pyran-4-yl)-1H-imidazol-2-yl]-3-methoxypyrazine;

Cpd 51, 3-[1-(4-Chlorophenyl)-4-(2,2,6,6-tetramethyltetrahydro-2H-pyran-4-yl)-1H-imidazol-2-yl]-2-ethoxypyridine;

Cpd 52, 3-[1-(3,4-Difluorophenyl)-4-(2,2,6,6-tetramethyltetrahydro-2H-pyran-4-yl)-1H-imidazol-2-yl]-2-ethoxypyridine;

Cpd 53, 5-[2-(2-Methoxyphenyl)-4-(2,2,6,6-tetramethyltetrahydro-2H-pyran-4-yl)-1H-imidazol-1-yl]-2-(trifluoromethyl)pyridine;

Cpd 54, 2-Methoxy-3-{4-(2,2,6,6-tetramethyltetrahydro-2H-pyran-4-yl)-1-[6-(trifluoromethyl)pyridin-3-yl]-1H-imidazol-2-yl}pyridine;

Cpd 55, 1-(4-Chlorophenyl)-2-(cyclopropylmethyl)-4-(2,2,6,6-tetramethyltetrahydro-2H-pyran-4-yl)-1H-imidazole;

Cpd 56, 1-(4-Chlorophenyl)-2-cyclopropyl-4-(2,2,6,6-tetramethyltetrahydro-2H-pyran-4-yl)-1H-imidazole;

Cpd 57, 4-[2-Cyclopropyl-4-(2,2,6,6-tetramethyltetrahydro-2H-pyran-4-yl)-1 H-imidazol-1-yl]benzonitrile;

Cpd 58, 4-[2-(Cyclopropylmethyl)-4-(2,2,6,6-tetramethyltetrahydro-2H-pyran-4-yl)-1H-imidazol-1-yl]benzonitrile;

Cpd 59, 5-[2-(Cyclopropylmethyl)-4-(2,2,6,6-tetramethyltetrahydro-2H-pyran-4-yl)-1H-imidazol-1-yl]-2-(trifluoromethyl)pyridine;

Cpd 60, 2-[1-(4-Chlorophenyl)-4-(2,2,6,6-tetramethyltetrahydro-2H-pyran-4-yl)-1H-imidazol-2-yl]-3-ethoxypyrazine;

Cpd 61, 1-(4-(difluoromethoxy)phenyl)-2-(2-methoxyphenyl)-4-(2,2,6,6-tetramethyltetrahydro-2H-pyran-4-yl)-1H-imidazole;

Cpd 62, 1-(4-Bromo-3-fluorophenyl)-2-(2-methoxyphenyl)-4-(2,2,6,6-tetramethyltetrahydro-2H-pyran-4-yl)-1H-imidazole;

Cpd 63, 1-(3-Bromo-4-fluorophenyl)-2-(2-methoxyphenyl)-4-(2,2,6,6-tetramethyltetrahydro-2H-pyran-4-yl)-1H-imidazole;

Cpd 64, 3-[1-(3-Bromo-4-fluorophenyl)-4-(2,2,6,6-tetramethyltetrahydro-2H-pyran-4-yl)-1H-imidazol-2-yl]-2-methoxypyridine;

Cpd 65, 3-[1-(4-Bromo-3-fluorophenyl)-4-(2,2,6,6-tetramethyltetrahydro-2H-pyran-4-yl)-1H-imidazol-2-yl]-2-methoxypyridine;

Cpd 66, 4-(1-(4-chlorophenyl)-4-(2,2,6,6-tetramethyltetrahydro-2H-pyran-4-yl)-1H-imidazol-2-yl)-3-methoxypyridine;

Cpd 67, 2-(1-(4-chlorophenyl)-4-(2,2,6,6-tetramethyltetrahydro-2H-pyran-4-yl)-1H-imidazol-2-yl)-3-methoxypyridine;

Cpd 68, 3-(1-(4-chlorophenyl)-4-(2,2,6,6-tetramethyltetrahydro-2H-pyran-4-yl)-1H-imidazol-2-yl)-4-methoxypyridine;

Cpd 69, 3-(1-(4-fluorophenyl)-4-(2,2,6,6-tetramethyltetrahydro-2H-pyran-4-yl)-1H-imidazol-2-yl)-4-methoxypyridine;

Cpd 70, 2-(1-(4-fluorophenyl)-4-(2,2,6,6-tetramethyltetrahydro-2H-pyran-4-yl)-1H-imidazol-2-yl)-3-methoxypyridine;

Cpd 71, 3-(1-(2,5-difluorophenyl)-4-(2,2,6,6-tetramethyltetrahydro-2H-pyran-4-yl)-1H-imidazol-2-yl)-2-methoxypyridine;

Cpd 72, 3-(1-(3,5-difluorophenyl)-4-(2,2,6,6-tetramethyltetrahydro-2H-pyran-4-yl)-1H-imidazol-2-yl)-2-methoxypyridine;

Cpd 73, 3-fluoro-5-(2-(2-methoxypyridin-3-yl)-4-(2,2,6,6-tetramethyltetrahydro-2H-pyran-4-yl)-1H-imidazol-1-yl)benzonitrile;

Cpd 74, 2-Fluoro-5-[2-(2-methoxy-phenyl)-4-(2,2,6,6-tetramethyl-tetrahydro-pyran-4-yl)-imidazol-1-yl]-benzonitrile;

Cpd 75, 3-[1-(6-Ethoxypyridin-3-yl)-4-(2,2,6,6-tetramethyltetrahydro-2H-pyran-4-yl)-1H-imidazol-2-yl]-2-methoxypyridine;

Cpd 76, 3-Fluoro-4-[2-(2-methoxypyridin-3-yl)-4-(2,2,6,6-tetramethyltetrahydro-2H-pyran-4-yl)-1H-imidazol-1-yl]benzonitrile;

Cpd 77, 2-Methoxy-4-[2-(2-methoxypyridin-3-yl)-4-(2,2,6,6-tetramethyltetrahydro-2H-pyran-4-yl)-1H-imidazol-1-yl]benzonitrile;

Cpd 78, 2-Chloro-4-[2-(2-methoxypyridin-3-yl)-4-(2,2,6,6-tetramethyltetrahydro-2H-pyran-4-yl)-1H-imidazol-1-yl]benzonitrile;

Cpd 79, 2-Fluoro-5-[2-(2-methoxypyridin-3-yl)-4-(2,2,6,6-tetramethyltetrahydro-2H-pyran-4-yl)-1H-imidazol-1-yl]benzonitrile;

Cpd 80, 2-Fluoro-4-[2-(2-methoxypyridin-3-yl)-4-(2,2,6,6-tetramethyltetrahydro-2H-pyran-4-yl)-1H-imidazol-1-yl]benzonitrile;

Cpd 81, 2-Fluoro-4-[2-(2-methoxyphenyl)-4-(2,2,6,6-tetramethyltetrahydro-2H-pyran-4-yl)-1H-imidazol-1-yl]benzonitrile;

Cpd 82, 2,6-difluoro-4-(2-(2-methoxypyridin-3-yl)-4-(2,2,6,6-tetramethyltetrahydro-2H-pyran-4-yl)-1H-imidazol-1-yl)benzonitrile;

Cpd 83, 3,5-difluoro-4-(2-(2-methoxyphenyl)-4-(2,2,6,6-tetramethyltetrahydro-2H-pyran-4-yl)-1H-imidazol-1-yl)benzonitrile;

Cpd 84, 2-Chloro-5-[2-(2-methoxypyridin-3-yl)-4-(2,2,6,6-tetramethyltetrahydro-2H-pyran-4-yl)-1H-imidazol-1-yl]benzonitrile;

Cpd 85, 2-Methoxy-5-[2-(2-methoxypyridin-3-yl)-4-(2,2,6,6-tetramethyltetrahydro-2H-pyran-4-yl)-1H-imidazol-1-yl]benzonitrile;

Cpd 86, 4-[2-(4-Methoxypyrimidin-5-yl)-4-(2,2,6,6-tetramethyltetrahydro-2H-pyran-4-yl)-1H-imidazol-1-yl]benzonitrile;

Cpd 87, 4-[2-(3-Methoxypyrazin-2-yl)-4-(2,2,6,6-tetramethyltetrahydro-2H-pyran-4-yl)-1H-imidazol-1-yl]benzonitrile;

Cpd 88, 2-fluoro-4-(2-(3-methoxypyrazin-2-yl)-4-(2,2,6,6-tetramethyltetrahydro-2H-pyran-4-yl)-1H-imidazol-1-yl)benzonitrile;

Cpd 89, 4-(2-(2-ethoxypyridin-3-yl)-4-(2,2,6,6-tetramethyltetrahydro-2H-pyran-4-yl)-1H-imidazol-1-yl)-2-fluorobenzonitrile;

Cpd 90, 1-(4-chlorophenyl)-2-(2-methoxyphenyl)-5-methyl-4-(2,2,6,6-tetramethyltetrahydro-2H-pyran-4-yl)-1H-imidazole;

Cpd 91, 4-[5-Chloro-2-(2-methoxypyridin-3-yl)-4-(2,2,6,6-tetramethyltetrahydro-2H-pyran-4-yl)-1H-imidazol-1-yl]benzonitrile;

Cpd 92, 3-[5-Chloro-1-(4-fluorophenyl)-4-(2,2,6,6-tetramethyltetrahydro-2H-pyran-4-yl)-1H-imidazol-2-yl]-2-methoxypyridine;

Cpd 93, 3-[5-Chloro-1-(4-chlorophenyl)-4-(2,2,6,6-tetramethyltetrahydro-2H-pyran-4-yl)-1H-imidazol-2-yl]-2-methoxypyridine;

Cpd 94, 2-(2-Methoxyphenyl)-4-(2,2,6,6-tetramethyltetrahydro-2H-pyran-4-yl)-1-[(trifluoromethyl)sulfonyl]-1H-imidazole;

Cpd 95, 1-(Cyclopropylsulfonyl)-2-(2-methoxyphenyl)-4-(2,2,6,6-tetramethyltetrahydro-2H-pyran-4-yl)-1H-imidazole;

Cpd 96, 2-(2-Methoxyphenyl)-1-[(2-methylpropyl)sulfonyl]-4-(2,2,6,6-tetramethyltetrahydro-2H-pyran-4-yl)-1H-imidazole;

Cpd 97, 1-[(4-Chlorophenyl)sulfonyl]-2-(2-methoxyphenyl)-4-(2,2,6,6-tetramethyltetrahydro-2H-pyran-4-yl)-1H-imidazole;

Cpd 98, 1-[(4-Fluorophenyl)sulfonyl]-2-(2-methoxyphenyl)-4-(2,2,6,6-tetramethyltetrahydro-2H-pyran-4-yl)-1H-imidazole;

Cpd 99, 4-{[2-(2-Methoxyphenyl)-4-(2,2,6,6-tetramethyltetrahydro-2H-pyran-4-yl)-1H-imidazol-1-yl]methyl}benzonitrile;

Cpd 100, 5-{[2-(2-Methoxyphenyl)-4-(2,2,6,6-tetramethyltetrahydro-2H-pyran-4-yl)-1H-imidazol-1-yl]methyl}pyrimidine;

Cpd 101, 3-{[2-(2-Methoxyphenyl)-4-(2,2,6,6-tetramethyltetrahydro-2H-pyran-4-yl)-1H-imidazol-1-yl]methyl}benzonitrile;

Cpd 102, 4-[1-(4-Chlorophenyl)-2-(2-methoxyphenyl)-1H-imidazol-4-yl]-2,2,6,6-tetramethyltetrahydro-2H-pyran-4-ol;

Cpd 103, 4-[1-(4-Chlorophenyl)-2-(4-methoxypyridin-3-yl)-1H-imidazol-4-yl]-2,2,6,6-tetramethyltetrahydro-2H-pyran-4-ol;

Cpd 104, 4-[1-(4-Chlorophenyl)-2-(3-methoxypyridin-2-yl)-1H-imidazol-4-yl]-2,2,6,6-tetramethyltetrahydro-2H-pyran-4-ol;

Cpd 105, 4-[1-(4-Chlorophenyl)-2-(2-methoxypyridin-3-yl)-1H-imidazol-4-yl]-2,2,6,6-tetramethyltetrahydro-2H-pyran-4-ol;

Cpd 106, 4-[1-(3-Bromo-4-fluorophenyl)-2-(2-methoxyphenyl)-1H-imidazol-4-yl]-2,2,6,6-tetramethyltetrahydro-2H-pyran-4-ol;

Cpd 107, 4-[1-(3,4-Difluorophenyl)-2-(2-methoxyphenyl)-1H-imidazol-4-yl]-2,2,6,6-tetramethyltetrahydro-2H-pyran-4-ol;

Cpd 108, 4-[1-(3,4-Difluorophenyl)-2-(2-methoxypyridin-3-yl)-1H-imidazol-4-yl]-2,2,6,6-tetramethyltetrahydro-2H-pyran-4-ol;

Cpd 109, 4-{2-(2-Methoxyphenyl)-1-[6-(trifluoromethyl)pyridin-3-yl]-1H-imidazol-4-yl}-2,2,6,6-tetramethyltetrahydro-2H-pyran-4-ol;

Cpd 110, 4-[1-(3-Chloro-4-fluorophenyl)-2-(2-methoxypyridin-3-yl)-1H-imidazol-4-yl]-2,2,6,6-tetramethyltetrahydro-2H-pyran-4-ol;

Cpd 111, 4-[1-(3-Chloro-4-fluorophenyl)-2-(2-methoxyphenyl)-1H-imidazol-4-yl]-2,2,6,6-tetramethyltetrahydro-2H-pyran-4-ol;

Cpd 112, 4-[1-(4-Chloro-3-fluorophenyl)-2-(2-methoxyphenyl)-1H-imidazol-4-yl]-2,2,6,6-tetramethyltetrahydro-2H-pyran-4-ol;

Cpd 113, 4-[1-(4-Chloro-3-fluorophenyl)-2-(2-methoxypyridin-3-yl)-1H-imidazol-4-yl]-2,2,6,6-tetramethyltetrahydro-2H-pyran-4-ol;

Cpd 114, 4-[1-(4-Chlorophenyl)-2-(2-ethoxypyridin-3-yl)-1H-imidazol-4-yl]-2,2,6,6-tetramethyltetrahydro-2H-pyran-4-ol;

Cpd 115, 4-[4-(4-Hydroxy-2,2,6,6-tetramethyltetrahydro-2H-pyran-4-yl)-2-(2-methoxypyridin-3-yl)-1H-imidazol-1-yl]benzonitrile;

Cpd 116, 2-Fluoro-5-[4-(4-hydroxy-2,2,6,6-tetramethyltetrahydro-2H-pyran-4-yl)-2-(2-methoxypyridin-3-yl)-1H-imidazol-1-yl]benzonitrile;

Cpd 117, 2-Fluoro-5-[4-(4-hydroxy-2,2,6,6-tetramethyltetrahydro-2H-pyran-4-yl)-2-(2-methoxyphenyl)-1H-imidazol-1-yl]benzonitrile;

Cpd 118, 2-Fluoro-4-[4-(4-hydroxy-2,2,6,6-tetramethyltetrahydro-2H-pyran-4-yl)-2-(2-methoxyphenyl)-1H-imidazol-1-yl]benzonitrile;

Cpd 119, 2-Fluoro-4-[4-(4-hydroxy-2,2,6,6-tetramethyltetrahydro-2H-pyran-4-yl)-2-(2-methoxypyridin-3-yl)-1H-imidazol-1-yl]benzonitrile;

Cpd 120, 4-[1-(4-Chlorophenyl)-2-(3-methoxypyridin-4-yl)-1H-imidazol-4-yl]-2,2,6,6-tetramethyltetrahydro-2H-pyran-4-ol;

Cpd 121, 4-[2-(2-Methoxyphenyl)-4-(2,2,6,6-tetramethyltetrahydro-2H-pyran-4-yl)-1H-imidazol-1-yl]-2-(trifluoromethyl)benzonitrile;

Cpd 122, 3-[1-(4-Chlorophenyl)-4-(2,2,6,6-tetramethyltetrahydro-2H-pyran-4-yl)-1H-imidazol-2-yl]pyridin-2-ol;

Cpd 123, 2-Chloro-4-[2-(2-methoxyphenyl)-4-(2,2,6,6-tetramethyltetrahydro-2H-pyran-4-yl)-1H-imidazol-1-yl]benzonitrile;

Cpd 124, 1-(4-Chlorophenyl)-2-(2-methoxyphenyl)-4-(2,2,6,6-tetramethyl-3,6-dihydro-2H-pyran-4-yl)-1H-imidazole;

Cpd 125, 1-(4-Bromo-3-fluorophenyl)-2-(2-methoxyphenyl)-4-(2,2,6,6-tetramethyl-3,6-dihydro-2H-pyran-4-yl)-1H-imidazole;

Cpd 126, 2-Fluoro-4-[2-(2-methoxyphenyl)-4-(2,2,6,6-tetramethyl-3,6-dihydro-2H-pyran-4-yl)-1H-imidazol-1-yl]benzonitrile;

and pharmaceutically acceptable salt forms thereof.

20. A pharmaceutical composition comprising a compound of claim 1 or 19 and at least one of a pharmaceutically acceptable carrier, a pharmaceutically acceptable excipient, and a pharmaceutically acceptable diluent.

21. The pharmaceutical composition of claim 20, wherein the composition is a solid oral dosage form.

22. The pharmaceutical composition of claim 20, wherein the composition is a syrup, an elixir or a suspension.

23. A method for treating peripheral neuropathic pain in a subject in need thereof, comprising:
administering to the subject a therapeutically effective amount of a compound of claim 1 or 19.

24. The method according of claim 23, wherein the peripheral neuropathic pain is a neuropathic pain associated with spinal cord injury.

* * * * *